US010556963B2

(12) United States Patent
Spits et al.

(10) Patent No.: US 10,556,963 B2
(45) Date of Patent: Feb. 11, 2020

(54) MEANS AND METHODS FOR COUNTERACTING MYELOPROLIFERATIVE OR LYMPHOPROLIFERATIVE DISORDERS

(71) Applicant: AIMM Therapeutics B.V., Amsterdam Zuidoost (NL)

(72) Inventors: Hergen Spits, Amsterdam Zuidoost (NL); Tim Beaumont, Amsterdam Zuidoost (NL); Marijn Aletta Gillissen, Amsterdam Zuidoost (NL); Adrianus Quirinus Bakker, Amsterdam Zuidoost (NL); Mette Deborah Hazenberg, Amsterdam Zuidoost (NL); Martijn Kedde, Amsterdam Zuidoost (NL)

(73) Assignee: AIMM THERAPEUTICS B.V., Amsterdam Zuidoost (NL)

( * ) Notice: Subject to any disclaimer, the term of this patent is extended or adjusted under 35 U.S.C. 154(b) by 220 days.

(21) Appl. No.: 15/105,076

(22) PCT Filed: Dec. 17, 2014

(86) PCT No.: PCT/NL2014/050873
§ 371 (c)(1),
(2) Date: Jun. 16, 2016

(87) PCT Pub. No.: WO2015/093949
PCT Pub. Date: Jun. 25, 2015

(65) Prior Publication Data
US 2016/0326261 A1    Nov. 10, 2016

(30) Foreign Application Priority Data
Dec. 17, 2013  (EP) .................................. 13197882

(51) Int. Cl.
| C07K 16/30 | (2006.01) |
| C07K 16/06 | (2006.01) |
| A61K 47/68 | (2017.01) |
| C07K 16/40 | (2006.01) |
| C12P 21/00 | (2006.01) |
| G01N 33/574 | (2006.01) |

(52) U.S. Cl.
CPC ...... *C07K 16/3061* (2013.01); *A61K 47/6851* (2017.08); *C07K 16/06* (2013.01); *C07K 16/40* (2013.01); *C12P 21/005* (2013.01); *G01N 33/57492* (2013.01); *C07K 2317/21* (2013.01); *C07K 2317/33* (2013.01); *C07K 2317/565* (2013.01); *C07K 2317/73* (2013.01); *C07K 2317/732* (2013.01); *C07K 2317/734* (2013.01); *G01N 2333/705* (2013.01)

(58) Field of Classification Search
None
See application file for complete search history.

(56) References Cited

U.S. PATENT DOCUMENTS

| 5,593,676 A | 1/1997 | Bhat et al. |
| 7,399,847 B1 | 7/2008 | Seed et al. |
| 9,005,974 B2 | 4/2015 | Spits |
| 2010/0203007 A1* | 8/2010 | Li ....................... C07D 487/04 424/85.1 |

FOREIGN PATENT DOCUMENTS

| EP | 1974017 B1 | 11/2013 |
| WO | 2002099059 A2 | 12/2002 |
| WO | 2006121240 A1 | 11/2006 |
| WO | 2007146172 A2 | 12/2007 |
| WO | 2013120012 A2 | 8/2013 |
| WO | 2015093949 A2 | 6/2015 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Borche, L., et al., 2005; CD43 monoclonal antibodies recognize the large sialoglycoprotein of human leukocytes; European Journal of Immunology, vol. 17, No. 10, pp. 1523-1526.
Hanly, W. Carey, et al., 1995; Review of Polyclonal Antibody Production Procedures in Mammals and Poultry; ILAR Journal, vol. 37, No. 3, pp. 93-118.
De Laurentiis, A., et al., 2011; Mass Spectrometry-Based Identification of the Tumor Antigen UN1 as the Transmembrane CD43 Sialoglycoprotein; Molecular & Cellular Proteomics, vol. 10, No. 5, M111.007898, pp. 1-12.
Malcovati, L., et al., 2013; Diagnosis and treatment of primary myelodysplastic syndromes in adults: recommendations from the European LeukemiaNet; Blood, vol. 122, No. 17, pp. 2943-2964.
Miller, P.H., et al., 2013; Enhanced normal short-term human myelopoiesis in mice engineered to express human-specific myeloid growth factors; Blood, vol. 121, No. 5, pp. e1-e4.
Schmid, K., et al., 1992; Amino acid sequence of human plasma galactoglycoprotein: Identity with the extracellular region of CD43 (sialophorin); Proceedings of the National Academy of Sciences of the United States of America, vol. 89, No. 2, pp. 663-667.
Shelley, C.S., et al., 1989; Molecular characterization of sialophorin (CD43), the lymphocyte surface sialoglycoprotein defective in Wiskott-Aldrich syndrome; Proceedings of the National Academy of Sciences of the United States of America, vol. 86, pp. 2819-2823.
Tuccillo, F.M., et al. , 2014; Cancer-associated CD43 glycoforms as target of immunotherapy; National Institute of Health, Mol Cancer Ther. vol. 13, No. 3; pp. 752-762.
Gillissen, M., et al., Dec. 6, 2014; Unique and Potent Tumor Specific Antibodies in Graft . . . ; Blood Journal, 124(21).

(Continued)

*Primary Examiner* — Brad Duffy
(74) *Attorney, Agent, or Firm* — Gianna J. Arnold; Saul Ewing Arnstein & Lehr LLP

(57) ABSTRACT

The invention provides human AML-specific binding compounds that are able to bind a cell surface component of AML cells. Therapeutic uses of binding compounds against AML are also provided.

16 Claims, 48 Drawing Sheets

Specification includes a Sequence Listing.

(56) References Cited

OTHER PUBLICATIONS

Tuccillo, F., et al.; Aberrant Glycosylation as Biomarker for Cancer: Focus on CD43; BioMed Research International; vol. 2014, Article ID 742831; pp. 1-13.
Buckley, S., et al., 2015; Update on Antigen-Specific Immunotherapy of Acute Myeloid Leukemia; Curr Hematol Malig Rep, vol. 10, pp. 65-75.
Kwakkenbos, M., et al., 2016; Stable long-term cultures of self-renewing B cells and their applications; Immunological Reviews, vol. 270, pp. 65-77.
Gillissen, M., et al., 2015; B lymphocytes are important effector cells in anti-AML responses after allogeneic hematopoietic stem cell transplantation; haematologica; vol. 100, p. 277.
Hazenberg, M., et al., 2016; Tumor-specific glycosylated CD43 is a novel and highly specific target for acute myeloid leukemia and myelodysplastic syndrome; haematologica; vol. 101, p. 191.
Kim, S., et al., Jun. 2014; Characterization of Two Novel mAbs Recognizing Different Epitopes on CD43; Immune Network; vol. 14, No. 3, pp. 164-170.
Hasegawa, K., et al., Mar. 24, 2016; Glycosylation Status of CD43 Protein is Associated with Resistance of Leukemia Cells to CTL-Mediated Cytolysis; PLOS ONE, vol. 10, No. 1371, pp. 1-14.
Matsuoka S., et al.; "A Novel Type of Cell Death of Lymphocytes Induced by a Monoclonal Antibody without Participation of Complement" The Journal of Experimental Medicine, Rockefeller University Press, US, vol. 181, Jun. 1, 1995, pp. 2007-2015.
Zhang C., et al.; "A cell surface receptor defined by a mAb mediates a unique type of cell death similar to oncosis;" Proceedings of the National Academy of Sciences, National Academy of Sciences, US, vol. 95, May 1, 1998, pp. 6290-6295.
International Search Report and Written Opinion, dated Nov. 13, 2015, issued in PCT/NL2014/050873.
Bakker, A.B., et al.; C-type lectin-like molecule-1: a novel myeloid cell surface marker associated with acute myeloid leukemia; Cancer Researc, Nov. 15, 2004, vol. 64, pp. 8443-8450.
Bennett, J.M., et al.; Proposals for the classification of the acute leukaemias; 1976, British Journal of Haematology, vol. 33, pp. 451-458.
Bhat, N.M., et al.; Rapid cytotoxicity of human B lymphocytes induced by VH4-34 (VH4.21) gene-encoded monoclonal antibodies, II; Clinical and Experimental Immunology, 1977, vol. 108, pp. 151-159.
Bernacki, M.A., et al.; Efficacious immune therapy in chronic myelogenous leukemia (CML) recognizes antigens that are expressed on CML progenitor cells; American Association for Cancer Research, Feb. 1, 2010, vol. 70, pp. 906-915.
Brady, Hugh J.M.; 2004 Methods in Molecular Biology, vol. 282.
Chen, Y., et al.; Selection and analysis of an optimized anti-VEGF antibody: crystal structure of an affinity-matured Fab in complex with antigen; Journal of Molecular Biology, 1999, vol. 293, pp. 865-881.
Diehl, S.A., et al.; STAT3-mediated up-regulation of BLIMP1 Is coordinated with BCL6 down-regulation to control human plasma cell differentiation; The Journal of Immunology, 2008, vol. 180, pp. 4805-4815.
Drexler, H.G., et al.; History and classification of human leukemia lymphoma cell lines; Leukemia and Lymphoma, 1998, vol. 31, pp. 305-316.

Hernandez, A.M., et al.; Anti-NeuGcGM3 Antibodies, Actively Elicited by Idiotypic Vaccination in Nonsmall Cell Lung Cancer Patients Induce Tumor Cell Death by an Oncosis-Like Mechanism; The Journal of Immunology, 2011, vol. 186, pp. 3735-3744.
Kattah, N.H., et al.; The U1-snRNP complex: structural properties relating to autoimmune pathogenesis in rheumatic diseases. Immunol Reviews; 2010, vol. 233, pp. 126-145.
Kepp, O., et al.; Cell death assays for drug discovery; Nature Reviews Drug Discovery, Mar. 2011, vol. 10, pp. 221-237.
Kwakkenbos, M.J., et al.; Generation of stable monoclonal antibody-producing B cell receptor-positive human memory B cells by genetic programming; Nature Medicine, Jan. 2010, vol. 16, No. 1, pp. 123-128.
Majeti, R., et al.; CD47 is an adverse prognostic factor and therapeutic antibody target on human acute myeloid leukemia stem cells; Cell, Jul. 24, 2009, vol. 138, pp. 286-299.
Schlenk, R.F., et al.; Mutations and treatment outcome in cytogenetically normal acute myeloid leukemia; The New England Journal of Medicine, May 1, 2008, vol. 358, pp. 1909-1918.
Schmid, C., et al; Donor lymphocyte infusion in the treatment of first hematological relapse after allogeneic stem-cell transplantation in adults with acute myeloid leukemia: a retrospective risk factors analysis and comparison with other strategies by the EBMT Acute Leukemia Working Party; Journal of Clinical Oncology, Nov. 1, 2007, vol. 25, No. 31, pp. 4938-4945.
Schmiedel, B.J., et al.; Generation and Preclinical Characterization of a Fc-optimized GITR-Ig Fusion Protein for Induction of NK Cell Reactivity Against Leukemia; The American Society of Gene & Cell Therapy, Molecular Therapy, Apr. 2013, vol. 21, No. 4, pp. 877-886.
Singh, R., et al. The non-steroidal anti-inflammatory drugs Sulindac sulfide and Diclofenac induce apoptosis and differentiation in human acute myeloid leukemia cells through an AP-1 dependent pathway; Apoptosis, 2011, vol. 16, pp. 889-901.
Tsuchiya, S., et al.; Establishment and characterization of a human acute monocytic leukemia cell line (THP-1); Int J Cancer, 1980, vol. 26, pp. 171-176.
Walther, R.B., et al.; Acute myeloid leukemia stem cells and CD33-targeted immunotherapy; Blood, 2012., vol. 119, No. 26, pp. 6198-208.
Willingham, S.B., et al.; The CD47-signal regulatory protein alpha (SIRPa) interaction is a therapeutic target for human solid tumors; Proceedings of the National Academy of Sciences, vol. 109:, No. 17, pp. 6662-6667.
Wu, C.J., et al.; Detection of a potent humoral response associated with immune-induced remission of chronic myelogenous leukemia, The Journal of Clinical Investigation, Sep. 2000, vol. 106, No. 5, pp. 705-714.
Imai, Norikazu, et al.; Program and Abstracts for Joint Symposium of 69th Annual Meeting of the Japanese Society of Hematology and the 49th Annual Meeting of the Japanese Society of Clinical Hematology; The Japanese Journal of Clinical Hematology, vol. 48, No. 9, Sep. 2007; Published by the Japanese Society of Clinical Hematology.
Mumada, Minoru; Acute Myelocytic Leukemia and Expectations for Molecular-Targeting Therapy—Novel Target Adhesion Molecule CD44 Emerges in America/Canada; Medicine and Drug Journal, vol. 43, No. 3, Mar. 2007; Published by Medicine and Drug Journal Co.

\* cited by examiner

FIG. 1

AIMM Therapeutics AML antibody panel
NB: CDR numbering according to Kabat et al (1991)

AT12-023 (11C9-22C11)

Heavy chain

Recombined from gene segments:
IGHV4-34*01 F
IGHD2-2*01 F
IGHJ6*03 F

AMINO ACID:
Fw1 QVQLQQWGAGLLKPSETLSLTCAVYGGSFS
CDR1 GYYWS
Fw2 WIRQPPGKGLEWIG
CDR2 EINHSGSTNYNPSLKS
Fw3 RVTISVDTSKNQFSLKLSSVTAADTAVYYCAR
CDR3 GRSTSPLDYYYYMDV
Fw4 WAKGTTVTVSS

NUCLEOTIDE:
Fw1 cag gtg cag cta cag cag tgg ggc gca gga ctg ttg aag cct tcg gag acc ctg tcc ctc acc tgc gct gtc tat ggt ggg tcc ttc agt CDR1 ggt tac tac tgg agc Fw2 tgg atc cgc cag ccc cca ggg aag ggg ctg gag tgg att ggg CDR2 gaa atc aat cat agt gga agc acc aac tac aac ccg tcc ctc aag agt Fw3 cga gtc acc ata tca gta gac acg tcc aag aac cag ttc tcc ctg aag ctg agc tct gtg acc gcc gcg gac acg gct gtg tat tac tgt gcg agg CDR3 ggc cgt agt acc agc ccg ctc gac tac tac tac tac tac atg gac gtc Fw4 tgg gcc aaa ggg acc acg gtc acc gtc tcc tca

Light chain

Recombined from gene segments:
IGLV3-19*01 F
IGLJ3*02 F

AMINO ACID:
Fw1 SSELTQDPAVSVALGQTVRITC
CDR1 QGDFLRSYYAS
Fw2 WYQQKPGQAPVLVIF
CDR2 GKNKRPS
Fw3 GIPDRFSGSSSGNTASLTITGAQAEDEADYYC
CDR3 NSRDRSGNHLV
Fw4 FGGGTKLTVL

NUCLEOTIDE:
Fw1 tct tct gag ctg act cag gac cct gct gtg tct gtg gcc ttg gga cag aca gtc agg atc aca tgc CDR1 caa gga gac ttc ctc aga agc tat tat gca agc Fw2 tgg tac cag cag aag cca gga cag gcc cct gta ctt gtc atc ttt CDR2 ggt aaa aac aag cgg ccc tca Fw3 ggg atc cca gac cga ttc tct ggc tcc agc tca gga aac aca gct tcc ttg acc atc act ggg gct cag gcg gaa gat gag gct gac tat tac tgt CDR3 aac tcc cgg gac cgc agt ggt aac cac ctg gtg Fw4 ttc ggc gga ggg acc aag ctg acc gtc cta

Heavy chain

Recombined from gene segments:
IGHV4-34*01 F
IGHD1-1*01 F
IGHJ4*02 F

AMINO ACID:
Fw1 QVQLQQWGAGLLKPSETLSLTCAVYGGSFS
CDR1 GYYWS
Fw2 WIRQPPGKGLEWIG
CDR2 EINHSGSTNYNPSLKS
Fw3 RVTISVDTSKNQFSLKLSSVTAADTAVYYCAR
CDR3 GSMARPKPFDY
Fw4 WGQGTLVTVSS

NUCLEOTIDE:
Fw1 cag gtg cag cta cag cag tgg ggc gca gga ctg ttg aag cct tcg gag acc ctg tcc ctc acc tgc gct gtc tat ggt ggg tcc ttc agt CDR1 ggt tat tac tgg agc Fw2 tgg atc cgc cag ccc cca ggg aag ggg ctg gag tgg att ggg CDR2 gaa atc aat cat agt gga agc acc aac tac aac ccg tcc ctc aag agt Fw3 cga gtc acc ata tca gta gac acg tcc aag aac cag ttc tcc ctg aag ctg agc tct gtg acc gcc gcg gac acg gct gtg tat tac tgt gcg aga CDR3 ggc tca atg gca aga ccc aag cca ttt gac tac Fw4 tgg ggc cag gga acc ctg gtc acc gtc tcc tca

Light chain

Recombined from gene segments:
IGKV1-39*01 F
IGKJ3*01 F

AMINO ACID:
Fw1 DIQMTQSPSSLSASVGDRVTITC
CDR1 RASQSISRYLN
Fw2 WYQQKPGKAPKLLIY
CDR2 AASSLQS
Fw3 GVPSRFSGSGSGTDFTLTISSLQPEDFATYYC
CDR3 QQSYSTPRT
Fw4 FGPGTKVDIK

NUCLEOTIDE:
Fw1 gac atc cag atg acc cag tct cca tcc tcc ctg tct gca tct gta gga gac aga gtc acc atc act tgc CDR1 cgg gca agt cag agc att agc agg tat tta aat Fw2 tgg tat cag cag aaa cca ggg aaa gcc cct aag ctc ctg atc tat CDR2 gct gca tcc agt ttg caa agt Fw3 ggg gtc cca tca agg ttc agt ggc agt gga tct ggg aca gat ttc act ctc acc atc agc agt ctg caa cct gaa gat ttt gca act tac tac tgt CDR3 caa cag agt tac agt acc cct cgc act Fw4 ttc ggc cct ggg acc aaa gtg gat atc aaa

Heavy chain

Recombined from gene segments:
IGHV3-30*02 F
IGHD3-22*01 F
IGHJ4*02 F

AMINO ACID:
Fw1 QVQLVESGGGVVQPGRSLRLSCAASGFTFS
CDR1 SYGMH
Fw2 WVRQAPGKGLEWVA
CDR2 FIRYDGSNKYFADSVRG
Fw3 RFTISRDNSKNTLFLQMNSLRAEDTAVYYCAK
CDR3 DPQERIYYSDTSGYLDY
Fw4 WGQGTLVTVSS

NUCLEOTIDE:
Fw1 cag gtg cag ctg gtg gag tct ggg gga ggc gtg gtc cag cct ggg agg tcc ctg aga ctc tcc tgt gca gcg tct gga ttc acc ttc agt CDR1 agc tat ggc atg cac Fw2 tgg gtc cgc cag gct cca ggc aag ggg ctg gag tgg gtg gca CDR2 ttt ata cgg tat gat gga agt aat aaa tac ttt gca gac tcc gtg agg ggc Fw3 cga ttc acc atc tcc aga gac aat tcc aag aac acg ctg ttt ctg caa atg aac agc ctg aga gct gag gac acg gct gtg tat tac tgt CDR3 gcg aaa gat ccc caa gag cgt att tat tac tct gat act agt ggt tac ctt gac tac Fw4 tgg ggc cag gga acc ctg gtc acc gtc tcc tca

Light chain

Recombined from gene segments:
IGKV1-5*03 F
IGKJ2*01 F

AMINO ACID:
Fw1 DIQMTQSPSTLSASVGDRVTITC
CDR1 RASQSISSWLA
Fw2 WYQQKPGKAPKLLIY
CDR2 KASSLES
Fw3 GVPSRFSGTGSGTEFTLTISSLQPDDFATYYC
CDR3 QQYNTYPYT
Fw4 FGQGTKLEIK

NUCLEOTIDE:
Fw1 gac atc cag atg acc cag tct cct tcc acc ctg tct gca tct gta gga gac aga gtc acc atc act tgc CDR1 cgg gcc agt cag agt att agt agc tgg ttg gcc Fw2 tgg tat cag cag aaa cca ggg aaa gcc cct aag ctc ctg atc tat CDR2 aag gcg tct agt tta gaa agt Fw3 ggg gtc cca tca agg ttc agc ggc act gga tct ggg aca gaa ttc act ctc acc atc agc agc ctg cag cct gat gat ttt gca act tat tac tgc CDR3 caa cag tat aat act tac ccg tac act Fw4 ttt ggc cag ggg acc aag ctg gag atc aaa

Heavy chain

Recombined from gene segments:
IGHV3-23*01 F
IGHD3-10*01 F
IGHJ4*02 F

AMINO ACID:
Fw1 EVHLLESGGGLVQPGGSLRLSCAASGFTFS
CDR1 SYAMS
Fw2 WVRQAPGKGLEWVS
CDR2 TIRASGGSTSYADSVKG
Fw3 RFTISRDNSQSRLYLQMNSLTAEDTAVYYCAK
CDR3 SPAMIRGVRGGDYFDY
Fw4 WGQGTLVTVSS

NUCLEOTIDE:
Fw1 gag gtg cac ctg ttg gag tct ggg gga ggc ttg gta cag cct ggg ggg tcc ctg aga ctc tcc tgt gca gcc tct gga ttc acc ttt agc CDR1 agc tat gcc atg agt Fw2 tgg gtc cgc cag gct cca ggg aag ggg ctg gag tgg gtc tca CDR2 act att agg gct agt ggt ggt agc aca agc tac gca gac tcc gtg aag ggc Fw3 cgg ttc acc atc tcc aga gac aat tcc cag agc agg ttg tat ctg caa atg aac agt ctg aca gcc gag gac acg gcc gta tat tac tgt gcg aaa CDR3 tct cct gct atg att cgg gga gtt agg ggg ggt gac tac ttt gac tac Fw4 tgg ggc cag gga acc ctg gtc acc gtc tcc tca

Light chain

Recombined from gene segments:
IGKV1-8*01 F
IGKJ2*01 F

AMINO ACID:
Fw1 AIRLTQSPSSVSASTGDRVTITC
CDR1 RASQAFSSYLV
Fw2 WYQQKPGKAPNLLIY
CDR2 ATSTLQG
Fw3 GVPSRFSGSGSGTDFTLTISNLQSEDFATYYC
CDR3 QQYYSYPPT
Fw4 FGQGTKLEIK

NUCLEOTIDE:
Fw1 gcc atc cgg ttg acc cag tct cca tcc tca gtc tct gca tct aca gga gac aga gtc acc atc act tgt CDR1 cgg gcg agt cag gct ttt agc agt tat tta gtc Fw2 tgg tat cag caa aaa cca ggg aaa gcc cct aac ctc ctg atc tac CDR2 gct aca tcc act ttg caa ggt Fw3 ggg gtc cca tca agg ttc agc ggc agt gga tct ggg aca gat ttc act ctc acc atc agc aac ctg cag tct gaa gat ttt gca act tat tac tgt CDR3 caa cag tat tat agt tac cct ccg act Fw4 ttt ggc cag ggg acc aag ttg gag atc aaa

Heavy chain

Recombined from gene segments:
IGHV3-30*03 F
IGHD2-15*01 F
IGHJ6*02 F

AMINO ACID:
Fw1 QVQLVESGGGVVQPGRSLRLSCAASGFTFS
CDR1 SYGMH
Fw2 WVRQAPGKGLEWVAV
CDR2 ISYDGSNKYYADSVKG
Fw3 RFTISRDNSKNTLYLQMNSLRAEDTAVYYCAK
CDR3 DGKGIVVIYYYYGMDV
Fw4 WGQGTTVTVSS

NUCLEOTIDE:
Fw1 cag gtg cag ctg gtg gag tct ggg gga ggc gtg gtc cag cct ggg agg tcc ctg aga ctc tcc tgt gca gcc tct gga ttc acc ttc agt CDR1 agc tat ggc atg cac Fw2 tgg gtc cgc cag gct cca ggc aag ggg ctg gag tgg gtg gca gtt CDR2 ata tca tat gat gga agt aat aaa tac tat gca gac tcc gtg aag ggc Fw3 cga ttc acc atc tcc aga gac aat tcc aag aac acg ctg tat ctg caa atg aac agc ctg aga gct gag gac acg gct gtg tat tac tgt gcg aaa CDR3 gat ggg aag ggg att gta gtt att tac tac tac tac ggt atg gac gtc Fw4 tgg ggc caa ggg acc acg gtc acc gtc tcc tca

Light chain

Recombined from gene segments:
IGLV3-1*01 F
IGLJ2*01 F

AMINO ACID:
Fw1 SYELTQPPSVSVSPGQTASITC
CDR1 SGDKLGDKYAC
Fw2 WYQQKPGQSPVLVIY
CDR2 QDSKRPS
Fw3 GIPERFSGSNSGNTATLTISGTQAMDEADYYC
CDR3 QAWDSSTVVF
Fw4 GGGTKLTVL

NUCLEOTIDE:
Fw1 tcc tat gag ctg act cag cca ccc tca gtg tcc gtg tcc cca gga cag aca gcc agc atc acc tgc CDR1 tct gga gat aaa ttg ggg gat aaa tat gct tgc Fw2 tgg tat cag cag aag cca ggc cag tcc cct gtg ctg gtc atc tat CDR2 caa gat agc aag cgg ccc tca Fw3 ggg atc cct gag cga ttc tct ggc tcc aac tct ggg aac aca gcc act ctg acc atc agc ggg acc cag gct atg gat gag gct gac tat tac tgt CDR3 cag gcg tgg gac agc agc act gtg gta ttc Fw4 ggc gga ggg acc aag ctg acc gtc cta

Heavy chain

Recombined from gene segments:
IGHV4-34*12 F
IGHD2-2*01 F
IGHJ4*02 F

AMINO ACID:
Fw1 QVQLQQWGAGLLKPSETLSLTCAVYGGSFS
CDR1 GYFWT
Fw2 WIRQPPGKGLEWIG
CDR2 ETVHSGGTNYNPSLKS
Fw3 RVTISVDTSKNQFSLRLNSVTAADTAVYYCVR
CDR3 GLNSPFDY
Fw4 WGQGTLVTVSS

NUCLEOTIDE:
Fw1 cag gta cag cta cag cag tgg ggc gca gga ctg ttg aag cct tcg gag acc ctg tcc ctc acc tgc gct gtc tat ggt ggg tcc ttc agt CDR1 ggt tac ttc tgg acc Fw2 tgg atc cgc cag ccc cca ggg aag ggg ctg gag tgg att ggg CDR2 gaa acc gtt cat agt gga ggc acc aac tac aac ccg tcc ctc aag agt Fw3 cga gtc acc ata tca gtc gac acg tcc aag aac cag ttc tcc ctg agg ctg aac tct gtg acc gcc gcg gac acg gct gtg tat tac tgt gtg aga CDR3 ggc ctt aac agc ccc ttt gac tac Fw4 tgg ggc cag gga acc cta gtc acc gtc tcc tca

Light chain

Recombined from gene segments:
IGKV1-17*01 F
IGKJ1*01 F

AMINO ACID:
Fw1 DIQMTQSPSSLSASVGDRVTITC
CDR1 RASQGIRNVLG
Fw2 WYQQKPGKAPKCLIY
CDR2 AASSLQS
Fw3 GVPSRFSGSGSGTEFTLTISSLQPEDFATYYC
CDR3 LQHNSHPRT
Fw4 FGQGTKVEIK

NUCLEOTIDE:
Fw1 gac atc cag atg acc cag tct cca tcc tcc ctg tct gca tct gta gga gac aga gtc acc atc act tgc CDR1 cgg gca agt cag ggc att aga aat gtt tta ggc Fw2 tgg tat cag cag aaa cca ggg aaa gcc cct aag tgc ctg atc tat CDR2 gct gca tcc agt ttg caa agt Fw3 ggg gtc cca tca agg ttc agc ggc agt gga tct ggg aca gaa ttc act ctc aca atc agc agc ctg cag cct gaa gat ttt gca act tat tac tgt CDR3 cta cag cat aat agt cac ccc cgg acg Fw4 ttc ggc caa ggg acc aag gtg gaa atc aaa

Heavy chain

Recombined from gene segments:
IGHV4-34*01 F
IGHD6-6*01 F
IGHJ4*02 F

AMINO ACID:
Fw1 QVQLQQWGAGLLKPSETLSLTCAVYGGSFS
CDR1 GYYWS
Fw2 WIRQPPGKGLEWIG
CDR2 EINHSGSTNYNPSLKS
Fw3 RVTISVDTSKKQFSLKLSSVTAADTAVYYCAR
CDR3 GPRGMYSSSSGDY
Fw4 WGQGTLVTVSS

NUCLEOTIDE:
Fw1 cag gtg cag cta cag cag tgg ggc gca gga ctg ttg aag cct tcg gag acc ctg tcc ctc acc tgc gct gtc tat ggt ggg tcc ttc agt CDR1 ggt tac tac tgg agc Fw2 tgg atc cgc cag ccc cca ggg aag ggg ctg gag tgg att ggg CDR2 gaa atc aat cat agt gga agc acc aac tac aac ccg tcc ctc aag agt Fw3 cga gtc acc ata tca gta gac acg tcc aag aag cag ttc tcc ctg aag ctg agc tct gtg acc gcc gcg gac acg gct gtg tat tat tgt gcg aga ggc CDR3 ccc cgg ggc atg tat agc agc tcg tcc ggg gac tac Fw4 tgg ggc cag gga acc ctg gtc acc gtc tcc tca

Light chain

Recombined from gene segments:
IGKV1-17*01 F
IGKJ2*02 F

AMINO ACID:
Fw1 DIQMTQSPSSLSASVGDRVTITC
CDR1 RASQGIRNDLG
Fw2 WYQQKPGKAPKRLIY
CDR2 AAVSLQS
Fw3 GVPSRFSGSGSGTEFTLTISSLQPEDFATYYC
CDR3 LQHNSYPRT
Fw4 FGQGTKLEIK

NUCLEOTIDE:
Fw1 gac atc cag atg acc cag tct cca tcc tcc ctg tct gca tct gta gga gac aga gtc acc atc act tgc CDR1 cgg gca agt cag ggc att aga aat gat tta ggc Fw2 tgg tat cag cag aaa cca ggg aaa gcc cct aag cgc ctg atc tat CDR2 gct gca gtc agt ttg caa agt Fw3 ggg gtc cca tca agg ttc agc ggc agt gga tct ggg aca gaa ttc act ctc aca atc agc agc ctg cag cct gaa gat ttt gca act tat tac tgt CDR3 cta cag cat aat agt tac cct cgg act Fw4 ttt ggc cag ggg acc aag ctg gag atc aaa

Heavy chain

Recombined from gene segments:
IGHV3-21*01 F
IGHD1-26*01 F
IGHJ6*03 F

AMINO ACID:
Fw1 EVQLVESGGGLVKPGGSLRLSCAASGFTFS
CDR1 TYSMN
Fw2 WVRQAPGKGLEWVS
CDR2 SISSSSGYIYYADSVKG
Fw3 RFTISRDNAKNSLYLQMNSLRAEDTAVYYCAR
CDR3 DGTFSYYYYMDV
Fw4 WGKGTTVTVSS

NUCLEOTIDE:
Fw1 gag gtg cag ctg gtg gag tct ggg gga ggc ctg gtc aag cct ggg ggg tcc ctg aga ctc tcc tgt gca gcc tct gga ttc acc ttc agt CDR1 acc tat agc atg aac Fw2 tgg gtc cgc cag gct cca ggg aag ggg ctg gag tgg gtc tca CDR2 tcc att agt agt agt agt ggt tac ata tac tac gca gac tca gtg aag ggc Fw3 cga ttc acc atc tcc aga gac aac gcc aag aac tca ctg tat ctg caa atg aac agc ctg aga gcc gag gac acg gct gtg tat tac tgt gcg aga CDR3 gat ggg act ttc tcc tac tac tac tac atg gac gtc Fw4 tgg ggc aaa ggg acc acg gtc acc gtc tcc tca

Light chain

Recombined from gene segments:
IGKV1-8*01 F
IGKJ1*01 F

AMINO ACID:
Fw1 AIRMTQSPSSFSASTGDRVTITC
CDR1 RASQDISSSLA
Fw2 WYQQKPGKAPKLLIY
CDR2 AASTLQS
Fw3 GVPSRFSGSGSGTDFTLTISCLQSEDFATYYC
CDR3 QQYYSYPPT
Fw4 FGQGTRLEIK

NUCLEOTIDE:
Fw1 gcc atc cgg atg acc cag tct cca tcc tca ttc tct gca tct aca gga gac aga gtc acc atc act tgt CDR1 cgg gcg agt cag gat att agc agt tct tta gcc Fw2 tgg tat cag caa aaa cca ggg aaa gcc cct aag ctc ctg atc tat CDR2 gct gca tcc act ttg caa agt Fw3 gga gtc cca tca agg ttc agc ggc agt gga tct ggg aca gac ttc act ctc acc atc agc tgc ctg cag tct gaa gat ttt gca act tat tac tgt CDR3 caa cag tat tat agt tac cct ccg acg Fw4 ttc ggc caa ggg acc agg ttg gaa atc aaa

Heavy chain

Recombined from gene segments:
IGHV3-30*03 F
IGHD4-23*01 ORF
IGHJ6*02 F

AMINO ACID:
Fw1 QVQLVESGGGVVQPGRSLRLSCAVSGLSFR
CDR1 NYGMH
Fw2 WVRQAPGKGLEWVA
CDR2 VISHDGSKTYYGHSVKG
Fw3 RFTISRDKSKTMLFLQMNSLRPEDTAVYYCAK
CDR3 AGLNYYGNLLSNYFYYGMDV
Fw4 WGQGTTVTVSS

NUCLEOTIDE:
Fw1 cag gtg cag ctg gtg gag tct ggg gga ggc gtg gtc cag cct ggg agg tcc ctg aga ctc tcc tgt gca gtc tct gga ctc agt ttc agg CDR1 aat tat ggc atg cac Fw2 tgg gtc cgc cag gct ccc ggc aag ggg ctg gag tgg gtg gca CDR2 gtc att tcg cat gat gga agt aag aca tac tat gga cac tcc gtg aag ggc Fw3 cga ttc acc ata tcc aga gac aaa tcc aag act atg ttg ttt ctc caa atg aac agc ctg aga cct gag gac acg gct gtt tat tac tgt gcg aaa CDR3 gcc ggg ttg aac tac tat gga aac cta tta tca aac tac ttc tac tac gga atg gac gtc Fw4 tgg ggc caa ggg acc aca gtc acc gtc tcg tca

Light chain

Recombined from gene segments:
IGLV2-8*01 F
IGLJ2*01 F

AMINO ACID:
Fw1 QSALTQPPSASGSPGQSVTISC
CDR1 TGTSSDIGGYNYVS
Fw2 WYQHHPGKAPKLMIY
CDR2 EVTKRPS
Fw3 GVPDRFSGSKSGNTASLTVSGLQAEDEAHYYC
CDR3 SSYAGSNDLL
Fw4 FGGGTKLTVL

NUCLEOTIDE:
Fw1 cag tct gcc ctg act cag cct ccc tcc gcg tcc ggg tct cct ggt cag tca gtc acc atc tcc tgt CDR1 act ggg acc agc agt gac att ggt ggt tat aac tat gtc tcc Fw2 tgg tac caa cac cac cca ggc aaa gcc ccc aaa ttg atg att tat CDR2 gag gtc act aag cgg ccc tca Fw3 ggg gtc cct gat cgt ttc tct ggc tcc aag tct ggc aac acg gcc tcc ctg acc gtc tct gga ctc cag gct gag gat gag gct cat tat tac tgc CDR3 agc tca tat gca ggc agc aac gat ttg cta Fw4 ttc ggc gga ggg acc aag ctg acc gtc ctg

Heavy chain

Recombined from gene segments:
IGHV3-33*01 F
IGHD2-15*01 F
IGHJ4*02 F

AMINO ACID:
Fw1 QVHLVESGGGVVQPGTSLRLSCAASEFTFS
CDR1 SHAIH
Fw2 WVRQAPGKGLEWVA
CDR2 LIWYDGSNNYYADSVKG
Fw3 RFTISRDSSKNTVHLQMNSLRVEDTAVYYC
CDR3 ARDGCTGGSCCYFDN
Fw4 WGQGTLVTVSS

NUCLEOTIDE:
Fw1 cag gtg cac ctg gtg gag tct ggg gga ggc gtg gtc cag cct ggg acg tcc ctg aga ctc tcc tgt gca gcg tct gaa ttc acc ttc agt CDR1 tcc cat gcc ata cac Fw2 tgg gtc cgc cag gct cca ggc aag ggg ctg gag tgg gtg gca CDR2 ctt ata tgg tat gat gga agt aat aat tat tat gca gac tcc gtg aag ggc Fw3 cga ttc acc atc tcc aga gac agt tcc aag aac acg gtg cat ctg caa atg aac agc ctg aga gtc gag gac acg gct gtg tat tac tgt CDR3 gcg aga gat ggt tgt act ggt ggt agc tgc tgc tat ttt gac aac Fw4 tgg ggc cag gga acc cta gtc acc gtc tcc tcg

Light chain

Recombined from gene segments:
IGKV3-15*01 F
IGKJ4*01 F

AMINO ACID:
Fw1 EVVMTQSPATLSVSPGERATLSC
CDR1 RASQSISNNLG
Fw2 WYQQKPGQAPRLLIY
CDR2 GASTRAT
Fw3 GIPGRFSGSGSGTEFTLTIYSLQSEDFAVYYC
CDR3 QQYNNWPRLT
Fw4 FGGGTKVEIK

NUCLEOTIDE:
Fw1 gaa gta gtg atg acg cag tct cca gcc acc ctg tct gtg tct cca ggg gaa aga gcc acc ctc tcc tgc CDR1 agg gcc agt cag agc att agc aac aac tta ggc Fw2 tgg tat cag cag aaa cct ggc cag gct ccc agg ctc ctc atc tac CDR2 ggt gca tcc acc agg gcc act Fw3 ggt atc cca ggc agg ttc agt ggc agt ggg tct ggg aca gag ttc act ctc acc atc tac agc ctg cag tct gag gat ttt gca gtt tat tac tgt CDR3 caa caa tat aat aac tgg cct cgg ctc act Fw4 ttc ggc gga ggg acc aag gtg gag atc aaa

<u>Heavy chain</u>

Recombined from gene segments:
IGHV3-30*03 F
IGHD3-10*01 F
IGHJ4*02 F

AMINO ACID:
Fw1 QVQLVESGGGVVQPGRSLRLSCAASGFTFS
CDR1 SYGMH
Fw2 WVRQAPGKGLEWVA
CDR2 VISYDGSNKYYADSVKG
Fw3 RFTISRDNSKNTLYLQMNSLRAEDTAVYYC
CDR3 AKDSYYYGSGRRWGYYFDY
Fw4 WGQGTLVTVSS

NUCLEOTIDE:
Fw1 cag gtg cag ctg gtg gag tct ggg gga ggc gtg gtc cag cct ggg agg tcc ctg aga ctc tcc tgt gca gcc tct gga ttc acc ttc agt CDR1 agc tat ggc atg cac Fw2 tgg gtc cgc cag gct cca ggc aag ggg ctg gag tgg gtg gca CDR2 gtt ata tca tat gat gga agt aat aaa tac tat gca gac tcc gtg aag ggc Fw3 cga ttc acc atc tcc aga gac aat tcc aag aac acg ctg tat ctg caa atg aac agc ctg aga gct gag gac acg gct gtg tat tac tgt CDR3 gcg aaa gac tcg tat tac tat ggt tcg ggg aga cga tgg ggc tac tac ttt gac tac Fw4 tgg ggc cag gga acc ctg gtc acc gtc tcc tca <u>Light chain</u>

Recombined from gene segments:
IGLV3-19*01 F
IGLJ2*01 F

AMINO ACID:
Fw1 SSELTQDPAVSVALGQTVRITC
CDR1 QGDSLRSYYAS
Fw2 WYQQKPGQAPVLVIY
CDR2 GKNNRPS
Fw3 GIPDRFSGSSSGNTASLTITGAQAEDEADYYC
CDR3 NSRDSSGNHVV
Fw4 FGGGTKLTVL

NUCLEOTIDE:
Fw1 tct tct gag ctg act cag gac cct gct gtg tct gtg gcc ttg gga cag aca gtc agg atc aca tgc CDR1 caa gga gac agc ctc aga agc tat tat gca agc Fw2 tgg tac cag cag aag cca gga cag gcc cct gta ctt gtc atc tat CDR2 ggt aaa aac aac cgg ccc tca Fw3 ggg atc cca gac cga ttc tct ggc tcc agc tca gga aac aca gct tcc ttg acc atc act ggg gct cag gcg gaa gat gag gct gac tat tac tgt CDR3 aac tcc cgg gac agc agt ggt aac cat gtg gta Fw4 ttc ggc gga ggg acc aag ctg acc gtc cta

Heavy chain

Recombined from gene segments:
IGHV3-21*01 F
IGHD5-24*01 ORF
IGHJ6*02 F

AMINO ACID:
Fw1 EVQLVESGGGLVKPGGSLRLSCAASGFTFS
CDR1 SYSMN
Fw2 WVRQAPGKGLEWVS
CDR2 SISSSSTYIYYADSVKG
Fw3 RFTISRDNARNSLYLQMNSLRAEDTAVYYC
CDR3 ARRREVGRDGYSLYPRGYHYGMDV
Fw4 WGQGTTVTVSS

NUCLEOTIDE:
Fw1 gag gtg cag ctg gtg gag tct ggg gga ggc ctg gtc aag cct ggg ggg tcc ctg aga ctc tcc tgt gca gcc tct gga ttc acc ttc agt CDR1 agt tat agc atg aac Fw2 tgg gtc cgc cag gct cca ggg aag ggg ctg gag tgg gtc tca CDR2 tcc att agt agt agt agt act tac ata tac tac gca gac tca gtg aag ggc Fw3 cga ttc acc atc tcc aga gac aac gcc agg aac tca ctg tat ctg caa atg aac agc ctg aga gcc gag gac acg gct gtg tat tat tgt CDR3 gcg aga agg agg gag gtc ggt aga gat ggc tac agt ttg tac ccc cgg ggg tac cac tac ggt atg gac gtc Fw4 tgg ggc caa ggg acc acg gtc acc gtc tcc tca

Light chain

Recombined from gene segments:
IGLV2-14*01 F
IGLJ2*01 F

AMINO ACID:
Fw1 QSALTQPASVSGSPRQSITISC
CDR1 TGTSSDVGGYNYVS
Fw2 WYQQLPGKAPKLMIY
CDR2 DVNDRPS
Fw3 GVSIRFSGSKSGNTASLTISGLQAEDEADYYC
CDR3 SSYTRSNTVI
Fw4 FGGGTKLTVL

NUCLEOTIDE:
Fw1 cag tct gcc ctg act cag cct gcc tcc gtg tct ggg tct cct aga cag tcg atc acc atc tcc tgc CDR1 act gga acc agc agt gac gtt ggt ggt tat aac tat gtc tcc Fw2 tgg tac caa caa ctc cca ggc aaa gcc ccc aaa ctc atg att tat CDR2 gat gtc aat gat cgg ccc tca Fw3 ggg gtt tct att cgc ttc tct ggc tcc aag tct ggc aac acg gcc tcc ctg acc atc tct ggg ctc cag gct gag gac gag gct gat tat tac tgc CDR3 agc tca tat aca aga agc aac act gtg ata Fw4 ttc ggc gga ggg acc aaa ctg acc gtc cta

Heavy chain

Recombined from gene segments:
IGHV3-33*01 F
IGHD5-12*01 F
IGHJ4*02 F

AMINO ACID:
Fw1 QVQLVESGGGVVQPGRSLRLSCAASGFTFS
CDR1 TYGMH
Fw2 WVRQAPGKGLEWVA
CDR2 VIWYDGSNTYYADSVKG
Fw3 RFTISRDNSKNTLYLQIKSLRAEDTAVYYC
CDR3 ARGRGYSAQGNRNRAYYFDY
Fw4 WGQGTLVTVSS

NUCLEOTIDE:
Fw1 cag gtg cag ctg gtg gag tct ggg gga ggc gtg gtc cag cct ggg agg tcc ctg aga ctc tcc tgt gca gcg tct gga ttc acc ttc agt CDR1 acc tat ggc atg cac Fw2 tgg gtc cgc cag gct cca ggc aag ggg ctt gag tgg gtg gca CDR2 gtt ata tgg tat gat gga agt aat aca tac tat gca gac tcc gtg aag ggc Fw3 cga ttc acc atc tcc aga gac aat tcc aag aac aca ctg tat ctg caa ata aag agc ctg aga gcc gag gac acg gct gtc tat tac tgt CDR3 gcg aga ggc cgt gga tat agt gcc caa ggg aat cgg aat agg gct tac tac ttt gac tac Fw4 tgg ggc cag gga acc ctg gtc acc gtc tcc tca

Light chain

Recombined from gene segments:
IGKV3-15*01 F
IGKJ2*01 F

AMINO ACID:
Fw1 EIVMTQSPATLSVSPGERVILSC
CDR1 RASQSVSSNLA
Fw2 WYQQKPGQPPRLLIY
CDR2 GAFTRVT
Fw3 GVPARFSGSGSGTEFTLTISSLQSEDFAVYYC
CDR3 QQYNDRPPYT
Fw4 FGQGTKLEIK

NUCLEOTIDE:
Fw1 gaa ata gtg atg acg cag tct cca gcc acc ctg tct gtg tct cca ggg gaa agg gtc atc ctc tcc tgc CDR1 agg gcc agt cag agt gtt agc agc aac tta gcc Fw2 tgg tac cag cag aaa cct ggc cag cct ccc agg ctc ctc atc tat CDR2 ggt gca ttc acg agg gtc act Fw3 ggt gtc cca gcc agg ttc agt ggc agt ggg tct ggg aca gaa ttc act ctc acc atc agc agc ctg cag tct gaa gat ttt gca gtt tat tac tgt CDR3 cag cag tac aat gac cgg ccc ccg tac act Fw4 ttt ggc cag ggg acc aag ctg gag atc aaa

Heavy chain

Recombined from gene segments:
IGHV4-4*02 F
IGHD6-19*01 F
IGHJ5*02 F

AMINO ACID:
Fw1 QGRLQESGPGLVKPSETLTLTCAVSGGSSVS
CDR1 SPNWWT
Fw2 WVRQAPGKGLEWIG
CDR2 EIYYGGRVSYNSALRS
Fw3 RVTISSDRSKEEFSLKLRSVTAADTAIYYC
CDR3 AGQKNIGCGYSSCFISWFDT
Fw4 WGQGIAVTVSS

NUCLEOTIDE:
Fw1 cag ggg cga ctg cag gag tcg ggc cca gga ctg gtg aag cct tcg gag acc ctg acc ctc acg tgc gct gtg tcc ggt ggc tcc tcc gtc agc CDR1 agt cct aac tgg tgg act Fw2 tgg gtc cgc cag gcc ccc ggg aag ggg ctg gag tgg att gga CDR2 gaa atc tat tat ggt ggg aga gtg agc tac aac tcg gcc ctc agg agt Fw3 cga gtc acc att tca tca gac agg tcc aaa gag gag ttc tcc ctg aaa ctg agg tct gtg acc gcc gcg gac acg gcc ata tat tat tgt CDR3 gcg ggt caa aaa aat att ggc tgt ggt tac agc agt tgc ttt atc agt tgg ttc gac acc Fw4 tgg gga cag gga att gcg gtc acc gtc tcc tca

Light chain

Recombined from gene segments:
IGKV4-1*01 F
IGKJ2*01 F

AMINO ACID:
Fw1 DIVMTQSPDSLAVSLGERATIAC
CDR1 KSSQTILQRSNHLNYLA
Fw2 WYQQKPGQPPKVLIY
CDR2 WASTRES
Fw3 GVPDRFSGSGSGTDFTLTINSLQAEDVAVYYC
CDR3 HQYYTTPQT
Fw4 FGQGTKVEIK

NUCLEOTIDE:
Fw1 gac atc gtg atg acc cag tct cca gac tcc ctg gct gtg tct ctg ggc gag agg gcc acc atc gcc tgc CDR1 aag tcc agc cag act att tta caa agg tcc aac cat ttg aac tac tta gct Fw2 tgg tac cag cag aaa cca gga cag cct cct aaa gtg ctc att tat CDR2 tgg gca tct acc cgg gaa tcc Fw3 ggg gtc cct gac cga ttc agt ggc agc ggg tct ggg aca gat ttc act ctc acc atc aac agc ctg cag gct gag gat gtg gca gtt tat tac tgt CDR3 cac caa tat tat act act ccg cag act Fw4 ttt ggc cag ggg acc aag gtg gag atc aaa

Heavy chain

Recombined from gene segments:
IGHV3-15*01 F
IGHD3-22*01 F
IGHJ4*02 F

AMINO ACID:
Fw1 EVQLVESGGGLVKPGGSLRLSCAASGFTFS
CDR1 DAWMS
Fw2 WVRQAPGKGLEWVG
CDR2 HINTKVDGGTTEYAAPVKG
Fw3 RFTISRDDSKNSLYLHMDSLKTEDTAVYYC
CDR3 TTEAIYDSSGYFHDY
Fw4 WGQGSLVTVSS

NUCLEOTIDE:
Fw1 gag gtg cag ctg gtg gag tct ggg gga ggt ttg gta aag cct ggg ggg tcc ctt aga ctc tcc tgt gca gcc tct gga ttc act ttc agt CDR1 gac gcc tgg atg agc Fw2 tgg gtc cgc cag gct cca ggg aag ggg ctg gag tgg gtt ggc CDR2 cat att aac acc aaa gtt gat ggt ggg aca aca gag tac gct gca ccc gtg aaa ggc Fw3 aga ttc acc atc tca aga gat gat tca aaa aat tcg ctg tat ctg cac atg gac agc ctg aaa acc gag gac aca gcc gtg tat tac tgt CDR3 acc aca gag gcg ata tat gat agt agt ggt tat ttc cat gac tat Fw4 tgg ggc cag gga tcc ctg gtc acc gtc tcc tca

Light chain

Recombined from gene segments:
IGKV4-1*01 F
IGKJ1*01 F

AMINO ACID:
Fw1 DIVMTQSPDSLAVSLGERATINC
CDR1 KSSRSVLYSSNNKNYLA
Fw2 WYQQKPGQPPKLLIY
CDR2 WASIRES
Fw3 GVPDRFSGSGSGTDFTLTINSLQAEDVAVYYC
CDR3 QQYSRPPT
Fw4 FGQGTKVEIK

NUCLEOTIDE:
Fw1 gac atc gtg atg acc cag tct cca gac tcc ctg gct gtg tct ctg ggc gag agg gcc acc atc aac tgc CDR1 aag tcc agc cgg agt gtt tta tac agc tcc aac aat aag aac tac tta gct Fw2 tgg tac cag cag aaa cca gga cag cct cct aag ctg ctc att tac CDR2 tgg gca tct atc cgg gaa tcc Fw3 ggg gtc cct gac cga ttc agt ggc agc ggg tct ggg aca gat ttc act ctc acc atc aac agc ctg cag gct gaa gat gtg gca gtt tat tac tgt CDR3 cag caa tat tct cgt cct ccg acg Fw4 ttc ggc caa ggg acc aag gtg gaa atc aaa

Heavy chain

Recombined from gene segments:
IGHV3-49*04 F
IGHD4-11*01 F
IGHJ6*03 F

AMINO ACID:
Fw1 EVQLVESGGGLAQPGRSLRLSCTASGFRFG
CDR1 DFAMS
Fw2 WVRQAPGKGLEWVG
CDR2 FIRTKANDGTTEYAASVKG
Fw3 RFIISRDDSKSIAYLQMNSLKTEDTAVYYC
CDR3 ASDPFMTTDYYYYMDV
Fw4 WGKGTTVTVSS

NUCLEOTIDE:
Fw1 gag gtg cag ctg gtg gag tcg ggg gga ggc ttg gca cag cca ggg cgg tcc ctg aga ctc tcc tgt aca gct tct gga ttc agg ttt ggt CDR1 gat ttt gct atg agt Fw2 tgg gtc cgc cag gct cca ggg aag gga ctg gag tgg gta ggt CDR2 ttc att aga acc aaa gct aat gat ggg aca aca gaa tac gcc gcg tct gtg aaa ggc Fw3 aga ttc atc atc tca aga gat gat tcc aaa agt atc gcc tat ctg caa atg aac agc ctg aaa acc gag gac aca gcc gtt tat tac tgt CDR3 gct agc gat ccc ttc atg act aca gac tat tac tac tac atg gac gtc Fw4 tgg ggc aaa ggg acc acg gtc acc gtc tcc tca

Light chain

Recombined from gene segments:
IGLV2-8*01 F
IGLJ2*01 F

AMINO ACID:
Fw1 QSALTQPPSASGSPGQSVTISC
CDR1 TGTSSDVGGYNSVS
Fw2 WYQHHPGKAPKLMIY
CDR2 EVYKRPL
Fw3 GVPDRFSGSKSGNTASLTVSGLQAEDEAYYYC
CDR3 SSYGGTVLF
Fw4 GGGTKLTVL

NUCLEOTIDE:
Fw1 cag tct gcc ctg act cag cct ccc tcc gcg tcc ggg tct cct gga cag tca gtc acc atc tcc tgc CDR1 act ggg acc agc agt gac gtt ggt ggt tat aac tct gtc tcc Fw2 tgg tac caa cat cac cca ggc aaa gcc ccc aaa ctc atg att tat CDR2 gag gtc tat aag cgg ccc tta Fw3 ggg gtc cct gat cgc ttc tct ggc tcc aag tct ggc aac acg gcc tcc ctg acc gtc tct ggg ctc cag gct gag gat gag gct tat tac tgc CDR3 agc tca tat gga ggc acc gtg cta ttc Fw4 ggc gga ggg acc aag ctg acc gtc cta

Heavy chain

Recombined from gene segments:
IGHV3-23*01 F
IGHD2-15*01 F
IGHJ3*02 F

AMINO ACID:
Fw1 EVQVLESGGDSVQPGGSLRLSCAASGFTFS
CDR1 SYAMT
Fw2 WVRQAPGKGLKWVS
CDR2 SISGSGGSTYYADSVRG
Fw3 RFTISRDNSKNTLYVQMNSLRAEDTAVYYC
CDR3 AKGYVGCSGGNCYSGGAFDI
Fw4 WGQGTVVTVSS

NUCLEOTIDE:
Fw1 gag gtg caa gtg ttg gag tct ggg gga gac tcg gta cag cct ggg ggg tcc ctg aga ctc tcc tgt gca gcc tct gga ttc acc ttt agc CDR1 agc tat gcc atg acc Fw2 tgg gtc cgc cag gct cca ggg aag ggg ctg aaa tgg gtc tca CDR2 agt att agt ggt agt ggt ggt agc aca tac tac gca gac tcc gtg agg ggc Fw3 cgg ttc acc atc tcc aga gac aat tcc aag aac acg ctg tat gtg cag atg aac agc ctg aga gcc gag gac acg gcc gta tat tac tgt CDR3 gcg aaa gga tat gtg ggg tgt agt ggt ggg aac tgc tac tcg ggg ggt gct ttt gat atc Fw4 tgg ggc caa ggg aca gtg gtc acc gtc tct tca

Light chain

Recombined from gene segments:
IGLV3-21*01 F
IGLJ2*01 F

AMINO ACID:
Fw1 SYVLTQPPSVSVAPGKTARITC
CDR1 GGNNIGSESVH
Fw2 WYQQKPGQAPVVVIY
CDR2 YDTDRPS
Fw3 GIPERFSGSNSGNTATLTISRVEAGDEADYYC
CDR3 QVWDNTSDHPVVF
Fw4 GGGTKLTVL

NUCLEOTIDE:
Fw1 tcc tat gtg ctg act cag cca ccc tca gtg tca gtg gcc cca gga aag acg gcc cgg att acc tgt CDR1 ggg ggg aac aac att gga agt gaa agt gtt cac Fw2 tgg tac cag cag aag cca ggc cag gcc cct gtg gtg gtc atc tat CDR2 tat gat acc gac cgg ccc tca Fw3 ggg atc cct gag cgc ttc tct ggc tcc aac tct ggg aac acg gcc acc ctg acc atc agc agg gtc gaa gcc ggg gat gag gcc gac tat tac tgt CDR3 cag gtg tgg gat aac act agt gat cat cct gtg gta ttc Fw4 ggc gga ggg acc aag ctg acc gtc cta

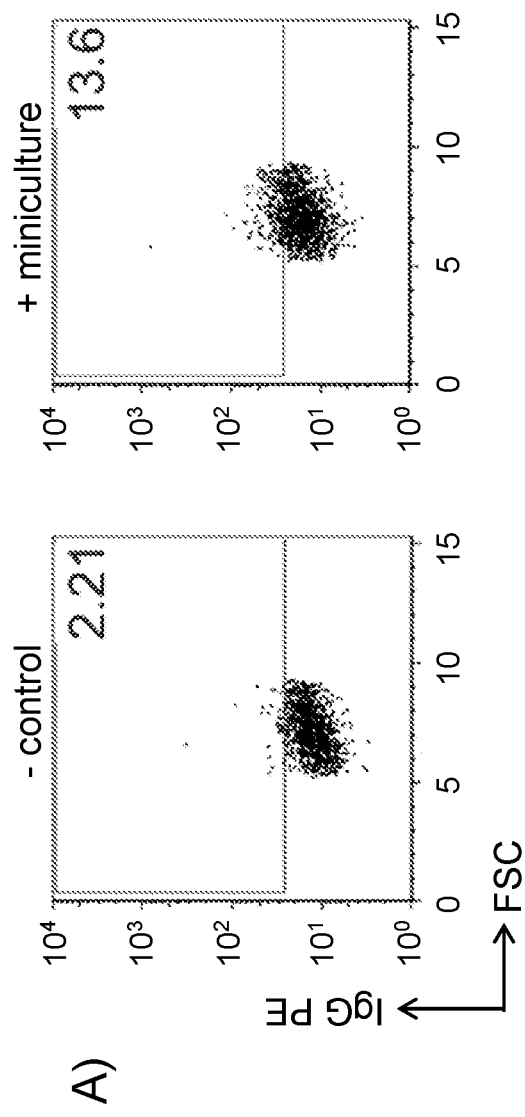
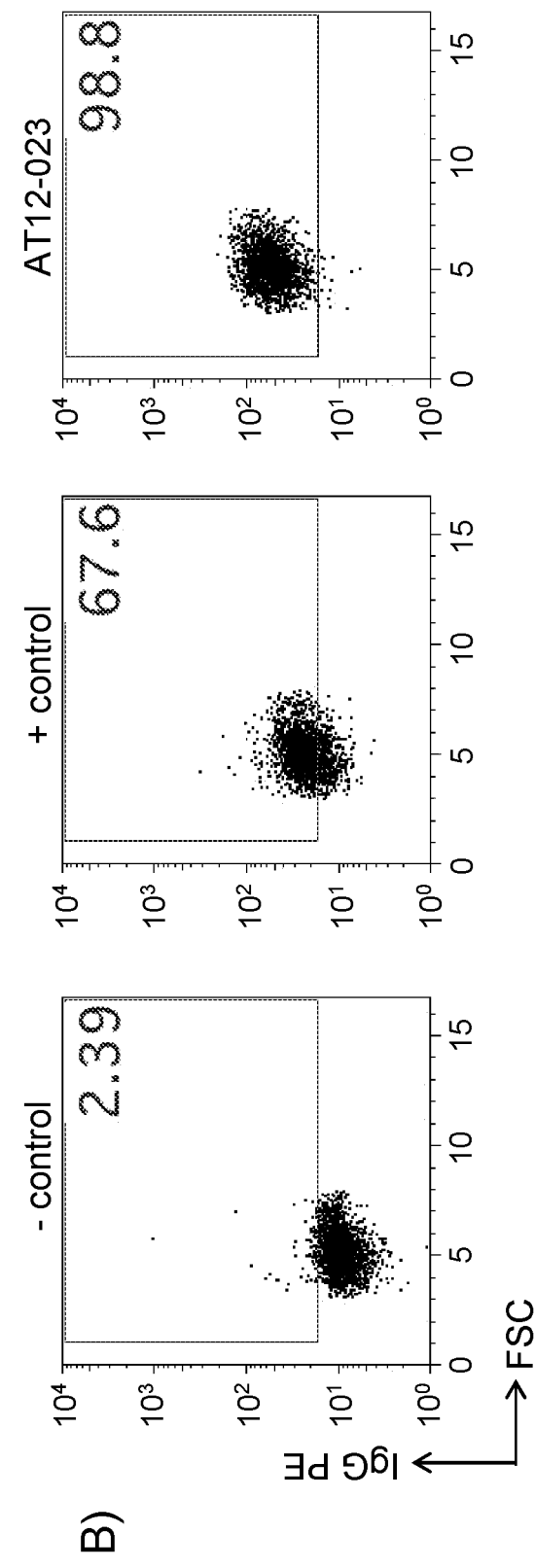
FIG. 3

*In vitro* activity of AT12-023

AT12-023 and AT12-025 reduce viability of THP-1

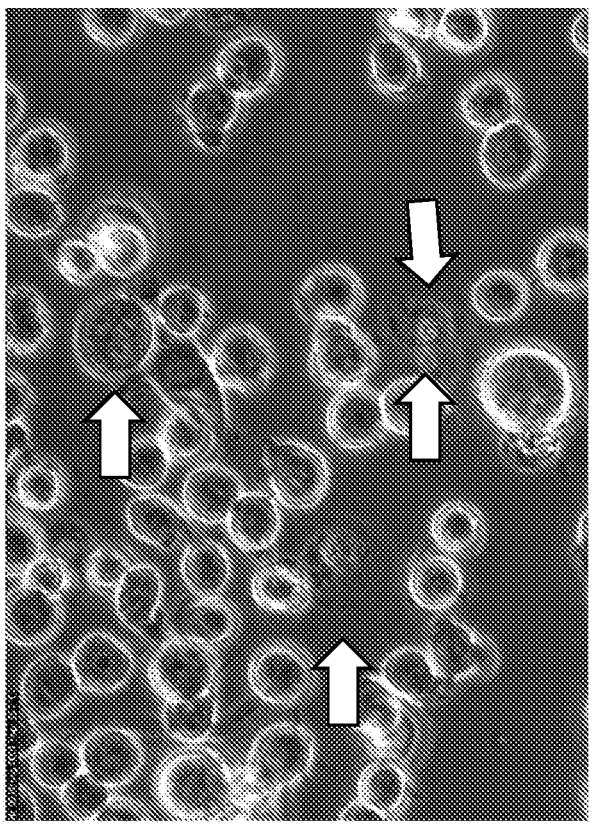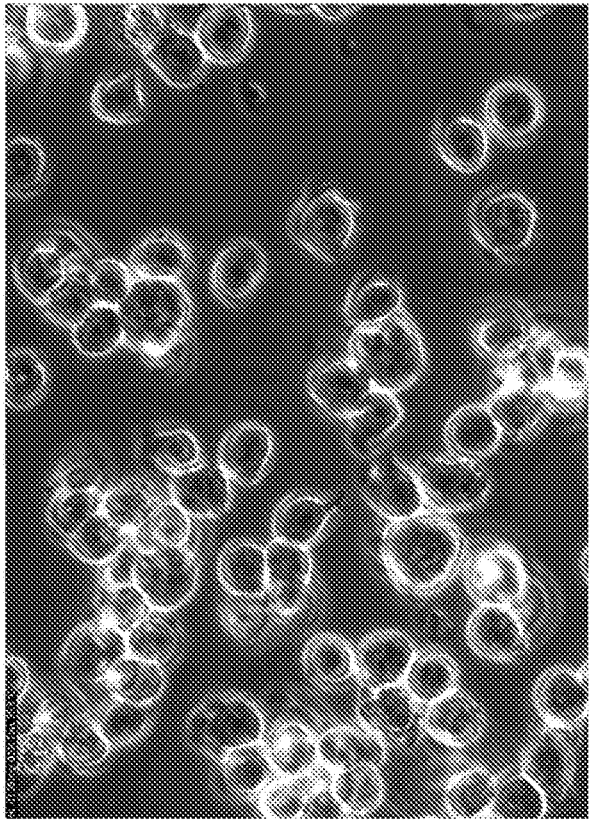
FIG. 17A
Cytotoxic AML-specific antibodies induce death of THP-1 cells (phase-contrast imaging)
AT13-037 (cytotoxic)
AT13-023 (non-cytotoxic)

MEANS AND METHODS FOR COUNTERACTING MYELOPROLIFERATIVE OR LYMPHOPROLIFERATIVE DISORDERS

CROSS REFERENCE TO RELATED APPLICATIONS

This application claims the priority of PCT/NL2014/050873, filed on Dec. 17, 2014, which claims priority to EP Application No. 13197882.7, filed Dec. 17, 2013, the entire contents of each of which are hereby incorporated in total by reference.

SEQUENCE LISTING

This application incorporates by reference the Sequence Listing contained in an ASCII text file named "362346_00034_SeqList.txt" submitted via EFS-Web on Jun. 16, 2016. The text file was created on Jun. 16, 2016, and is 87 kb in size.

The invention relates to the fields of biology, immunology, medicine and cancer therapy, in particular therapy against myeloproliferative or lymphoproliferative disorders. More in particular, the invention relates to antibodies against acute myeloid leukemia cells.

Acute myeloid leukemia (AML) is a high risk malignancy with five year survival rates of 40-50% in patients younger than 60 years of age. For patients over 65 years of age outcomes are even worse, with only less than 20% of patients obtaining durable remissions. Allogeneic stem cell transplantation is frequently applied in the treatment of acute leukemia. It was initially designed to rescue patients from otherwise lethal myeloablative chemotherapy but was subsequently found to be complicated by alloreactive immune response related complications (graft versus host disease; GvHD). T cell depletion of grafts before reinfusion averted GvHD but the observation that T cell depleted graft recipients, similar to monozygotic twin donor transplant recipients, experienced much higher rates of relapse made it increasingly clear that the success of allogeneic SCT is dependent on the induction of an anti-leukemic immune response (graft versus leukemia (GvL)). This has led to the development of strategies to apply allogeneic stem cell transplantation without myeloablative conditioning (reduced intensity stem cell transplantation, RIST), to reduce cytotoxicity and to allow allogeneic SCT in a larger group of patients including older patients and heavily pretreated patients. Preparative regimens in RIST are aimed at decimating the recipients adaptive immune system to prevent graft rejection, without complete ablation of the recipients bone marrow thereby reducing early SCT toxicity. Following transplantation, donor stem cells gradually replace stem cells of the recipient and full donor chimerism is usually achieved within three months after SCT. Although allogeneic SCT is curative in significant numbers of patients, and much progress has been made in the supportive care of SCT recipients, still 15-30% of patients die as a result of transplantation related complications such as GvHD and infectious complications (arising as a result of slow immune recovery following SCT or as a complication of immunosuppressive therapy of GvHD).

Hence, although SCT is potentially curative when potent graft versus leukemia (GvL) responses are induced, its therapeutic success is limited by anti-host immune responses leading to GvHD which causes high morbidity and mortality.

About 70% of SCT patients develop GvHD at one point following SCT, with target organs including the skin, liver, intestine and lung. GvHD is treated with local or systemic immunosuppressive therapy including corticosteroids. A significant number of GvHD patients is not responsive to steroid therapy, and about half of these patients also respond poorly to alternative (and partly still experimental) measures such as mesenchymal stromal cell (MSC) transplantation or T cell modulating therapy such as anti-tumor necrosis factor α (anti-TNFα; infliximab). Extensive and long-term immunosuppressive therapy is undesirable, since it may hamper the development of therapeutic antileukemia responses. Indeed, when an AML relapse occurs while the patient is still on immunosuppressive therapy, the first step is to rapidly taper immunosuppressants. This may induce a curative GvL response, often at the expense of GvHD. In relapsed patients on immunosuppressive therapy who do not respond to tapering of immunosuppressants or relapsed patients in whom immunosuppressants were already phased out before relapse occurred but who had not developed GvHD, tumor load reduction by chemotherapy, followed by increasing doses of donor-lymphocyte infusions (DLI) may lead to durable remission of disease. While the absence of diagnostic tests to demonstrate the presence of a robust GvL makes it difficult to estimate exactly how often allogeneic SCT induce GvL responses in primary or relapsed AML, some studies provided compelling evidence of the induction of such a response in a considerable number of patients. For example, Schmid and colleagues demonstrated potent GvL responses by DLI in 50% of a small group of AML patients with disease relapse who were in second remission following chemotherapy (Schmid et al., 2007). Schlenk and colleagues convincingly showed the additive value of allogeneic SCT in primary AML, with a doubling of the 5-year disease free survival in patients with high risk AML who received an allogeneic SCT from a sibling, compared with patients who did not have a suitable sibling donor (Schlenk et al., 2008). Thus, GvL responses often occur at the cost of GvHD, and the observation that T cell depletion from the graft reduced GvHD incidence but increased disease relapse rates suggested that both are primarily mediated by T cell dependent immune responses against recipient-antigens.

In view of the high GvHD incidence after allogeneic stem cell transplantation, resulting in death of 15-30% of the patients, as well as the fact that a suitable donor is not always available for a given patient, alternative treatment approaches are needed. It is an object of the present invention to provide alternative means and methods for counteracting and/or preventing AML.

The present invention provides patient-derived, AML-specific, human antibodies that are able to bind intact AML cells. Importantly, the antibodies are derived from human AML patients that received an allogeneic SCT and are in complete remission indicating that the antibodies are effective against AML. Indeed, in the Examples it has been demonstrated that antibodies according to the present invention are able to bind intact AML cells. The AML-specific human antibodies according to the present invention are, therefore, particularly suitable for use in anti AML therapy. For instance, an antibody according to the invention is provided with a toxic moiety. After administration, AML cells will be bound and/or internalised and the toxic moiety will exert its toxic effect on the AML cell. Alternatively, in some embodiments antibody-dependent cell-mediated cytotoxicity (ADCC) or complement-dependent cytotoxicity (CDC) is induced using an antibody according to the present invention, optionally bound to an immunomodulatory compound. The fact that human antibodies are provided, or functional parts or functional equivalents of human antibodies, diminishes the chance of side effects in human beings, which is an important advantage. Hence, with the antibodies provided by the present invention, novel AML treatment options have become available which can be used in addition to existing AML therapy, or as an alternative.

An important embodiment of the present invention provides human AML-specific antibodies that are capable of diminishing proliferation of AML cells. Administration of such antibodies to an AML patient will counteract AML cells without the need to add additional (toxic) moieties to the antibody. A particularly preferred embodiment provides human AML-specific antibodies that are capable of diminishing proliferation of AML cells independently from antibody-dependent cell-mediated cytotoxicity (ADCC), complement-dependent cytotoxicity (CDC), apoptosis or phagocytosis by tumor-associated myeloid cells such as macrophages or dendritic cells. Preferably, such antibodies are capable of diminishing proliferation of AML cells (essentially) independently from any other immune cells, or complement or apoptosis. As shown in the Examples, such antibodies are capable of directly diminishing or inhibiting AML cell growth, or are even capable of killing AML cells, in the absence of immune cells like NK cells or macrophages, and in the absence of complement. This embodiment is in contrast to prior art approaches such as for instance described in Majeti et al., 2009 and Willingham et al., 2012, wherein a CD47-specific antibody is used in order to enable macrophage phagocytosis of tumor cells. WO 2009/051974 describes the use of C-type lectin-like molecule-1 (CLL-1)-specific antibodies, which are capable of inducing CDC against AML cells in vitro in the presence of rabbit complement. Bakker et al., 2004, however, does not envision that antibody-dependent cell-mediated cytotoxicity or complement-dependent cytotoxicity via CLL-1 will be an effective targeting mechanism, and proposes toxin-conjugated CLL-1 antibodies for use against AML. WO 2012/098407 discloses the use of antibodies specific for IL1RAP for inducing antibody-dependent cell-mediated cytotoxicity against AML cells, by recruiting NK cells which induce AML cell death. Hence, the above described prior art focuses on the use of antibodies in order to activate other immune cells, which may not provide the desired results in immune compromised individuals such as AML patients who have undergone chemotherapy with or without an allogeneic SCT.

WO 2013/071068 describes anti-CXCR4 antibodies that were raised in transgenic transchromosomic mice expressing human antibody genes. The obtained antibodies bind a broad range of hematopoietic cells and are capable of inhibiting growth of an AML cell line in vitro. These anti-CXCR4 antibodies induce apoptosis of various AML cell lines.

Anti-CD33 monoclonal antibody therapy against AML has also been described (Walther et al., 2012). For instance, CD33-specific antibodies coupled to a drug conjugate are described.

WO 2010/102244 describes a humaneered anti-EphA3 antibody that is capable of inducing apoptosis of AML cells. Furthermore, Biernacki et al., 2010 and Wu et al., 2000 describe antibodies obtained from AML patients that are specific for intracellular antigens such as RAB38, TBCE, DUSP12 and RAFTK.

In conclusion, several publications describe AML antibodies that bind intracellular antigens. Such antibodies are not a first choice for combating living, intact AML cells in vivo due to the unreachability of such intracellular targets when the AML cells are intact. Other publications describe antibodies that bind a broad range of hematopoietic cells, for instance through CD33, CXCR4, CD47 or CLL-1. Antibodies which bind a broad range of (hematopoietic) cells involve the risk of severe side-effects.

Several antibodies described in the art act by inducing phagocytosis, ADCC or CDC, meaning that other immune cells or complement components are required for counteracting AML cells. The use of such antibodies is, therefore, limited in immune compromised individuals. Moreover, some of the described antibodies are not human, which involves a high risk of side effects. Other publications (such as WO 2013/071068 and WO 2010/102244) describe antibodies that induce apoptosis of AML cells.

In contrast to the above-mentioned publications, the present inventors have taken a different approach. Instead of artificially producing antibodies against a component that is present on, amongst other things, AML cells, the inventors have isolated antibodies from human AML patients who, after receiving an allogeneic SCT, mounted a potent graft versus leukemia response as they maintained in complete remission. These antibodies are capable of specifically binding intact AML cells. Hence, instead of using artificially developed antibodies, the present inventors have elegantly taken advantage of the natural immune defenses elicited in human AML patients after receiving an allogeneic SCT. The humoral response found in nature results in a very adequate selection and outgrowth of B-cells that produce effective antibodies in vivo. The antibodies according to the present invention, or functional parts or functional derivatives thereof, are therefore particularly suitable for binding AML cells in AML patients. The fact that the antibodies are specific for intact AML cells, instead of intracellular antigens, makes them particularly suitable for AML therapy.

As described, an antibody or functional part or functional equivalent according to the invention can be coupled to a toxic moiety. Such toxic moiety will then be directed to AML cells in vivo through the binding of the antibody to AML cells. One embodiment of the present invention provides human antibodies, or functional parts or functional equivalents thereof, which are able to bind intact AML cells and which are able to diminish proliferation of AML cells. Such antibody obviates the need of coupling the antibody to an additional, toxic component (although the use of a toxic moiety can still be useful for providing additional anti-AML effects). In one particularly preferred embodiment, human antibodies, or functional parts or functional equivalents thereof, according to the invention are provided which are able to bind intact AML cells and which are able to diminish proliferation of AML cells independently from antibody-dependent cell-mediated cytotoxicity (ADCC), complement-dependent cytotoxicity (CDC) or phagocytosis by tumor-associated myeloid cells such as macrophages or dendritic cells. Preferably, such antibodies are capable of diminishing proliferation of AML cells independently from, or essentially independently from, other immune cells or complement components. The use of such antibodies, having a strong anti-AML activity, is preferred, especially in immune-compromised individuals. One preferred aspect of the present invention therefore provides an isolated, synthetic or recombinant human antibody, or a functional part or a functional equivalent thereof, which is able to bind a cell surface component of acute myeloid leukemia (AML) cells and which is able to diminish proliferation of AML cells independently from, or essentially independently from, antibody-dependent cell-mediated cytotoxicity (ADCC), complement-dependent cytotoxicity (CDC) or phagocytosis by tumor-associated myeloid cells such as macrophages or dendritic cells. Preferably, such antibodies are capable of diminishing proliferation of AML cells (essentially) independently from any other immune cells or complement. As shown in the Examples, at least antibodies AT12-023, AT12-025 and AT13-024 have these characteristics. These are, therefore, preferred antibodies according to the present invention.

In a further preferred embodiment, human antibodies, or functional parts or functional equivalents thereof, according to the invention are provided which are able to bind intact AML cells and which are able to diminish proliferation of AML cells independently from apoptosis. As shown in the Examples, at least antibodies AT12-023, AT13-031 and AT13-037 have this characteristic. This is clear from the fact that these antibodies can induce death of AML cells in the presence of apoptosis inhibitors such as the pan caspase inhibitors Q-VD-OPh or Z-VAD-fmk, and from the fact that most of these antibodies (except antibody AT13-031) maintain their cytotoxic properties at 4° C. According to the present invention, antibodies such as AT12-023, AT13-031 and AT13-037 kill their AML target cells via necrosis (such as oncosis or necroptosis). This provides the advantage over currently known apoptosis-inducing antibodies that the necrosis-inducing antibodies according to the present invention will enhance a patient's immune response more than apoptosis-inducing antibodies. This is due to the fact that necrosis causes more exposure of the cell contents to an individual's immune system. Further provided is therefore an isolated, synthetic or recombinant human antibody, or a functional part or a functional equivalent thereof, which is able to bind a cell surface component of acute myeloid leukemia (AML) cells and which is able to diminish proliferation of AML cells independently from, or essentially independently from, apoptosis.

In a further preferred embodiment, human antibodies, or functional parts or functional equivalents thereof, according to the invention are provided which are able to diminish proliferation of AML cells independently from both apoptosis and the above-mentioned immune cells and complement. Further provided is therefore an isolated, synthetic or recombinant human antibody, or a functional part or a functional equivalent thereof, which is able to bind a cell surface component of acute myeloid leukemia (AML) cells and which is able to diminish proliferation of AML cells essentially independently from antibody-dependent cell-mediated cytotoxicity (ADCC), complement-dependent cytotoxicity (CDC), apoptosis, or phagocytosis by macrophages or dendritic cells.

An antibody or functional part or functional equivalent according to the invention is preferably capable of binding intact AML cells. Preferably, such antibody or functional part or functional equivalent is able to bind a cell surface component that is specific for AML cells. This typically means that non-hematopoietic cells or non-malignant hematopoietic cells, such as for instance hepatocytes, colon cells, fibroblasts, endothelial cells, healthy peripheral blood mononuclear cells (PBMC) and healthy bone marrow cells, are not, or to a significantly lesser extent, recognized as compared to the binding affinity of an antibody or functional part or functional equivalent according to the invention for AML cells. This means that the binding of an antibody or functional part or functional equivalent according to the invention to non-hematopoietic cells or non-malignant hematopoietic cells is typically in the same range as binding of an irrelevant control antibody to these cells (wherein the control antibody is not specific for said cells). Some reactivity towards other types of malignant hematopoietic cells is, however, embraced within the term "AML-specific". For instance, it is shown in Table 4 and FIG. 6 that antibodies AT13-031 and AT12-023 are capable of binding patient-derived B-non-Hodgkin lymphoma cells. A use of antibody AT13-031 or antibody AT12-023, or a functional part or functional derivative of any of these antibodies, for the preparation of a medicament or prophylactic agent against B-non-Hodgkin lymphoma is therefore also provided, as well as antibody AT13-031 or antibody AT12-023, or a functional part or functional derivative of any of these antibodies, for use in a method for at least in part treating or preventing B-non-Hodgkin lymphoma. Similarly, antibodies AT13-024, AT13-031 and AT12-019 are capable to bind lymphoma- and/or multiple myeloma cell lines (Table 4). A use of antibody AT13-024 or antibody AT13-031 or antibody AT12-019, or a functional part or functional derivative of any of these antibodies, for the preparation of a medicament or prophylactic agent against lymphoma and/or myeloma is therefore also provided, as well as antibody AT13-024 or antibody AT13-031 or antibody AT12-019, or a functional part or functional derivative of any of these antibodies, for use in a method for at least in part treating or preventing lymphoma and/or myeloma.

As used herein, the term "AML cells" embraces natural AML cells, such as primary AML blasts that are present in AML patients, as well as AML cell lines such as for instance THP-1, Mono-Mac 6 and Molm13.

The term "antibody" as used herein, refers to an immunoglobulin protein comprising at least a heavy chain variable region (VH), paired with a light chain variable region (VL), that is specific for a target epitope.

A "functional part of an antibody" is defined herein as a part that has at least one shared property as said antibody in kind, not necessarily in amount. Said functional part is capable of binding the same antigen as said antibody, albeit not necessarily to the same extent. In one embodiment a functional part of an antibody comprises at least a heavy chain variable domain (VH). Non-limiting examples of a functional part of an antibody are a single domain antibody, a single chain antibody, a nanobody, an unibody, a single chain variable fragment (scFv), a Fab fragment and a F(ab')$_2$ fragment.

A "functional equivalent of an antibody" is defined herein as an artificial binding compound, comprising at least one CDR sequence of an antibody, preferably a heavy chain CDR3 sequence. Said functional equivalent preferably comprises the heavy chain CDR3 sequence of an antibody, as well as the light chain CDR3 sequence of said antibody. More preferably, said functional equivalent comprises the heavy chain CDR1, CDR2 and CDR3 sequences of an antibody, as well as the light chain CDR1, CDR2 and CDR3 sequences of said antibody. A functional equivalent of an antibody is for instance produced by altering an antibody such that at least an antigen-binding property of the resulting compound is essentially the same in kind, not necessarily in amount. This is done in many ways, for instance through conservative amino acid substitution, whereby an amino acid residue is substituted by another residue with generally similar properties (size, hydrophobicity, etc), such that the overall functioning of the antibody is essentially not affected.

As is well known by the skilled person, a heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain is often, but not always, together with the variable domain of the heavy chain involved in antigen binding.

Complementary-determining regions (CDRs) are the hypervariable regions present in heavy chain variable domains and light chain variable domains. In case of whole antibodies, the CDRs 1-3 of a heavy chain and the CDRs 1-3 of the connected light chain together form the antigen-binding site.

As used herein, the term "an antibody or functional part or functional equivalent according to the invention" is also referred to as "a binding compound according to the invention".

The term "cell surface component of AML cells" means any component that is at least in part present in or on the cell surface of AML cells, or a component that is attached to an AML cell surface. Non-limiting examples of cell surface components of AML cells are (trans)membrane proteins, glycoproteins, and any compound attached thereto.

The terms "specific for" and "capable of specifically binding" are used herein interchangeably and refer to the interaction between an antibody, or functional part or functional equivalent thereof, and its epitope. This means that said antibody, or functional part or functional equivalent thereof, preferentially binds to said epitope over other antigens or amino acid sequences. Thus, although the antibody, functional part or equivalent may non-specifically bind to other antigens or amino acid sequences, the binding affinity of said antibody or functional part or functional equivalent for its epitope is significantly higher than the non-specific binding affinity of said antibody or functional part or functional equivalent for other antigens or amino acid sequences.

An antibody or functional part or functional equivalent according to the invention that is able to bind a particular epitope of AML cells can also be specific for other, non-AML cells if said epitope of AML cells is also present on other cells (for instance other leukemic cells, myeloma cells or lymphoma cells). In that case an antibody referred to herein as being specific for AML cells is also specific for said other cells comprising the same epitope. Preferably, human AML antibodies and functional parts and functional equivalents thereof, as provided herewith, do not significantly bind non-hematopoietic cells and non-malignant hematopoietic cells.

"Binding affinity" refers to the strength of the total sum of the noncovalent interactions between a single binding site of an antibody or functional part or functional equivalent and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the equilibrium dissociation constant ($K_D$), which is calculated as the $k_a$ to $k_d$ ratio, see, e.g., Chen, Y., et al., (1999) *J. Mol Biol* 293:865-881. Affinity can be measured by common methods known in the art, such as for instance a surface plasmon resonance (SPR) assay such as BiaCore or IBIS-iSPR instrument at IBIS Technologies BV (Hengelo, the Netherlands) or solution phase assays, such as Kinexa. Preferably an antibody according to the invention has a binding affinity for an epitope at or on the cell surface of AML cells characterized by a dissociation constant ($K_D$) of at most 100 nM, more preferably at most 50 nM, more preferably at most 25 nM, more preferably at most 10 nM, more preferably at most 5 nM, more preferably at most 2 nM, more preferably at most 1 nM, more preferably at most 0.5 nM, more preferably at most 0.3 nM, more preferably at most 0.1 nM.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. Methods and computer programs for the alignment are well known in the art, for example "Align 2".

In a particularly preferred embodiment, an antibody or functional part or functional equivalent according to the invention is provided which is able to induce death of primary AML blasts. Since primary AML blasts are directly derived from an AML patient, as opposed to commercially available cell lines, the activity of an antibody against such AML blasts is even more indicative for an in vivo situation. As shown in the Examples, at least antibodies AT13-024 and AT12-025 have this characteristic. These antibodies are, therefore, preferred. In a particularly preferred embodiment, an antibody or functional part or functional equivalent according to the invention is provided which is able to induce death of primary AML blasts independently from, or essentially independently from, antibody-dependent cell-mediated cytotoxicity (ADCC), complement-dependent cytotoxicity (CDC), apoptosis, and/or phagocytosis by macrophages or dendritic cells. Preferably, such binding compounds are capable of inducing death of AML blasts essentially independently from other immune cells, or complement or apoptosis. Antibodies AT13-024 and AT12-025 also have this preferred characteristic.

As used herein, the term "essentially independently from ADCC, CDC or phagocytosis by tumor-associated myeloid cells such as macrophages or dendritic cells" means that ADCC, CDC or phagocytosis by tumor-associated myeloid cells such as macrophages or dendritic cells are not required for an anti-AML effect induced by a binding compound according to the present invention, even though in an in vivo situation ADCC, CDC or phagocytosis by tumor-associated myeloid cells such as macrophages or dendritic cells may also occur. Hence, in this embodiment, ADCC, CDC and phagocytosis by tumor-associated myeloid cells such as macrophages or dendritic cells is not excluded, but not essential either. Likewise, the term "essentially independently from other immune cells or complement" means that a binding compound according to the invention is, in principle, capable of exerting an anti-AML effect without the presence of other immune cells or complement, even though in an in vivo situation other immune cells or complement may also have an anti-AML activity. The term "essentially independently from apoptosis" means that the anti-AML effect is exerted by a binding compound according to the present invention via a mechanism other than apoptosis. Preferably, said anti-AML effect is exerted via necrosis.

In a further preferred embodiment, an antibody or functional part or functional equivalent according to the invention is provided which is able to diminish proliferation of AML cells in vitro within 7 days, preferably within 5 days, more preferably within 3 days and even more preferably within 1 day. This indicates a quick therapeutic effect.

The present invention provides isolated, synthetic and recombinant human antibodies, and functional parts or functional equivalents thereof, which are able to bind intact AML cells. Said AML cells preferably belong to a French-American-British (FAB) classification selected from the group consisting of M5, M0, M1, M2, M3 and M4. More preferably, said AML cells belong to the FAB classification M5 or M1 or M0 or M4, preferably M5. These are the FAB classifications commonly found in AML patients.

In a further preferred embodiment, isolated, synthetic and recombinant human antibodies, or functional parts or functional equivalents thereof, are provided which are able to bind different AML cells of at least two, preferably at least three, more preferably at least four different FAB classifications. Such antibodies are useful for different AML patients having different FAB classifications, so that these antibodies are broadly applicable. As shown in Table 3, antibody AT12-025 is capable of binding AML cells of at least two FAB classifications (M5+M1). This is, therefore, a preferred antibody according to the invention. Antibodies AT13-024, AT12-019, AT13-023, and AT13-022 are capable of binding AML cells of at least three FAB classifications (M5+M0+M1). Antibody AT13-031 is also capable of binding AML cells of at least three FAB classifications (M5+M1+M4). These antibodies are, therefore, even more preferred. Furthermore, antibody AT12-023 is capable of binding AML cells of at least four FAB classifications (M5+M0+M1+M4). This antibody is, therefore, even more broadly applicable and is, therefore, particularly preferred.

In one particularly preferred embodiment, an antibody or functional part or functional equivalent according to the invention is provided wherein said antibody is of the IgG isotype, preferably IgG1 or IgG3. This is beneficial for medical applications in humans.

Tables 1A and 1B, and FIG. 1, provide an overview of the variable heavy and light chain sequences, as well as the individual CDR sequences, of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016. These are preferred antibodies according to the invention, obtained from three human AML patients. The terms "AT12-023", "AT12-025", "AT13-024", "AT12-019", "AT13-022", "AT13-023", "AT13-031", "AT12-020", "AT13-033", "AT13-034", "AT13-035", "AT13-036", "AT13-037", "AT14-013", "AT14-014", "AT14-015" and "AT14-016" as used herein encompass all antibodies and functional parts and functional equivalents having at least the heavy and light chain CDR1-3 regions, preferably the variable heavy chain and light chain sequences, of these antibodies as depicted in Tables 1A and 1B and FIG. 1, such as for instance isolated and/or purified antibodies or recombinantly produced antibodies.

As used herein, any reference to "Table 1" includes a reference to Table 1A and/or Table 1B.

Based on the antibodies depicted in Table 1 and FIG. 1, it is possible to produce an antibody or functional part or functional equivalent thereof comprising at least one CDR sequence of an antibody depicted in Table 1 or FIG. 1, which is specific for AML cells. Provided is therefore an isolated, recombinant and/or synthetic antibody or a functional part or functional equivalent thereof comprising at least one CDR sequence of an antibody as depicted in Table 1. Said CDR sequence is preferably a CDR3 sequence of an antibody according to the present invention. Preferably, binding compounds are provided which comprise at least two CDRs, more preferably at least three CDRs, of the heavy and light chains of the same antibody indicated in Table 1 or FIG. 1. Hence, preferably at least two or three CDRs of the heavy and light chains of antibody AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 or AT14-016 are jointly present in one binding compound according to the invention. Preferably, a binding compound according to the invention comprises all three heavy chain CDRs and all three light chain CDRs of the same antibody depicted in Table 1 or FIG. 1. Optionally, at least one of said CDR sequences is optimized, thereby generating a variant binding compound, preferably in order to improve binding efficacy, selectivity, or stability. This is for instance done by mutagenesis procedures where after the stability and/or binding efficacy of the resulting compounds are preferably tested and an improved AML-specific binding compound is selected. A skilled person is well capable of generating variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. Preferably, an antibody or functional part or functional equivalent is provided comprising a CDR sequence which is at least 80% identical to a CDR sequence as depicted in Table 1 or FIG. 1, so that the favourable AML-binding and/or AML-killing characteristic of an AML-specific antibody as depicted in Table 1 or FIG. 1 is maintained or even improved. Variant binding compounds comprising an amino acid sequence which is at least 80% identical to a CDR sequence as depicted in Table 1 or FIG. 1 are therefore also within the scope of the present invention. Preferably, said binding compounds comprise heavy chain and light chain CDR 1-3 sequences which are at least 80% identical to the heavy and light chain CDR 1-3 sequences of the same antibody depicted in Table 1 or FIG. 1. Preferably, the CDR sequences differ in no more than three, preferably in no more than two, preferably in no more than one amino acid from the original CDR sequences of an antibody according to the invention.

Besides optimizing CDR sequences in order to improve binding efficacy or stability, at least one sequence in at least one of the framework regions can be optimized. This is preferably done in order to improve binding efficacy or stability. Framework sequences are for instance optimized by mutating a nucleic acid molecule encoding such framework sequence where after the characteristics of the resulting antibody—or functional part or functional equivalent—are preferably tested. This way, it is possible to obtain improved binding compounds. In a preferred embodiment, human germline sequences are used for framework regions in antibodies according to the invention. The use of human germline sequences minimizes the risk of immunogenicity of said antibodies, because these sequences are less likely to contain somatic alterations which are unique to individuals from which the framework regions are derived, and may cause an immunogenic response when applied to another human individual. Further provided is therefore a synthetic or recombinant antibody or functional part or functional equivalent according to the invention, comprising at least one non-natural mutation in a framework region. Additionally, or alternatively, a synthetic or recombinant antibody or functional part or functional equivalent according to the invention is provided that comprises at least one non-natural mutation in a constant region. By a "non-natural mutation" is meant that the resulting amino acid sequence does not occur in nature. Instead, it has been artificially produced. In one embodiment, an IgG3 Fc region of antibody AT12-023, AT12-025, AT13-024, AT13-022, AT12-020, AT14-014, AT14-015 or AT14-016 is at least partly replaced by an IgG1 Fc region. This typically increases the stability and half life of the resulting immunoglobulin.

A binding compound according to the present invention preferably comprises a human variable region. More preferably, said binding compound comprises a human constant region and a human variable region. Most preferably, said binding compound is a human antibody. The use of human AML-specific antibodies is advantageous over the use of non-human antibodies. The in vivo use of non-human antibodies for diagnosis and/or treatment of human diseases is hampered by a number of factors. In particular, the human body may recognize non-human antibodies as foreign, which will result in an immunogenic response against the non-human antibodies, resulting in adverse side effects and/or rapid clearance of the antibodies from the circulation. A human antibody diminishes the chance of side-effects when administered to a human individual and often results in a longer half-life in the circulation because of reduced clearance when compared to non-human antibodies. In another embodiment a binding compound according to the invention is a humanized antibody. In another embodiment a binding compound according to the invention is a chimeric antibody. In a chimeric antibody, sequences of interest, such as for instance an additional binding site of interest, are included into a binding compound according to the invention.

Further, binding compounds according to the invention are preferably monoclonal antibodies. A monoclonal antibody is an antibody consisting of a single molecular species. Monoclonal antibodies can be produced in large quantities by monoclonal antibody-producing cells or recombinant DNA technology.

Hence, variant binding compounds based on the preferred antibodies depicted in Table 1 and FIG. 1 can also be generated, using techniques known in the art such as for instance mutagenesis. Typically, sequence variations between 80 and 99% are tolerated while maintaining a certain antigen specificity. Binding compounds according to the invention comprising a sequence that has at least 80% sequence identity to at least a CDR sequence of any of the antibodies of Table 1 or FIG. 1 are therefore also provided herein. Since the antigen specificity of an antibody is typically dominated by the CDR3 sequences, a variant antibody according to the invention preferably comprises at least a heavy chain CDR3 sequence having at least 80% sequence identity with a heavy chain CDR3 sequence as depicted in Table 1 or FIG. 1. Said variant antibody preferably comprises a heavy chain CDR3 sequence and a light chain CDR3 sequence having at least 80% sequence identity with the heavy and light chain CDR3 sequences of the same antibody, selected from the group consisting of AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016.

Further provided is, therefore, an isolated, synthetic or recombinant antibody, or a functional part or a functional equivalent thereof, which comprises at least a heavy chain CDR3 sequence having at least 80% sequence identity with a sequence selected from the group consisting of SEQ ID NOs: 27-39 and 217-220, and a light chain CDR3 sequence having at least 80% sequence identity with a sequence selected from the group consisting of SEQ ID NOs: 66-78 and 229-232. These are the CDR3 sequences of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016 depicted in Table 1 and FIG. 1. Preferably, said sequence identity is at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As said before, a binding compound according to the present invention preferably comprises a heavy and light chain CDR3 sequence having at least 80% sequence identity with the heavy and light chain CDR3 sequences of the same antibody, selected from Table 1 or FIG. 1.

Typically, at least 1, 2 or 3 amino acid residues of a given CDR sequence may vary while retaining the same kind of binding activity (in kind, not necessarily in amount). Hence, a binding compound according to the invention preferably contains a heavy chain and light chain CDR3 sequence wherein at most 3, preferably at most 2, more preferably at most 1 amino acid deviates from a heavy and light chain CDR 3 sequence from the same antibody selected from the group consisting of AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016.

The invention further provides an isolated, synthetic or recombinant antibody, or a functional part or a functional equivalent thereof, which comprises:
  a heavy chain CDR1 sequence comprising a sequence which has at least 80% sequence identity with a sequence selected from the group consisting of SEQ ID NOs: 1-13 and 209-212; and/or
  a heavy chain CDR2 sequence comprising a sequence which has at least 80% sequence identity with a sequence selected from the group consisting of SEQ ID NOs: 14-26 and 213-216; and/or
  a heavy chain CDR3 sequence comprising a sequence which has at least 80% sequence identity with a sequence selected from the group consisting of SEQ ID NOs: 27-39 and 217-220; and/or
  a light chain CDR1 sequence comprising a sequence which has at least 80% sequence identity with a sequence selected from the group consisting of SEQ ID NOs: 40-52 and 221-224; and/or
  a light chain CDR2 sequence comprising a sequence which has at least 80% sequence identity with a sequence selected from the group consisting of SEQ ID NOs: 53-65 and 225-228; and/or
  a light chain CDR3 sequence comprising a sequence which has at least 80% sequence identity with a sequence selected from the group consisting of SEQ ID NOs: 66-78 and 229-232.

These are the heavy and light chain CDR sequences of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016, depicted in Table 1A and 1B and in FIG. 1.

The above mentioned heavy and light chain CDR 1 to 3 sequences are preferably from the same antibody selected from Table 1 or FIG. 1. Preferably, said antibody or functional part or equivalent comprises heavy chain CDR1, CDR2 and CDR3 sequences and light chain CDR1, CDR2 and CDR3 sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100% identical to the above recited CDR sequences (SEQ ID NOs 1-78 and 209-232).

In a preferred embodiment, the heavy chain CDR1 and CDR2 and CDR3 sequences, as well as the light chain CDR1 and CDR2 and CDR3 sequences, of the same antibody, selected from the group consisting of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016 are present in a given binding compound according to the invention.

A preferred antibody according to the present invention is antibody AT12-023. This antibody is preferred because it is capable of efficiently binding and killing cells of the AML cell line THP-1, as shown in the Examples and FIGS. 7 and 8. This antibody is, therefore, particularly suitable for AML therapy and/or diagnosis. Interestingly, AT12-023 is of the IgG3 isotype and belongs to the VH4-34 family, which is a family of VH sequences known for their potential killing properties (Bhat et al, 1997). Antibody AT12-023 is also capable of efficiently binding primary AML blasts of at least four different FAB classifications (Table 3). The heavy chain CDR1, CDR2 and CDR3 sequences, and the light chain CDR1, CDR2 and CDR3 sequences of antibody AT12-023 are SEQ ID NOs 1, 14, 27, 40, 53 and 66, respectively, as depicted in Table 1. The invention therefore further provides an isolated, synthetic or recombinant antibody, or a functional part or a functional equivalent thereof, which comprises:

a heavy chain CDR1 sequence comprising a sequence which has at least 85% sequence identity with SEQ ID NO: 1; and
a heavy chain CDR2 sequence comprising a sequence which has at least 85% sequence identity with SEQ ID NO: 14; and
a heavy chain CDR3 sequence comprising a sequence which has at least 85% sequence identity with SEQ ID NO: 27; and
a light chain CDR1 sequence comprising a sequence which has at least 85% sequence identity with SEQ ID NO: 40; and
a light chain CDR2 sequence comprising a sequence which has at least 85% sequence identity with SEQ ID NO: 53; and
a light chain CDR3 sequence comprising a sequence which has at least 85% sequence identity with SEQ ID NO: 66. Preferably, said sequence identities are at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described herein before, at least 1, 2 or 3 amino acid residues in the recited CDR sequences may vary while retaining the same kind of binding activity (in kind, not necessarily in amount). Hence, said heavy and light chain CDR 1, 2 and 3 sequences preferably contain antibody AT12-023-derived CDR sequences that deviate in no more than three, preferably no more than two, more preferably no more than one amino acid from the recited AT12-023 CDR sequences.

Another preferred antibody according to the present invention is antibody AT12-025. This antibody is preferred because it is capable of efficiently binding and killing cells of the AML cell line THP-1, as well as patient-derived primary AML blasts, as shown in the Examples and FIGS. 8 and 10. This antibody is, therefore, particularly suitable for AML therapy and/or diagnosis. Interestingly, AT12-025 is of the IgG3 isotype and belongs to the VH4-34 family, which is a family of VH sequences known for their potential killing properties (Bhat et al, 1997). The heavy chain CDR1, CDR2 and CDR3 sequences and the light chain CDR1, CDR2 and CDR3 sequences of antibody AT12-025 are SEQ ID NOs 2, 15, 28, 41, 54 and 67, respectively, as depicted in Table 1. The invention therefore further provides an isolated, synthetic or recombinant antibody, or a functional part or a functional equivalent thereof, which comprises:

a heavy chain CDR1 sequence comprising a sequence which has at least 80% sequence identity with SEQ ID NO: 2; and
a heavy chain CDR2 sequence comprising a sequence which has at least 80% sequence identity with SEQ ID NO: 15; and
a heavy chain CDR3 sequence comprising a sequence which has at least 80% sequence identity with SEQ ID NO: 28; and
a light chain CDR1 sequence comprising a sequence which has at least 80% sequence identity with SEQ ID NO: 41; and
a light chain CDR2 sequence comprising a sequence which has at least 80% sequence identity with SEQ ID NO: 54; and
a light chain CDR3 sequence comprising a sequence which has at least 80% sequence identity with SEQ ID NO: 67. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT12-025 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT12-025 CDR sequences.

Another preferred antibody according to the present invention is antibody AT13-024. This antibody is preferred because it is capable of binding and killing patient-derived primary AML blasts, as shown in the Examples and FIG. 10. This antibody is, therefore, particularly suitable for AML therapy and/or diagnosis. Interestingly, AT13-024 is of the IgG3 isotype and belongs to the VH3-30 family. The heavy chain CDR 1, CDR2 and CDR3 sequences and the light chain CDR1, CDR2 and CDR3 sequences of antibody AT13-024 are SEQ ID NOs 3, 16 29, 42, 55 and 68, respectively, as depicted in Table 1. The invention therefore further provides an isolated, synthetic or recombinant antibody, or a functional part or a functional equivalent thereof, which comprises:
- a heavy chain CDR1 sequence comprising a sequence which has at least 80% sequence identity with SEQ ID NO: 3; and
- a heavy chain CDR2 sequence comprising a sequence which has at least 80% sequence identity with SEQ ID NO: 16; and
- a heavy chain CDR3 sequence comprising a sequence which has at least 80% sequence identity with SEQ ID NO: 29; and
- a light chain CDR1 sequence comprising a sequence which has at least 80% sequence identity with SEQ ID NO: 42; and
- a light chain CDR2 sequence comprising a sequence which has at least 80% sequence identity with SEQ ID NO: 55; and
- a light chain CDR3 sequence comprising a sequence which has at least 80% sequence identity with SEQ ID NO: 68. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-024 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-024 CDR sequences.

The invention further provides an isolated, synthetic or recombinant antibody, or a functional part or a functional equivalent thereof, which comprises:
- a heavy chain CDR1 sequence comprising a sequence which has at least 80% sequence identity with SEQ ID NO: 4; and
- a heavy chain CDR2 sequence comprising a sequence which has at least 80% sequence identity with SEQ ID NO: 17; and
- a heavy chain CDR3 sequence comprising a sequence which has at least 80% sequence identity with SEQ ID NO: 30; and
- a light chain CDR1 sequence comprising a sequence which has at least 80% sequence identity with SEQ ID NO: 43; and
- a light chain CDR2 sequence comprising a sequence which has at least 80% sequence identity with SEQ ID NO: 56; and
- a light chain CDR3 sequence comprising a sequence which has at least 80% sequence identity with SEQ ID NO: 69. These are the CDR sequences of antibody AT12-019. Antibody AT12-019, derived from a human AML patient in complete remission, is capable of efficiently binding intact AML cells, which makes a binding compound containing AT12-019-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT12-019 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT12-019 CDR sequences.

The invention further provides an isolated, synthetic or recombinant antibody, or a functional part or a functional equivalent thereof, which comprises:
- a heavy chain CDR1 sequence comprising a sequence which has at least 80% sequence identity with SEQ ID NO: 5; and
- a heavy chain CDR2 sequence comprising a sequence which has at least 80% sequence identity with SEQ ID NO: 18; and
- a heavy chain CDR3 sequence comprising a sequence which has at least 80% sequence identity with SEQ ID NO: 31; and
- a light chain CDR1 sequence comprising a sequence which has at least 80% sequence identity with SEQ ID NO: 44; and
- a light chain CDR2 sequence comprising a sequence which has at least 80% sequence identity with SEQ ID NO: 57; and
- a light chain CDR3 sequence comprising a sequence which has at least 80% sequence identity with SEQ ID NO: 70. These are the CDR sequences of antibody AT13-022. Interestingly, antibody AT13-022 is of the IgG3 isotype. Antibody AT13-022, derived from a human AML patient in complete remission, is capable of specifically binding intact AML cells, which makes a binding compound containing AT13-022-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-022CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-022 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 6; and
  a heavy chain CDR2 sequence comprising a sequence which has at least 80% sequence identity with SEQ ID NO: 19; and
  a heavy chain CDR3 sequence comprising a sequence which has at least 80% sequence identity with SEQ ID NO: 32; and
  a light chain CDR1 sequence comprising a sequence which has at least 80% sequence identity with SEQ ID NO: 45; and
  a light chain CDR2 sequence comprising a sequence which has at least 80% sequence identity with SEQ ID NO: 58; and
  a light chain CDR3 sequence comprising a sequence which has at least 80% sequence identity with SEQ ID NO: 71. These are the CDR sequences of antibody AT13-023. Interestingly, AT13-023 belongs to the VH4-34 family, which is a family of VH sequences known for their potential killing properties (Bhat et al, 1997). Antibody AT13-023, derived from a human AML patient in complete remission, is capable of specifically binding intact AML cells, which makes a binding compound containing AT13-023-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-023 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-023 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 7; and
  a heavy chain CDR2 sequence comprising a sequence which has at least 80% sequence identity with SEQ ID NO: 20; and
  a heavy chain CDR3 sequence comprising a sequence which has at least 80% sequence identity with SEQ ID NO: 33; and
  a light chain CDR1 sequence comprising a sequence which has at least 80% sequence identity with SEQ ID NO: 46; and
  a light chain CDR2 sequence comprising a sequence which has at least 80% sequence identity with SEQ ID NO: 59; and
  a light chain CDR3 sequence comprising a sequence which has at least 80% sequence identity with SEQ ID NO: 72. These are the CDR sequences of antibody AT13-031. Interestingly, AT13-031 belongs to the VH4-34 family, which is a family of VH sequences known for their potential killing properties (Bhat et al, 1997). Antibody AT13-031, derived from a human AML patient in complete remission, is capable of specifically binding intact AML cells. Moreover, this antibody is preferred because it is capable of efficiently binding and killing cells of the AML cell line THP-1. Hence, a binding compound containing AT13-031-derived CDR sequences is particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-031 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-031 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 8; and a heavy chain CDR2 sequence comprising a sequence which has at least 80% sequence identity with SEQ ID NO: 21; and a heavy chain CDR3 sequence comprising a sequence which has at least 80% sequence identity with SEQ ID NO: 34; and a light chain CDR1 sequence comprising a sequence which has at least 80% sequence identity with SEQ ID NO: 47; and a light chain CDR2 sequence comprising a sequence which has at least 80% sequence identity with SEQ ID NO: 60; and a light chain CDR3 sequence comprising a sequence which has at least 80% sequence identity with SEQ ID NO: 73. These are the CDR sequences of antibody AT12-020. Interestingly, antibody AT12-020 is of the IgG3 isotype. Antibody AT12-020, derived from a human AML patient in complete remission, is capable of specifically binding intact AML cells, which makes a binding compound containing AT12-020-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT12-020 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT12-020 CDR sequences.

The invention further provides an isolated, synthetic or recombinant antibody, or a functional part or a functional equivalent thereof, which comprises:

a heavy chain CDR1 sequence comprising a sequence which has at least 80% sequence identity with SEQ ID NO: 9; and a heavy chain CDR2 sequence comprising a sequence which has at least 80% sequence identity with SEQ ID NO: 22; and a heavy chain CDR3 sequence comprising a sequence which has at least 80% sequence identity with SEQ ID NO: 35; and a light chain CDR1 sequence comprising a sequence which has at least 80% sequence identity with SEQ ID NO: 48; and a light chain CDR2 sequence comprising a sequence which has at least 80% sequence identity with SEQ ID NO: 61; and a light chain CDR3 sequence comprising a sequence which has at least 80% sequence identity with SEQ ID NO: 74. These are the CDR sequences of antibody AT13-033. Antibody AT13-033, derived from a human AML patient in complete remission, is capable of specifically binding intact AML cells. Moreover, this antibody is preferred because it is capable of efficiently binding and killing cells of the AML cell line THP-1. Hence, a binding compound containing AT13-033-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-033 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-033 CDR sequences.

The invention further provides an isolated, synthetic or recombinant antibody, or a functional part or a functional equivalent thereof, which comprises:

a heavy chain CDR1 sequence comprising a sequence which has at least 80% sequence identity with SEQ ID NO: 10; and a heavy chain CDR2 sequence comprising a sequence which has at least 80% sequence identity with SEQ ID NO: 23; and a heavy chain CDR3 sequence comprising a sequence which has at least 80% sequence identity with SEQ ID NO: 36; and a light chain CDR1 sequence comprising a sequence which has at least 80% sequence identity with SEQ ID NO: 49; and a light chain CDR2 sequence comprising a sequence which has at least 80% sequence identity with SEQ ID NO: 62; and a light chain CDR3 sequence comprising a sequence which has at least 80% sequence identity with SEQ ID NO: 75. These are the CDR sequences of antibody AT13-034. Antibody AT13-034, derived from a human AML patient in complete remission, is capable of specifically binding intact AML cells, which makes a binding compound containing AT13-034-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-034 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-034 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 11; and
  a heavy chain CDR2 sequence comprising a sequence which has at least 80% sequence identity with SEQ ID NO: 24; and
  a heavy chain CDR3 sequence comprising a sequence which has at least 80% sequence identity with SEQ ID NO: 37; and
  a light chain CDR1 sequence comprising a sequence which has at least 80% sequence identity with SEQ ID NO: 50; and
  a light chain CDR2 sequence comprising a sequence which has at least 80% sequence identity with SEQ ID NO: 63; and
  a light chain CDR3 sequence comprising a sequence which has at least 80% sequence identity with SEQ ID NO: 76. These are the CDR sequences of antibody AT13-035. Antibody AT13-035, derived from a human AML patient in complete remission, is capable of specifically binding intact AML cells. Moreover, this antibody is preferred because it is capable of efficiently binding and killing cells of the AML cell line THP-1. Hence, a binding compound containing AT13-035-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-035 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-035 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 12; and
  a heavy chain CDR2 sequence comprising a sequence which has at least 80% sequence identity with SEQ ID NO: 25; and
  a heavy chain CDR3 sequence comprising a sequence which has at least 80% sequence identity with SEQ ID NO: 38; and
  a light chain CDR1 sequence comprising a sequence which has at least 80% sequence identity with SEQ ID NO: 51; and
  a light chain CDR2 sequence comprising a sequence which has at least 80% sequence identity with SEQ ID NO: 64; and
  a light chain CDR3 sequence comprising a sequence which has at least 80% sequence identity with SEQ ID NO: 77. These are the CDR sequences of antibody AT13-036. Antibody AT13-036, derived from a human AML patient in complete remission, is capable of specifically binding intact AML cells. Moreover, this antibody is preferred because it is capable of efficiently binding and killing cells of the AML cell line THP-1. Hence, a binding compound containing AT13-036-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-036 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-036 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 13; and
  a heavy chain CDR2 sequence comprising a sequence which has at least 80% sequence identity with SEQ ID NO: 26; and
  a heavy chain CDR3 sequence comprising a sequence which has at least 80% sequence identity with SEQ ID NO: 39; and
  a light chain CDR1 sequence comprising a sequence which has at least 80% sequence identity with SEQ ID NO: 52; and
  a light chain CDR2 sequence comprising a sequence which has at least 80% sequence identity with SEQ ID NO: 65; and
  a light chain CDR3 sequence comprising a sequence which has at least 80% sequence identity with SEQ ID NO: 78. These are the CDR sequences of antibody AT13-037. Antibody AT13-037, derived from a human AML patient in complete remission, is capable of specifically binding intact AML cells. Moreover, this antibody is preferred because it is capable of efficiently binding and killing cells of the AML cell line THP-1, as well as patient-derived primary AML blasts, as shown in the Examples. Hence, a binding compound containing AT13-037-derived CDR sequences particularly suitable for AML therapy and/or diagnosis. Such binding compound is for instance used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT13-037 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT13-037 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 209; and
  a heavy chain CDR2 sequence comprising a sequence which has at least 80% sequence identity with SEQ ID NO: 213; and
  a heavy chain CDR3 sequence comprising a sequence which has at least 80% sequence identity with SEQ ID NO: 217; and
  a light chain CDR1 sequence comprising a sequence which has at least 80% sequence identity with SEQ ID NO: 221; and
  a light chain CDR2 sequence comprising a sequence which has at least 80% sequence identity with SEQ ID NO: 225; and
  a light chain CDR3 sequence comprising a sequence which has at least 80% sequence identity with SEQ ID NO: 229. These are the CDR sequences of antibody AT14-013. Antibody AT14-013, derived from a human AML patient in complete remission, is capable of specifically binding primary AML blasts of at least three different FAB classifications, which makes a binding compound containing AT14-013-derived CDR sequences particularly suitable for AML therapy and/or diagnosis. Such binding compound is for instance used for diminishing proliferation of AML cells, preferably independently from apoptosis and/or independently from ADCC, CDC or phagocytosis by macrophages or dendritic cells. Preferably, said binding compound is used for inducing death of AML cells. In some embodiments, such binding compound is used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT14-013 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT14-013 CDR sequences.

The invention further provides an isolated, synthetic or recombinant antibody, or a functional part or a functional equivalent thereof, which comprises:
  a heavy chain CDR1 sequence comprising a sequence which has at least 80% sequence identity with SEQ ID NO: 210; and
  a heavy chain CDR2 sequence comprising a sequence which has at least 80% sequence identity with SEQ ID NO: 214; and
  a heavy chain CDR3 sequence comprising a sequence which has at least 80% sequence identity with SEQ ID NO: 218; and a light chain CDR1 sequence comprising a sequence which has at least 80% sequence identity with SEQ ID NO: 222; and a light chain CDR2 sequence comprising a sequence which has at least 80% sequence identity with SEQ ID NO: 226; and a light chain CDR3 sequence comprising a sequence which has at least 80% sequence identity with SEQ ID NO: 230. These are the CDR sequences of antibody AT14-014. Interestingly, antibody AT14-014 is of the IgG3 isotype. Antibody AT14-014, derived from a human AML patient in complete remission, is capable of specifically binding intact AML cells, which makes a binding compound containing AT14-014-derived CDR sequences particularly suitable for AML therapy and/or diagnosis. Such binding compound is for instance used for diminishing proliferation of AML cells, preferably independently from apoptosis and/or independently from ADCC, CDC or phagocytosis by macrophages or dendritic cells. Preferably, said binding compound is used for inducing death of AML cells. In some embodiments, such binding compound is used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT14-014 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT14-014 CDR sequences.

The invention further provides an isolated, synthetic or recombinant antibody, or a functional part or a functional equivalent thereof, which comprises:

a heavy chain CDR1 sequence comprising a sequence which has at least 80% sequence identity with SEQ ID NO: 211; and a heavy chain CDR2 sequence comprising a sequence which has at least 80% sequence identity with SEQ ID NO: 215; and a heavy chain CDR3 sequence comprising a sequence which has at least 80% sequence identity with SEQ ID NO: 219; and a light chain CDR1 sequence comprising a sequence which has at least 80% sequence identity with SEQ ID NO: 223; and a light chain CDR2 sequence comprising a sequence which has at least 80% sequence identity with SEQ ID NO: 227; and a light chain CDR3 sequence comprising a sequence which has at least 80% sequence identity with SEQ ID NO: 231. These are the CDR sequences of antibody AT14-015. Interestingly, antibody AT14-015 is of the IgG3 isotype. Antibody AT14-015, derived from a human AML patient in complete remission, is capable of specifically binding intact AML cells, which makes a binding compound containing AT14-015-derived CDR sequences particularly suitable for AML therapy and/or diagnosis. Such binding compound is for instance used for diminishing proliferation of AML cells, preferably independently from apoptosis and/or independently from ADCC, CDC or phagocytosis by macrophages or dendritic cells. Preferably, said binding compound is used for inducing death of AML cells. In some embodiments, such binding compound is used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT14-015 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT14-015 CDR sequences.

The invention further provides an isolated, synthetic or recombinant antibody, or a functional part or a functional equivalent thereof, which comprises:

a heavy chain CDR1 sequence comprising a sequence which has at least 80% sequence identity with SEQ ID NO: 212; and a heavy chain CDR2 sequence comprising a sequence which has at least 80% sequence identity with SEQ ID NO: 216; and a heavy chain CDR3 sequence comprising a sequence which has at least 80% sequence identity with SEQ ID NO: 220; and a light chain CDR1 sequence comprising a sequence which has at least 80% sequence identity with SEQ ID NO: 224; and a light chain CDR2 sequence comprising a sequence which has at least 80% sequence identity with SEQ ID NO: 228; and a light chain CDR3 sequence comprising a sequence which has at least 80% sequence identity with SEQ ID NO: 232. These are the CDR sequences of antibody AT14-016. Interestingly, antibody AT14-016 is of the IgG3 isotype. Antibody AT14-016, derived from a human AML patient in complete remission, is capable of specifically binding intact AML cells, which makes a binding compound containing AT14-016-derived CDR sequences particularly suitable for AML therapy and/or diagnosis. Such binding compound is for instance used for diminishing proliferation of AML cells, preferably independently from apoptosis and/or independently from ADCC, CDC or phagocytosis by macrophages or dendritic cells. Preferably, said binding compound is used for inducing death of AML cells. In some embodiments, such binding compound is used as an antibody-drug conjugate (ADC), such that a toxic compound will be directed to AML cells, or it is used by inducing CDC and/or ADCC. Alternatively, or additionally, such binding compound can be used to mark AML cells for specific phagocytosis by tumor-associated myeloid cells such as macrophages or dendritic cells, which cells can subsequently induce an AML specific immune response. Again, said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%. As described above, at least 1, 2 or 3 amino acid residues in the recited AT14-016 CDR sequences may vary while retaining the same kind of binding activity (in kind, not necessarily in amount). Hence, the above mentioned heavy and light chain CDR 1, 2 and 3 sequences preferably contain CDR sequences that deviate in no more than three, preferably no more than two, more preferably no more than one amino acid from the recited AT14-016 CDR sequences.

Preferably, an antibody according to the invention comprises a variable heavy chain sequence and/or a variable light chain sequence as depicted in Table 1 or FIG. 1, or a sequence which has at least 80% sequence identity thereto. As shown in Table 1, the variable heavy chain sequences of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016 are SEQ ID NOs 79-91 and 233-236, respectively. The variable light chain sequences of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016 are SEQ ID NOs 92-104 and 237-240, respectively. Also provided is, therefore, an antibody or functional part or equivalent thereof according to the invention, comprising a variable heavy chain sequence having at least 80% sequence identity with a sequence selected from the group consisting of SEQ ID NOs: 79-91 and 233-236, and/or comprising a variable light chain sequence having at least 80% sequence identity with a sequence selected from the group consisting of SEQ ID NOs: 92-104 and 237-240, or sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, or even 100% identical to any one of these heavy chain or light chain sequences. The higher the identity, the more closely an antibody resembles an antibody depicted in FIG. 1. Preferably, a binding compound according to the invention comprises the variable heavy chain sequence of any one of the antibodies depicted in FIG. 1, together with the variable light chain sequence of the same antibody, or heavy and light chain sequences that are at least 80%, preferably at least 85%, or at least 86%, or at least 87%, or at least 88%, or at least 89%, or at least 90%, or 91%, or at least 92%, or at least 93%, or at least 94%, or at least 95%, or at least 96%, or at least 97%, or at least 98%, or at least 99%, thereto.

For instance, antibody AT12-023 has the variable heavy chain sequence of SEQ ID NO: 79 and the variable light chain sequence of SEQ ID NO: 92 as depicted in Table 1. A binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 79 is therefore preferably provided. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 92.

Antibody AT12-025 has the variable heavy chain sequence of SEQ ID NO: 80 and the variable light chain sequence of SEQ ID NO: 93 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 80. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 93.

Antibody AT13-024 has the variable heavy chain sequence of SEQ ID NO: 81 and the variable light chain sequence of SEQ ID NO: 94 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 81. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 94.

Antibody AT12-019 has the variable heavy chain sequence of SEQ ID NO: 82 and the variable light chain sequence of SEQ ID NO: 95 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 82. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 95.

Antibody AT13-022 has the variable heavy chain sequence of SEQ ID NO: 83 and the variable light chain sequence of SEQ ID NO: 96 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 83. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 96.

Antibody AT13-023 has the variable heavy chain sequence of SEQ ID NO: 84 and the variable light chain sequence of SEQ ID NO: 97 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 84. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 97.

Antibody AT13-031 has the variable heavy chain sequence of SEQ ID NO: 85 and the variable light chain sequence of SEQ ID NO: 98 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 85. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 98.

Antibody AT12-020 has the variable heavy chain sequence of SEQ ID NO: 86 and the variable light chain sequence of SEQ ID NO: 99 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 86. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 99.

Antibody AT13-033 has the variable heavy chain sequence of SEQ ID NO: 87 and the variable light chain sequence of SEQ ID NO: 100 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 87. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 100.

Antibody AT13-034 has the variable heavy chain sequence of SEQ ID NO: 88 and the variable light chain sequence of SEQ ID NO: 101 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 88. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 101.

Antibody AT13-035 has the variable heavy chain sequence of SEQ ID NO: 89 and the variable light chain sequence of SEQ ID NO: 102 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 89. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 102.

Antibody AT13-036 has the variable heavy chain sequence of SEQ ID NO: 90 and the variable light chain sequence of SEQ ID NO: 103 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 90. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 103.

Antibody AT13-037 has the variable heavy chain sequence of SEQ ID NO: 91 and the variable light chain sequence of SEQ ID NO: 104 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 91. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 104.

Antibody AT14-013 has the variable heavy chain sequence of SEQ ID NO: 233 and the variable light chain sequence of SEQ ID NO: 237 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 233. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 237.

Antibody AT14-014 has the variable heavy chain sequence of SEQ ID NO: 234 and the variable light chain sequence of SEQ ID NO: 238 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 234. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 238.

Antibody AT14-015 has the variable heavy chain sequence of SEQ ID NO: 235 and the variable light chain sequence of SEQ ID NO: 239 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 235. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 239.

Antibody AT14-016 has the variable heavy chain sequence of SEQ ID NO: 236 and the variable light chain sequence of SEQ ID NO: 240 as depicted in Table 1. Further provided is therefore a binding compound according to the present invention, having a variable heavy chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with SEQ ID NO: 236. Preferably, said binding compound also comprises a variable light chain sequence having at least 80%, preferably at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, sequence identity with SEQ ID NO: 240.

In one particularly preferred embodiment, an antibody or functional part or functional equivalent according to the invention is provided, which is able to bind snRNP200. snRNP200, also known as U5-snRNP, is a protein complex that is part of the spliceosome in all eukaryotic cells. Normally, snRNP200 is located in the nucleus. However, the present invention provides the surprising insight that snRNP200 is also present on the surface of AML cells. This antigen is bound by at least antibodies AT12-023, AT13-031 and AT13-037, and functional parts and functional equivalents thereof. Hence, snRNP200 is an important target for anti-AML therapy and snRNP200-specific antibodies according to the invention are therefore particularly suitable for counteracting these cells.

The invention further provides an isolated, synthetic or recombinant nucleic acid molecule with a length of at least 15 nucleotides, or a functional equivalent thereof, encoding at least one CDR sequence of an antibody or functional part or functional equivalent according to the invention. Preferably a nucleic acid molecule according to the invention has a length of at least 30 nucleotides, more preferably at least 50 nucleotides, more preferably at least 75 nucleotides. A nucleic acid molecule according to the invention is for instance isolated from a B-cell which is capable of producing an antibody according to the invention. Said B-cell preferably produces antibody AT12-023, AT12-025, AT13-024, AT12-019, AT13-022, AT13-023, AT13-031, AT12-020, AT13-033, AT13-034, AT13-035, AT13-036, AT13-037 AT14-013, AT14-014, AT14-015, or AT14-016. In a preferred embodiment a nucleic acid molecule encoding at least the heavy chain CDR3 sequence and the light chain CDR3 sequence of an antibody according to the invention is provided.

As used herein the term "an isolated, synthetic or recombinant nucleic acid molecule with a length of at least 15 nucleotides, or a functional equivalent thereof, encoding at least one CDR sequence of an antibody or functional part or functional equivalent according to the invention" is herein also referred to as "a nucleic acid molecule or functional equivalent according to the invention".

As used herein, a nucleic acid molecule or nucleic acid sequence of the invention preferably comprises a chain of nucleotides, more preferably DNA, cDNA or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid molecule" thus encompasses a chain comprising non-natural nucleotides, modified nucleotides and/or non-nucleotide building blocks which exhibit the same function as natural nucleotides.

Nucleic acid sequences encoding heavy chain and light chain CDRs of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016 are depicted in Table 1. Nucleic acid molecules encoding a heavy or light chain CDR of an antibody according to the invention which differ from the CDR nucleic acid sequences depicted in Table 1 but have nucleic acid codons which encode the same amino acids of said heavy or light chain CDR are also encompassed by the invention. Such nucleic acid molecules for instance comprise nucleic acid sequences that have been codon optimized for a producer cell, such as for instance *E. coli* or Chinese hamster ovary (CHO) cells, NSO cells (a mouse myeloma) or 293(T) cells, enabling high scale production of binding compounds according to the invention. It should be noted that antibody production can be done by any recombinant antibody production system; the four producer cell systems mentioned here are only a few examples of the many systems that are available to date. As used herein, the term "codon" means a triplet of nucleotides (or functional equivalents thereof) that encode a specific amino acid residue. The term "codon optimized" means that one or more codons from the original, human nucleic acid sequence are replaced by one or more codons that are preferred by a certain antibody production system. These replacement codons preferably encode the same amino acid residue as the original human codon that has been replaced. Alternatively, one or more replacement codons encode a different amino acid residue. This preferably results in conservative amino acid substitution, although this is not necessary. Typically, in constant regions and framework regions one or more amino acid substitutions are generally allowed. In CDR regions, preferably codons are used that encode the same amino acid residue as the original human codon that has been replaced.

Furthermore, nucleic acid molecules encoding a heavy or light chain CDR which is not identical to, but based on, a CDR sequence of an antibody depicted in Table 1 are also encompassed by the invention, as long as the resulting CDR has at least 80% sequence identity with a CDR sequence depicted in Table 1.

Further provided is, therefore, a nucleic acid molecule or functional equivalent thereof or a vector, comprising a sequence which has at least 80% sequence identity with a sequence selected from the group consisting of SEQ ID NOs: 105-182 and 241-264. Preferably, the resulting CDR differs in no more than three, preferably in no more than two, preferably in only one amino acid from the original CDR sequence of an antibody according to the invention.

Preferred nucleic acid molecules or functional equivalents or vectors according to the invention comprise:
   a heavy chain CDR1 encoding nucleic acid sequence which has at least 80% sequence identity to a sequence which is selected from the group consisting of SEQ ID NO's: 105-117 and 241-244, and/or
   a heavy chain CDR2 encoding sequence which has at least 80% sequence identity to a sequence which is selected from the group consisting of SEQ ID NO's: 118-130 and 245-248, and/or
   a heavy chain CDR3 encoding sequence which has at least 80% sequence identity to a sequence which is selected from the group consisting of SEQ ID NO's: 131-143 and 249-252, and/or
   a light chain CDR1 encoding sequence which has at least 80% sequence identity to a sequence which is selected from the group consisting of SEQ ID NO's: 144-156 and 253-256, and/or
   a light chain CDR2 encoding sequence which has at least 80% sequence identity to a sequence which is selected from the group consisting of SEQ ID NO's: 157-169 and 257-260, and/or
   a light chain CDR3 encoding sequence which has at least 80% sequence identity to a sequence which is selected from the group consisting of SEQ ID NO's: 170-182 and 261-264.

Said sequence identities are preferably at least 85%, more preferably at least 90%, most preferably at least 95% sequence, most preferably 100%. A nucleic acid molecule according to the invention preferably comprises heavy chain CDR 1-3-encoding sequences and light chain CDR 1-3-encoding sequences from the same antibody, wherein said antibody is selected from the group consisting of AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016, and heavy chain CDR 1-3-encoding sequences and light chain CDR 1-3-encoding sequences that have at least 80% sequence identity thereto.

Further provided is a nucleic acid molecule or functional equivalent or one or more vectors that comprise(s):
   a heavy chain CDR1 encoding nucleic acid sequence which has at least 80% sequence identity to SEQ ID NO: 105, and
   a heavy chain CDR2 encoding sequence which has at least 80% sequence identity to SEQ ID NO: 118, and
   a heavy chain CDR3 encoding sequence which has at least 80% sequence identity to SEQ ID NO: 131, and a light chain CDR1 encoding sequence which has at least 80% sequence identity to SEQ ID NO: 144, and
a light chain CDR2 encoding sequence which has at least 80% sequence identity to SEQ ID NO: 157, and
a light chain CDR3 encoding sequence which has at least 80% sequence identity to SEQ ID NO: 170. The recited SEQ ID NOs are the heavy and light chain CDR1-3 sequences of antibody AT12-023. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT12-023.

Further provided is a nucleic acid molecule or functional equivalent or one or more vectors that comprise(s):
a heavy chain CDR1 encoding nucleic acid sequence which has at least 80% sequence identity to SEQ ID NO: 106, and
a heavy chain CDR2 encoding sequence which has at least 80% sequence identity to SEQ ID NO: 119, and
a heavy chain CDR3 encoding sequence which has at least 80% sequence identity to SEQ ID NO: 132, and
a light chain CDR1 encoding sequence which has at least 80% sequence identity to SEQ ID NO: 145, and
a light chain CDR2 encoding sequence which has at least 80% sequence identity to SEQ ID NO: 158, and
a light chain CDR3 encoding sequence which has at least 80% sequence identity to SEQ ID NO: 171. The recited SEQ ID NOs are the heavy and light chain CDR1-3 sequences of antibody AT12-025. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT12-025.

Further provided is a nucleic acid molecule or functional equivalent or one or more vectors that comprise(s):
a heavy chain CDR1 encoding nucleic acid sequence which has at least 80% sequence identity to SEQ ID NO: 107, and
a heavy chain CDR2 encoding sequence which has at least 80% sequence identity to SEQ ID NO: 120, and
a heavy chain CDR3 encoding sequence which has at least 80% sequence identity to SEQ ID NO: 133, and
a light chain CDR1 encoding sequence which has at least 80% sequence identity to SEQ ID NO: 146, and
a light chain CDR2 encoding sequence which has at least 80% sequence identity to SEQ ID NO: 159, and
a light chain CDR3 encoding sequence which has at least 80% sequence identity to SEQ ID NO: 172. The recited SEQ ID NOs are the heavy and light chain CDR1-3 sequences of antibody AT13-024. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-024.

Further provided is a nucleic acid molecule or functional equivalent or one or more vectors that comprise(s):
a heavy chain CDR1 encoding nucleic acid sequence which has at least 80% sequence identity to SEQ ID NO: 108, and
a heavy chain CDR2 encoding sequence which has at least 80% sequence identity to SEQ ID NO: 121, and
a heavy chain CDR3 encoding sequence which has at least 80% sequence identity to SEQ ID NO: 134, and
a light chain CDR1 encoding sequence which has at least 80% sequence identity to SEQ ID NO: 147, and
a light chain CDR2 encoding sequence which has at least 80% sequence identity to SEQ ID NO: 160, and
a light chain CDR3 encoding sequence which has at least 80% sequence identity to SEQ ID NO: 173. The recited SEQ ID NOs are the heavy and light chain CDR1-3 sequences of antibody AT12-019. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT12-019.

Further provided is a nucleic acid molecule or functional equivalent or one or more vectors that comprise(s):
a heavy chain CDR1 encoding nucleic acid sequence which has at least 80% sequence identity to SEQ ID NO: 109, and
a heavy chain CDR2 encoding sequence which has at least 80% sequence identity to SEQ ID NO: 122, and
a heavy chain CDR3 encoding sequence which has at least 80% sequence identity to SEQ ID NO: 135, and
a light chain CDR1 encoding sequence which has at least 80% sequence identity to SEQ ID NO: 148, and
a light chain CDR2 encoding sequence which has at least 80% sequence identity to SEQ ID NO: 161, and
a light chain CDR3 encoding sequence which has at least 80% sequence identity to SEQ ID NO: 174. The recited SEQ ID NOs are the heavy and light chain CDR1-3 sequences of antibody AT13-022. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-022.

Further provided is a nucleic acid molecule or functional equivalent or one or more vectors that comprise(s):
a heavy chain CDR1 encoding nucleic acid sequence which has at least 80% sequence identity to SEQ ID NO: 110, and
a heavy chain CDR2 encoding sequence which has at least 80% sequence identity to SEQ ID NO: 123, and
a heavy chain CDR3 encoding sequence which has at least 80% sequence identity to SEQ ID NO: 136, and
a light chain CDR1 encoding sequence which has at least 80% sequence identity to SEQ ID NO: 149, and
a light chain CDR2 encoding sequence which has at least 80% sequence identity to SEQ ID NO: 162, and
a light chain CDR3 encoding sequence which has at least 80% sequence identity to SEQ ID NO: 175. The recited SEQ ID NOs are the heavy and light chain CDR1-3 sequences of antibody AT13-023. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-023.

Further provided is a nucleic acid molecule or functional equivalent or one or more vectors that comprise(s):
- a heavy chain CDR1 encoding nucleic acid sequence which has at least 80% sequence identity to SEQ ID NO: 111, and
- a heavy chain CDR2 encoding sequence which has at least 80% sequence identity to SEQ ID NO: 124, and
- a heavy chain CDR3 encoding sequence which has at least 80% sequence identity to SEQ ID NO: 137, and
- a light chain CDR1 encoding sequence which has at least 80% sequence identity to SEQ ID NO: 150, and
- a light chain CDR2 encoding sequence which has at least 80% sequence identity to SEQ ID NO: 163, and
- a light chain CDR3 encoding sequence which has at least 80% sequence identity to SEQ ID NO: 176. The recited SEQ ID NOs are the heavy and light chain CDR1-3 sequences of antibody AT13-031. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-031.

Further provided is a nucleic acid molecule or functional equivalent or one or more vectors that comprise(s):
- a heavy chain CDR1 encoding nucleic acid sequence which has at least 80% sequence identity to SEQ ID NO: 112, and
- a heavy chain CDR2 encoding sequence which has at least 80% sequence identity to SEQ ID NO: 125, and
- a heavy chain CDR3 encoding sequence which has at least 80% sequence identity to SEQ ID NO: 138, and
- a light chain CDR1 encoding sequence which has at least 80% sequence identity to SEQ ID NO: 151, and
- a light chain CDR2 encoding sequence which has at least 80% sequence identity to SEQ ID NO: 164, and
- a light chain CDR3 encoding sequence which has at least 80% sequence identity to SEQ ID NO: 177. The recited SEQ ID NOs are the heavy and light chain CDR1-3 sequences of antibody AT12-020. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT12-020.

Further provided is a nucleic acid molecule or functional equivalent or one or more vectors that comprise(s):
- a heavy chain CDR1 encoding nucleic acid sequence which has at least 80% sequence identity to SEQ ID NO: 113, and
- a heavy chain CDR2 encoding sequence which has at least 80% sequence identity to SEQ ID NO: 126, and
- a heavy chain CDR3 encoding sequence which has at least 80% sequence identity to SEQ ID NO: 139, and
- a light chain CDR1 encoding sequence which has at least 80% sequence identity to SEQ ID NO: 152, and
- a light chain CDR2 encoding sequence which has at least 80% sequence identity to SEQ ID NO: 165, and
- a light chain CDR3 encoding sequence which has at least 80% sequence identity to SEQ ID NO: 178. The recited SEQ ID NOs are the heavy and light chain CDR1-3 sequences of antibody AT13-033. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-033.

Further provided is a nucleic acid molecule or functional equivalent or one or more vectors that comprise(s):
- a heavy chain CDR1 encoding nucleic acid sequence which has at least 80% sequence identity to SEQ ID NO: 114, and
- a heavy chain CDR2 encoding sequence which has at least 80% sequence identity to SEQ ID NO: 127, and
- a heavy chain CDR3 encoding sequence which has at least 80% sequence identity to SEQ ID NO: 140, and
- a light chain CDR1 encoding sequence which has at least 80% sequence identity to SEQ ID NO: 153, and
- a light chain CDR2 encoding sequence which has at least 80% sequence identity to SEQ ID NO: 166, and
- a light chain CDR3 encoding sequence which has at least 80% sequence identity to SEQ ID NO: 179. The recited SEQ ID NOs are the heavy and light chain CDR1-3 sequences of antibody AT13-034. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-034.

Further provided is a nucleic acid molecule or functional equivalent or one or more vectors that comprise(s):
- a heavy chain CDR1 encoding nucleic acid sequence which has at least 80% sequence identity to SEQ ID NO: 115, and
- a heavy chain CDR2 encoding sequence which has at least 80% sequence identity to SEQ ID NO: 128, and
- a heavy chain CDR3 encoding sequence which has at least 80% sequence identity to SEQ ID NO: 141, and
- a light chain CDR1 encoding sequence which has at least 80% sequence identity to SEQ ID NO: 154, and
- a light chain CDR2 encoding sequence which has at least 80% sequence identity to SEQ ID NO: 167, and
- a light chain CDR3 encoding sequence which has at least 80% sequence identity to SEQ ID NO: 180. The recited SEQ ID NOs are the heavy and light chain CDR1-3 sequences of antibody AT13-035. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-035.

Further provided is a nucleic acid molecule or functional equivalent or one or more vectors that comprise(s):
- a heavy chain CDR1 encoding nucleic acid sequence which has at least 80% sequence identity to SEQ ID NO: 116, and
- a heavy chain CDR2 encoding sequence which has at least 80% sequence identity to SEQ ID NO: 129, and
- a heavy chain CDR3 encoding sequence which has at least 80% sequence identity to SEQ ID NO: 142, and
- a light chain CDR1 encoding sequence which has at least 80% sequence identity to SEQ ID NO: 155, and a light chain CDR2 encoding sequence which has at least 80% sequence identity to SEQ ID NO: 168, and a light chain CDR3 encoding sequence which has at least 80% sequence identity to SEQ ID NO: 181. The recited SEQ ID NOs are the heavy and light chain CDR1-3 sequences of antibody AT13-036. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-036.

Further provided is a nucleic acid molecule or functional equivalent or one or more vectors that comprise(s):

a heavy chain CDR1 encoding nucleic acid sequence which has at least 80% sequence identity to SEQ ID NO: 117, and a heavy chain CDR2 encoding sequence which has at least 80% sequence identity to SEQ ID NO: 130, and a heavy chain CDR3 encoding sequence which has at least 80% sequence identity to SEQ ID NO: 143, and a light chain CDR1 encoding sequence which has at least 80% sequence identity to SEQ ID NO: 156, and a light chain CDR2 encoding sequence which has at least 80% sequence identity to SEQ ID NO: 169, and a light chain CDR3 encoding sequence which has at least 80% sequence identity to SEQ ID NO: 182. The recited SEQ ID NOs are the heavy and light chain CDR1-3 sequences of antibody AT13-037. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT13-037.

Further provided is a nucleic acid molecule or functional equivalent or one or more vectors that comprise(s):

a heavy chain CDR1 encoding nucleic acid sequence which has at least 80% sequence identity to SEQ ID NO: 241, and a heavy chain CDR2 encoding sequence which has at least 80% sequence identity to SEQ ID NO: 245, and a heavy chain CDR3 encoding sequence which has at least 80% sequence identity to SEQ ID NO: 249, and a light chain CDR1 encoding sequence which has at least 80% sequence identity to SEQ ID NO: 253, and a light chain CDR2 encoding sequence which has at least 80% sequence identity to SEQ ID NO: 257, and a light chain CDR3 encoding sequence which has at least 80% sequence identity to SEQ ID NO: 261. The recited SEQ ID NOs are the heavy and light chain CDR1-3 sequences of antibody AT14-013. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT14-013.

Further provided is a nucleic acid molecule or functional equivalent or one or more vectors that comprise(s):

a heavy chain CDR1 encoding nucleic acid sequence which has at least 80% sequence identity to SEQ ID NO: 242, and a heavy chain CDR2 encoding sequence which has at least 80% sequence identity to SEQ ID NO: 246, and a heavy chain CDR3 encoding sequence which has at least 80% sequence identity to SEQ ID NO: 250, and a light chain CDR1 encoding sequence which has at least 80% sequence identity to SEQ ID NO: 254, and a light chain CDR2 encoding sequence which has at least 80% sequence identity to SEQ ID NO: 258, and a light chain CDR3 encoding sequence which has at least 80% sequence identity to SEQ ID NO: 262. The recited SEQ ID NOs are the heavy and light chain CDR1-3 sequences of antibody AT14-014. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT14-014.

Further provided is a nucleic acid molecule or functional equivalent or one or more vectors that comprise(s):

a heavy chain CDR1 encoding nucleic acid sequence which has at least 80% sequence identity to SEQ ID NO: 243, and a heavy chain CDR2 encoding sequence which has at least 80% sequence identity to SEQ ID NO: 247, and a heavy chain CDR3 encoding sequence which has at least 80% sequence identity to SEQ ID NO: 251, and a light chain CDR1 encoding sequence which has at least 80% sequence identity to SEQ ID NO: 255, and a light chain CDR2 encoding sequence which has at least 80% sequence identity to SEQ ID NO: 259, and a light chain CDR3 encoding sequence which has at least 80% sequence identity to SEQ ID NO: 263. The recited SEQ ID NOs are the heavy and light chain CDR1-3 sequences of antibody AT14-015. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT14-015.

Further provided is a nucleic acid molecule or functional equivalent or one or more vectors that comprise(s):

a heavy chain CDR1 encoding nucleic acid sequence which has at least 80% sequence identity to SEQ ID NO: 244, and a heavy chain CDR2 encoding sequence which has at least 80% sequence identity to SEQ ID NO: 248, and a heavy chain CDR3 encoding sequence which has at least 80% sequence identity to SEQ ID NO: 252, and a light chain CDR1 encoding sequence which has at least 80% sequence identity to SEQ ID NO: 256, and a light chain CDR2 encoding sequence which has at least 80% sequence identity to SEQ ID NO: 260, and a light chain CDR3 encoding sequence which has at least 80% sequence identity to SEQ ID NO: 264. The recited SEQ ID NOs are the heavy and light chain CDR1-3 sequences of antibody AT14-016. Again, said sequence identities are preferably at least 80%, more preferably at least 85%, more preferably at least 90%, most preferably at least 95%, most preferably 100%. Preferably, the resulting CDR sequences differ in no more than three, preferably in no more than two, preferably in only one amino acid from the original CDR sequences of antibody AT14-016.

A preferred nucleic acid molecule or vector(s) according to the invention encode(s) at least the variable heavy chain sequence and/or the variable light chain sequence of an antibody or functional part or functional equivalent according to the invention. Preferably, said nucleic acid molecule(s) or vector(s) encode(s) at least the variable heavy chain sequence and the variable light chain sequence of an antibody or functional part or functional equivalent according to the invention. In one embodiment, a nucleic acid molecule or functional equivalent or one or more vectors according to the invention are provided which comprise(s) a sequence which has at least 80% sequence identity with a sequence selected from the group consisting of SEQ ID NOs 183-195 and 265-268 and/or a sequence which has at least 80% sequence identity with a sequence selected from the group consisting of SEQ ID NOs 196-208 and 269-272. Said sequence identities are preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably 100%.

More preferably, a nucleic acid molecule or a functional equivalent or one or more vectors according to the invention comprise(s) a variable heavy chain encoding sequence as well as a variable light chain encoding sequence which resemble the variable heavy and light chain encoding sequences of the same antibody depicted in Table 1. Thus, in a preferred embodiment a nucleic acid molecule or functional equivalent or vector(s) according to the invention comprise(s) the variable heavy chain encoding sequence of antibody AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 or AT14-016, and the variable light chain encoding sequence of the same antibody, or sequences that are at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In some embodiments, nucleic acid molecules and functional equivalents thereof and vectors are provided that encode an antibody or functional part or functional equivalent according to the invention. Further provided is therefore a nucleic acid molecule, or functional equivalent thereof, or one or more vectors, that encode(s) antibody AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 or AT14-016, or functional part or functional equivalent thereof. In some embodiments, said nucleic acid molecule or functional equivalent or vector(s) is/are codon optimized for a non-human recombinant expression system.

Further provided is a vector comprising a nucleic acid molecule or functional equivalent according to the invention. As used herein "a vector comprising a nucleic acid molecule or functional equivalent according to the invention" is also referred to as "a vector according to the invention". These terms encompass one or more vector(s) according to the invention, comprising one or more nucleic acid molecule(s) or functional equivalent(s) according to the invention. As used herein, the singular term "a" encompasses the term "one or more".

Methods for constructing vectors comprising one or more nucleic acid molecule(s) or functional equivalent(s) according to the invention are well known in the art. Non-limiting examples of vectors suitable for generating a vector of the invention are retroviral and lentiviral vectors. Such vectors are suitable for a variety of applications. For instance, one or more vectors of the invention comprising a therapeutically beneficial nucleic acid sequence according to the invention is/are suitable for prophylactic or therapeutic applications against AML. Administration of such vector(s) to an individual, preferably a human, in need thereof results in expression of said prophylactic or therapeutic nucleic acid sequence in vivo resulting in at least partial treatment or prophylaxis against AML. Said vector(s) can also be used in applications involving in vitro expression of a nucleic acid molecule of interest, for instance for (commercial) production of antibodies or functional equivalents according to the invention. Also provided is therefore an isolated or recombinant cell, or a non-human animal, comprising at least one nucleic acid molecule or functional equivalent, or at least one vector, according to the invention.

A nucleic acid molecule or a vector according to the invention is particularly useful for generating antibodies or functional parts or functional equivalents according to the invention, which are specific for AML. This is for instance done by introducing such nucleic acid molecule or vector(s) into a cell so that the cell's nucleic acid translation machinery will produce the encoded antibodies or functional parts or functional equivalents. In one embodiment, a nucleic acid molecule or vector encoding a heavy and/or light chain according to the invention is expressed in so called producer cells, such as for instance *E. coli*, CHO, NSO or 293(T) cells, some of which are adapted to commercial antibody production. Of note, any recombinant antibody production system is suitable; these four producer cell systems mentioned are only a few examples of the many systems that are available to date. As described herein before, in such cases it is preferred to use nucleic acid molecules wherein the original human sequences as provided herein are codon optimized for the producer cell. Proliferation of said producer cells results in a producer cell line capable of producing binding compounds according to the invention. Preferably, said producer cell line is suitable for producing antibodies for use in humans. Hence, said producer cell line is preferably free of pathogenic agents such as pathogenic micro-organisms. Most preferably, antibodies consisting of human sequences are generated using at least one nucleic acid molecule or vector according to the invention.

An isolated or recombinant antibody producing cell capable of producing a binding compound according to the invention is therefore also provided. Such cell typically comprises at least one nucleic acid molecule or vector according to the invention, which preferably contains a nucleic acid sequence that is codon optimized for said cell. An antibody producing cell is defined herein as a cell which is capable of producing and/or secreting antibodies or functional parts or functional equivalents thereof, and/or which is capable of developing into a cell which is capable of producing and/or secreting antibodies or functional parts or functional equivalents thereof. An antibody producing cell according to the invention is preferably a producer cell which is adapted to commercial antibody production. As explained above, said producer cell is preferably suitable for producing antibodies for use in humans. A method for producing an antibody or functional part or functional equivalent according to the invention is therefore also provided, said method comprising providing a cell, preferably an antibody producing cell, with a nucleic acid molecule or functional equivalent or a vector according to the invention, and allowing said cell to translate said nucleic acid molecule or functional equivalent or vector, thereby producing said antibody or functional part or functional equivalent according to the invention. A method according to the invention preferably further comprises a step of harvesting, purifying and/or isolating said antibody or functional part or functional equivalent according to the invention. Obtained binding compounds according to the invention are preferably used in human therapy, optionally after additional purifying, isolation or processing steps.

Another aspect of the invention provides an antibody or functional part or functional equivalent according to the invention, which is coupled to another compound. In one embodiment, a binding compound according to the invention is coupled to another therapeutic moiety, such as a chemotherapeutic drug or other toxic compound or radioactive compound, to form a so called "antibody-drug conjugate". In another embodiment, a moiety that is coupled to a binding compound according to the invention is an immunomodulatory molecule such as for instance a CD3-specific antibody. Such CD3-specific antibody is capable of binding T cells and, if coupled to a binding compound according to the invention, it will target T cells to AML cells, thereby enhancing an anti-leukemic T-cell response. This provides an even stronger anti-AML effect. One preferred embodiment of the invention therefore provides a bispecific or multispecific binding compound, comprising an AML-specific binding compound according to the present invention and an immunomodulatory molecule, preferably a CD3-specific binding compound. Another preferred embodiment provides an anti-AML compound, said compound comprising a binding compound according to the present invention, which is specific for AML cells, and a toxic moiety. In some other embodiments, a binding compound according to the present invention is coupled to a label. This allows detection of myeloproliferative cells, such as AML cells, using such labeled binding compound. Other embodiments provide a binding compound according to the invention that is coupled to another AML-binding compound. In some embodiments, such other AML-binding compound is also a binding compound according to the present invention. Provided is therefore a compound comprising two binding compounds according to the invention that are coupled to each other. This is, however, not necessary since a binding compound according to the invention can also be coupled to other AML-binding compounds, such as currently known antibodies that bind AML cells. Bispecific compounds according to the invention allow, for instance, for increased binding of AML cells, especially when the two coupled binding compounds are specific for different epitopes on AML cells. Such bispecific compound is thus very suitable for therapeutic or diagnostic applications. It is also possible to use bispecific compounds according to the invention in assays wherein different AML cells are bound to the same bispecific binding compound.

In one embodiment, a synthetic or recombinant antibody is provided, or a functional part or a functional equivalent thereof, which comprises one Fab fragment of an antibody according to the present invention, and one Fab fragment of another antibody according to the invention. The resulting binding compound is specific for AML cells, but each Fab arm will typically bind its own epitope. In some embodiments, the epitopes recognized by the Fab fragments are different from each other. In another embodiment, the epitopes are the same. The Fab arms may bind the epitopes with different affinity. Alternatively, the Fab arms bind their epitopes with essentially the same affinity, meaning that the $K_D$ of the Fab arms differ no more than 30%, preferably no more than 20% or no more than 10% from each other.

Said other moiety, for example a chemotherapeutic agent or a CD3-specific antibody, is preferably coupled to a binding compound according to the invention via a linker such as for instance an acid-labile hydrazone linker, or via a peptide linker like citruline-valine, or through a thioether linkage, or by sortase catalized transamidation, which is described in detail in WO 2010/087994.

Sortase catalized transamidation involves engineering of a sortase recognition site (LPETGG) on the heavy chain of an antibody, preferably on the C-terminal part of the heavy chain, and on the moiety to be coupled to said antibody. The antibody and the moiety further typically contain a GGGGS sequence and a tag for purification purposes, such as a HIS tag. Subsequently sortase mediated transamidation is performed followed by click chemistry linkage. In a sortase catalized transaminidation, "click chemistry linkage" typically involves chemical coupling of, for instance, an alkyne-containing reagent and, for instance, an azide-containing reagent which are added by sortase through addition of glycines to the sortase motif on the heavy chain of the antibody and to a sortase motif on the moiety (such as a protein, peptide or antibody) to be coupled to the antibody. In one embodiment, the invention therefore provides an antibody according to the invention wherein a sortase recognition site (LPETGG) is engineered on the heavy chain of the antibody, preferably on the C-terminal part of the heavy chain, the antibody preferably further containing a GGGGS sequence and a purification tag, such as a HIS tag.

In another embodiment a binding compound according to the invention is coupled to another moiety via a thioether linkage. In such case, one or more cysteines are preferably incorporated into a binding compound according to the invention. Cysteines contain a thiol group and, therefore, incorporation of one or more cysteines into a binding compound according to the invention, or replacement of one or more amino acids by one or more cysteines of a binding compound according to the invention, enable coupling of said binding compound to another moiety. Said one or more cysteines are preferably introduced into a binding compound according to the invention at a position where it does not significantly influence folding of said binding compound, and does not significantly alter antigen binding or effector function. The invention therefore also provides a binding compound according to the invention wherein at least one amino acid other than cysteine has been replaced by a cysteine.

In one embodiment, an AML-specific binding compound according to the present invention is coupled to at least one other AML-specific binding compound according to the present invention. Such bispecific or multispecific binding compound provides a stronger anti-AML effect.

Binding compounds according to the present invention are suitable for use against myeloproliferative disorders such as AML, or acute leukemia's that developed from myelodysplastic syndrome, chronic myeloid leukemia, myelofibrosis or other, non-malignant myeloproliferative syndromes. As some of the antibodies also bind to non-myeloid, lymphoproliferative malignancies such as multiple myeloma and B-non Hodgkin lymphoma (B-NHL), they are suitable for use against these disorders as well. Binding compounds according to the present invention are therefore particularly suitable for use as a medicine or prophylactic agent. Preferably, binding compounds according to the invention are used which consist of human sequences, in order to reduce the chance of adverse side effects when human individuals are treated. Such human sequences can be isolated from a human or synthetically or recombinantly produced based on the sequence of human antibodies, optionally using codon optimized nucleic acid sequences that encode the same amino acids as the original human nucleic acid sequence. Provided is therefore an antibody or functional part or functional equivalent according to the invention for use as a medicament and/or prophylactic agent. Said antibody preferably comprises an antibody selected from the group consisting of AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016. Also provided is a nucleic acid molecule or functional equivalent thereof according to the invention or a vector according to the invention comprising such nucleic acid or functional equivalent, or a cell according to the invention, for use as a medicament and/or prophylactic agent. When (a vector comprising) one or more nucleic acid molecule(s) or functional equivalent(s) according to the invention is/are administered, the nucleic acid molecule(s) or functional equivalent(s) will be translated in situ by the host's machinery into a binding compound according to the invention. Produced binding compounds according to the invention are capable of preventing and/or counteracting myeloproliferative disorders such as AML and lymphoproliferative disorders such as for instance lymphoma, B-NHL and multiple myeloma. Further provided is therefore an antibody or functional part or functional equivalent according to the invention, or a nucleic acid molecule or functional equivalent according to the invention, or a vector or a cell according to the invention, for use in a method for at least in part treating or preventing a myeloproliferative or lymphoproliferative disorder. As described herein before, such disorder can be treated or prevented by using cytotoxic binding compounds according to the invention. As demonstrated in the Examples, at least antibodies AT13-033, AT13-035, AT13-036, AT13-037, AT12-023, AT12-025 and AT13-031 have cytotoxic activity. Further provided is therefore an antibody selected from the group consisting of antibodies AT13-033, AT13-035, AT13-036, AT13-037, AT12-023, AT12-025 and AT13-031, and functional parts and functional equivalents thereof, or a nucleic acid molecule or functional equivalent or one or more vectors encoding therefore, for use in a method for at least in part treating or preventing a myeloproliferative or lymphoproliferative disorder. Preferably, said disorder is AML.

In some embodiments, a binding compound according to the invention is coupled to a therapeutic moiety, such as a chemotherapeutic drug or other toxic compound or a radioactive compound or an immunomodulatory molecule such as for instance a CD3-specific antibody, to form a so called "antibody-drug conjugate" or a "chimeric antigen receptor (CAR) T cell", respectively, which is able to counteract a myeloproliferative or lymphoproliferative disorder.

In some embodiments, said lymphoproliferative disorder is treated with one or more antibodies selected from the group consisting of antibodies AT12-019, AT12-023, AT12-025, AT13-024 and AT13-031, and functional parts and functional equivalents thereof. Further provided is therefore an antibody selected from the group consisting of antibodies AT12-019, AT12-023, AT12-025, AT13-024 and AT13-031, and functional parts and functional equivalents thereof, or a nucleic acid molecule or functional equivalent or one or more vectors encoding therefore, for use in a method for at least in part treating or preventing a lymphoproliferative disorder. Preferably, said lymphoproliferative disorder is lymphoma, B-NHL or multiple myeloma.

A binding compound according to the invention, or a nucleic acid molecule or functional equivalent thereof according to the invention, or at least one vector or cell according to the invention, is preferably used for at least in part treating and/or preventing AML. As used herein the term "at least in part treating and/or preventing AML" includes counteracting AML tumor growth and/or alleviating symptoms resulting from the presence of AML cells in a patient. Also provided is therefore a use of an antibody or functional part or functional equivalent according to the invention, or of a nucleic acid molecule or functional equivalent according to the invention, or of at least one vector or cell according to the invention, for the preparation of a medicament and/or prophylactic agent for at least in part treating and/or preventing AML. Further provided is an antibody or functional part or functional equivalent according to the invention, or a nucleic acid molecule or functional equivalent according to the invention, or at least one vector or cell according to the invention, for use in a method for at least in part treating and/or preventing AML.

Preferred antibodies for use in any of the recited methods are antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016.

The invention further provides a composition comprising an antibody or functional part or functional equivalent according to the invention. A composition comprising a nucleic acid molecule or functional equivalent according to the invention is also provided, as well as a composition comprising a vector or a cell according to the invention. In some embodiments a composition according to the invention comprises at least two antibodies, functional parts or functional equivalents according to the invention.

A composition according to the present invention preferably comprises a pharmaceutical composition. Said pharmaceutical composition preferably also comprises a pharmaceutical acceptable carrier, diluent and/or excipient. Non-limiting examples of suitable carriers for instance comprise keyhole limpet haemocyanin (KLH), serum albumin (e.g. BSA or RSA) and ovalbumin. In one preferred embodiment said suitable carrier comprises a solution, like for example saline. A pharmaceutical composition according to the invention is preferably suitable for human use.

The invention further provides a method for at least in part treating and/or preventing a myeloproliferative or lymphoproliferative disorder, comprising administering to an individual in need thereof a therapeutically effective amount of an antibody or functional part or functional equivalent according to the invention, and/or a nucleic acid molecule or functional equivalent thereof according to the invention, and/or a vector or cell according to the invention, and/or a composition according to the invention. As used herein, an "individual" or "subject" is a human or an animal, preferably a human AML patient. Said composition is preferably a pharmaceutical composition according to the invention.

A binding compound and/or composition according to the present invention is particularly suitable for administering to immune compromised individuals with an increased risk of complications, such as individuals that have undergone chemotherapy, particularly infants and elderly people. A binding compound, or a nucleic acid molecule or functional equivalent thereof, or a vector, and/or a pharmaceutical composition according to the invention is preferably administered via one or more injections. Typical doses of administration of a binding compound according to the invention are between 0.1 and 10 mg per kg body weight.

A binding compound according to the invention is also particularly suitable for diagnostic use. For instance, if an individual, preferably a human, is suspected of suffering from a myeloproliferative disorder such as AML or a lymphoproliferative disorder such as B-NHL or multiple myeloma, a sample, such as a blood or tissue sample, from said individual can be tested for the presence of myeloproliferative cells or lymphoproliferative cells, using a binding compound according to the invention. Preferably, said sample is mixed with a binding compound according to the invention, which will specifically bind to myeloproliferative cells. Myeloproliferative cells or lymphoproliferative cells bound to a binding compound according to the invention can be isolated from the sample and/or detected using any method known in the art, for example, but not limited to, isolation using magnetic beads, streptavidin-coated beads, or isolation through the use of secondary antibodies immobilized on a column. Alternatively, or additionally, a binding compound according to the invention is labeled in order to be able to detect said antibody, for instance, but not limited to, fluorescently labeled, enzymatically labeled, or radioactively labeled. Alternatively, a binding compound according to the invention is detected using a labeled secondary antibody which is directed against said binding compound. If binding of said antibody is detected, it is indicative for the presence of myeloproliferative or lymphoproliferative cells. The invention therefore provides an antibody or functional part or functional equivalent according to the invention, or a nucleic acid molecule or functional equivalent according to the invention, or a vector or a cell according to the invention, for use in detecting myeloproliferative cells or lymphoproliferative cells. Also provided is an antibody or functional part or functional equivalent according to the invention, or a nucleic acid molecule or functional equivalent according to the invention, or a vector or a cell according to the invention, for use in diagnosis of a myeloproliferative disorder or lymphoproliferative disorder. Said myeloproliferative disorder is preferably AML. In some embodiments, said lymphoproliferative disorder is lymphoma, B-NHL or multiple myeloma. Lymphoproliferative cells are preferably detected with one or more antibodies selected from the group consisting of AT12-019, AT12-023, AT12-025, AT13-024 and AT13-031, and functional parts and functional equivalents thereof.

A use of an antibody or functional part or functional equivalent according to the invention, or use of a nucleic acid molecule or functional equivalent according to the invention, or use of a vector or a cell according to the invention, for determining whether a sample comprises myeloproliferative cells or lymphoproliferative cells is also provided, as well as a method for detecting myeloproliferative cells or lymphoproliferative cells using an antibody or functional part or functional equivalent according to the invention. The invention further provides a method for determining whether myeloproliferative cells or lymphoproliferative cells are present in a sample comprising:
contacting said sample with an antibody or functional part or functional equivalent according to the invention, and
allowing said antibody or functional part or functional equivalent to bind myeloproliferative cells or lymphoproliferative cells, if present, and
determining whether or not myeloproliferative cells or lymphoproliferative cells are bound to said antibody or functional part or functional equivalent, thereby determining whether or not myeloproliferative cells or lymphoproliferative cells are present in said sample.

In a preferred embodiment, said myeloproliferative cells are AML cells. In another preferred embodiment, said lymphoproliferative cells are lymphoma, B-NHL or multiple myeloma cells. Lymphoproliferative cells are preferably detected with one or more antibodies selected from the group consisting of AT12-019, AT12-023, AT12-025, AT13-024 and AT13-031, and functional parts and functional equivalents thereof.

In a further embodiment it is determined whether an individual is suffering from a myeloproliferative or lymphoproliferative disorder. Also provided is therefore a method for determining whether an individual is suffering from a myeloproliferative disorder or a lymphoproliferative disorder, comprising:
contacting a sample from said individual with an antibody or functional part or functional equivalent according to the invention, and
allowing said antibody or functional part or functional equivalent to bind myeloproliferative cells or lymphoproliferative cells, if present, and
determining whether or not myeloproliferative cells or lymphoproliferative cells are bound to said antibody or functional part or functional equivalent, thereby determining whether or nor said individual is suffering from a myeloproliferative disorder or a lymphoproliferative disorder. Preferably said individual is a human. In some embodiments, said myeloproliferative disorder is AML. In other embodiments, said lymphoproliferative disorder is lymphoma, B-NHL or multiple myeloma.

As described herein before, the present invention provides the surprising insight that snRNP200 is present on the surface of AML cells, whereas snRNP200 is normally located in the nucleus only. Hence, snRNP200 is an important target for anti-AML therapy. Moreover, antibodies AT12-023 and AT13-031, which are specific for snRNP200, also bind B-NHL cells and multiple myeloma cells. This indicates that surface expression of snRNP200 also occurs on B-NHL cells and multiple myeloma cells. Now that this insight has been provided, many applications have become possible. For instance, snRNP200-specific binding compounds can now be used for treating or preventing myeloproliferative or lymphoproliferative disorders. Further provided is therefore a use of an snRNP200-specific binding compound for the preparation of a medicament for the treatment or prophylaxis of a myeloproliferative or lymphoproliferative disorder, such as AML, B-NHL or multiple myeloma. An snRNP200-specific binding compound for use in a method for at least in part treating or preventing a myeloproliferative or lymphoproliferative disorder is also provided, as well as a method for at least in part treating and/or preventing a myeloproliferative or lymphoproliferative disorder, comprising administering to an individual in need thereof a therapeutically effective amount of an snRNP200-specific binding compound.

Novel detection methods have also become available. Since snRNP200 is normally only present in the nucleus, but appears to be also present at the surface of myeloproliferative and lymphoproliferative cells, these cells can now be detected and distinguished from healthy cells by determining whether snRNP200 is present at their surface. Further provided is therefore a method for determining whether a myeloid cell or lymphoid cell is a myeloproliferative cell or lymphoproliferative cell, the method comprising determining whether snRNP200 is present on the surface of said cell, wherein the presence of snRNP200 on the surface of said cell indicates that said cell is myeloproliferative or lymphoproliferative. Also provided is a method for identifying myeloproliferative or lymphoproliferative cells, comprising detecting the presence of snRNP200 on the surface of said cells. As used herein, the expression "present at the surface of a cell" or "present on the surface of a cell" means that at least part of snRNP200 is present on, or within, the cell surface, or associated therewith.

In some embodiments, a cell-containing sample of an individual is typed. Such sample, which typically contains lymphoid cells and/or myeloid cells, is in some embodiments tested for the presence of snRNP200 on the surface of these cells. If snRNP200 appears to be present on the surface of cells, the sample is typed as containing myeloproliferative or lymphoproliferative cells. Further provided is therefore a method for typing a myeloid cell-containing sample or a lymphoid cell-containing sample of an individual, the method comprising determining whether snRNP200 is present on the surface of cells of said sample. If this is the case, it indicates that myeloproliferative cells or lymphoproliferative cells are present in said sample.

In some embodiments, the individual is suffering from, or suspected of suffering from, a myeloproliferative or lymphoproliferative disorder. This is however not necessary, since such typing method can also be part of a general screening test, for instance for health checks.

Said sample can be any sample that contains myeloid and/or lymphoid cells, such as for instance a bone marrow sample, a tissue sample or a lymph fluid sample. Preferably, said sample comprises peripheral blood mononuclear cells, since a blood sample is easily obtainable with little discomfort for the individual.

The present invention provides the insight that at least a subpopulation of patients who suffer from a myeloproliferative or lymphoproliferative disorder produce antibodies that are specific for snRNP200. The presence of such antibodies in a sample from an individual is thus indicative for a myeloproliferative or lymphoproliferative disorder. Further provided is therefore a method for determining whether an individual is suffering from a myeloproliferative or lymphoproliferative disorder, comprising determining whether a sample from said individual comprises antibodies that are specific for snRNP200. In some embodiments such method comprises the steps of:
  contacting a sample from said individual with snRNP200 or an epitope thereof;
  allowing said snRNP200 or epitope to bind snRNP200-specific antibodies from said sample, if present, and
  determining whether or not said snRNP200 or epitope is bound to snRNP200-specific antibodies, wherein binding of said snRNP200 or epitope to snRNP200-specific antibodies indicates that said individual is suffering from a myeloproliferative or lymphoproliferative disorder.

Screening assays as provided herein can be performed using methods such as for instance enzyme-linked immunosorbent assays (ELISA), radio-immuno assays (RIA), Western Blot assays and immunohistochemical staining assays. These assays are well known in the art and therefore need no further explanation. Variations or adaptations of ELISA, RIA, Western blot assay and immunohistochemical staining assay are also known in the art.

Another aspect of the invention provides a method for determining whether a patient suffering from a myeloproliferative or lymphoproliferative disorder has an improved chance of a positive outcome of treatment with an antibody, functional part or functional equivalent according to the invention, as compared to the mean population of patients suffering from a myeloproliferative or lymphoproliferative disorder, the method comprising determining whether snRNP200 is present on the surface of myeloproliferative cells or lymphoproliferative cells of said patient. If this is the case, snRNP200-specific antibodies such as AT12-023, AT13-031 and AT13-037 are particularly suitable for counteracting such myeloproliferative or lymphoproliferative disorder. Therefore, if it is known that myeloproliferative or lymphoproliferative cells of an individual express snRNP200 at their surface, the chance of successful treatment is increased. Such method according to the invention preferably comprises the steps of:
  contacting a myeloproliferative cell- or lymphoproliferative cell-containing sample from said individual with an antibody or functional part or functional equivalent that is specific for snRNP200;
  allowing said antibody or functional part or functional equivalent to bind myeloproliferative cells or lymphoproliferative cells of said sample, and
  determining whether or not said a snRNP200-specific antibody or functional part or functional equivalent is bound to myeloproliferative cells or lymphoproliferative cells of said sample, wherein binding of said snRNP200-specific antibody or functional part or functional equivalent to myeloproliferative cells or lymphoproliferative cells of said sample indicates that said patient has an improved chance of a positive outcome of treatment with an antibody, functional part or functional equivalent according to the invention, as compared to the mean population of patients suffering from a myeloproliferative or lymphoproliferative disorder. Said treatment preferably comprises the use of antibodies AT12-023, AT13-031 or AT13-037, or functional parts or functional equivalents thereof, since at least these antibodies are able to bind snRNP200. Further provided is therefore an antibody according to the invention, or an antibody for use according to the invention, or a use or a method according to the invention, wherein said antibody is AT12-023, AT13-031, AT13-037, or a functional part or a functional equivalent thereof.

If the use of antibody AT12-023, AT13-031 and/or AT13-037 is contemplated, it is preferably determined beforehand if a certain patient contains malignant cells that express snRNP200 at their surface. Some embodiments therefore provide a method for determining whether a patient suffering from a myeloproliferative disorder or lymphoproliferative disorder is a candidate for treatment with antibody AT12-023, AT13-031 or AT13-037, or a functional part or a functional equivalent thereof, the method comprising determining whether snRNP200 is present on the surface of myeloproliferative cells or lymphoproliferative cells of said patient.

In a method according to the invention, said myeloproliferative disorder is preferably AML and said myeloproliferative cells are preferably AML cells. Moreover, said lymphoproliferative disorder is preferably lymphoma, B-non-Hodgkin lymphoma or multiple myeloma and said lymphoproliferative cells are preferably lymphoma, B-non-Hodgkin lymphoma or multiple myeloma cells.

The above-mentioned procedures for detecting myeloproliferative or lymphoproliferative cells using binding compounds according to the present invention are for instance particularly suitable for determining whether a patient suffering from a myeloproliferative disorder or lymphoproliferative disorder who has received medical treatment, such as for instance an AML patient who has been treated against AML, for instance an AML patient who has received immunotherapy such as a stem cell transplantation or donor-lymphocyte infusion, has a GvL response. Until to date, there are no diagnostic tools to test for the presence of a potent GvL response in a treated patient. Such diagnostic tool is much needed, for instance because: 1) It will allow early identification of allogeneic SCT recipients at high risk for relapse, at a time-point before relapse has occurred thereby allowing earlier interventions such as tapering of immunosuppressants or donor-lymphocyte infusions; 2) It will allow titrating such donor lymphocyte infusions until anti-leukemia antibodies do appear; and 3) It will offer hope for allogeneic SCT recipients at a time they often suffer from one of many SCT-related complications when the presence of a potent GvL response can be demonstrated. Nowadays patients have to wait and see whether or not a relapse occurs, and there is no way to predict relapse of disease. The availability of a test for determining whether a patient has a GvL response will therefore greatly improve the clinical care of SCT patients, affecting prognosis and quality of life. Further provided is, therefore, a use of a binding compound according to the invention for determining whether a sample is indicative for a GvL response. Also provided is a use of a binding compound according to the invention for determining whether or not an AML patient has a GvL response, and a use of a binding compound according to the invention for determining whether a treatment against a myeloproliferative or lymphoproliferative disease, such as for instance anti-AML therapy, anti-B-NHL therapy or anti-multiple myeloma therapy, is efficaceous. This is for instance done by determining whether a sample (for instance a blood or tissue sample) from a patient (that has for instance received a SCT or DLI or any other form of immunotherapy) contains myeloproliferative or lymphoproliferative cells, for instance AML cells, B-NHL cells or multiple myeloma cells. The absence of myeloproliferative or lymphoproliferative cells indicates that said patient has a GvL response. Further provided is, therefore, a method for determining whether a patient suffering from a myeloproliferative disorder or a lymphoproliferative disorder who has received immunotherapy against said disorder has a GvL response, the method comprising contacting a sample from said patient with an antibody or functional part or functional equivalent according to the invention, and allowing said antibody or functional part or functional equivalent to bind myeloproliferative or lymphoproliferative cells, if present, and determining whether or not myeloproliferative cells or lymphoproliferative cells are bound to said antibody or functional part or functional equivalent, thereby determining whether or not said individual has a GvL response, whereby the absence of myeloproliferative or lymphoproliferative cells is indicative for a GvL response and the presence of myeloproliferative or lymphoproliferative cells is indicative for a lack of, or insufficient (ineffective), GvL response. In some embodiments, said lymphoproliferative disorder is lymphoma, B-NHL, or multiple myeloma. In some embodiments, said myeloproliferative disorder is AML. Also provided is, therefore, a method for determining whether an AML patient that has received anti-AML immunotherapy has a GvL response, the method comprising contacting a sample from said AML patient with an antibody or functional part or functional equivalent according to the invention, and allowing said antibody or functional part or functional equivalent to bind AML cells, if present, and determining whether or not AML cells are bound to said antibody or functional part or functional equivalent, thereby determining whether or nor said individual has a GvL response, whereby the absence of AML cells is indicative for a GvL response and the presence of AML response is indicative for a lack of, or insufficient (ineffective), GvL response. Preferably said individual is a human. Alternatively, binding compounds according to the present invention that are labeled with a detectable moiety, such as for instance with a copper compound, are administered to an AML patient that has received anti-AML immunotherapy such as a SCT or DLI, and it is subsequently determined whether said labeled antibody is bound to AML cells of said patient in vivo, for instance using a PET scan. The absence of bound binding compounds is indicative for a GvL response and the presence of bound binding compounds is indicative for a lack of, or insufficient (ineffective), GvL response.

It is also possible to determine the amount of antibody belonging to the VH4-34 family before and after anti-AML immunotherapy. If the amount of antibody belonging to the VH4-34 family, which is a family of VH sequences known for their potential killing properties (Bhat et al, 1997), is significantly raised after immunotherapy, it indicates that a GvL response is present. Further provided is, therefore, a method for determining whether an AML patient that has received anti-AML immunotherapy has a GvL response, the method comprising determining the amount of antibody belonging to the VH4-34 family before and after anti-AML immunotherapy, and determining whether the amount of antibody belonging to the VH4-34 family is significantly raised after immunotherapy. If this is the case, it is concluded that a GvL response is present in said patient. If this is not the case, it is concluded that a GvL response is lacking, or not sufficient.

The invention is further explained in the following examples. These examples do not limit the scope of the invention, but merely serve to clarify the invention.

BRIEF DESCRIPTION OF THE DRAWINGS

FIG. 1. Sequences of antibodies AT12-023, AT12-025, AT13-024, AT12-019, AT13-022, AT13-023, AT13-031, AT12-020, AT13-033, AT13-034, AT13-035, AT13-036, AT13-037, AT14-013, AT14-014, AT14-015 and AT14-016.

FIG. 3. a) Supernatant of one of the minicultures (20 or 40 cells per well) binding to the AML cell line THP-1. b) B cells from this miniculture were plated into 1 cell/well solutions and supernatants again screened for binding to THP-1. THP-1 express HLA-DR, that was used in this screening experiment as a positive control. As a negative control an influenza-specific monoclonal antibody was used.

EXAMPLES

Example 1

Materials & Methods

Patient and Healthy Human Materials

Figure 2:
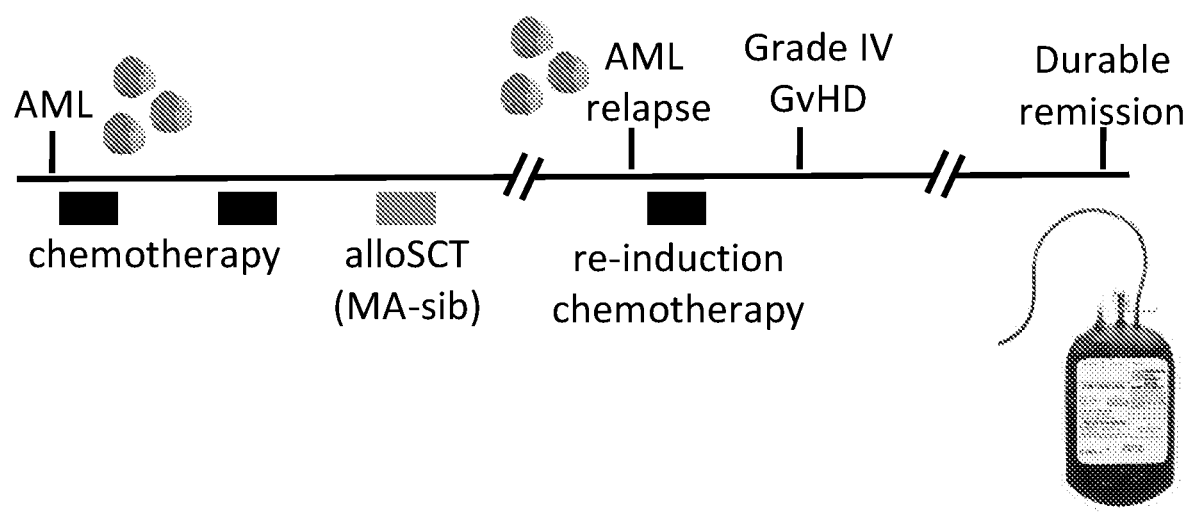
FIG. 2. 36 year old patient with AML, who obtained complete remission after the first cycle of induction chemotherapy and received a myeloablative (MA) allogeneic stem cell transplantation (SCT) from her HLA-matched brother (sib) as consolidation therapy. AML relapse occurred however 5 months post-transplantation. Re-induction chemotherapy resulted again in complete remission and in severe, grade IV graft versus host disease (GvHD) of the liver and grade I GvHD of the skin. The observation that she has remained in complete remission for more than three years now implies that she has developed a potent graft versus leukemia response. B lymphocytes were isolated from a phlebotomy product obtained about 1.5 years after the one cycle of re-induction chemotherapy.

Study protocols were approved by the Medical Ethical Committee of the Academic Medical Centre. All participants signed informed consent. We selected two patients who had received an allogeneic stem cell transplantation (myeloablative sibling transplant for donor 59 and a matched unrelated donor-reduced intensity stem cell transplantation for donor 58) for AML and who, based on their clinical histories, can be assumed to have generated strong graft versus leukemia responses. These two SCT recipients donated 500 ml peripheral blood each, the products of one of many phlebotomies they underwent for post-transfusion hyperferritinemia. In addition, patients admitted to our clinic with newly diagnosed AML consented to donate 2-5 ml bone marrow or blood containing AML blasts to be used for antibody binding assays. Healthy bone marrow was donated by patients undergoing thoracotomy for cardiac surgery in our institute. B-non Hodgkin's lymphoma cells were obtained as rest material from biopsies of patients with newly diagnosed B-non Hodgkin's lymphoma. These B-non Hodgkin's lymphoma cells were used to test for binding of our antibodies as described below. Rest material of human umbilical vein endothelial cells (HUVECS), that were freshly isolated at the Department of Ophthalmology (AMC, Amsterdam, The Netherlands) were directly used for binding assays as described below. For purity, cells were co stained with and selected for anti human CD14+.

Mononuclear cells were isolated from peripheral blood and bone marrow of healthy individuals and AML patients by Ficoll separation. Extra markers like CD45, CD33, CD34, CD14, CD3 and CD19 were used to isolate specific cell populations (AML blasts, monocytes, T and B lymphocytes, respectively, obtained from blood bank donors).

Isolation of B Cells

We obtained B cells from peripheral blood by Ficoll separation and CD22 MACS microbeads (Miltenyi Biotech). Subsequently we sorted these cells for CD27- or CD27+CD19+CD3–IgM–IgA– (naïve or memory IgG cells, respectively) and CD19+CD3–CD27+IgG–IgA– (memory IgM cells) on a FACSAria (Becton Dickinson).

Cell Culture

We maintained B cells ($2 \times 10^5$ cells/ml) in IMDM (Gibco) culture medium containing 8% FBS (HyClone) and penicillin/streptomycin (Roche), supplemented with recombinant mouse IL-21 (50 ng/ml, in house produced) and co-cultured them on γ-irradiated (50Gy) mouse L cell fibroblasts stably expressing CD40L (CD40L-L cells, $10^5$ cells/ml). The cultures were tested routinely for the presence of mycoplasma by PCR (data not shown).

Retroviral Transduction

Retroviral transduction was performed as described in Kwakkenbos ea, Nat Med 2010. Briefly, naïve and memory IgG and memory IgM B cells were cultured and activated during 36 hours on CD40L-L cells in the presence of mIL-21. Then, BCL6 and Bcl-xL retroviral constructs that include the marker gene for GFP were used to transduce the B cells as described before (Diehl ea, J Immunol 2008), with the addition that we centrifuged cells and virus at room temperature for 60 min at 360×g (1800 RPM). Transduction efficiency ranged from 69-90%.

Culture of Target Cell Lines

Target AML cell lines THP-1 (ATCC; density of $2 \times 10^5$ cells/ml to $1 \times 10^6$ cells/ml) and Mono-Mach (a kind gift from Dr. Hamann of the Experimental Immunology department, density of $2 \times 10^5$ cells/ml to $2 \times 10^6$ cells/ml) were maintained in RPMI 1640 (Gibco) culture medium, containing 10% FBS (HyClone) and penicillin/streptomycin (Roche). Culture medium of Mono-Mach was enriched with non-essential amino acids (Invitrogen), 1 mM sodium pyruvate (Invitrogen) and 10 µg/ml human insulin (Sigma). The AML cell line Molm13 was maintained at a density of $5 \times 10^5$ cells/ml to $1,5 \times 10^6$ cells/ml in RPMI 1640 (Gibco) culture medium, containing 20% FBS (HyClone) and penicillin/streptomycin (Roche). The liver cell lines HepG2 and Huh7 and the colon cell line HT29 (a kind gift from the Tytgat Institute, AMC, Amsterdam, The Netherlands) were cultured in DMEM (Gibco) culture medium, containing 8% FBS (HyClone) and penicillin/streptomycin (Roche). The acute T-cell leukemia cell line Jurkat (ATCC) was maintained in RPMI 1640 (Gibco) culture medium, containing 10% FBS (HyClone) and penicillin/streptomycin (Roche) at a density of $1 \times 10^5$ cells/ml to $2 \times 10^6$ cells/ml. Skin primary fibroblasts (a kind gift of the University of Leiden, The Netherlands) were cultured twice a week in DMEM (Gibco) culture medium, containing 10% FBS (HyClone) and penicillin/streptomycin (Roche). Cells were passaged no more then 10 times. The diffuse large cell B cell lymphoma (DLBCL) cell lines OCI-Ly1 and OCI-Ly7 (DSMZ and ATCC, respectively) were maintained in IMDM (Gibco) culture medium containing 8% FBS (HyClone) and penicillin/streptomycin (Roche). The cultures were maintained at $0.5$-$2\times10^6$ cells/ml. Finally, the multiple myeloma (MM) cell lines U266 and NCI-H929 were maintained and cultured as described for THP-1 cells.

Generation of AML-Specific Clones

Transduced naïve and memory IgG and IgM B cells of each patient were seeded at concentrations of 20 or 40 cells per well (hereafter named microcultures) and expanded with IL-21 and CD40L. Supernatants of expanded B cell micro cultures were then screened for antibody binding to leukemia cell lines (THP-1, MonoMac6 and the cell lines depicted in Table 4), to liver- and colon cell lines, and some supernatants also to the primary blasts isolated from patients with AML-M0, M1, M4 and M5, by FACS, using human-IgG-PE (Southern Biotech) or human IgG H+L AF647 (Life Technologies) as a secondary antibody. Several in-house generated antibodies were used as negative control antibodies, such as anti-CD30 (expressed on activated B and T lymphocytes), anti-CD33 (expressed on monocytes, myeloid progenitor cells and myeloid leukaemias), D25 (against RSV; described in WO 2008/147196), AT10-002, AT10-004 (against influenza; described in WO 2013/081463), and F1 (against MRSA; described in WO 2011/008092). In addition, some commercially available antibodies were used, such as Rituximab (anti-CD20), Palivizumab (anti-RSV), Panitumumab (anti-EGFR) and HLA-DR. Microcultures binding to AML cell lines but not to liver- and colon cell lines were selected and seeded at a concentration of 1 cell/well and their supernatants tested again for specificity for AML cell lines. Clones with supernatants specifically binding AML cell lines and not liver- or colon cell lines, or healthy PBMC and bone marrow were selected for sequencing. Clones were expanded under normal culture conditions in the presence of FBS IgG low serum (Hyclone) and antibodies purified from the supernatants of these cultures as described below for the recombinant antibodies.

Cloning of AML-Specific Antibodies

To produce recombinant antibodies we isolated total RNA with the RNeasy® mini kit (Qiagen), generated cDNA, performed PCR and cloned the heavy and light chain variable regions into the pCR2.1 TA cloning vector (Invitrogen). To rule out reverse transcriptase or DNA polymerase induced mutations, we performed several independent cloning experiments. To produce recombinant mAb we cloned heavy and light variable regions of each antibody in frame with human IgG1 or IgG3 and Kappa constant regions into a pcDNA3.1 (Invitrogen) based vector and transiently transfected 293T cells. We purified recombinant antibodies from the culture supernatant with Protein A or G, depending on the Ig subtype of the clone.

In Vitro Activity of AML-Specific Antibodies

To measure the in vitro effect of AML-specific antibodies on AML cells we used several approaches. First, THP-1 cells ($2\times10^4$) were seeded in flat bottom 96 well plates (Costar). AML or control-antibodies were added on day 1, in a concentration of 5-10 µg/ml. Numbers of cells per well were counted daily. Induction of cell death on both THP-1 cells and primary leukemic cells by AML-specific antibodies was measured in parallel by costaining an aliquot of cells for Annexin V (BD Pharmingen) and 7-Aminoactinomycin D (7-AAD; Beckman Coulter), double-negative cells being the viable cells. In addition, we used a specific lysis assay. Target cells (THP-1) were labeled with Calcein AM (Becton Dickinson), a green fluorescent dye that is released from the cytoplasm when cells die. Briefly, 2 million THP-1 cells were incubated with 2 ml of 2 µM Calcein AM for 30 minutes at 37° C. AML or control antibodies were added for 4 hours, after which green fluorescence was measured using a fluoresence plate reader. The proportion of specific lysis was calculated as (experimental value-low control)/(high control-low control)×100, where low control means the spontaneous release of Calcein AM by unaffected cells and high control means the maximum amount of released Calcein AM when all cells are lysed. In addition to the Calcein AM release assay we applied the lactate dehydrogenase (LDH) release assay to measure the killing activity of AML specific antibodies. LDH is released by damaged cells, from the cytosol. Leukemic blasts, isolated at diagnosis from a patient with AML-M0, were incubated with AT13-024 at a maximum concentration of 10 µg/ml per 10.000 blasts. LDH release is measured after adding Reaction mixture and Stop Solution (Roche Diagnostics/Applied Science) according to the manufacturer's protocol on an ELISA reader. The percent cytotoxicity is calculated as the (experimental value-low control)/(high control-low control)×100, where low control means the spontaneous release of LDH by unaffected cells and high control means the maximum amount of LDH when all cells are lysed. To quantify death of target cells induced by AML-specific antibodies we used a FACS-based leukemia cell lysis assay as previously described (Schmiedel et al, 2013). In brief, FACS calibration beads (Accudrop Fluorescent Beads, BD Biosciences) were added to the cells in a 50/50 ratio after which a standard amount of beads was acquired with FACS. As an equal assay volume was ascertained by the calibration beads, the amount of dead or vanished cells can then be calculated as follows: 100−((Dapi negative cells in respective treatment/Dapi negative cells in control)×100).

Finally, to discern between apoptotic and non-apoptotic pathways of cell death induced by our antibodies we co-stained target cells with DiOC6 and propidium iodide (PI). DiOC6 (3,3-dihexyloxacabocyanine iodide) is a cell-permeant, green-fluorescent, lipophilic dye that is selective for the mitochondria of live cells, when used at low concentrations. Apoptotic cells will lose their mitochondrial membrane potential (loss of DiOC6 stain) before the cell membrane becomes permeable (PI positive); necrotic cells become PI positive before they loose their mitochondrial membrane potential (and become DiOC6-negative). The methods used for staining were adapted from Hugh J. M et al., 2004. In brief, THP-1 cells were stained with 40 nM of DiOC6 (Invitrogen) for 20 minutes at 37° C. PI was added after which the samples were analyzed immediately by flow cytometry.

Flow Cytometry

Stained cells were analyzed on FACSAria (BD), FACSCanto (BD), FACS LSRFortessa X-20 (BD) and Guava (Millipore) flowcytometers and flow cytometry data were processed with FlowJo software (Tree Star).

Phase Contrast Imaging

THP-1 cells were added to a two chambered Cover glass system (LabTek). Using a phase contrast-imaging microscope (in-house manufactured), four fields of interest per chamber were chosen. The software was set to take a picture of every field of interest every other minute. Just prior to the run, the THP-1 binding, non-cytotoxic antibody AT13-023 and the THP-1 binding, cytotoxic antibody AT13-037 were added to their respective wells at a concentration of 10 ug/ml.

Target Verification: Immunoprecipitation and Flow Cytometry

THP-1 cells were lysed and precleared with an irrelevant antibody (in-house generated RSV antibody D25) and beads to remove non specific binding proteins. Precleared lysate was then incubated with bead-labeled AML-specific antibodies or with the influenza specific antibody AT10-002 as a negative control (3 hrs at 4° C.). Antibody-incubated lysates were washed five times, bound proteins were eluted from the THP-1 lysate and then run on an SDS-PAGE gel. Proteins were blotted and stained with Ponseau S to reveal total protein. The blot was blocked with BSA and incubated with mouse-anti-snRNP200 (Millipore, clone 3B6.1) or Rabbit-anti-HMGB1 (Abcam) for Western blot analysis. Intracelllar staining for snRNP200 was performed after fixing and permeabilizing THP-1 cells with methanol (Sigma) and permeabilization buffer containing triton X-100 (Sigma), EDTA (Gibco) and BSA (Roche), followed by incubation with rabbit-anti-human snRNP200 antibody (Sigma) overnight at 4° C.

Target Conformation: snRNP200 ELISA

HEK 293T cells were transfected with an expression vector containing the full-length open reading frame of snRNP200 with an N-terminal FLAG tag. At 2 days after transfection cells were harvested and lysed in lysis buffer containing protease inhibitors. This lysate was cleared and protein concentration was measured. AML specific antibodies AT12-019, AT12-023, AT13-031 and AT13-037 or commercially available snRNP200 specific antibodies (Bethyl labs) were then coated on an ELISA plate. The lysate was added at a concentration of 3 µg/ml for capturing. After extensive washing, captured snRNP200-flag was detected with a monoclonal mouse anti-flag HRP antibody (Sigma-Aldrich, clone M2).

Results

Generation of AML-Specific Antibodies

In our project we use a unique technology that was recently developed in our laboratory (WO 2007/067046; incorporated herein by reference) that allows for selection of naturally occurring leukemia-specific B cells and the antibodies produced by these cells. We employed this technology to generate leukemia-specific B cell lines from two AML patients who developed potent GvL responses in parallel with severe GvHD of the liver and skin. With our B cell immortalization technique, it became possible to identify B cell responses of leukemia patients and to create leukemia-specific B cell lines that allow functional studies of the antibodies these cell lines produce and allow generation of larger numbers of antibodies, as compared to other methods known in the art, with diagnostic and therapeutic potential.

First, we applied our technique as described in WO 2007/067046 to perform a set of pilot experiments, where we isolated and immortalized B lymphocytes from a carefully selected patient (donor 59) who developed a potent GvL response following extensive GvHD of liver and skin. This patient was diagnosed with AML at the age of 36 years. She obtained complete remission after the first of two courses induction chemotherapy after which she received a myeloablative, HLA-matched sibling donor SCT as consolidation therapy. Only 5 months after SCT, shortly after immunosuppressive therapy had been tapered, her AML relapsed. With one cycle of high-dose cytarabine she obtained complete remission again, after which she spontaneously, before the scheduled donor-lymphocyte infusion, developed stage III GvHD of the liver and stage II GvHD of the skin. She was successfully treated with high-dose corticosteroid therapy but during tapering of therapy hepatic GvHD relapsed twice. In the end, corticosteroid therapy was successfully phased out about 6 months before the current experiments were started (1.5 yrs after AML relapse) and she has remained in complete remission from her leukemia for more than three years now (FIG. 2).

From this patient, we generated B cell clones using our technique to immortalize B cells. Briefly, PBMC were isolated from the peripheral blood by ficoll centrifugation, and B lymphocytes sorted by FACS. Isolated B lymphocytes were then cultured with IL21 and CD40L and transduced with BCL6 and BCL-xL, with a transduction efficiency of around 70%. Using this technique, unique B cell clones that concurrently express the B cell receptor and secrete monoclonal antibodies were generated. Immortalized CD27− naïve and CD27+ memory IgG+ B cells were seeded at concentrations of 20 or 40 cells per well and expanded with IL21 and CD40L. Supernatants of expanded B cell micro cultures were then screened for antibody binding to leukemia-, liver- and colon cell lines by FACS, using human-IgG-PE as a secondary detection antibody.

As the patient had been diagnosed with AML-M5 according to the French-American-British (FAB) classification (Bennett et al., 1976), we selected the THP-1 cell line that morphologically and phenotypically is roughly similar to AML-M5 for these screening essays (Tsuchiya et al., 1988). In addition, because the patient suffered from extensive GvHD of the liver we screened for the identification of liver-binding B cell clones using the liver cell line HepG2. As a negative control, and to select out cross-binding B cell clones we used the colon cell lines HT-29 and LSTR. Micro cultures with the highest binding to either of these cell lines were then sorted and single cells were deposited in 96 well formats, expanded and the supernatants of these expanded clones were again screened for binding against leukemia cell lines (FIG. 3).

Properties of AML-Specific Antibodies

Figure 4A:
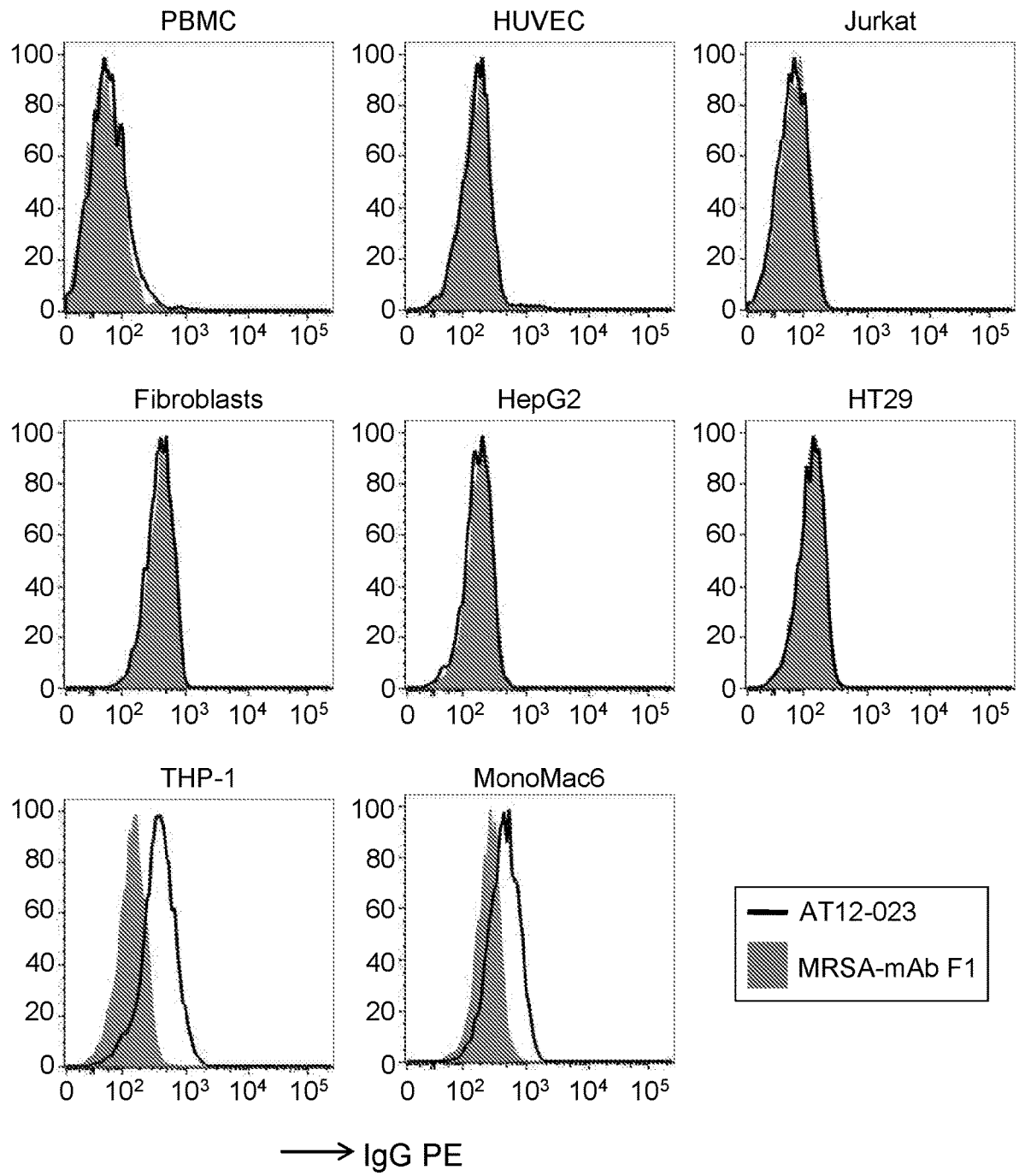
FIG. 4. Two examples of the AML specific antibodies identified. AT12-023 (a) and AT13-031 (b) bind to AML cell lines THP-1 and MonoMac6, but not to healthy peripheral blood mononuclear cells (PBMC), endothelial cells (human umbilical vein endothelial cells: HUVEC), the T cell line Jurkat, primary fibroblasts, hepatocytes (liver hepatocellular carcinoma cell line: HepG2) or the colon adenocarcinoma cell line HT-29. The MRSA-mAb F1 is an in-house generated human IgG3 mAb that is used as control antibody.
Figure 4B:
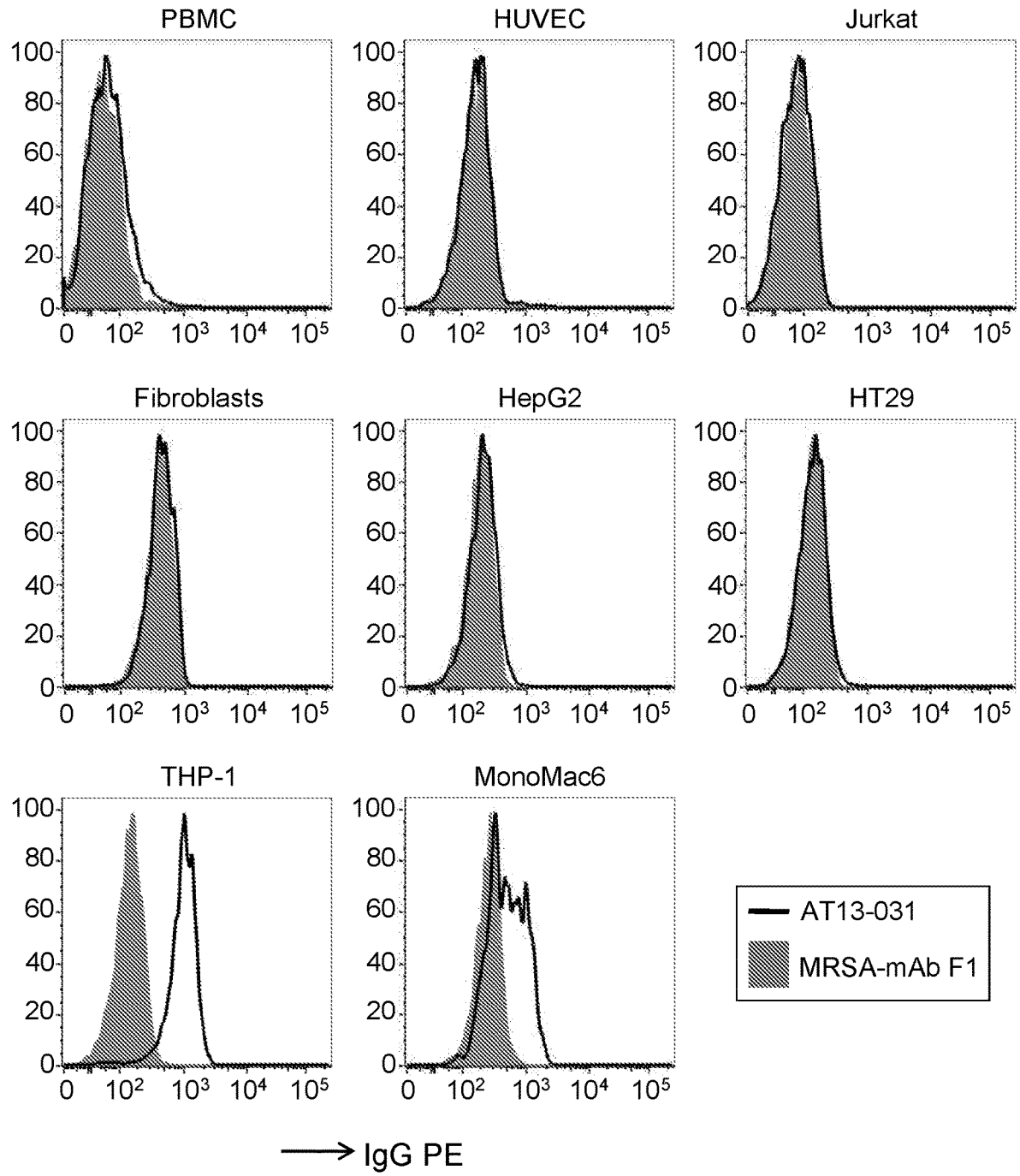

With this approach we generated eight B cell lines from this one patient, producing antibodies that bind to THP-1 (FIG. 3) but not liver or colon cell lines, fibroblasts, endothelial cells (human umbilical vein endothelial cells or HUVEC), healthy PBMC or bone marrow (Table 2 and FIG. 4). These are antibodies AT12-019, AT12-023, AT12-025, AT13-022, AT13-023, AT13-024, AT13-031 and AT12-020. The heavy and light chain variable regions of these antibodies are depicted in Table 1 and FIG. 1.

Interestingly, the antibodies are of the IgG1 and IgG3 isotypes, and several of the DNA sequences showed somatic hypermutations. Antibodies AT12-023, AT12-025, AT13-023 and AT13-031 belong to the VH4-34 family, which is a family of VH sequences known for their potential killing properties (Bhat et al, 1997). The antibodies are of donor-origin, as confirmed by microchimerism analyses.

We then determined the breadth of binding within the spectrum of AML subtypes, and tested the generated AML-specific B cell clones for binding to other AML FAB classification types. Selected leukemia-specific clones also bound to the AML-M5 cell line MonoMac6 (Table 3) (see for review of AML cell lines (Drexler and Minowada, 1998)).

Figure 5:
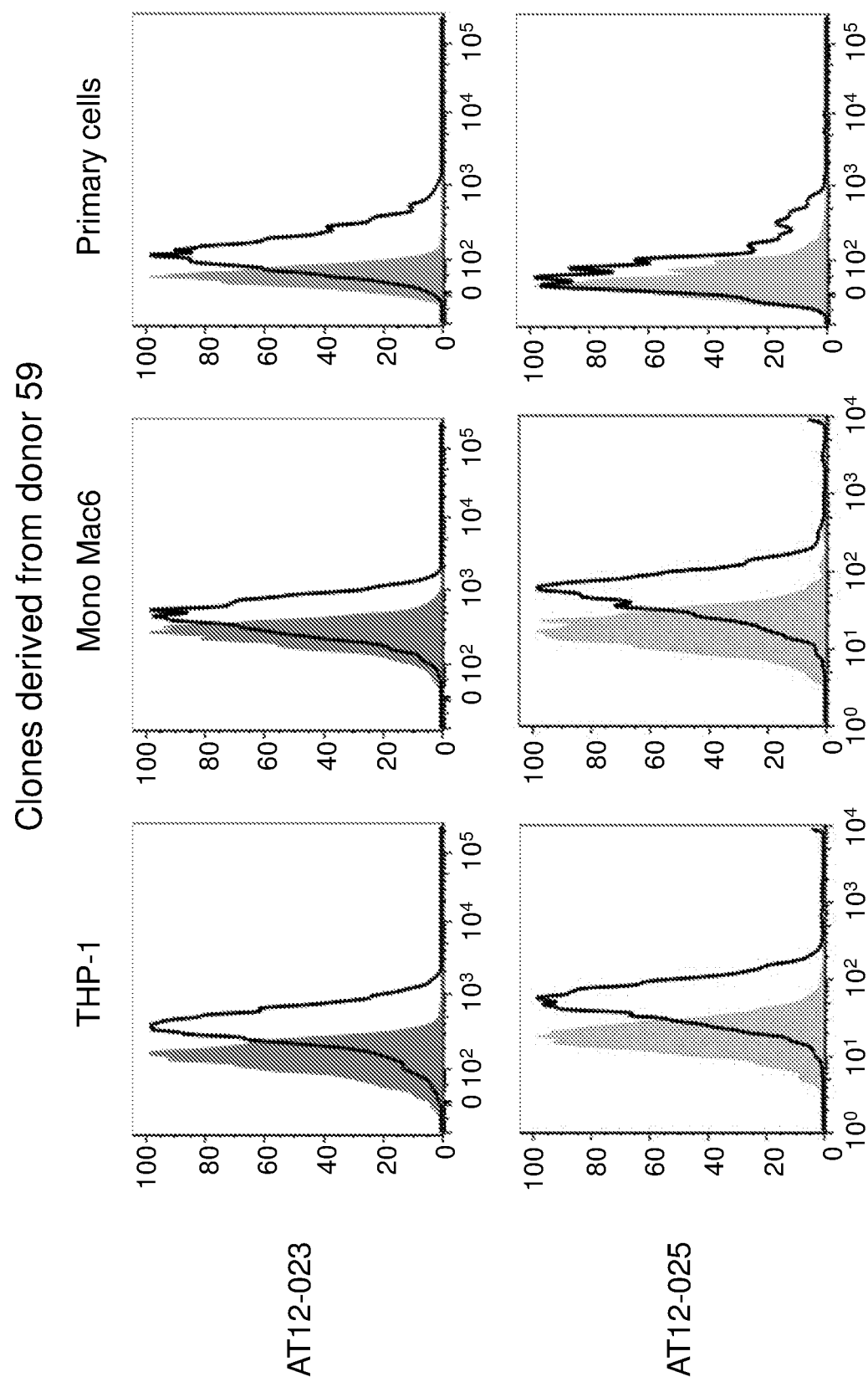
FIG. 5. Antibodies derived from donor 59 bind to the AML cell lines THP-1 and MonoMac6, and to primary leukemic blasts isolated from newly diagnosed AML patients (ranging from FAB classification M0-M4). See also table 3 for a more detailed overview.
Figure 5:
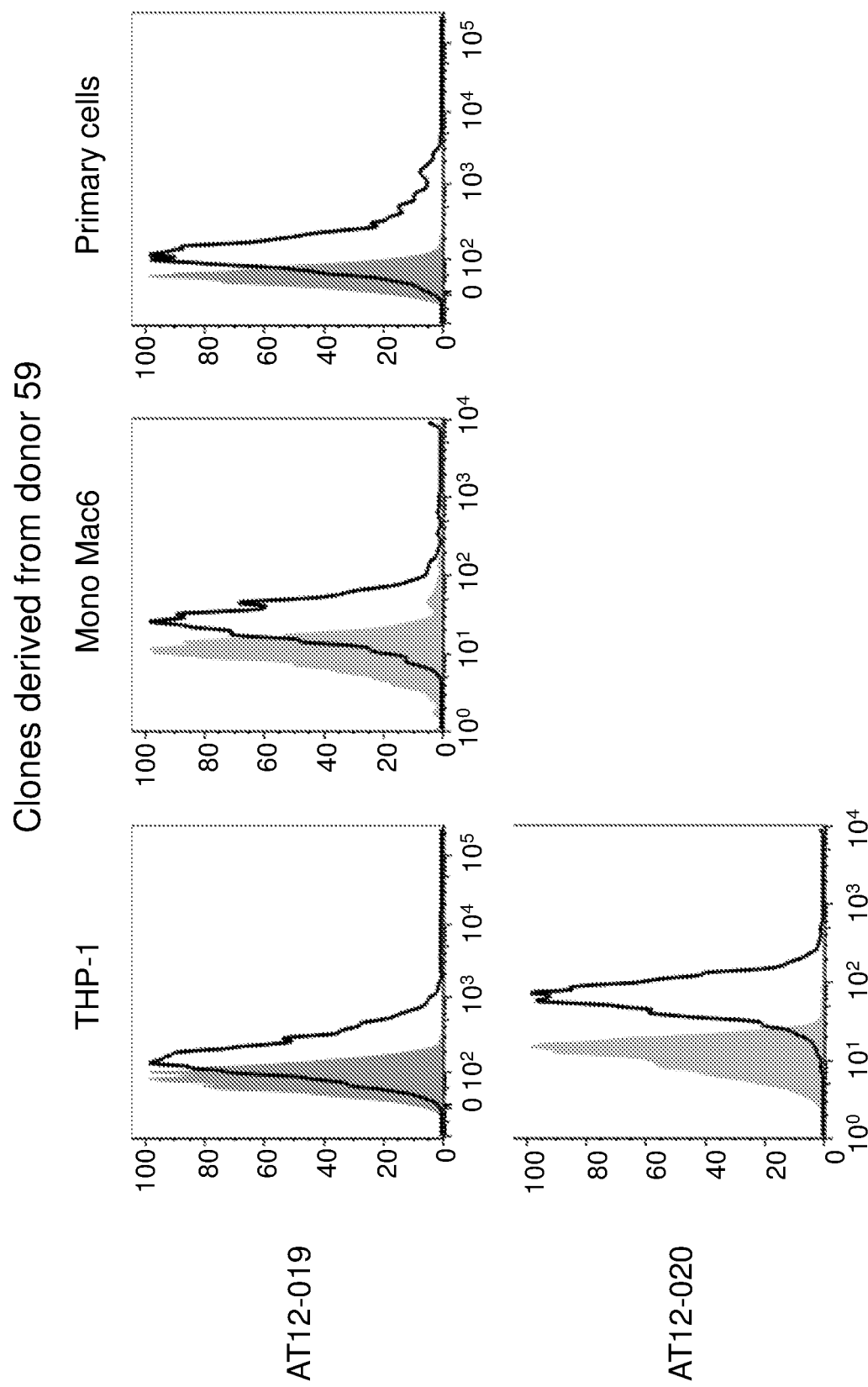
Figure 5:
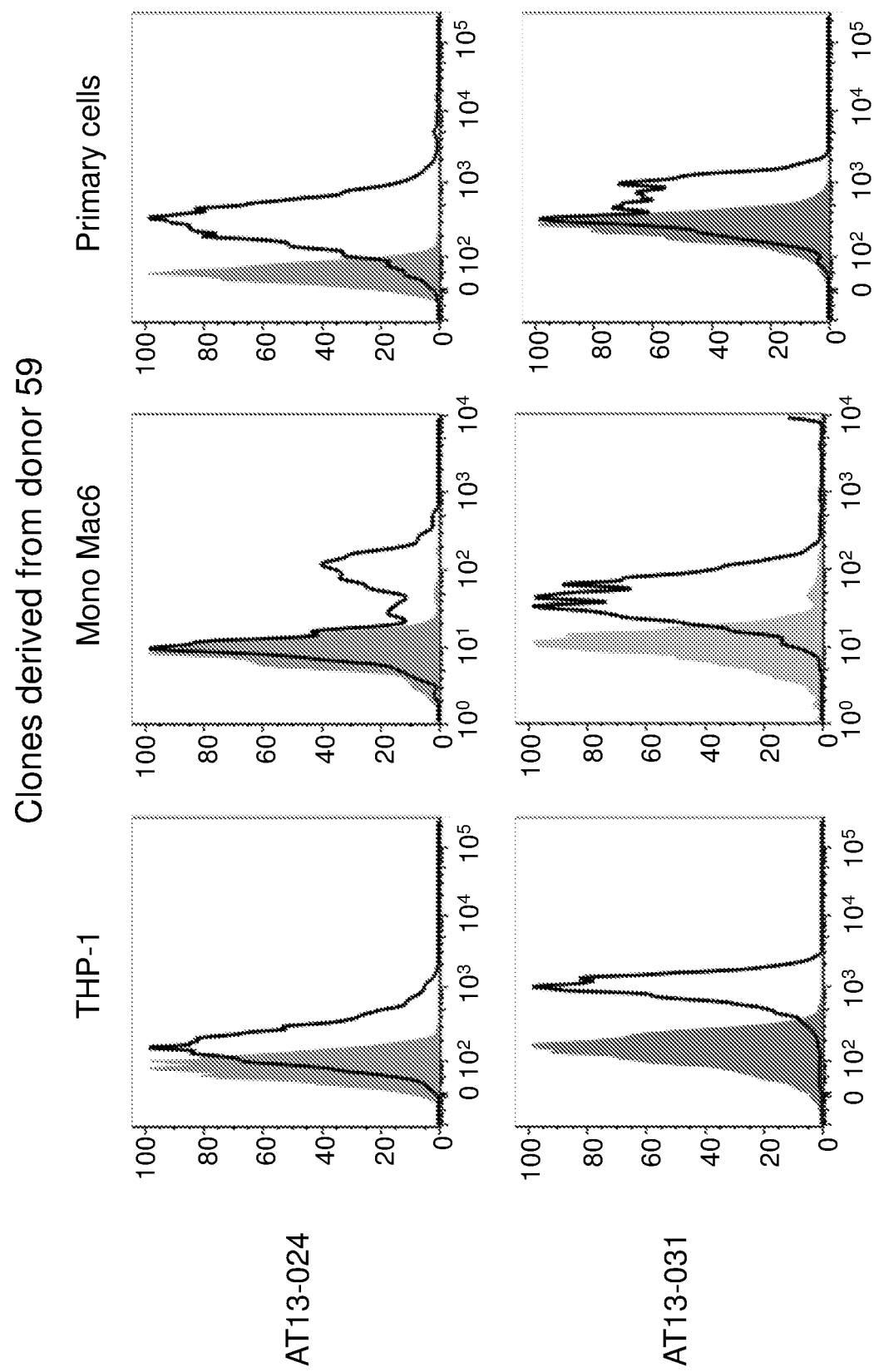
Figure 5:
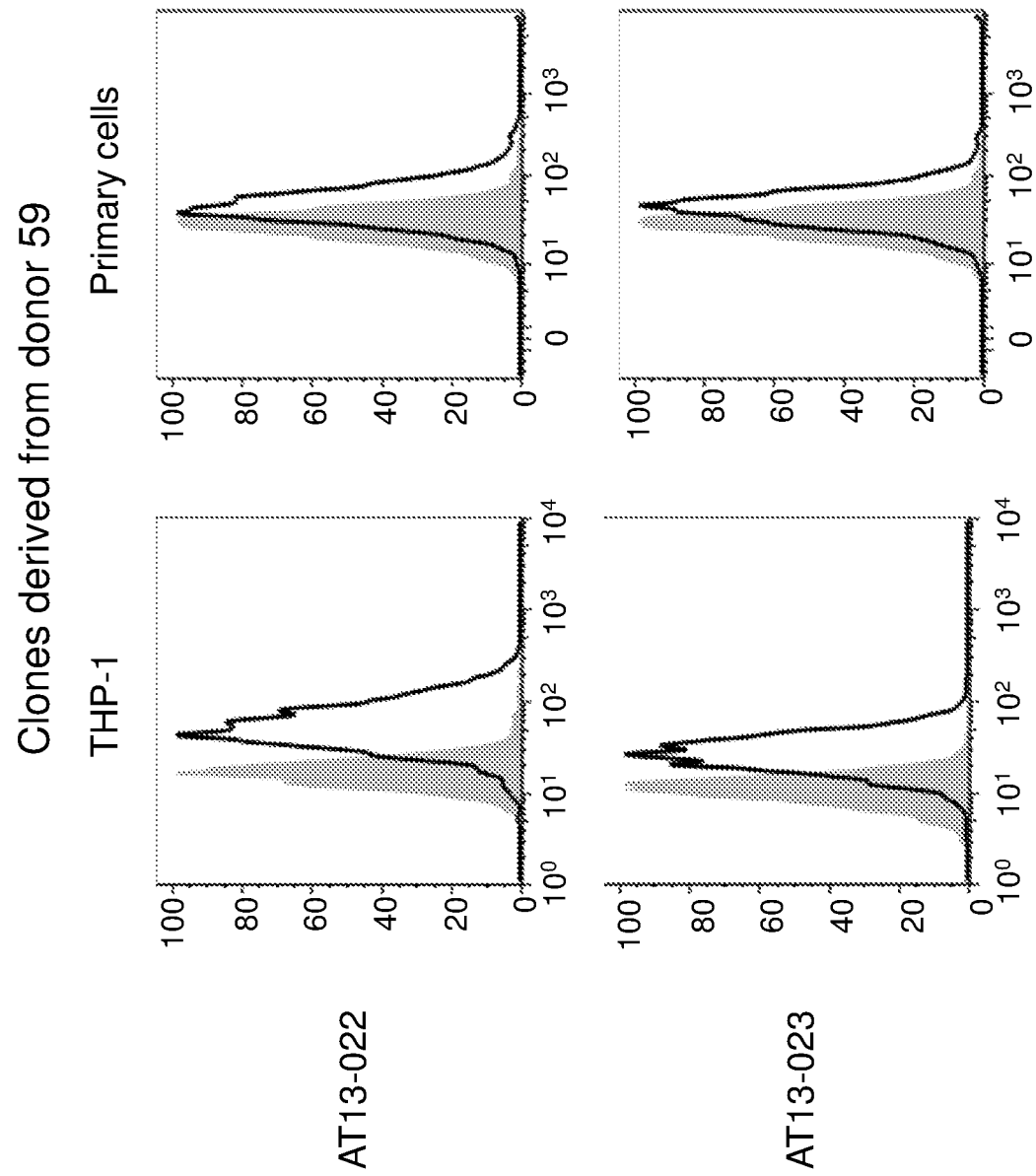

Our AML-specific antibodies also bound to freshly isolated AML blasts of newly diagnosed patients (Table 3 and FIG. 5).

Figure 6:
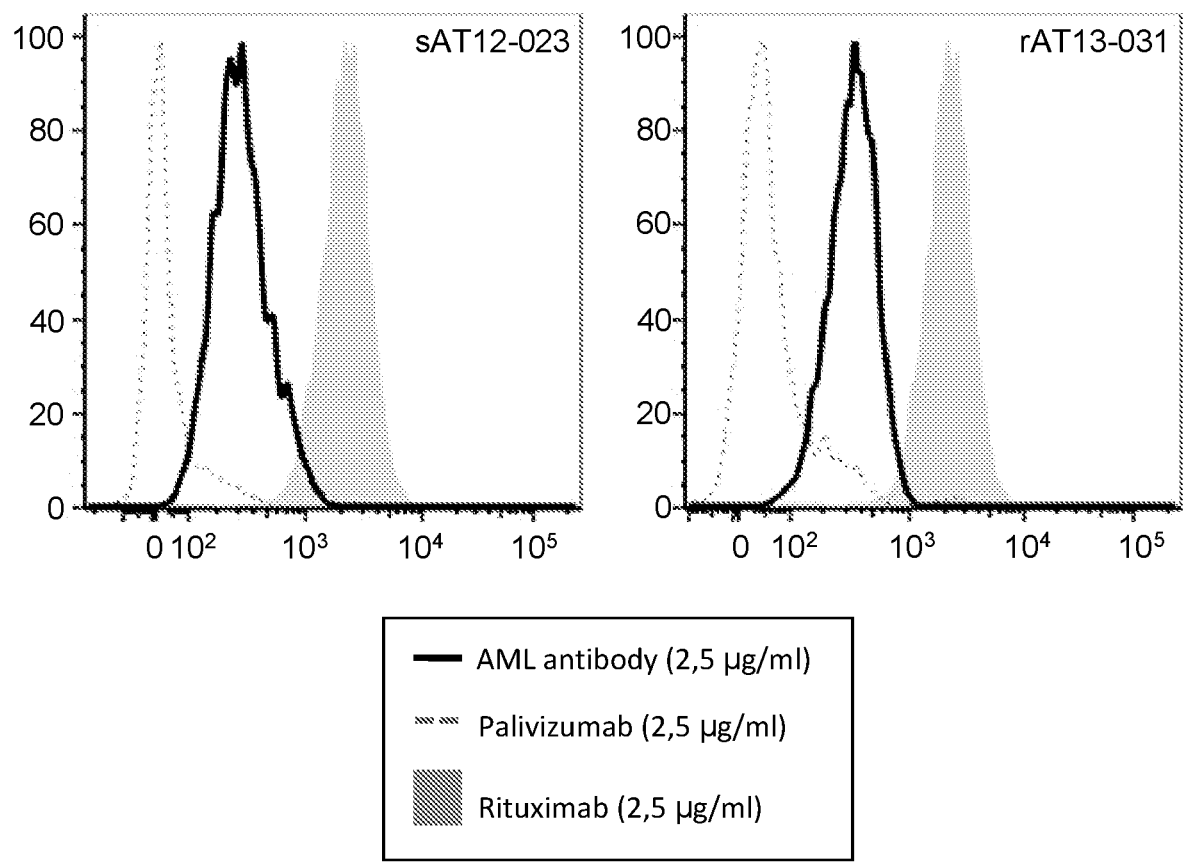
FIG. 6. Some of the antibodies also bind to other hematological malignancies. Here, binding of AT12-023 (antibodies isolated from supernatant of B cell clone) and AT13-031 (recombinant antibody) to B-non Hodgkin lymphoma (B-NHL) cells that were freshly isolated from a lymphoma patient is shown. The antibodies did not bind to non-malignant B cells (not shown in this experiment). The RSV antibody Palivizumab was used as a negative control, and Rituximab, a CD20-antibody specifically binding B-cell lymphoma, as a positive control. See for more details of antibody binding to other hematologic malignancies table 4.

Furthermore, some antibodies also bound other hematopoietic malignancy-cell lines, such as the diffuse large cell B cell lymphoma cell lines OCI-Ly1 and OCI-Ly7 and the multiple myeloma cell lines U266 and NCI-H929, and/or patient-derived hematologic tumor cells (Table 4 and FIG. 6).

In Vitro Activity of AML Specific Antibodies

While testing the specificity of the AML-binding antibodies, we made a striking observation. Three of the eight antibodies spontaneously induced death of the leukemic cells they were binding to. THP-1 cells were killed by AT12-023 and AT12-025, and primary AML blasts isolated from patients diagnosed with AML were killed by AT12-025 and AT12-024 (Table 5 and FIGS. 7-10).

Figure 7:
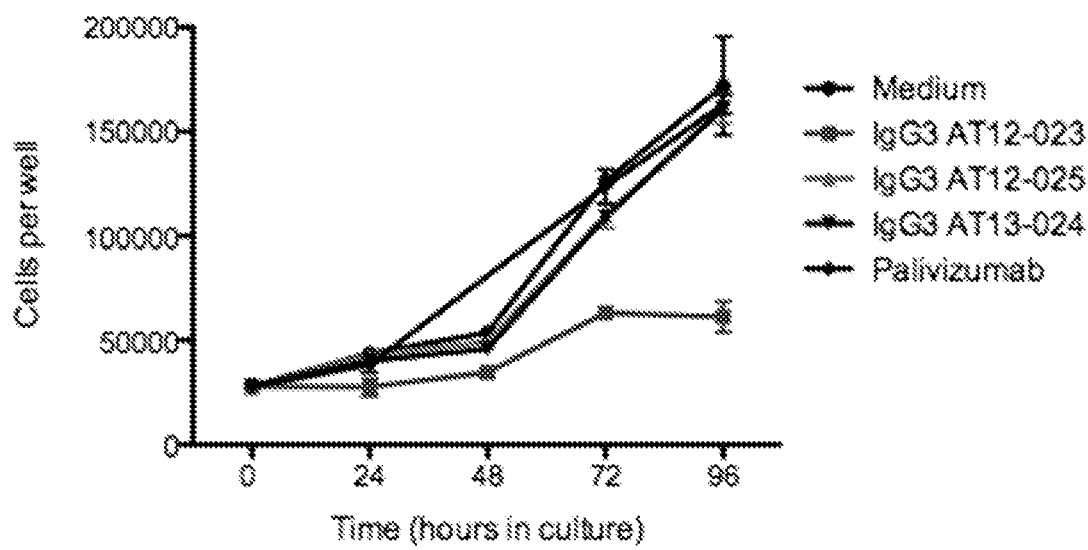
FIG. 7. THP-1 cells were cultered in medium alone or with antibodies added at a concentration of 5 µg/ml at day 0. In the presence of AT12-023, THP-1 cells showed significant growth inhibition. Depicted are total cell numbers in culture.
Figure 8:
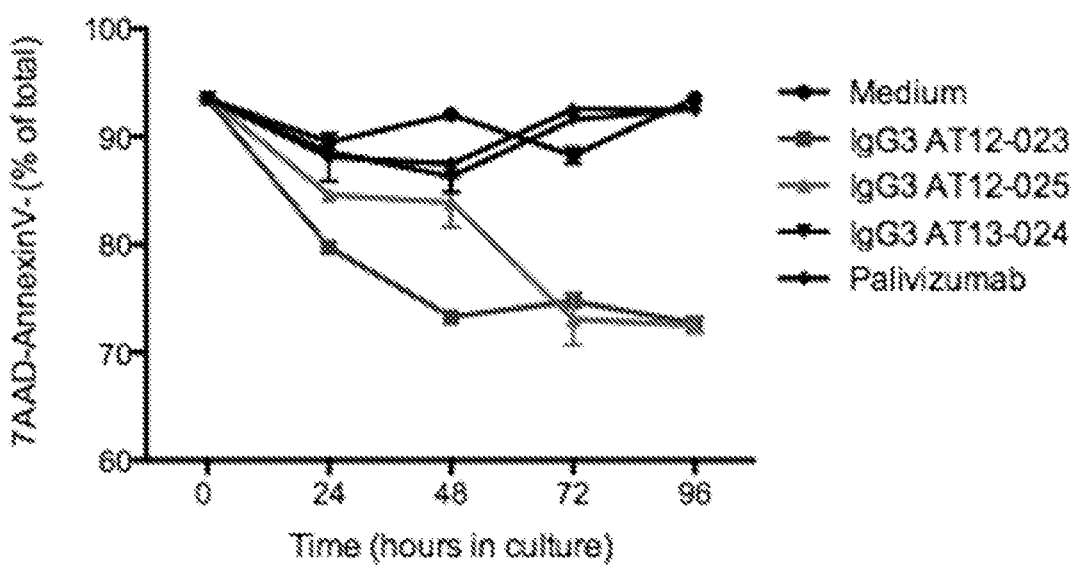
FIG. 8. When added at day 0 of the culture, antibodies AT12-023 and AT12-025 strongly reduced the viability of THP-1 cells. Viability is depicted as the proportion of cells double-negative for cell-death markers Annexin V and 7AAD.

FIG. 7 shows rapid killing of THP-1 cells by AT12-023. Dying blasts expressed 7-AAD and Annexin V. Strikingly, while co-culture of THP-1 with AT12-025 at first did not affect total cell numbers in the cultures (FIG. 7), this antibody appeared to also induce death of THP-1 cells, albeit with a little delay compared to AT12-023 (FIG. 8). The observation that some of the antibodies show direct killing activity against leukemic cells is highly exciting and has to the best of our knowledge not been reported before.

Figure 11:
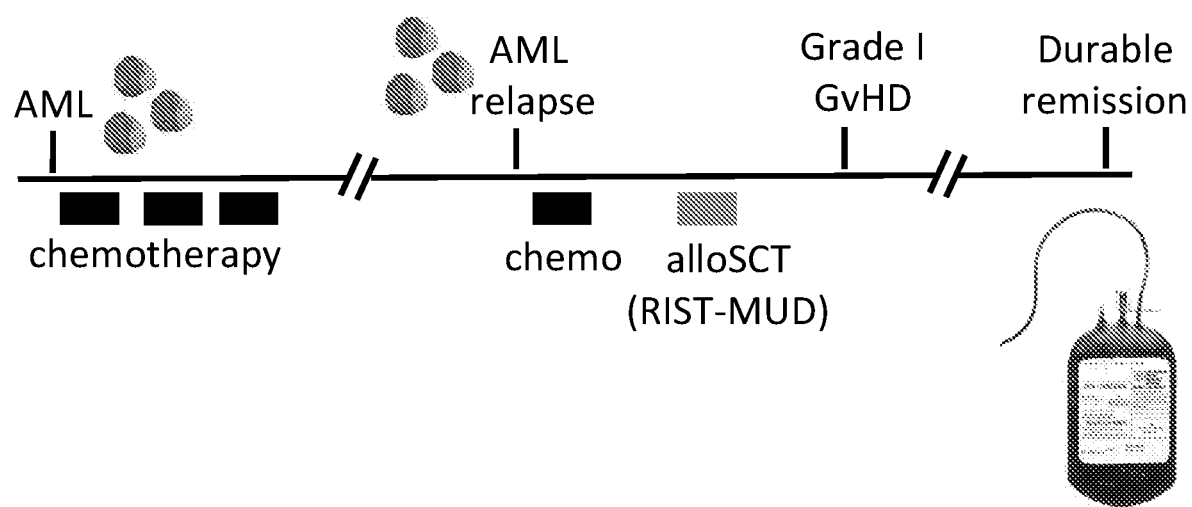
FIG. 11. Donor 58 was diagnosed with AML-M5, for which she received three cycles of chemotherapy. She remained in complete remission for about a year, after which the AML relapsed. She received one cycle of re-induction chemotherapy, followed by an allogeneic reduced intensity stem cell transplantation (RIST) from a matched unrelated donor (MUD). She developed GvHD grade I of the liver and has remained in complete remission for almost 4 years now, implicating that she has developed a potent graft versus leukemia response. B cells were isolated from a phlebotomy product obtained from this patient about 3 years post-SCT.
Figure 12:
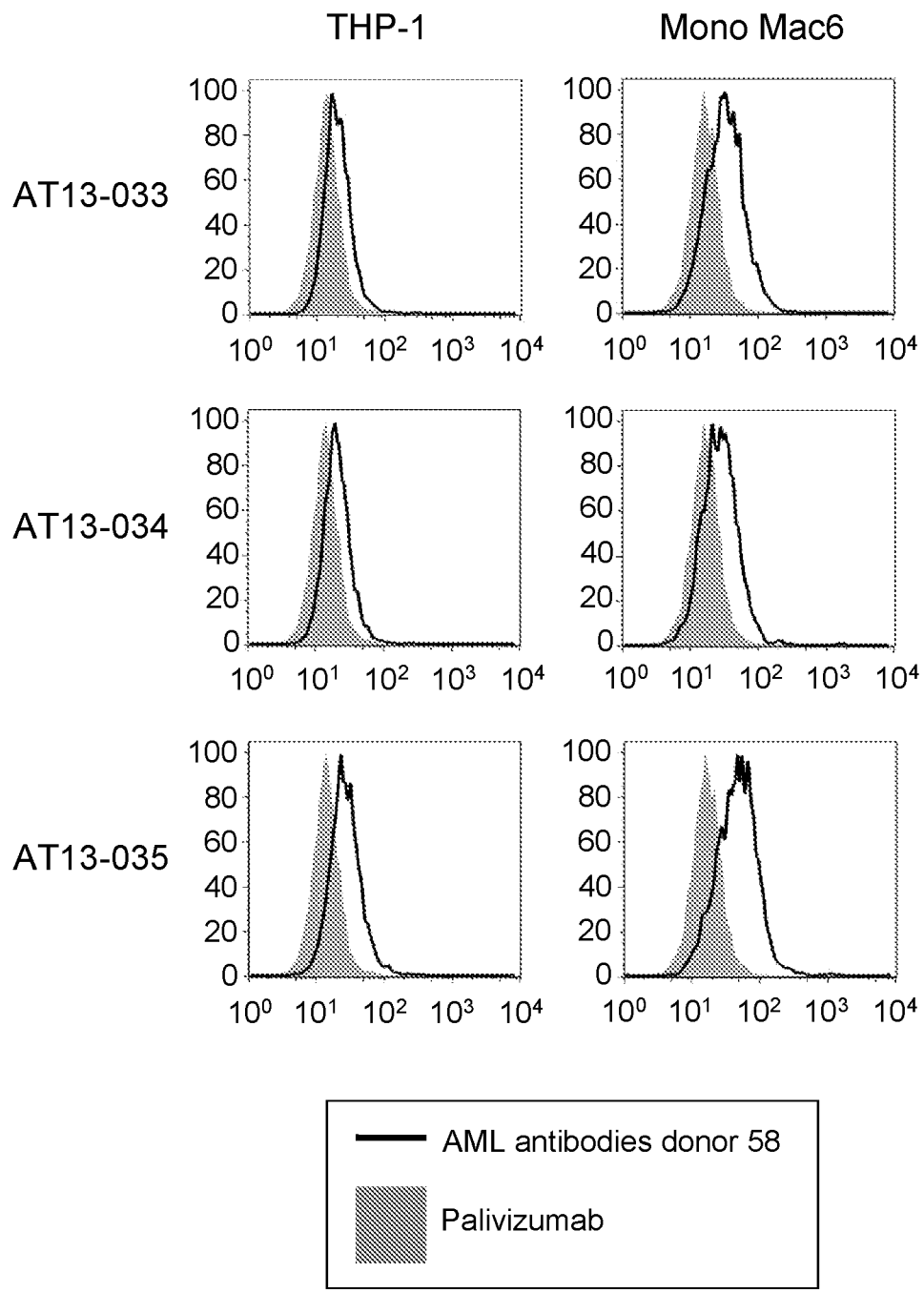
FIG. 12. Antibodies derived from donor 58 bind to the AML cell lines THP-1 and MonoMac6. Palivizumab, the commercially available RSV specific antibody, was used as a negative control.
Figure 12:
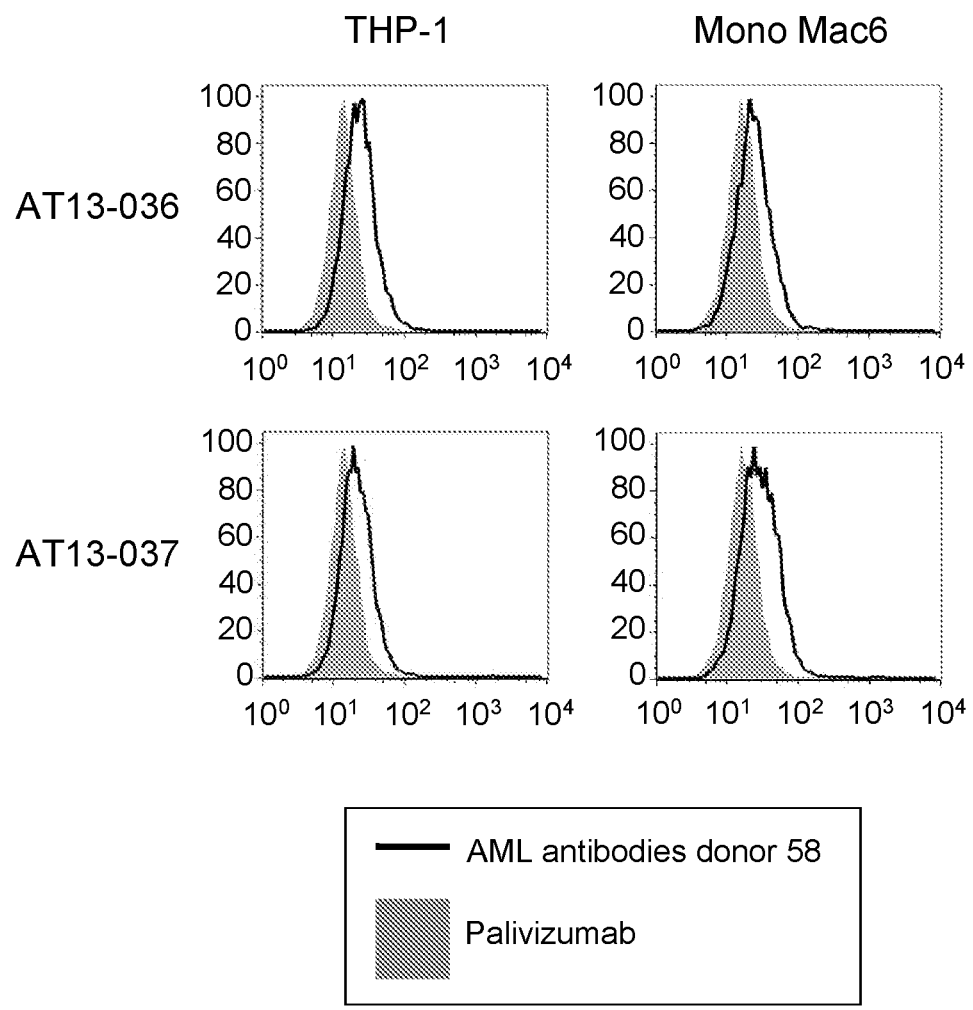

Confirmation of Our Findings by Generating AML-Specific B Cell Lines from a Second Patient About 0.05 to 0.1% of the B cells that we screened from the first patient were found to be AML-specific. To confirm our findings, we selected a second patient with relapsed AML who obtained durable remission after an allogeneic SCT (donor 58; FIG. 11). Also this patient developed GvHD of the skin and liver for which she was treated with oral steroids. After steroids were phased out, about one year after the SCT, PBMC were isolated, B cells immortalized, and B cell lines screened for binding to AML cell lines as described above. Five B cell clones have been generated from this patient that bind to the AML cell lines THP-1 and Mono-Mac6 (FIG. 12), but not to liver or gut cell lines, fibroblasts or healthy PBMC (Table 6). These clones produce antibodies AT13-033, AT13-034, AT13-035, AT13-036 and AT13-037. Interestingly, all these antibodies are of the IgG3 isotype. The sequences of the heavy and light chain variable regions of these antibodies are also depicted in Table 1 and FIG. 1. These data confirm the achievability of our project; despite the low frequencies of the B cells we are aiming at, we were able to isolate them and to generate robust antibody-producing B cell lines that were specific for AML.

Discussion

These preliminary date are highly exciting, as—to the best of our knowledge—we are the first to generate several human, non-chimeric, leukemia-specific B lymphocyte clones from patients that developed a robust, lasting GvL response against AML. The observation that some of these antibodies spontaneously show killing activity against leukemic blasts in vitro is highly exciting and very promising. In addition, the observation that some of the antibodies have a germline sequence and are of the IgG3 subclass, a type of antibody that can be induced without T cell help, warrants further attention as these findings demonstrate that 'natural' antibodies generated in a T-cell-independent way affect GvL responses in SCT patients. Importantly, these data offer proof of concept that using this technique, we can select leukemia-specific B cell clones.

Example 2

AML-Specific Antibodies from a Third Patient

Figure 13:
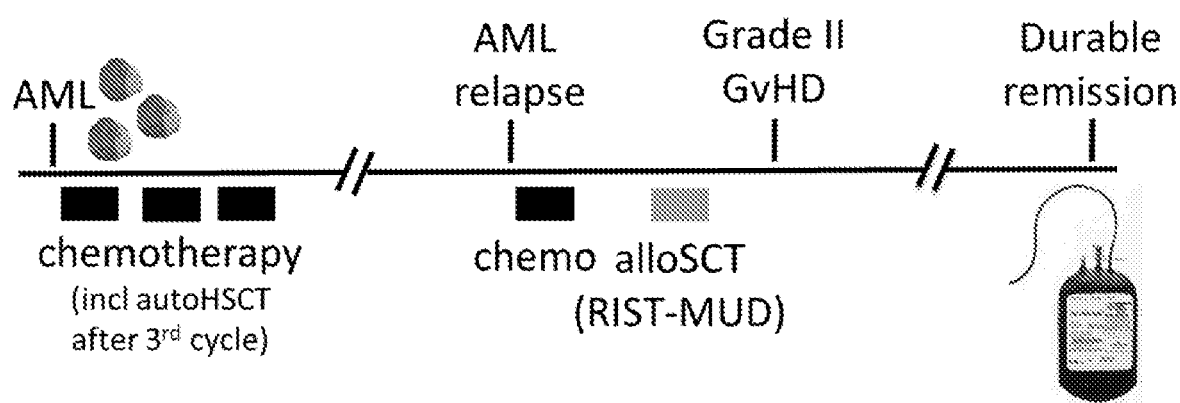
FIG. 13. Clinical history of a third patient with a potent GvL response. Donor 101 was diagnosed with an intermediate-risk AML (no cytogenetic or molecular abnormalities; FAB classification AML-M5) at the age of 49 years. He received two courses of chemotherapy and one course of consolidation chemotherapy followed by an autologous HSCT, as there was no HLA-matched sibling stem cell donor available. Fourteen months after the first diagnosis his disease relapsed. He obtained complete remission after one cycle of high-dose cytarabine, after which he received a rediced-intensity allogeneic HSCT with a matched unrelated donor (RIST-MUD). Six weeks later he developed acute GvHD of skin, liver and intestine (stage 1; grade II) that responded well to corticosteroid therapy. B cells were isolated from a phlebotomy product obtained from this patient 38 months after the allogeneic HSCT. He has maintained durable remission until today.

To further confirm our approach and to show this anti-AML response is not only reserved for female patients, we selected a male patient as well. This patient (FIG. 13), donor 101, was diagnosed with an intermediate-risk AML (no cytogenetic or molecular abnormalities; FAB classification AML-M5) at the age of 49 years. He received two courses of chemotherapy (cytarabine, idarubicine, amsacrine) and one course of consolidation chemotherapy (busulphan, cyclophosphamide) followed by an autologous HSCT, as there was no HLA-matched sibling stem cell donor available. Fourteen months after the first diagnosis his disease relapsed. He obtained complete remission after one cycle of high-dose cytarabine, after which he received a reduced intensity allogeneic HSCT of a matched, unrelated donor (RIST-MUD). Six weeks later he developed acute GvHD of skin, liver and intestine (stage 1; grade II) that responded well to corticosteroid therapy. B cells were isolated from a phlebotomy product obtained from this patient 38 months post-SCT.

Figure 14:
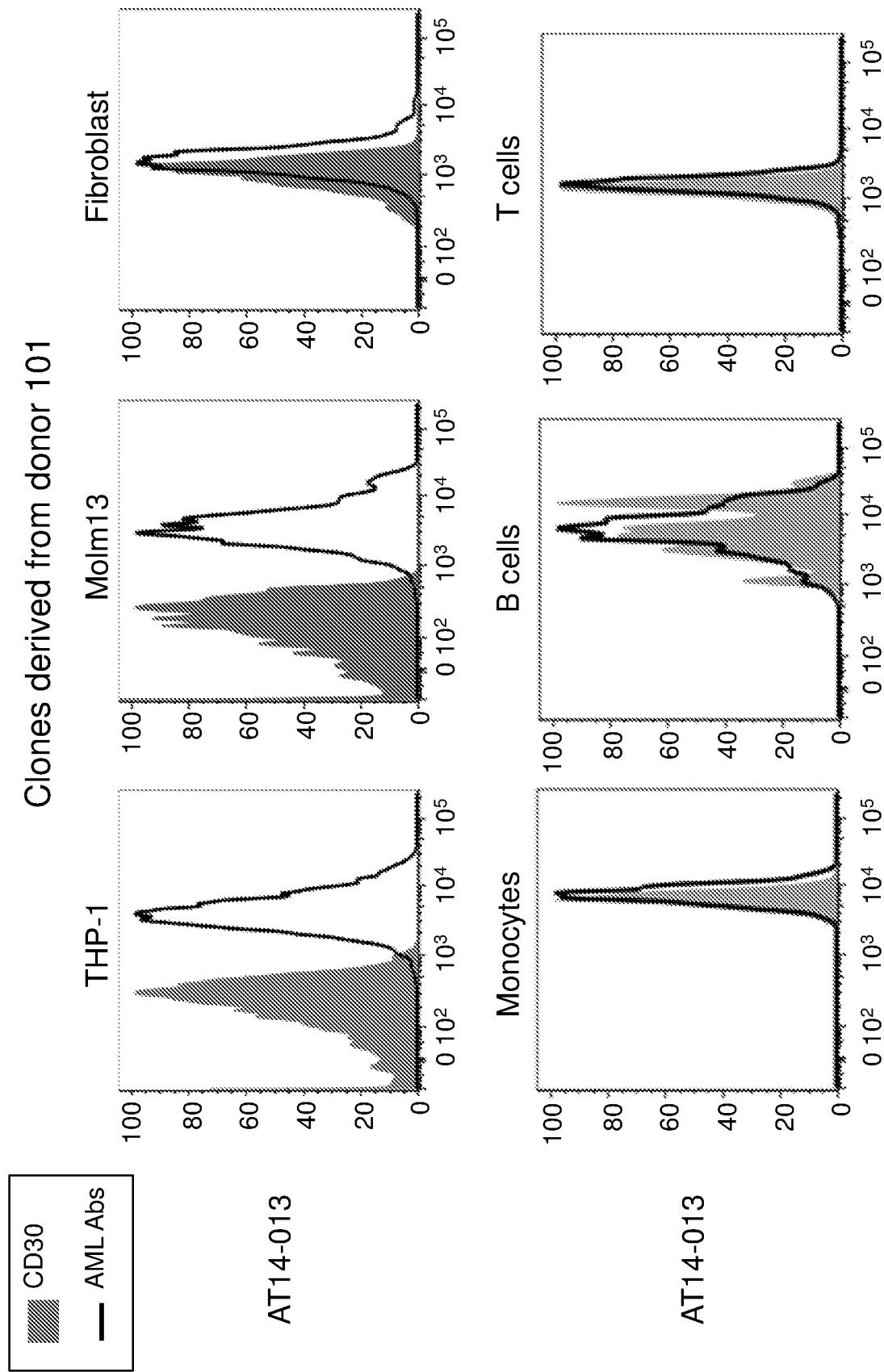
FIG. 14. Antibodies derived from donor 101 bind to the AML cell lines THP-1 and Molm13, but not to fibroblasts, monocytes, B cells and T cells. An in-house produced human antibody against CD30 was used as a negative control. AT14-013 showed minor reactivity with fibroblasts, compared to its high binding to the AML cell lines. See tables 7 and 8 for an overview of the binding capacities of the antibodies derived from donor 101.
Figure 14:
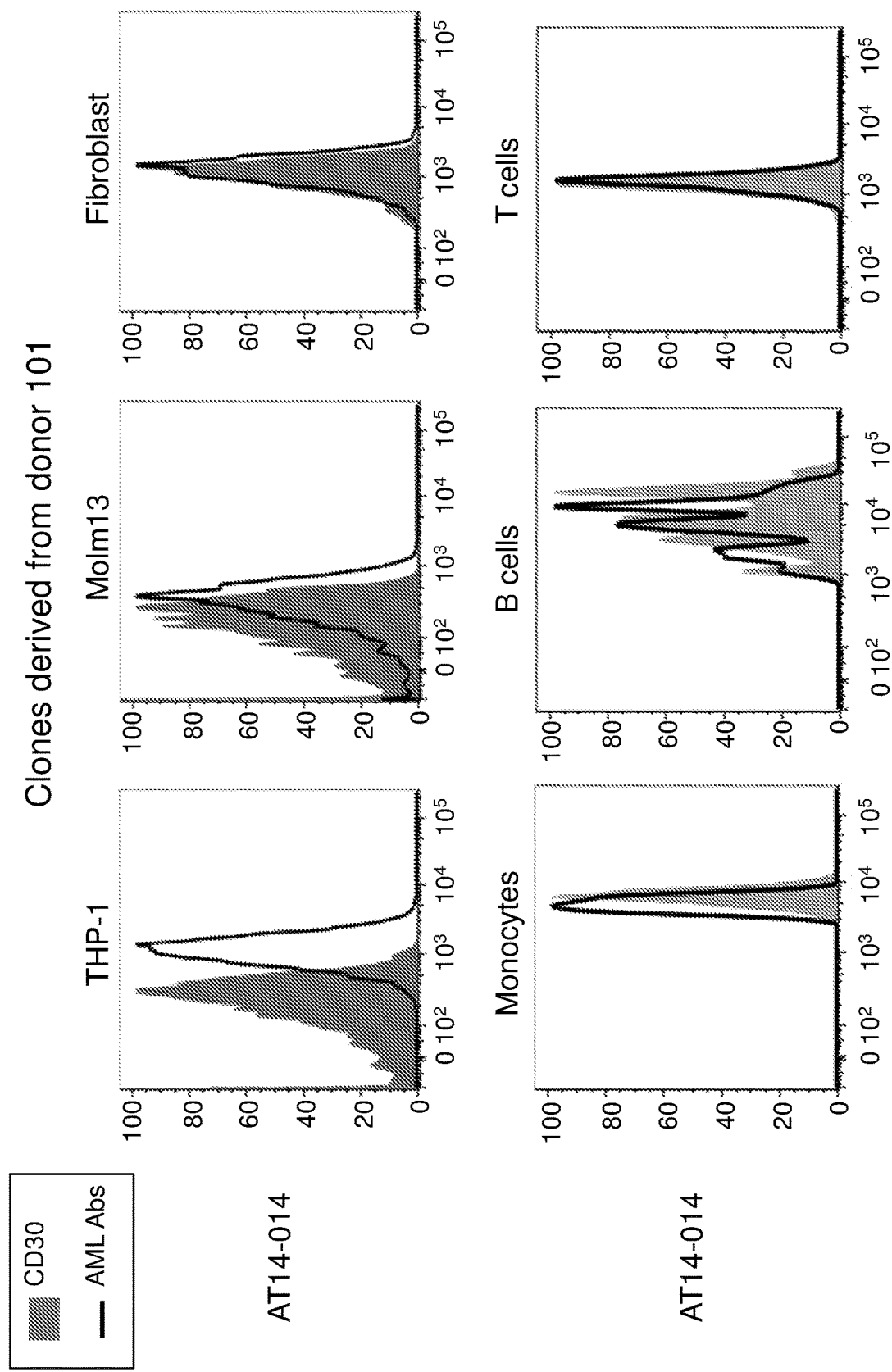
Figure 14:
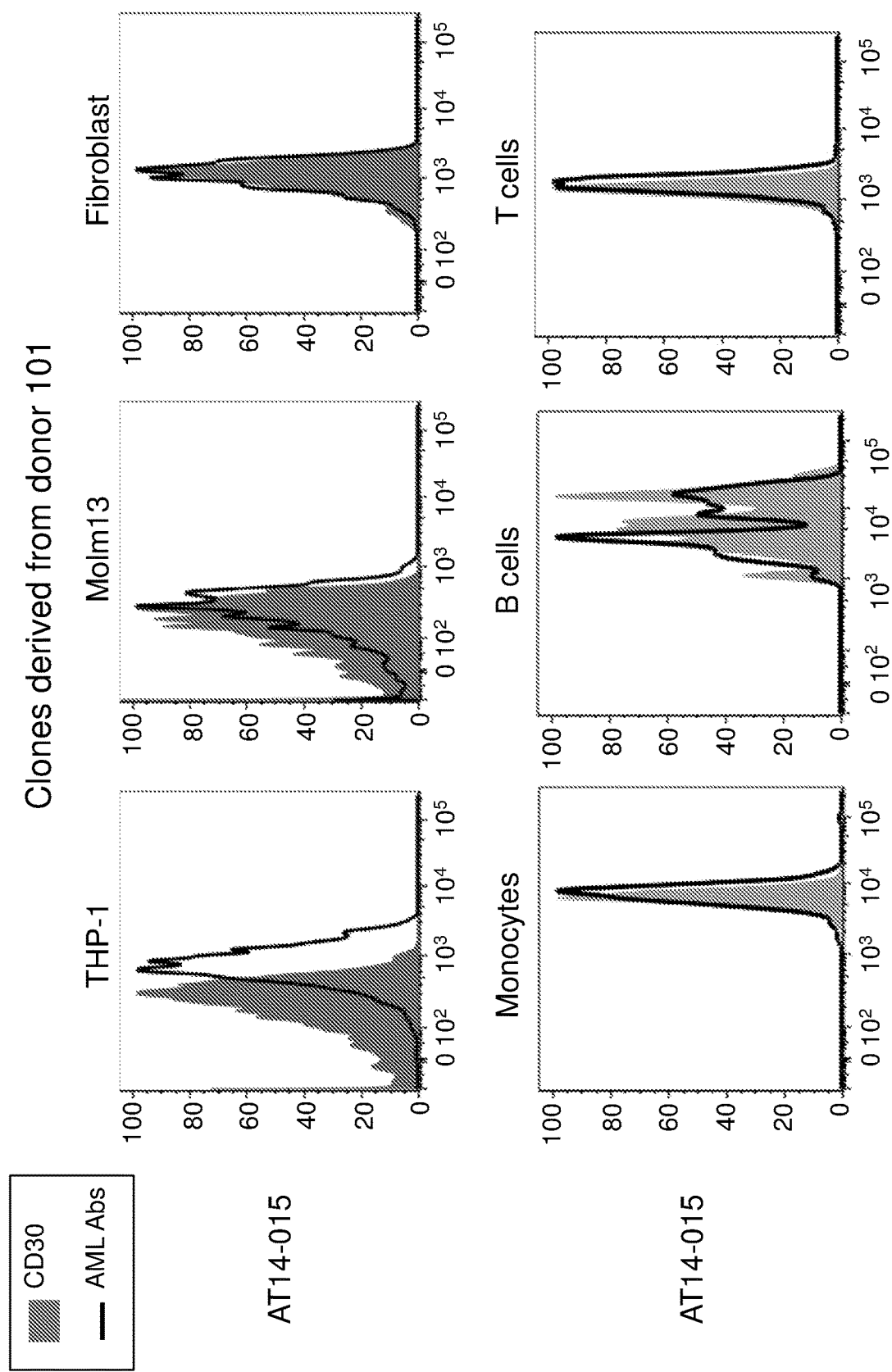
Figure 14:
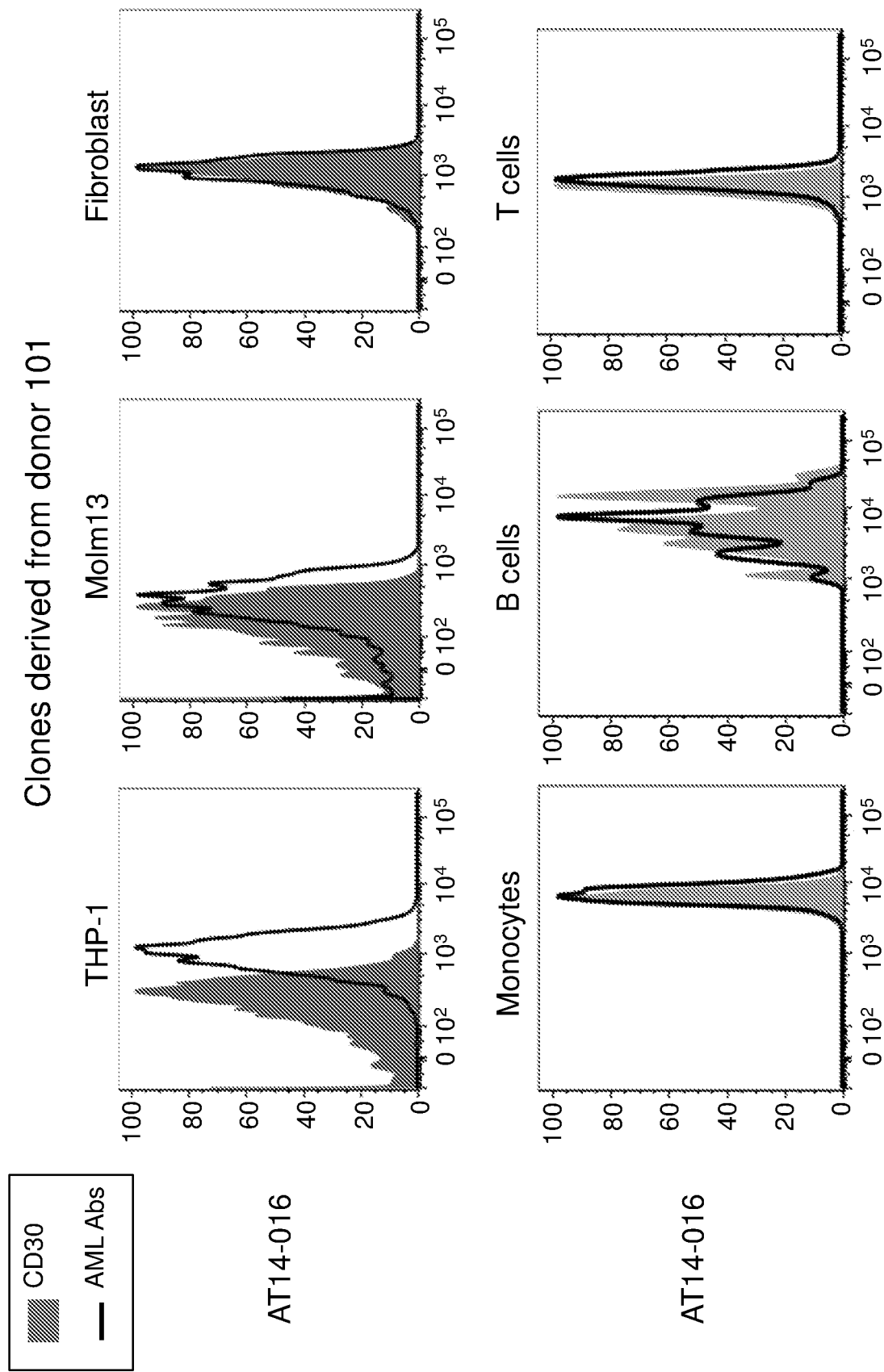

Using the same methods as described in Example 1, four B cell clones have been generated from this patient that bind to the AML cell lines THP-1 and/or Molm13 (FIG. 14 and Table 7) but not to (fetal) liver or gut cell lines, fibroblasts or healthy PBMC (Table 8). These clones produce antibodies AT14-013 (IgG1), AT14-014 (IgG3), AT14-015 (IgG3) and AT14-016 (IgG3). Interestingly, again the majority of the antibodies is of the IgG3 isotype. The sequences of the heavy and light chain variable regions of these antibodies show high amounts of somatic hypermutations and are depicted in Table 1B and FIG. 1. Clone AT14-013 shows very minor reactivity with the hepatocellular carcinoma cell line Huh7, but not to the hepatocellular carcinoma cell line HepG2 or healthy fetal liver cells. Also minor reactivity to fibroblasts is observed, however, the binding of this antibody to these tissue specific cells, compared to the binding to primary leukemic blasts is negligible (FIG. 14).

Figure 15:
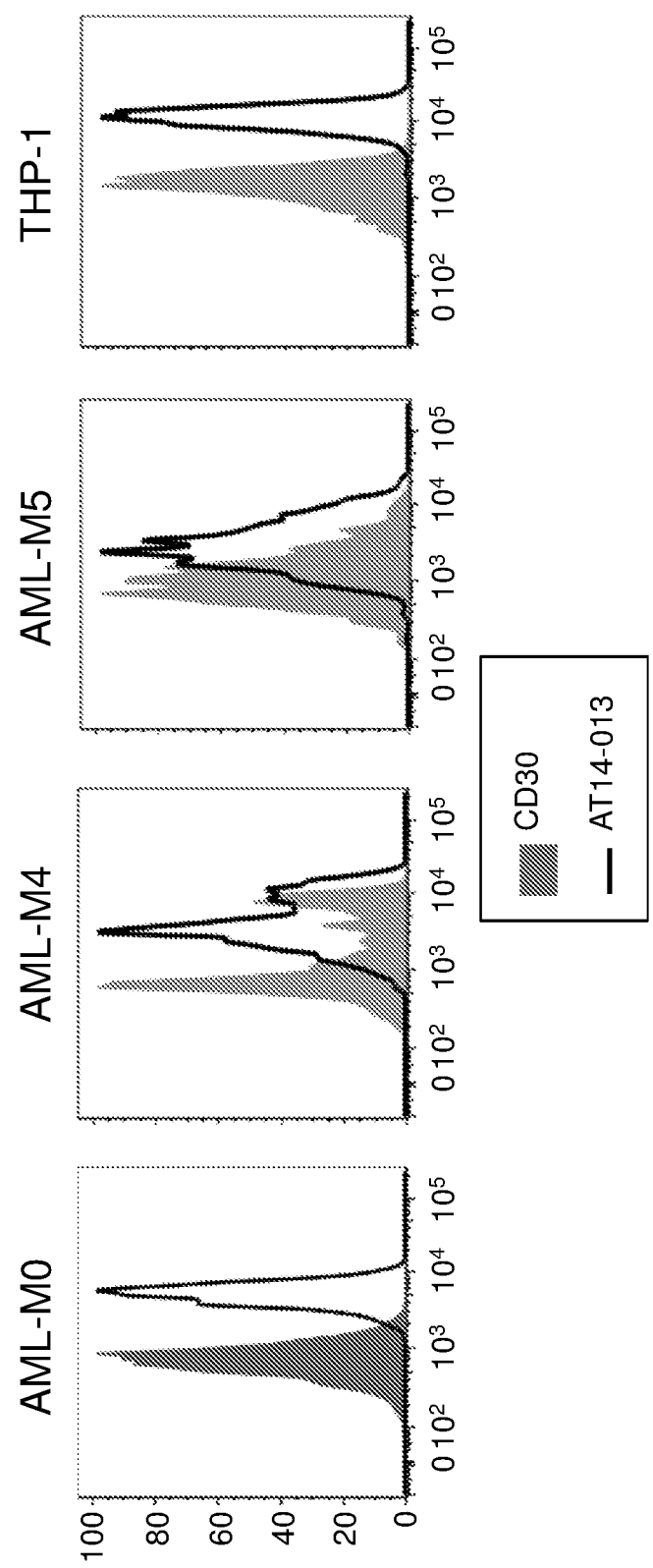
FIG. 15. AML-specific antibody AT14-013 (donor 101) binds primary leukemic blasts isolated from newly diagnosed AML patients (FAB classifications M0-M5). Negative control: in-house generated CD30 antibody. See table 7 for an overview of the primary AML blast binding capacities of the antibodies derived from donor 101.

It was also tested whether the four antibodies of donor 101 could bind primary AML blasts (Materials & Methods: see Example 1). FIG. 15 and Table 7 show that antibody AT14-013 appears to bind primary blasts of at least three different FAB classifications (AML-M0, M4 and M5). Antibodies AT14-015 and AT14-016 are able to bind primary AML blasts of the M4 classification.

Example 3

In Vitro Activity of AML-Specific Antibodies of Donors 59, 58 and 101

In Example 1, the breadth of binding of the antibodies of donor 59 within the spectrum of AML subtypes was determined (Table 3). Using the same methods, this has also been determined for the antibodies of donor 58. The results are shown in Table 9A: all five antibodies of donor 58 (AT13-033, AT13-034, AT13-035, AT13-036 and AT13-037) bound to the AML-M5 cell line THP-1, as well as to the AML-M5 cell line MonoMac6. These AML-specific antibodies did not significantly bind to freshly isolated AML blasts of newly diagnosed patients of FAB classification M0, M1 or M4. AT13-034 could only weakly bind M0 blasts. This indicates that these antibodies have a specificity for (at least) AML M5 blasts.

Figure 9:
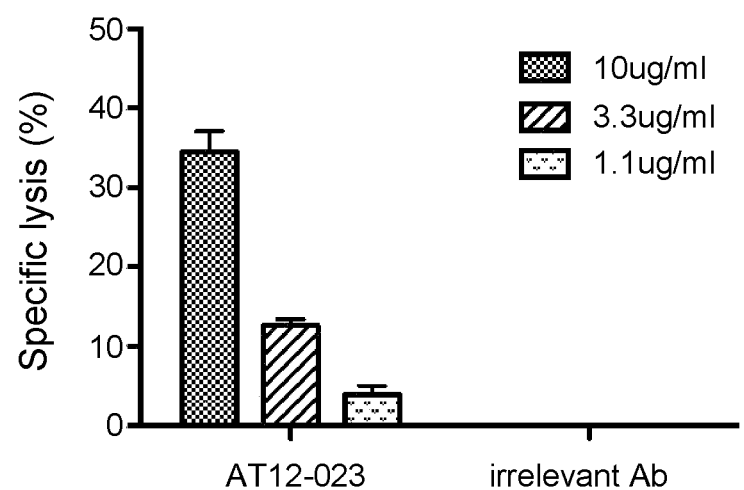
FIG. 9. To quantify the amount of THP-1 cells specifically killed by AT12-023 we used a calcein AM release assay. Briefly, before THP-1 cells were incubated with AT12-023, the THP-1 cells were loaded with calcein AM, that is released when cells are dying and the cell membrane becomes instable. Lysis was read out after 4 hours of incubation and was related to the background death of calcein-loaded cells as measured with an irrelevant antibody.
Figure 10A:
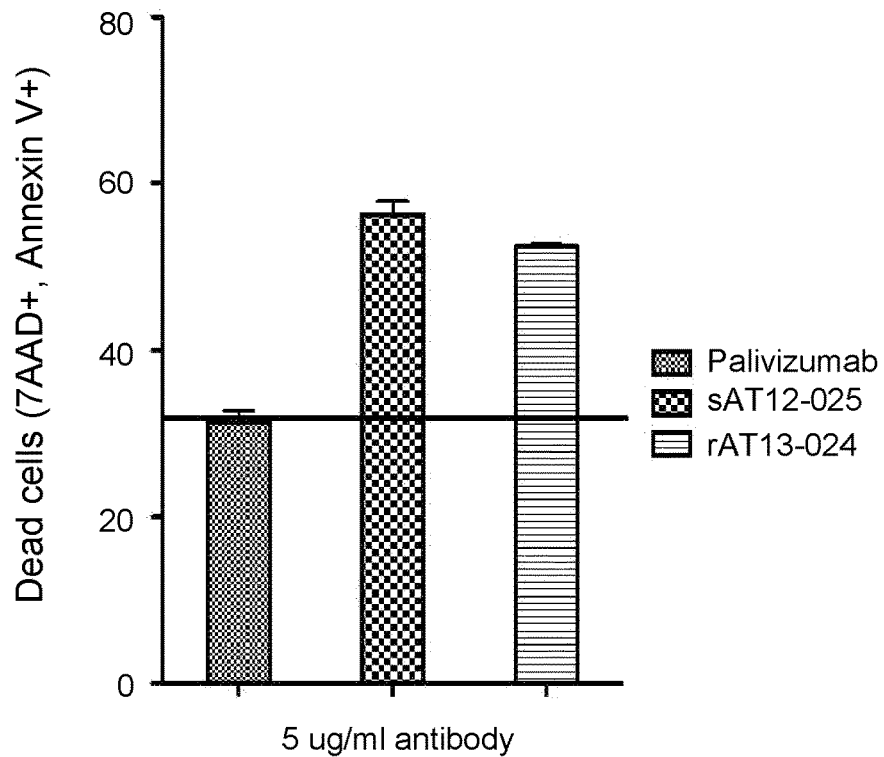
FIG. 10. a) Besides killing of THP-1 cells, AT12-025 does also induce death of primary tumor cells, similar to AT13-024. Leukemic blasts, isolated from a patient with AML-M5 at diagnosis, were incubated with AT12-025 or AT13-024 (5 ug/ml) for 24 hours at 37° C., after which cells were stained with 7AAD and AnnexinV to determine the amount of dead cells (7AAD and Annexin V double-positive). b) In addition, Lactate dehydrogenase (LDH) can be used as a marker to determine dying cells. Leukemic blasts, isolated from a patient with AML-M0, were incubated with AT13-024 or the RSV antibody palivizumab for 18 hrs, after which LDH release was measured. These two experiments show that AT13-024, but not palivizumab, induced death of leukemic blasts and that this property was not restricted to one type of AML but includes different FAB classifications (M0 to M5).
Figure 10B:
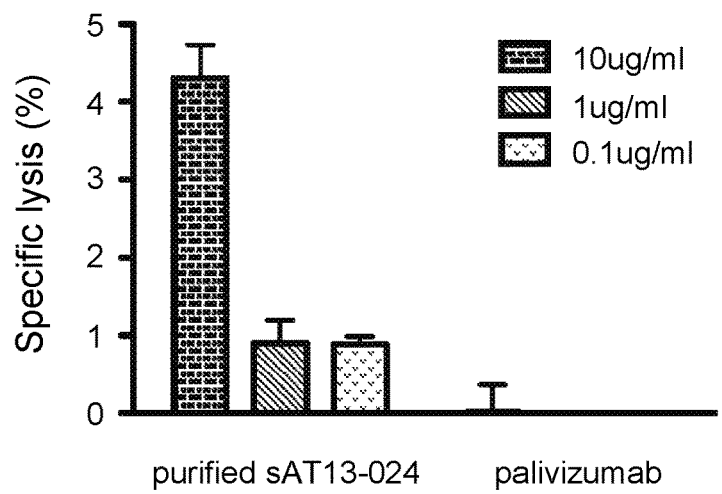

In Example 1, it was also determined that antibodies AT12-023 and AT12-025 of donor 59 killed THP-1 cells (Table 5 and FIGS. 7-9). Subsequently, we have tested whether the other antibodies of donor 59, as well as the antibodies of donor 58, could also kill THP-1 cells, using the same Materials & Methods as in Example 1. As shown in Tables 9B-10, in addition to AT12-023 and AT12-025 also antibody AT13-031 (donor 59), as well as antibodies AT13-033, AT13-035, AT13-036 and AT13-037 (donor 58) appear to be able to kill THP-1 cells.

Figure 16:
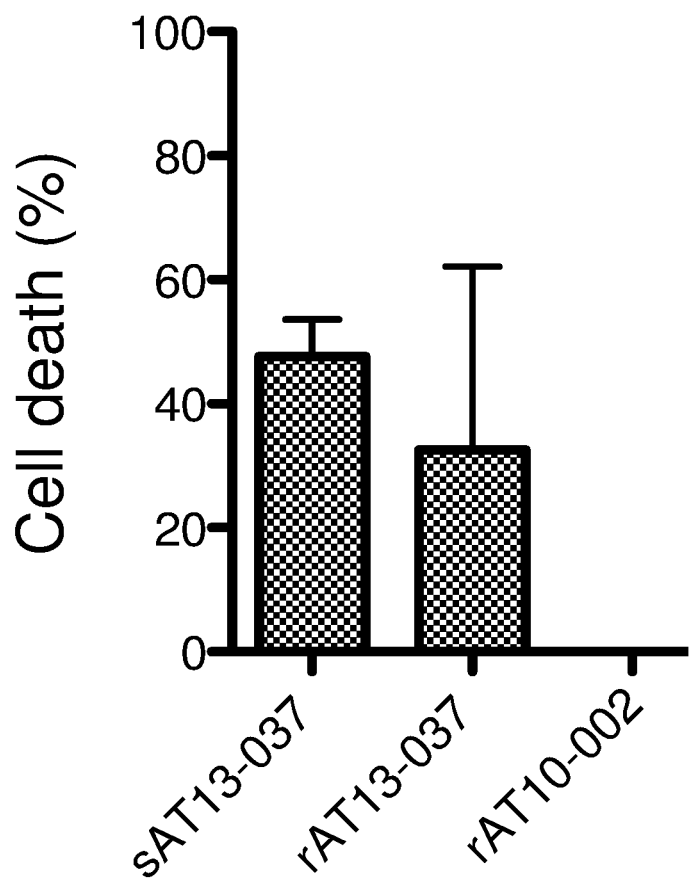
FIG. 16. Antibody AT13-037 induces death of primary blasts. Leukemic blasts, isolated from an AML patient at diagnosis (BL-038; AML-M5), were incubated with antibodies purified from the supernatants of the parental B cell clone (sAT13-037) or with the recombinant antibody (rAT13-037) at a concentration of 5 ug/ml for 4 hours at 37° C., after which cells were stained with the death cell marker Dapi. To quantify death of cells a standard amount of beads was added. Recombinant influenza specific rAT10-002 was used as a negative control.

The capability of inducing death of primary AML blasts was also tested (Materials & Methods: see Example 1). Similar to some of the antibodies obtained from donor 59, some of the antibodies derived from donor 58 are also capable of inducing cell death of primary AML cells. This is shown in FIG. 16 for antibody AT13-037, in both forms (purified B cell supernatant (sAT13-037) and recombinant produced antibody (rAT13-037); both in the IgG3 confirmation). The leukemic cells are derived from the bone marrow of a newly diagnosed AML patient, FAB classification AML-M5.

Example 4

Figure 17B:
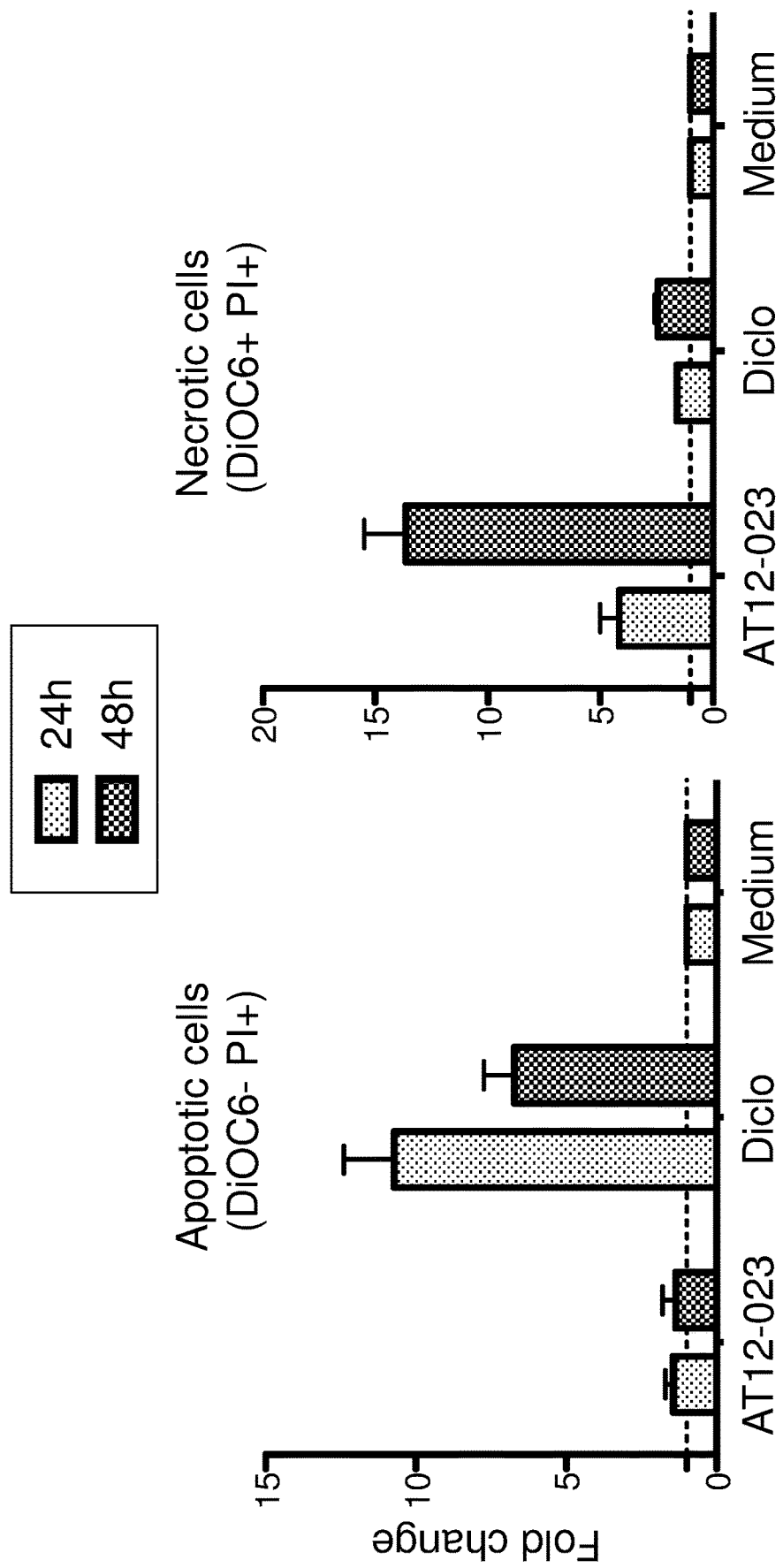
FIG. 17. Cytotoxic antibodies induced a non-apoptotic death pathway. a) Phase contrast imaging of THP-1 cells. THP-1 cells were incubated with the non-cytotoxic AML-specific antibody AT13-023 (left panel) or the cytotoxic antibody AML-specific AT13-037 (right panel). Interaction was visualized using time-lapse imaging and demonstrated swelling of target cells after which cells died. Stills were taken after 4 hours of incubation, with blue arrows indicating large cells that are dead. b) Double staining with DiOC6 and PI showed that cytotoxic antibodies do not induce apoptosis. THP-1 cells were incubated with the cytotoxic AML-specific antibody AT12-023, with diclofenac (that induces apoptosis in THP-1 cells) or with medium only. Cells undergoing apoptosis first loose their mitochondrial membrane potential (loss of DiOC6 stain) after which they become permeable (PI positive), as can be seen after incubation of THP-1 cells with diclofenac. THP-1 cells incubated with AT12-023 showed increased membrane permeability (PI+) but maintained mitochondrial membrane potential (DioC6+), indicating the induction of a non-apoptotic cell death pathway. c) To confirm the non-apoptotic nature of the death pathway induced we tested the involvement of caspases in cell death induction. Cell death of THP-1 cells by AML-specific antibodies could not be prevented with the pan caspase inhibitors Q-VD-OPh (left panel) or Z-VAD-fmk (right panel).
Figure 17C:
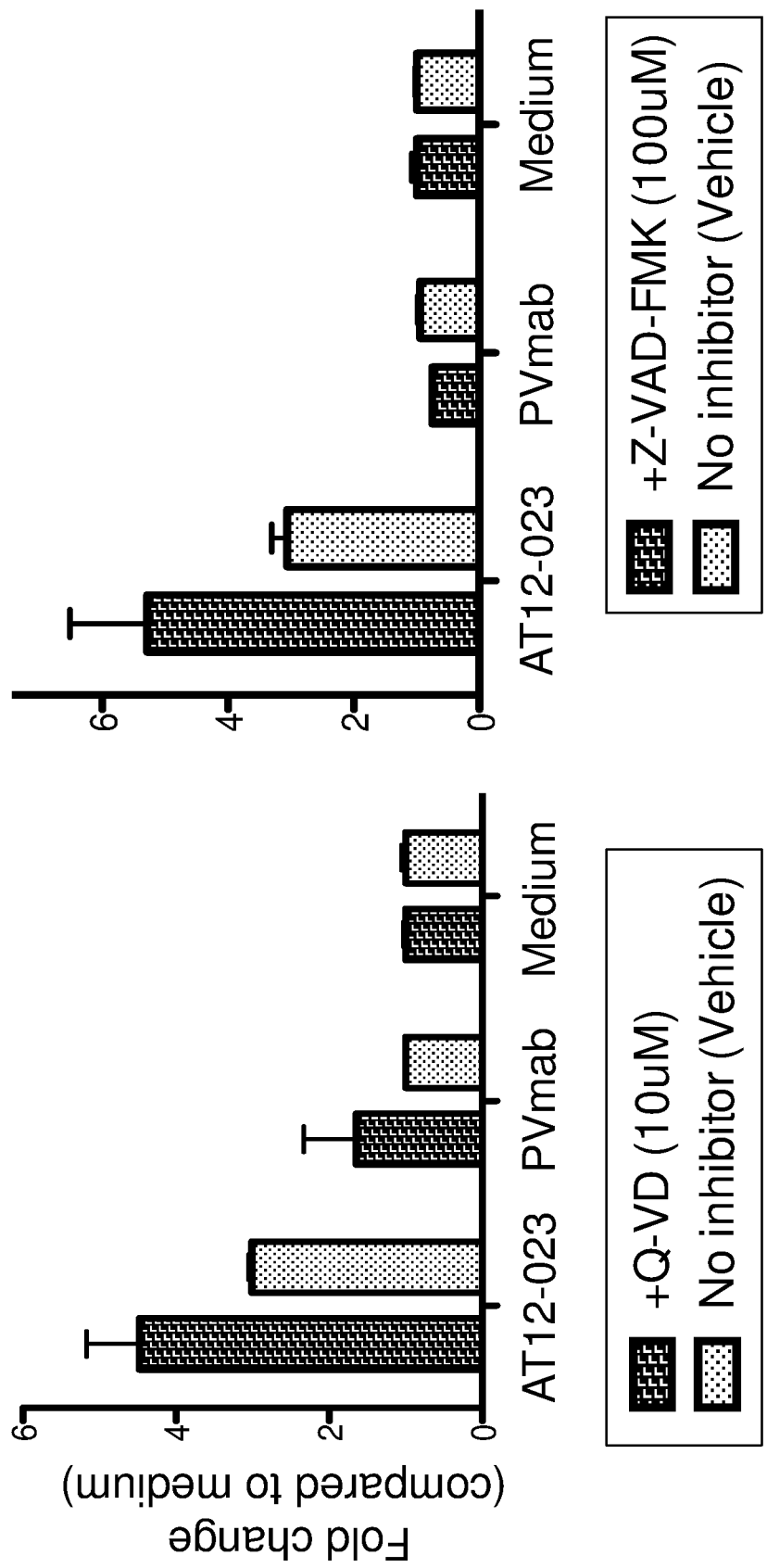

In Vitro Activity of AML Antibodies is Rapid and Involves a Non-Apoptotic Cell Death Pathway To investigate the pathway through which several of the above-mentioned antibodies induced death of their target cells, we visualized death of target cells with time-lapse microscopy (FIG. 17a). We observed that within a few minutes after incubation with antibody AT13-037, cells started to swell and then died. This suggested that antibodies according to the invention activated pathways other than the classical apoptosis pathways, as apoptotic cells shrink rather than swell. To further investigate this we performed double staining with the cell death markers DiOC6 and propidiumiodide (PI). Cells engaged to undergo apoptosis first loose mitochondrial charge (which can be visualized by the loss of DiOC6 binding) before membrane permeability increases (visualized by propidium iodide (PI) staining), while cells undergoing necrosis loose their membrane integrity (PI positive) but not immediately the mitochondrial membrane potential. As diclofenac is known to induce apoptosis of THP-1 cells, we used diclofenac as a positive control. Diclofenac-treated, apoptotic THP-1 cells became DiOC6-negative (lost mitochondrial membrane potential), but maintained membrane integrity. Upon incubation with the AML-specific cytotoxic antibody AT12-023 mitochondrial membrane potential was maintained (DiOC6-positive) while the membrane permeability of THP-1 cells increased (PI-positive). Thus, AML-antibody treated THP-1 cells became PI-positive while maintaining mitochondrial membrane potential (FIG. 17b, right panel) indicating the activation of a non-apoptotic death pathway. Indeed, death of THP-1 cells by cytotoxic AML-specific antibody treatment could not be prevented by incubating the cells with the pan caspase inhibitors Z-VAD-fmk or QVD-OPh (FIG. 17c).

Cell Death Mediated Through Interference with the Target Cell Membrane

Figure 18:
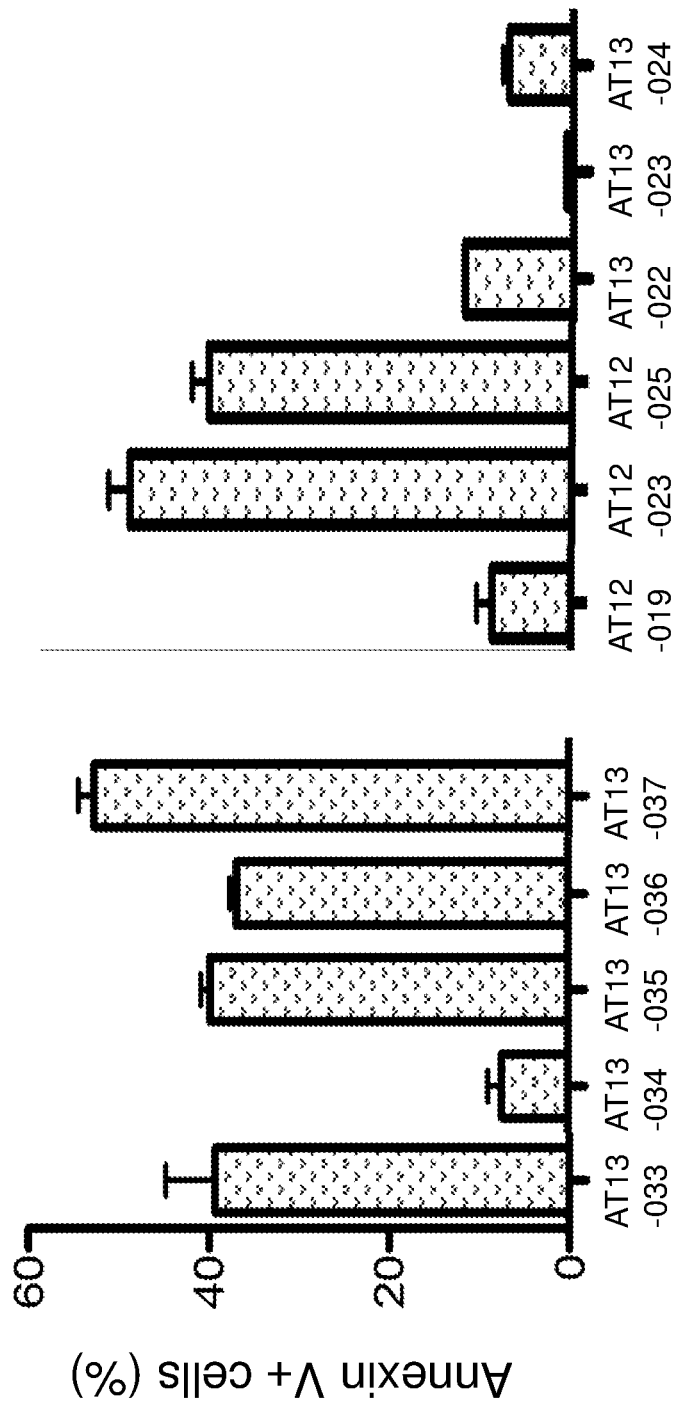
FIG. 18. Cell death induced by AML-specific antibodies also occurred at 4° C., suggesting the involvement of a passive process. This was true for all antibodies except AT13-031, which is cytotoxic at 37° C. only (not shown). Negative controls included the AML-specific non-cytotoxic antibodies AT13-034, AT12-019, AT13-022, AT13-023 and AT13-024.

Non-apoptotic death pathways include necroptosis and oncosis. Necroptosis is, similar to apoptosis, an active cell death pathway that depends on the activation of defined molecular pathways including the activation of receptor-interacting protein kinase 3 (RIPK3). To investigate whether AML-antibody-induced cell death was dependent on the activation of intracellular molecular pathways we tested whether antibody-induced cytotoxicity was dependent of temperature. We found that under these experimental conditions the cytotoxic activities of at least antibodies AT13-033, AT13-035, AT13-036, AT13-037, AT12-023 and AT12-025 were equally potent at 4° C. as compared to their activities at 37° C. (FIG. 18), suggesting that at least these antibodies induced cell death by a passive process. Of note, the cytotoxic activity of antibody AT13-031 was significantly more potent at 37° C. as compared to 4° C. However, since antibody AT13-031 does induce death of AML cells in the presence of apoptosis inhibitors (such as the pan caspase inhibitors Q-VD-OPh or Z-VAD-fmk), it is clear that antibody AT13-031 is also able to diminish proliferation of AML cells independently from apoptosis.

Figure 19A:
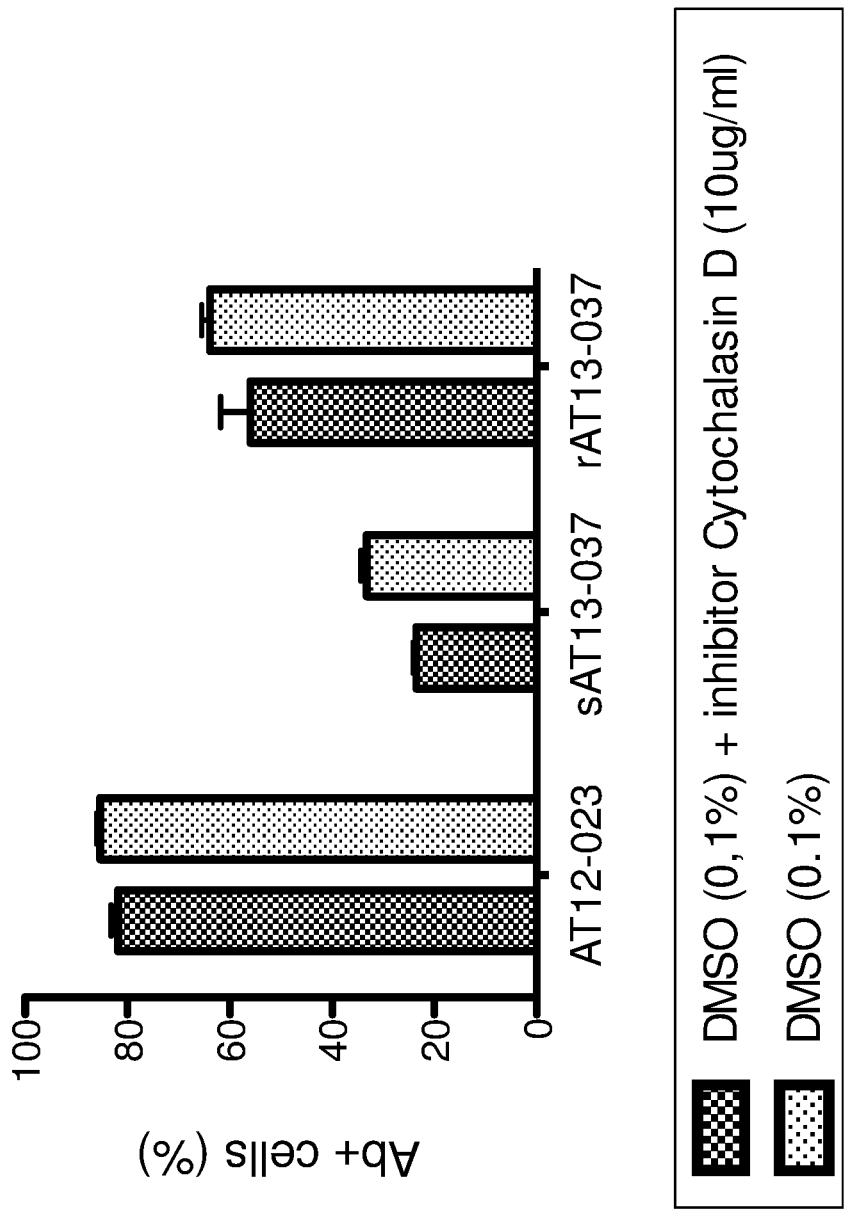
FIG. 19. (a) Incubation of target cells with cytochalasin D did not inhibit binding of the antibodies. THP-1 cells were incubated with cytochalasin D, after which AML-specific antibodies AT12-023, AT13-031 and AT13-037 were added. (b) Pre-incubation of the target cells with the membrane stabilizing agent cytocholasin D did protect the THP-1 cells against cell death by the AML-specific cytotoxic antibodies.
Figure 19B:
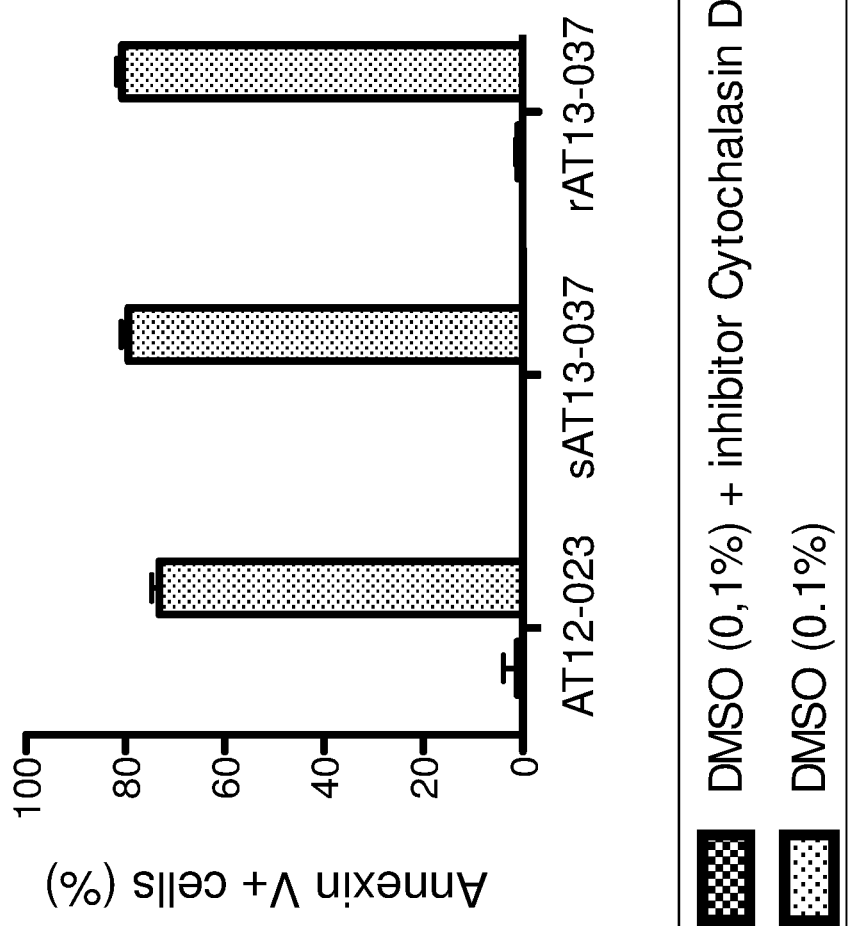

Oncosis is a mode of cell death characterized by swelling of the cell, through selective membrane injury, resulting in increased membrane permeability and ultimately cell death. Oncosis-inducing antibodies have been described that mediate cell death by forming large pores in the membrane through destabilization of the membrane (Hernandez et al, 2011). Cytocholasin D is an actin polymerization inhibitor that can stabilize the cytoskeleton. Treatment of the target cell line THP-1 with cytochalasin D did not prevent antibody binding to these cells (FIG. 19a), however, it did prevent death of the target cells (FIG. 19b). Thus, membrane stabilisation protects the target cells against the cytotoxic activity of our antibodies.

Example 5

One of the Targets Recognized by Our Antibodies is snRNP200

Figure 20A:
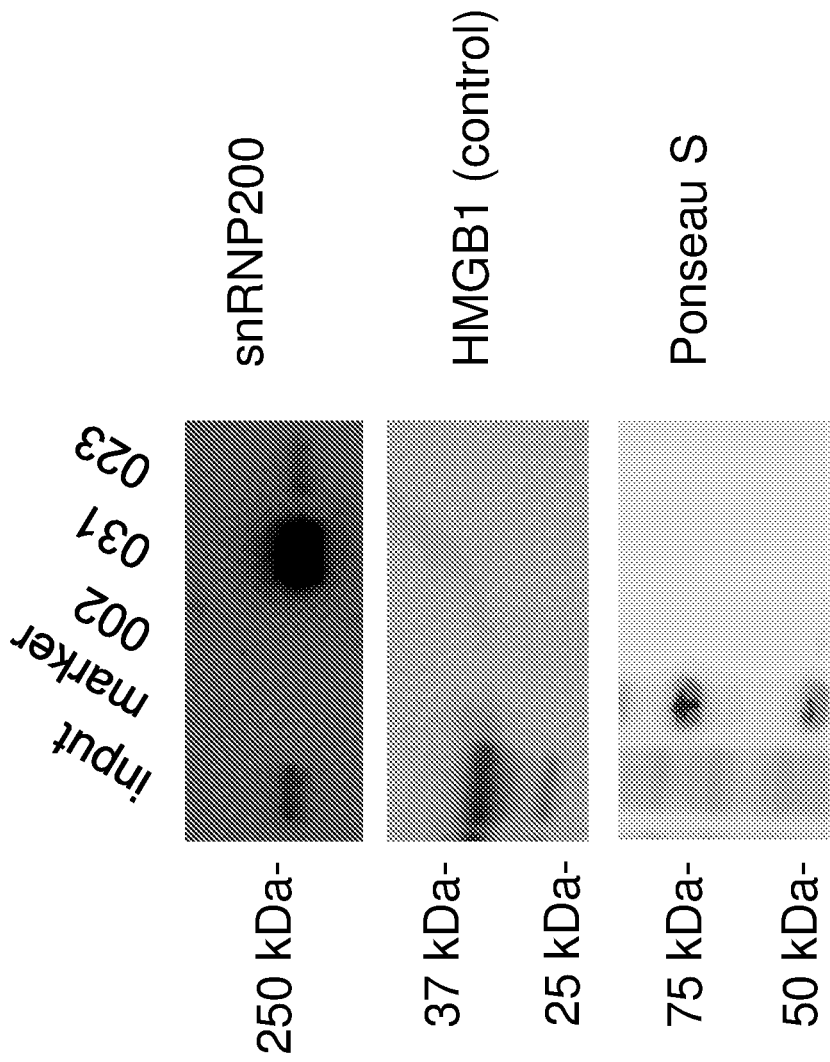
FIG. 20. Target verification of AT12-023, AT13-031 and AT13-037. a) THP-1 membrane lysate was incubated with AT12-023 and AT13-031, with the influenza-specific antibody AT10-002 or with marker alone. Western blot analysis including mouse-anti-human snRNP200 (and HMGB1 as a negative control) revealed specific binding of AT12-023 and AT13-031 to snRNP200. b) AML specific antibodies AT12-019, AT12-023, AT13-031 and AT13-037 or commercially available snRNP200-specific antibodies snRNP200 453 and snRNP200 454 were coated on an ELISA plate, incubated with a snRNP200-flag construct for capturing and with anti-flag HRP for detection. AT12-023, AT13-031 and AT13-037 specifically bound snRNP200, whereas negative controls and for example AT12-019 did not.
Figure 20B:
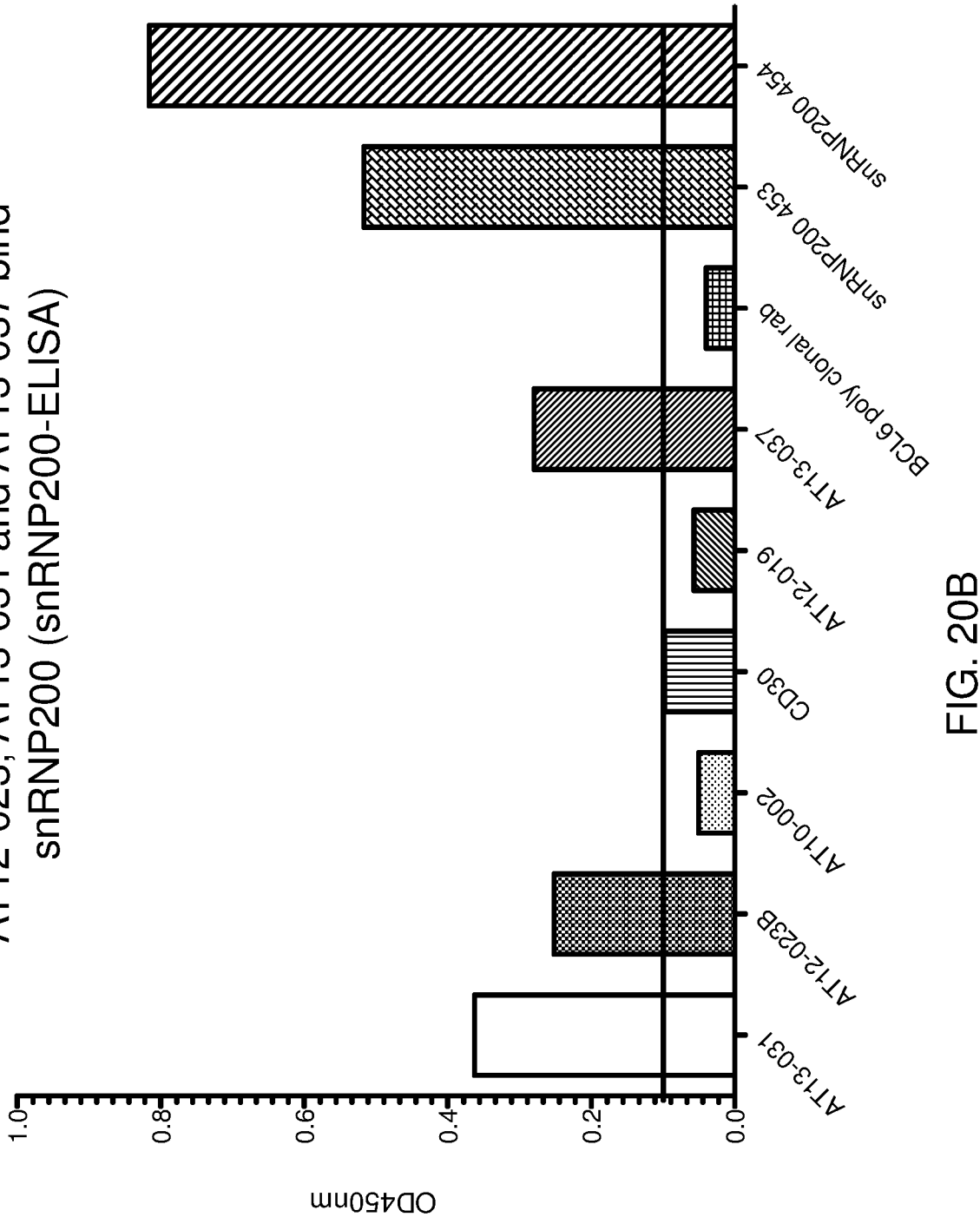
Figure 21:
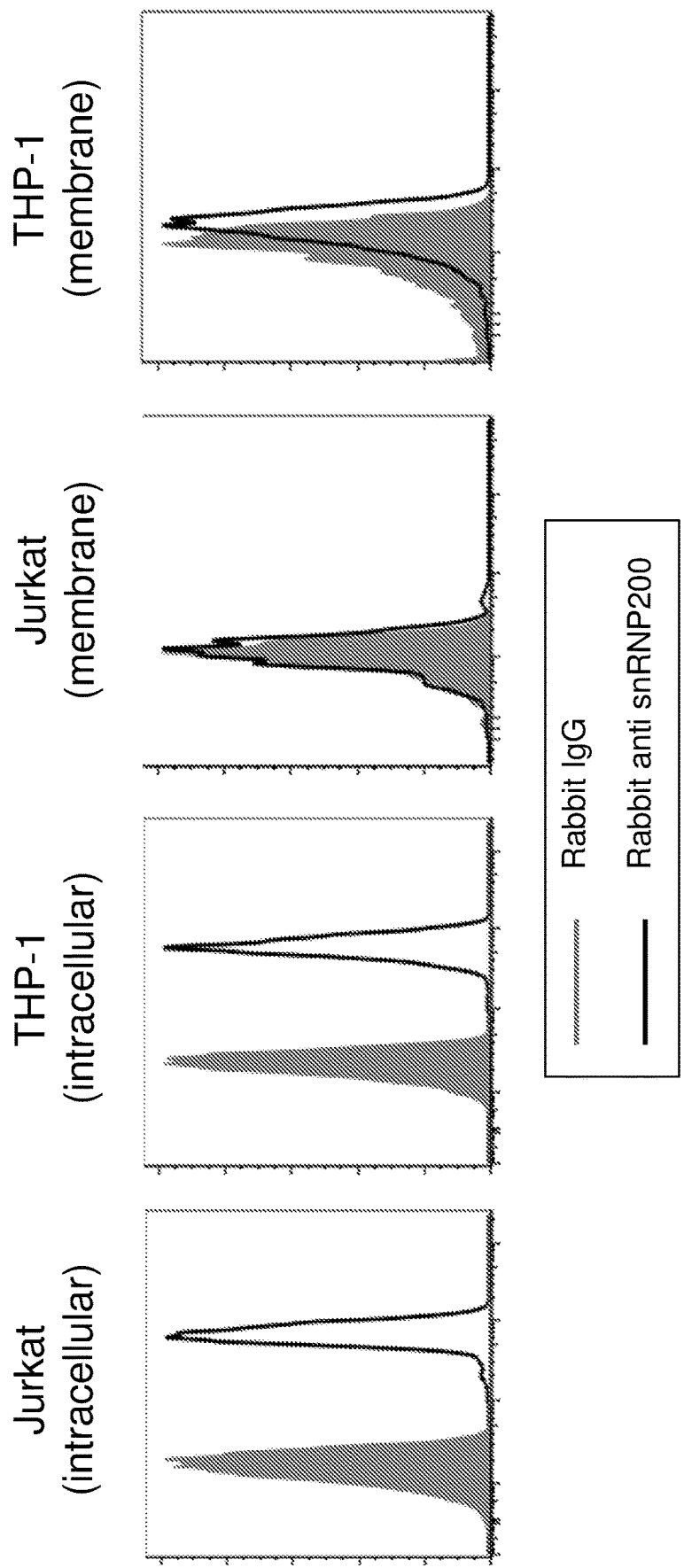
FIG. 21. THP-1 cells express snRNP200 on their membrane. THP-1 cells and Jurkat cells were stained with a commercially available human-anti-mouse snRNP200 antibody. Intracellular staining of Jurkat cells and THP-1 cells showed nuclear staining, as expected (left panels). However, membrane staining of snRNP200 was restricted to THP-1 cells (right panels).

We then set out to determine the target recognized by several AML-specific antibodies. For this we used immunoprecipitation of cell membrane lysates of THP-1 cells with AT12-023 and AT13-031. We found a clear protein band at 250 kD that was sent for mass-spectometry analysis which revealed snRNP200 as the target antigen which could be confirmed by Western blot analysis (FIG. 20a). We developed an ELISA, to verify snRNP200 as the target of some of the AML antibodies. With this ELISA we found that in addition to AT12-023 and AT13-031, AT13-037 specifically recognizes snRNP200 (FIG. 20b). Other AML specific antibodies like AT12-019 did not recognize snRNP200 as target antigen.

snRNP200 is part of the spliceosome in all eukaryotic cells and is therefore expected to be located in the nucleus. To confirm that AML cells express this protein on their cell surface we stained the cell membrane of THP-1 cells with a commercially available, anti-snRNP200 antibody. FIG. 21 shows that the anti snRNP200 antibody is indeed binding to the membrane of the AML cells, but not to the Jurkat cell line. As expected, as snRNP200 is a nuclear protein, it did bind intracellularly to the Jurkat and THP-1 cell lines (FIG. 21).

All eukaryotic cells have snRNP200 (also known as U5-snRNP) protein in the nucleus, as part of the spliceosome (Kattah, 2010). The spliceosome consists of a number of proteins. At least one of these proteins, U1-snRNP, has been described to be expressed on apoptotic cells in patients with systemic lupus erythematosus (SLE) and mixed connective tissue disease (MCTD) leading to autoimmune responses (Kattah, 2010).

We propose that snRNP200 expression by AML cells has triggered an allo-immune response (graft vs leukemia response) that has kept the patients in durable remission. Therefore, this protein can now be used as a new AML target. Moreover, since antibodies AT12-023 and AT13-031 specifically recognize snRNP200 and also recognize B-NHL cells, snRNP200 can now also be used as a target for B-NHL.

TABLE 1A

Preferred anti-AML antibodies according to the invention
(CDR numbering according to Kabat et al. 1991)

| SEQ ID NO. | Antibody | Identity | Sequence |
|---|---|---|---|
| 1 | AT12-023 | Heavy chain CDR1 | GYYWS |
| 2 | AT12-025 | Heavy chain CDR1 | GYYWS |
| 3 | AT13-024 | Heavy chain CDR1 | SYGMH |
| 4 | AT12-019 | Heavy chain CDR1 | SYAMS |
| 5 | AT13-022 | Heavy chain CDR1 | SYGMH |
| 6 | AT13-023 | Heavy chain CDR1 | GYFWT |
| 7 | AT13-031 | Heavy chain CDR1 | GYYWS |
| 8 | AT12-020 | Heavy chain CDR1 | TYSMN |
| 9 | AT13-033 | Heavy chain CDR1 | NYGMH |
| 10 | AT13-034 | Heavy chain CDR1 | SHAIH |
| 11 | AT13-035 | Heavy chain CDR1 | SYGMH |
| 12 | AT13-036 | Heavy chain CDR1 | SYSMN |
| 13 | AT13-037 | Heavy chain CDR1 | TYGMH |
| 14 | AT12-023 | Heavy chain CDR2 | EINHSGSTNYNPSLKS |
| 15 | AT12-025 | Heavy chain CDR2 | EINHSGSTNYNPSLKS |
| 16 | AT13-024 | Heavy chain CDR2 | FIRYDGSNKYFADSVRG |
| 17 | AT12-019 | Heavy chain CDR2 | TIRASGGSTSYADSVKG |
| 18 | AT13-022 | Heavy chain CDR2 | ISYDGSNKYYADSVKG |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 19 | AT13-023 | Heavy chain CDR2 | ETVHSGGTNYNPSLKS |
| 20 | AT13-031 | Heavy chain CDR2 | EINHSGSTNYNPSLKS |
| 21 | AT12-020 | Heavy chain CDR2 | SISSSSGYIYYADSVKG |
| 22 | AT13-033 | Heavy chain CDR2 | VISHDGSKTYYGHSVKG |
| 23 | AT13-034 | Heavy chain CDR2 | LIWYDGSNNYYADSVKG |
| 24 | AT13-035 | Heavy chain CDR2 | VISYDGSNKYYADSVKG |
| 25 | AT13-036 | Heavy chain CDR2 | SISSSSTYIYYADSVKG |
| 26 | AT13-037 | Heavy chain CDR2 | VIWYDGSNTYYADSVKG |
| 27 | AT12-023 | Heavy chain CDR3 | GRSTSPLDYYYYMDV |
| 28 | AT12-025 | Heavy chain CDR3 | GSMARPKPFDY |
| 29 | AT13-024 | Heavy chain CDR3 | DPQERIYYSDTSGYLDY |
| 30 | AT12-019 | Heavy chain CDR3 | SPAMIRGVRGGDYFDY |
| 31 | AT13-022 | Heavy chain CDR3 | DGKGIVVIYYYYGMDV |
| 32 | AT13-023 | Heavy chain CDR3 | GLNSPFDY |
| 33 | AT13-031 | Heavy chain CDR3 | GPRGMYSSSSGDY |
| 34 | AT12-020 | Heavy chain CDR3 | DGTFSYYYYMDV |
| 35 | AT13-033 | Heavy chain CDR3 | AGLNYYGNLLSNYFYYGMDV |
| 36 | AT13-034 | Heavy chain CDR3 | ARDGCTGGSCCYFDN |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 37 | AT13-035 | Heavy chain CDR3 | AKDSYYYGSGRRWGYYFDY |
| 38 | AT13-036 | Heavy chain CDR3 | ARRREVGRDGYSLYPRGYHYGMDV |
| 39 | AT13-037 | Heavy chain CDR3 | ARGRGYSAQGNRNRAYYFDY |
| 40 | AT12-023 | Light chain CDR1 | QGDFLRSYYAS |
| 41 | AT12-025 | Light chain CDR1 | RASQSISRYLN |
| 42 | AT13-024 | Light chain CDR1 | RASQSISSWLA |
| 43 | AT12-019 | Light chain CDR1 | RASQAFSSYLV |
| 44 | AT13-022 | Light chain CDR1 | SGDKLGDKYAC |
| 45 | AT13-023 | Light chain CDR1 | RASQGIRNVLG |
| 46 | AT13-031 | Light chain CDR1 | RASQGIRNDLG |
| 47 | AT12-020 | Light chain CDR1 | RASQDISSSLA |
| 48 | AT13-033 | Light chain CDR1 | TGTSSDIGGYNYVS |
| 49 | AT13-034 | Light chain CDR1 | RASQSISNNLG |
| 50 | AT13-035 | Light chain CDR1 | QGDSLRSYYAS |
| 51 | AT13-036 | Light chain CDR1 | TGTSSDVGGYNYVS |
| 52 | AT13-037 | Light chain CDR1 | RASQSVSSNLA |
| 53 | AT12-023 | Light chain CDR2 | GKNKRPS |
| 54 | AT12-025 | Light chain CDR2 | AASSLQS |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 55 | AT13-024 | Light chain CDR2 | KASSLES |
| 56 | AT12-019 | Light chain CDR2 | ATSTLQG |
| 57 | AT13-022 | Light chain CDR2 | QDSKRPS |
| 58 | AT13-023 | Light chain CDR2 | AASSLQS |
| 59 | AT13-031 | Light chain CDR2 | AAVSLQS |
| 60 | AT12-020 | Light chain CDR2 | AASTLQS |
| 61 | AT13-033 | Light chain CDR2 | EVTKRPS |
| 62 | AT13-034 | Light chain CDR2 | GASTRAT |
| 63 | AT13-035 | Light chain CDR2 | GKNNRPS |
| 64 | AT13-036 | Light chain CDR2 | DVNDRPS |
| 65 | AT13-037 | Light chain CDR2 | GAFTRVT |
| 66 | AT12-023 | Light chain CDR3 | NSRDRSGNHLV |
| 67 | AT12-025 | Light chain CDR3 | QQSYSTPRT |
| 68 | AT13-024 | Light chain CDR3 | QQYNTYPYT |
| 69 | AT12-019 | Light chain CDR3 | QQYYSYPPT |
| 70 | AT13-022 | Light chain CDR3 | QAWDSSTVVF |
| 71 | AT13-023 | Light chain CDR3 | LQHNSHPRT |
| 72 | AT13-031 | Light chain CDR3 | LQHNSYPRT |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 73 | AT12-020 | Light chain CDR3 | QQYYSYPPT |
| 74 | AT13-033 | Light chain CDR3 | SSYAGSNDLL |
| 75 | AT13-034 | Light chain CDR3 | QQYNNWPRLT |
| 76 | AT13-035 | Light chain CDR3 | NSRDSSGNHVV |
| 77 | AT13-036 | Light chain CDR3 | SSYTRSNTVI |
| 78 | AT13-037 | Light chain CDR3 | QQYNDRPPYT |
| 79 | AT12-023 | Heavy chain | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRSTSPLDYYYYMDVWAKGTTVTVSS |
| 80 | AT12-025 | Heavy chain | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGSMARPKPFDYWGQGTLVTVSS |
| 81 | AT13-024 | Heavy chain | QVQLVESGGGVVQPGRSLRLSCAASGFTFSSYGMHWVRQAPGKGLEWVAFIRYDGSNKYFADSVRGRFTISRDNSKNTLFLQMNSLRAEDTAVYYCAKDPQERIYYSDTSGYLDYWGQGTLVTVSS |
| 82 | AT12-019 | Heavy chain | EVHLLESGGGLVQPGGSLRLSCAASGFTFSSYAMSWVRQAPGKGLEWVSTIRASGGSTSYADSVKGRFTISRDNSQSRLYLQMNSLTAEDTAVYYCAKSPAMIRGVRGGDYFDYWGQGTLVTVSS |
| 83 | AT13-022 | Heavy chain | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKDGKGIVVIYYYYGMDVWGQGTTVTVSS |
| 84 | AT13-023 | Heavy chain | QVQLQQWGAGLLKPSETLSLTCAVYGGSFSGYFWTWIRQPPGKGLEWIGETVHSGGTNYNPSLKSRVTISVDTSKNQFSLRLNSVTAADTAVYYCVRGLNSPFDYWGQGTLVTVSS |
| 85 | AT13-031 | Heavy chain | QVQLQQWGAGLLKPSETLSLTCAVYGGSFSGYYWSWIRQPPGKGLEWIGEINHSGSTNYNPSLKSRVTISVDTSKKQFSLKLSSVTAADTAVYYCARGPRGMYSSSSGDYWGQGTLVTVSS |
| 86 | AT12-020 | Heavy chain | EVQLVESGGGLVKPGGSLRLSCAASGFTFSTYSMNWVRQAPGKGLEWVSSISSSSGYIYYADSVKGRFTISRDNAKNSLYLQMNSLRAEDTAVYYCARDGTFSYYYYMDVWGKGTTVTVSS |
| 87 | AT13-033 | Heavy chain | QVQLVESGGGVVQPGRSLRLSCAVSGLSFRNYGMHWVRQAPGKGLEWVAVISHDGSKTYYGHSVKGRFTISRDKSKTMLFLQMNSLRPEDTAVYYCAKAGLNYYGNLLSNYFYYGMDVWGQGTTVTVSS |
| 88 | AT13-034 | Heavy chain | QVHLVESGGGVVQPGTSLRLSCAASEFTFSSHAIHWVRQAPGKGLEWVALIWYDGSNNYYADSVKGRFTISRDSSKNTVHLQMNSLRVEDTAVYYCARDGCTGGSCCYFDNWGQGTLVTVSS |
| 89 | AT13-035 | Heavy chain | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKDSYYYGSGRRWGYYFDYWGQGTLVTVSS |
| 90 | AT13-036 | Heavy chain | EVQLVESGGGLVKPGGSLRLSCAASGFTFSSYSMNWVRQAPGKGLEWVSSISSSSTYIYYADSVKGRFTISRDNARNSLYLQMNSLRAEDTAVYYCARRREVGRDGYSLYPRGYHYGMDVWGQGTTVTVSS |
| 91 | AT13-037 | Heavy chain | QVQLVESGGGVVQPGRSLRLSCAASGFTFSTYGMHWVRQAPGKGLEWVAVIWYDGSNTYYADSVKGRFTISRDNSKNTLYLQIKSLRAEDTAVYYCARGRGYSAQGNRNRAYYFDYWGQGTLVTVSS |
| 92 | AT12-023 | Light chain | SSELTQDPAVSVALGQTVRITCQGDFLRSYYASWYQQKPGQAPVLVIFGKNKRPSGIPDRFSGSSSGNTASLTITGAQAEDEADYYCNSRDRSGNHLVFGGGTKLTVL |
| 93 | AT12-025 | Light chain | DIQMTQSPSSLSASVGDRVTITCRASQSISRYLNWYQQKPGKAPKLLIYAASSLQSGVPSRFSGSGSGTDFTLTISSLQPEDFATYYCQQSYSTPRTFGPGTKVDIK |
| 94 | AT13-024 | Light chain | DIQMTQSPSTLSASVGDRVTITCRASQSISSWLAWYQQKPGKAPKLLIYKASSLESGVPSRFSGTGSGTEFTLTISSLQPDDFATYYCQQYNTYPYTFGQGTKLEIK |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 95 | AT12-019 | Light chain | AIRLTQSPSSVSASTGDRVTITCRASQAFSSYLWYQQKPGKAPNLLIYATSTLQGGVPSRFSGSGSGTDFTL TISNLQSEDFATYYCQQYYSYPPTFGQGTKLEIK |
| 96 | AT13-022 | Light chain | SYELTQPPSVSVSPGQTASITCSGDKLGDKYACWYQQKPGQSPVLVIYQDSKRPSGIPERFSGSNSGNTATL TISGTQAMDEADYYCQAWDSSTVVFGGGTKLTVL |
| 97 | AT13-023 | Light chain | DIQMTQSPSSLSASVGDRVTITCRASQGIRNVLGWYQQKPGKAPKCLIYAASSLQSGVPSRFSGSGSGTEFTL TISSLQPEDFATYYCLQHNSHPRTFGQGTKVEIK |
| 98 | AT13-031 | Light chain | DIQMTQSPSSLSASVGDRVTITCRASQGIRNDLGWYQQKPGKAPKRLIYAAVSLQSGVPSRFSGSGSGTEFT LTISSLQPEDFATYYCLQHNSYPRTFGQGTKLEIK |
| 99 | AT12-020 | Light chain | AIRMTQSPSSFSASTGDRVTITCRASQDISSSLAWYQQKPGKAPKLLIYAASTLQSGVPSRFSGSGSGTDFTL TISCLQSEDFATYYCQQYYSYPPTFGQGTRLEIK |
| 100 | AT13-033 | Light chain | QSALTQPPSASGSPGQSVTISCTGTSSDIGGYNYVSWYQHHPGKAPKLMIYEVTKRPSGVPDRFSGSKSGNT ASLTVSGLQAEDEAHYYCSSYAGSNDLLFGGGTKLTVL |
| 101 | AT13-034 | Light chain | EVVMTQSPATLSVSPGERATLSCRASQSISNNLGWYQQKPGQAPRLLIYGASTRATGIPGRFSGSGSGTEFT LTIYSLQSEDFAVYYCQQYNNWPRLTFGGGTKVEIK |
| 102 | AT13-035 | Light chain | SSELTQDPAVSVALGQTVRITCQGDSLRSYYASWYQQKPGQAPVLVIYGKNNRPSGIPDRFSGSSSGNTASL TITGAQAEDEADYYCNSRDSSGNHVVFGGGTKLTVL |
| 103 | AT13-036 | Light chain | QSALTQPASVSGSPRQSITISCTGTSSDVGGYNYVSWYQQLPGKAPKLMIYDVNDRPSGVSIRFSGSKSGNT ASLTISGLQAEDEADYYCSSYTRSNTVIFGGGTKLTVL |
| 104 | AT13-037 | Light chain | EIVMTQSPATLSVSPGERVILSCRASQSVSSNLAWYQQKPGQPPRLLIYGAFTRVTGVPARFSGSGSGTEFTL TISSLQSEDFAVYYCQQYNDRPPYTFGQGTKLEIK |
| 105 | AT12-023 | Heavy chain CDR1 | ggt tac tac tgg agc |
| 106 | AT12-025 | Heavy chain CDR1 | ggt tat tac tgg agc |
| 107 | AT13-024 | Heavy chain CDR1 | agc tat ggc atg cac |
| 108 | AT12-019 | Heavy chain CDR1 | agc tat gcc atg agt |
| 109 | AT13-022 | Heavy chain CDR1 | agc tat ggc atg cac |
| 110 | AT13-023 | Heavy chain CDR1 | ggt tac ttc tgg acc |
| 111 | AT13-031 | Heavy chain CDR1 | ggt tac tac tgg agc |
| 112 | AT12-020 | Heavy chain CDR1 | acc tat agc atg aac |
| 113 | AT13-033 | Heavy chain CDR1 | aat tat ggc atg cac |
| 114 | AT13-034 | Heavy chain CDR1 | tcc cat gcc ata cac |
| 115 | AT13-035 | Heavy chain CDR1 | agc tat ggc atg cac |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 116 | AT13-036 | Heavy chain CDR1 | agt tat agc atg aac |
| 117 | AT13-037 | Heavy chain CDR1 | acc tat ggc atg cac |
| 118 | AT12-023 | Heavy chain CDR2 | gaa atc aat cat agt gga agc acc aac tac aac ccg tcc ctc aag agt |
| 119 | AT12-025 | Heavy chain CDR2 | gaa atc aat cat agt gga agc acc aac tac aac ccg tcc ctc aag agt |
| 120 | AT13-024 | Heavy chain CDR2 | ttt ata cgg tat gat gga agt aat aaa tac ttt gca gac tcc gtg agg ggc |
| 121 | AT12-019 | Heavy chain CDR2 | act att agg gct agt ggt ggt agc aca agc tac gca gac tcc gtg aag ggc |
| 122 | AT13-022 | Heavy chain CDR2 | ata tca tat gat gga agt aat aaa tac tat gca gac tcc gtg aag ggc |
| 123 | AT13-023 | Heavy chain CDR2 | gaa acc gtt cat agt gga ggc acc aac tac aac ccg tcc ctc aag agt |
| 124 | AT13-031 | Heavy chain CDR2 | gaa atc aat cat agt gga agc acc aac tac aac ccg tcc ctc aag agt |
| 125 | AT12-020 | Heavy chain CDR2 | tcc att agt agt agt agt ggt tac ata tac tac gca gac tca gtg aag ggc |
| 126 | AT13-033 | Heavy chain CDR2 | gtc att tcg cat gat gga agt aag aca tac tat gga cac tcc gtg aag ggc |
| 127 | AT13-034 | Heavy chain CDR2 | ctt ata tgg tat gat gga agt aat aat tat tat gca gac tcc gtg aag ggc |
| 128 | AT13-035 | Heavy chain CDR2 | gtt ata tca tat gat gga agt aat aaa tac tat gca gac tcc gtg aag ggc |
| 129 | AT13-036 | Heavy chain CDR2 | tcc att agt agt agt agt act tac ata tac tac gca gac tca gtg aag ggc |
| 130 | AT13-037 | Heavy chain CDR2 | gtt ata tgg tat gat gga agt aat aca tac tat gca gac tcc gtg aag ggc |
| 131 | AT12-023 | Heavy chain CDR3 | ggc cgt agt acc agc ccg ctc gac tac tac tac tac tac atg gac gtc |
| 132 | AT12-025 | Heavy chain CDR3 | ggc tca atg gca aga ccc aag cca ttt gac tac |
| 133 | AT13-024 | Heavy chain CDR3 | gcg aaa gat ccc caa gag cgt att tat tac tct gat act agt ggt tac ctt gac tac |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 134 | AT12-019 | Heavy chain CDR3 | tct cct gct atg att cgg gga gtt agg ggg ggt gac tac ttt gac tac |
| 135 | AT13-022 | Heavy chain CDR3 | gat ggg aag ggg att gta gtt att tac tac tac tac ggt atg gac gtc |
| 136 | AT13-023 | Heavy chain CDR3 | ggc ctt aac agc ccc ttt gac tac |
| 137 | AT13-031 | Heavy chain CDR3 | ccc cgg ggc atg tat agc agc tcg tcc ggg gac tac |
| 138 | AT12-020 | Heavy chain CDR3 | gat ggg act ttc tcc tac tac tac tac atg gac gtc |
| 139 | AT13-033 | Heavy chain CDR3 | gcc ggg ttg aac tac tat gga aac cta tta tca aac tac ttc tac tac gga atg gac gtc |
| 140 | AT13-034 | Heavy chain CDR3 | gcg aga gat ggt tgt act ggt ggt agc tgc tgc tat ttt gac aac |
| 141 | AT13-035 | Heavy chain CDR3 | gcg aaa gac tcg tat tac tat ggt tcg ggg aga cga tgg ggc tac tac ttt gac tac |
| 142 | AT13-036 | Heavy chain CDR3 | gcg aga agg agg gag gtc ggt aga gat ggc tac agt ttg tac ccc cgg ggg tac cac tac ggt atg gac gtc |
| 143 | AT13-037 | Heavy chain CDR3 | gcg aga ggc cgt gga tat agt gcc caa ggg aat cgg aat agg gct tac tac ttt gac tac |
| 144 | AT12-023 | Light chain CDR1 | caa gga gac ttc ctc aga agc tat tat gca agc |
| 145 | AT12-025 | Light chain CDR1 | cgg gca agt cag agc att agc agg tat tta aat |
| 146 | AT13-024 | Light chain CDR1 | cgg gcc agt cag agt att agt agc tgg ttg gcc |
| 147 | AT12-019 | Light chain CDR1 | cgg gcg agt cag gct ttt agc agt tat tta gtc |
| 148 | AT13-022 | Light chain CDR1 | tct gga gat aaa ttg ggg gat aaa tat gct tgc |
| 149 | AT13-023 | Light chain CDR1 | cgg gca agt cag ggc att aga aat gtt tta ggc |
| 150 | AT13-031 | Light chain CDR1 | cgg gca agt cag ggc att aga aat gat tta ggc |
| 151 | AT12-020 | Light chain CDR1 | cgg gcg agt cag gat att agc agt tct tta gcc |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 152 | AT13-033 | Light chain CDR1 | act ggg acc agc agt gac att ggt ggt tat aac tat gtc tcc |
| 153 | AT13-034 | Light chain CDR1 | agg gcc agt cag agc att agc aac aac tta ggc |
| 154 | AT13-035 | Light chain CDR1 | caa gga gac agc ctc aga agc tat tat gca agc |
| 155 | AT13-036 | Light chain CDR1 | act gga acc agc agt gac gtt ggt ggt tat aac tat gtc tcc |
| 156 | AT13-037 | Light chain CDR1 | agg gcc agt cag agt gtt agc agc aac tta gcc |
| 157 | AT12-023 | Light chain CDR2 | ggt aaa aac aag cgg ccc tca |
| 158 | AT12-025 | Light chain CDR2 | gct gca tcc agt ttg caa agt |
| 159 | AT13-024 | Light chain CDR2 | aag gcg tct agt tta gaa agt |
| 160 | AT12-019 | Light chain CDR2 | gct aca tcc act ttg caa ggt |
| 161 | AT13-022 | Light chain CDR2 | caa gat agc aag cgg ccc tca |
| 162 | AT13-023 | Light chain CDR2 | gct gca tcc agt ttg caa agt |
| 163 | AT13-031 | Light chain CDR2 | gct gca gtc agt ttg caa agt |
| 164 | AT12-020 | Light chain CDR2 | gct gca tcc act ttg caa agt |
| 165 | AT13-033 | Light chain CDR2 | gag gtc act aag cgg ccc tca |
| 166 | AT13-034 | Light chain CDR2 | ggt gca tcc acc agg gcc act |
| 167 | AT13-035 | Light chain CDR2 | ggt aaa aac aac cgg ccc tca |
| 168 | AT13-036 | Light chain CDR2 | gat gtc aat gat cgg ccc tca |
| 169 | AT13-037 | Light chain CDR2 | ggt gca ttc acg agg gtc act |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 170 | AT12-023 | Light chain CDR3 | aac tcc cgg gac cgc agt ggt aac cac ctg gtg |
| 171 | AT12-025 | Light chain CDR3 | caa cag agt tac agt acc cct cgc act |
| 172 | AT13-024 | Light chain CDR3 | caa cag tat aat act tac ccg tac act |
| 173 | AT12-019 | Light chain CDR3 | caa cag tat tat agt tac cct ccg act |
| 174 | AT13-022 | Light chain CDR3 | cag gcg tgg gac agc agc act gtg gta ttc |
| 175 | AT13-023 | Light chain CDR3 | cta cag cat aat agt cac ccc cgg acg |
| 176 | AT13-031 | Light chain CDR3 | cta cag cat aat agt tac cct cgg act |
| 177 | AT12-020 | Light chain CDR3 | caa cag tat tat agt tac cct ccg acg |
| 178 | AT13-033 | Light chain CDR3 | agc tca tat gca ggc agc aac gat ttg cta |
| 179 | AT13-034 | Light chain CDR3 | caa caa tat aat aac tgg cct cgg ctc act |
| 180 | AT13-035 | Light chain CDR3 | aac tcc cgg gac agc agt ggt aac cat gtg gta |
| 181 | AT13-036 | Light chain CDR3 | agc tca tat aca aga agc aac act gtg ata |
| 182 | AT13-037 | Light chain CDR3 | cag cag tac aat gac cgg ccc ccg tac act |
| 183 | AT12-023 | Heavy chain | cag gtg cag cta cag cag tgg ggc gca gga ctg ttg aag cct tcg gag acc ctg tcc ctc acc tgc gct gtc tat ggt ggg tcc ttc agt ggt tac tac tgg agc tgg atc cgc cag ccc cca ggg aag ggg ctg gag tgg att ggg gaa atc aat cat agt gga agc acc aac tac aac ccg tcc ctc aag agt cga gtc acc ata tca gta gac acg tcc aag aac cag ttc tcc ctg aag ctg agc tct gtg acc gcc gcg gac acg gct gtg tat tac tgt gcg agg ggc cgt agt acc agc ccg ctc gac tac tac tac tac atg gac gtc tgg gcc aaa ggg acc acg gtc acc gtc tcc tca |
| 184 | AT12-025 | Heavy chain | cag gtg cag cta cag cag tgg ggc gca gga ctg ttg aag cct tcg gag acc ctg tcc ctc acc tgc gct gtc tat ggt ggg tcc ttc agt ggt tat tac tgg agc tgg atc cgc cag ccc cca ggg aag ggg ctg gag tgg att ggg gaa atc aat cat agt gga agc acc aac tac aac ccg tcc ctc aag agt cga gtc acc ata tca gta gac acg tcc aag aac cag ttc tcc ctg aag ctg agc tct gtg acc gcc gcg gac acg gct gtg tat tac tgt gcg aga ggc tca atg gca aga ccc aag cca ttt gac tac tgg ggc cag gga acc ctg gtc acc gtc tcc tca |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 185 | AT13-024 | Heavy chain | cag gtg cag ctg gtg gag tct ggg gga ggc gtg gtc cag cct ggg agg tcc ctg aga ctc tcc tgt gca gcg tct gga ttc acc ttc agt agc tat ggc atg cac tgg gtc cgc cag gct cca ggc aag ggg ctg gag tgg gtg gca ttt ata cgg tat gat gga agt aat aaa tac ttt gca gac tcc gtg agg ggc cga ttc acc atc tcc aga gac aat tcc aag aac acg ctg ttt ctg caa atg aac agc ctg aga gct gag gac acg gct gtg tat tac tgt gcg aaa gat ccc caa gag cgt att tat tac tct gat act agt ggt tac ctt gac tac tgg ggc cag gga acc ctg gtc acc gtc tcc tca |
| 186 | AT12-019 | Heavy chain | gag gtg cac ctg ttg gag tct ggg gga ggc ttg gta cag cct ggg ggg tcc ctg aga ctc tcc tgt gca gcc tct gga ttc acc ttt agc agc tat gcc atg agt tgg gtc cgc cag gct cca ggg aag ggg ctg gag tgg gtc tca act att agg gct agt ggt ggt agc aca agc tac gca gac tcc gtg aag ggc cgg ttc acc atc tcc aga gac aat tcc cag agc agg ttg tat ctg caa atg aac agt ctg aca gcc gag gac acg gcc gta tat tac tgt gcg aaa tct cct gct atg att cgg gga gtt agg ggg ggt gac tac ttt gac tac tgg ggc cag gga acc ctg gtc acc gtc tcc tca |
| 187 | AT13-022 | Heavy chain | cag gtg cag ctg gtg gag tct ggg gga ggc gtg gtc cag cct ggg agg tcc ctg aga ctc tcc tgt gca gcc tct gga ttc acc ttc agt agc tat ggc atg cac tgg gtc cgc cag gct cca ggc aag ggg ctg gag tgg gtg gca gtt ata tca tat gat gga agt aat aaa tac tat gca gac tcc gtg aag ggc cga ttc acc atc tcc aga gac aat tcc aag aac acg ctg tat ctg caa atg aac agc ctg aga gct gag gac acg gct gtg tat tac tgt gcg aaa gat ggg aag ggg att gta gtt att tac tac tac ggt atg gac gtc tgg ggc caa ggg acc acg gtc acc gtc tcc tca |
| 188 | AT13-023 | Heavy chain | cag gta cag cta cag cag tgg ggc gca gga ctg ttg aag cct tcg gag acc ctg tcc ctc acc tgc gct gtc tat ggt ggg tcc ttc agt ggt tac ttc tgg acc tgg atc cgc cag ccc cca ggg aag ggg ctg gag tgg att ggg gaa acc gtt cat agt gga acc aac tac aac ccg tcc ctc aag agt cga gtc acc ata tca gtc gac acg tcc aag aac cag ttc tcc ctg agg ctg aac tct gtg acc gcc gcg gac acg gct gtg tat tac tgt gtg aga ggc ctt aac agc ccc ttt gac tac tgg ggc cag gga acc cta gtc acc gtc tcc tca |
| 189 | AT13-031 | Heavy chain | cag gtg cag cta cag cag tgg ggc gca gga ctg ttg aag cct tcg gag acc ctg tcc ctc acc tgc gct gtc tat ggt ggg tcc ttc agt ggt tac tac tgg agc tgg atc cgc cag ccc cca ggg aag ggg ctg gag tgg att ggg gaa atc aat cat agt gga agc acc aac tac aac ccg tcc ctc aag agt cga gtc acc ata tca gta gac acg tcc aag aag cag ttc tcc ctg aag ctg agc tct gtg acc gcc gcg gac acg gct gtg tat tgt gcg aga ggc ccc cgg ggc atg tat agc agc tcg tcc ggg gac tac tgg ggc cag gga acc ctg gtc acc gtc tcc tca |
| 190 | AT12-020 | Heavy chain | gag gtg cag ctg gtg gag tct ggg gga ggc ctg gtc aag cct ggg ggg tcc ctg aga ctc tcc tgt gca gcc tct gga ttc acc ttc acc agt agc atg aac tgg gtc cgc cag gct cca ggg aag ggg ctg gag tgg gtc tca tcc att agt agt agt agt ggt tac ata tac tac gca gac tca gtg aag ggc cga ttc acc atc tcc aga gac aac gcc aag aac tca ctg tat ctg caa atg aac agc ctg aga gcc gag gac acg gct gtg tat tac tgt gcg aga gat ggg act ttc tcc tac tac tac atg gac gtc tgg ggc aaa ggg acc acg gtc acc gtc tcc tca |
| 191 | AT13-033 | Heavy chain | cag gtg cag ctg gtg gag tct ggg gga ggc gtg gtc cag cct ggg agg tcc ctg aga ctc tcc tgt gca gtc tct gga ttc agt ttc agg aat tat ggc atg cac tgg gtc cgc cag gct ccc ggc aag ggg ctg gag tgg gtg gca gtc att tcg cat gat gga agt aag aca tac tat gga cac tcc gtg aag ggc cga ttc acc ata tcc aga gac aaa tcc aag act atg ttg ttt ctc caa atg aac agc ctg aga cct gag gac acg gct gtt tat tac tgt gcg aaa gcc ggg ttg aac tac tat gga aac cta tta tca aac tac ttc tac tac gga atg gac gtc tgg ggc caa ggg acc aca gtc acc gtc tcg tca |
| 192 | AT13-034 | Heavy chain | cag gtg cac ctg gtg gag tct ggg gga ggc gtg gtc cag cct ggg acg tcc ctg aga ctc tcc tgt gca gcg tct gaa ttc acc ttc agt tcc cat gcc ata cac tgg gtc cgc cag gct cca ggg aag ggg ctg gag tgg gtg gca ctt ata tgg tat gat gga agt aat aat tat tat gca gac tcc gtg aag ggc cga ttc acc atc tcc aga gac agt ccc aag aac acg gtg cat ctg caa atg aac agc ctg aga gtc gag gac acg gct gtg tat tac tgt gcg aga gat ggt tgt act ggt ggt agc tgc tgc tat ttt gac aac tgg ggc cag gga acc cta gtc acc gtc tcc tcg |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 193 | AT13-035 | Heavy chain | cag gtg cag ctg gtg gag tct ggg gga ggc gtg gtc cag cct ggg agg tcc ctg aga ctc tcc tgt gca gcc tct gga ttc acc ttc agt agc tat ggc atg cac tgg gtc cgc cag gct cca ggc aag ggg ctg gag tgg gtg gca gtt ata tca tat gat gga agt aat aaa tac tat gca gac tcc gtg aag ggc cga ttc acc atc tcc aga gac aat tcc aag aac acg ctg tat ctg caa atg aac agc ctg aga gct gag gac acg gct gtg tat tac tgt gcg aaa gac tcg tat tac tat ggt tcg ggg aga cga tgg ggc tac tac ttt gac tac tgg ggc cag gga acc ctg gtc acc gtc tcc tca |
| 194 | AT13-036 | Heavy chain | gag gtg cag ctg gtg gag tct ggg gga ggc ctg gtc aag cct ggg ggg tcc ctg aga ctc tcc tgt gca gcc tct gga ttc acc ttc agt agt tat agc atg aac tgg gtc cgc cag gct cca ggg aag ggg ctg gag tgg gtc tca tcc att agt agt agt agt act tac ata tac tac gca gac tca gtg aag ggc cga ttc acc atc tcc aga gac aac gcc agg aac tca ctg tat ctg caa atg aac agc ctg aga gcc gag gac acg gct gtg tat tat tgt gcg aga agg agg gag tcg gta aga gat ggc tac agt ttg tac ccc cgg ggg tac cac tac ggt atg gac gtc tgg ggc caa ggg acc acg gtc acc gtc tcc tca |
| 195 | AT13-037 | Heavy chain | cag gtg cag ctg gtg gag tct ggg gga ggc gtg gtc cag cct ggg agg tcc ctg aga ctc tcc tgt gca gcg tct gga ttc acc ttc agt acc tat ggc atg cac tgg gtc cgc cag gct cca ggc aag ggg ctt gag tgg gtg gca gtt ata tgg tat gat gga agt aat aca tac tat gca gac tcc gtg aag ggc cga ttc acc atc tcc aga gac aat tcc aag aac aca ctg tat ctg caa ata aag agc ctg aga gcc gag gac acg gct gtc tat tac tgt gcg aga ggc cgt gga tat agt gcc caa ggg aat cgg aat agg gct tac tac ttt gac tac tgg ggc cag gga acc ctg gtc acc gtc tcc tca |
| 196 | AT12-023 | Light chain | tct tct gag ctg act cag gac cct gct gtg tct gtg gcc ttg gga cag aca gtc agg atc aca tgc caa gga gac ttc ctc aga tat tat gca agc tgg tac cag cag aag cca gga cag gcc cct gta ctt gtc atc ttt ggt aaa aac aag cgg ccc tca ggg atc cca gac cga ttc tct ggc tcc agc tca gga aac aca gct tcc ttg acc atc act ggg gct cag gcg gaa gat gag gct gac tat tac tgt aac tcc cgg gac cgc agt ggt aac cac ctg gtg ttc ggc gga ggg acc aag ctg acc gtc cta |
| 197 | AT12-025 | Light chain | gac atc cag atg acc cag tct cca tcc tcc ctg tct gca tct gta gga gac aga gtc acc atc act tgc cgg gca agt cag agc att agc agg tat tta aat tgg tat cag cag aaa cca ggg aaa gcc cct aag ctc ctg atc tat gct gca tcc agt ttg caa agt ggg gtc cca tca agg ttc agt ggc agt gga tct ggg aca gat ttc act ctc acc atc agc agt ctg caa cct gaa gat ttt gca act tac tac tgt caa cag agt tac agt acc cct cgc act ttc ggc cct ggg acc aaa gtg gat atc aaa |
| 198 | AT13-024 | Light chain | gac atc cag atg acc cag tct cct tcc acc ctg tct gca tct gta gga gac aga gtc acc atc act tgc cgg gcc agt cag agt att agt tgg ttg gcc tgg tat cag cag aaa cca ggg aaa gcc cct aag ctc ctg atc tat aag gcg tct agt tta gaa agt ggg gtc cca tca agg ttc agc ggc act gga tct ggg aca gaa ttc act ctc acc atc agc agc ctg cag cct gat gat ttt gca act tat tac tgc caa cag tat aat act tac ccg tac act ttt ggc cag ggg acc aag ctg gag atc aaa |
| 199 | AT12-019 | Light chain | gcc atc cgg ttg acc cag tct cca tcc tca gtc tct gca tct aca gga gac aga gtc acc atc act tgt cgg gcg agt cag gct ttt agc agt tat tta gtc tgg tat cag caa aaa cca ggg aaa gcc cct aac ctc ctg atc tac gct aca tcc act ttg caa ggt ggg gtc cca tca agg ttc agc ggc agt gga tct ggg aca gat ttc act ctc acc atc agc aac ctg cag tct gaa gat ttt gca act tat tac tgt caa cag tat tat agt tac cct ccg act ttt ggc cag ggg acc aag ttg gag atc aaa |
| 200 | AT13-022 | Light chain | tcc tat gag ctg act cag cca ccc tca gtg tcc gtg tcc cca gga cag aca gcc agc atc acc tgc tct gga gat aaa ttg ggg gat aaa tat gct tgc tgg tat cag cag aag cca ggc cag tcc cct gtg ctg gtc atc tat caa gat agc aag cgg ccc tca ggg atc cct gag cga ttc tct ggc tcc aac tct ggg aac aca gcc act ctg acc atc agc ggg acc cag gct atg gat gag gct gac tat tac tgt cag gcg tgg gac agc agc act gtg gta ttc ggc gga ggg acc aag ctg acc gtc cta |

TABLE 1A-continued

Preferred anti-AML antibodies according to the invention
(CDR numbering according to Kabat et al. 1991)

| SEQ ID NO. | Antibody | Identity | Sequence |
|---|---|---|---|
| 201 | AT13-023 | Light chain | gac atc cag atg acc cag tct cca tcc tcc ctg tct gca tct gta gga gac aga gtc acc atc act tgc cgg gca agt cag ggc att aga aat gtt tta ggc tgg tat cag cag aaa cca ggg aaa gcc cct aag tgc ctg atc tat gct gca tcc agt ttg caa agt ggg gtc cca tca agg ttc agc ggc agt gga tct ggg aca gaa ttc act ctc aca atc agc agc ctg cag cct gaa gat ttt gca act tat tac tgt cta cag cat aat agt cac ccc cgg acg ttc ggc caa ggg acc aag gtg gaa atc aaa |
| 202 | AT13-031 | Light chain | gac atc cag atg acc cag tct cca tcc tcc ctg tct gca tct gta gga gac aga gtc acc atc act tgc cgg gca agt cag ggc att aga aat gat tta ggc tgg tat cag cag aaa cca ggg aaa gcc cct aag cgc ctg atc tat gct gca gtc agt ttg caa agt ggg gtc cca tca agg ttc agc ggc agt gga tct ggg aca gaa ttc act ctc aca atc agc agc ctg cag cct gaa gat ttt gca act tat tac tgt cta cag cat aat agt tac cct cgg act ttt ggc cag ggg acc aag ctg gag atc aaa |
| 203 | AT12-020 | Light chain | gcc atc cgg atg acc cag tct cca tcc tca ttc tct gca tct aca gga gac aga gtc acc atc act tgt cgg gcg agt cag gat att agc agt tct tta gcc tgg tat cag caa aaa cca ggg aaa gcc cct aag ctc ctg atc tat gct gca tcc act ttg caa agt gga gtc cca tca agg ttc agc ggc agt gga tct ggg aca gac ttc act ctc acc atc agc tgc ctg cag tct gaa gat ttt gca act tat tac tgt caa cag tat tat agt tac cct ccg acg ttc ggc caa ggg acc agg ttg gaa atc aaa |
| 204 | AT13-033 | Light chain | cag tct gcc ctg act cag cct ccc tcc gcg tcc ggg tct cct ggt cag tca gtc acc atc tcc tgt act ggg acc agc agt gac att ggt ggt tat aac tat gtc tcc tgg tac caa cac cac cca ggc aaa gcc ccc aaa ttg atg att tat gag gtc act aag cgg ccc tca ggg gtc cct gat cgt ttc tct ggc tcc aag tct ggc aac acg gcc tcc ctg acc gtc tct gga ctc cag gct gag gat gag gct cat tat tac tgc agc tca tat gca ggc agc aac gat ttg cta ttc ggc gga ggg acc aag ctg acc gtc ctg |
| 205 | AT13-034 | Light chain | gaa gta gtg atg acg cag tct cca gcc acc ctg tct gtg tct cca ggg gaa aga gcc acc ctc tcc tgc agg gcc agt cag agc att agc aac aac tta ggc tgg tat cag cag aaa cct ggc cag gct ccc agg ctc ctc atc tac ggt gca tcc acc agg gcc act ggt atc cca gcc agg ttc agt ggc agt ggg tct ggg aca gag ttc act ctc acc atc tac agc ctg cag tct gag gat ttt gca gtt tat tac tgt caa caa tat aat aac tgg cct cgg ctc act ttc ggc gga ggg acc aag gtg gag atc aaa |
| 206 | AT13-035 | Light chain | tct tct gag ctg act cag gac cct gct gtg tct gtg gcc ttg gga cag aca gtc agg atc aca tgc caa gga gac agc ctc aga agc tat tat gca agc tgg tac cag cag aag cca gga cag gcc cct gta ctt gtc atc tat ggt aaa aac aac cgg ccc tca ggg atc cca gac cga ttc tct ggc tcc agc tca gga aac aca gct tcc ttg acc atc act ggg gct cag gcg gaa gat gag gct gac tat tac tgt aac tcc cgg gac agc agt ggt aac cat gtg gta ttc ggc gga ggg acc aag ctg acc gtc cta |
| 207 | AT13-036 | Light chain | cag tct gcc ctg act cag cct gcc tcc gtg tct ggg tct cct aga cag tcg atc acc atc tcc tgc act gga acc agc agt gac gtt ggt ggt tat aac tat gtc tcc tgg tac caa caa ctc cca ggc aaa gcc ccc aaa ctc atg att tat gat gtc aat gat cgg ccc tca ggg gtt tct att cgc ttc tct ggc tcc aag tct ggc aac acg gcc tcc ctg acc atc tct ggg ctc cag gct gag gac gag gct gat tat tac tgc agc tca tat aca aga agc aac act gtg ata ttc ggc gga ggg acc aaa ctg acc gtc cta |
| 208 | AT13-037 | Light chain | gaa ata gtg atg acg cag tct cca gcc acc ctg tct gtg tct cca ggg gaa agg gtc atc ctc tcc tgc agg gcc agt cag agt gtt agc agc aac tta gcc tgg tac cag cag aaa cct ggc cag cct ccc agg ctc ctc atc tat ggt gca ttc acg agg gtc act ggt gtc cca gcc agg ttc agt ggc agt ggg tct ggg aca gaa ttc act ctc acc atc agc agc ctg cag tct gaa gat ttt gca gtt tat tac tgt cag cag tac aat gac cgg ccc ccg tac act ttt ggc cag ggg acc aag ctg gag atc aaa |

TABLE 1B

Preferred anti-AML antibodies according to the invention (CDR numbering according to Kabat et al. 1991)

| SEQ ID NO. | Antibody | Identity | Sequence |
|---|---|---|---|
| 209 | AT14-013 | Heavy chain CDR1 | SPNWWT |
| 210 | AT14-014 | Heavy chain CDR1 | DAWMS |
| 211 | AT14-015 | Heavy chain CDR1 | DFAMS |
| 212 | AT14-016 | Heavy chain CDR1 | SYAMT |
| 213 | AT14-013 | Heavy chain CDR2 | EIYYGGRVSYNSALRS |
| 214 | AT14-014 | Heavy chain CDR2 | HINTKVDGGTTEYAAPVKG |
| 215 | AT14-015 | Heavy chain CDR2 | FIRTKANDGTTEYAASVKG |
| 216 | AT14-016 | Heavy chain CDR2 | SISGSGGSTYYADSVRG |
| 217 | AT14-013 | Heavy chain CDR3 | AGQKNIGCGYSSCFISWFDT |
| 218 | AT14-014 | Heavy chain CDR3 | TTEAIYDSSGYFHDY |
| 219 | AT14-015 | Heavy chain CDR3 | ASDPFMTTDYYYYMDV |
| 220 | AT14-016 | Heavy chain CDR3 | AKGYVGCSGGNCYSGGAFDI |
| 221 | AT14-013 | Light chain CDR1 | KSSQTILQRSNHLNYLA |
| 222 | AT14-014 | Light chain CDR1 | KSSRSVLYSSNNKNYLA |
| 223 | AT14-015 | Light chain CDR1 | TGTSSDVGGYNSVS |
| 224 | AT14-016 | Light chain CDR1 | GGNNIGSESVH |
| 225 | AT14-013 | Light chain CDR2 | WASTRES |
| 226 | AT14-014 | Light chain CDR2 | WASIRES |

TABLE 1B-continued

Preferred anti-AML antibodies according to the invention (CDR numbering according to Kabat et al. 1991)

| SEQ ID NO. | Antibody | Identity | Sequence |
|---|---|---|---|
| 227 | AT14-015 | Light chain CDR2 | EVYKRPL |
| 228 | AT14-016 | Light chain CDR2 | YDTDRPS |
| 229 | AT14-013 | Light chain CDR3 | HQYYTTPQT |
| 230 | AT14-014 | Light chain CDR3 | QQYSRPPT |
| 231 | AT14-015 | Light chain CDR3 | SSYGGTVLF |
| 232 | AT14-016 | Light chain CDR3 | QVWDNTSDHPVVF |
| 233 | AT14-013 | Heavy chain | QGRLQESGPGLVKPSETLTLTCAVSGGSSVSSPNWWTWVRQAPGKGLEWIGEIYYGGRVSYNSALRSRVTI SSDRSKEEFSLKLRSVTAADTAIYYCAGQKNIGCGYSSCFISWFDTWGQGIAVTVSS |
| 234 | AT14-014 | Heavy chain | EVQLVESGGGLVKPGGSLRLSCAASGFTFSDAWMSWVRQAPGKGLEWVGHINTKVDGGTTEYAAPVKGR FTISRDDSKNSLYLHMDSLKTEDTAVYYCTTEAIYDSSGYFHDYWGQGSLVTVSS |
| 235 | AT14-015 | Heavy chain | EVQLVESGGGLAQPGRSLRLSCTASGFRFGDFAMSWVRQAPGKGLEWVGFIRTKANDGTTEYAASVKGRF IISRDDSKSIAYLQMNSLKTEDTAVYYCASDPFMTTYYYYYMDVWGKGTTVTVSS |
| 236 | AT14-016 | Heavy chain | EVQVLESGGDSVQPGGSLRLSCAASGFTFSSYAMTWVRQAPGKGLKWVSSISGSGGSTYYADSVRGRFTISR DNSKNTLYVQMNSLRAEDTAVYYCAKGYVGCSGGNCYSGGAFDIWGQGTVVTVSS |
| 237 | AT14-013 | Light chain | DIVMTQSPDSLAVSLGERATIACKSSQTILQRSNHLNYLAWYQQKPGQPPKVLIYWASTRESGVPDRFSGSG SGTDFTLTINSLQAEDVAVYYCHQYYTTPQTFGQGTKVEIK |
| 238 | AT14-014 | Light chain | DIVMTQSPDSLAVSLGERATINCKSSRSVLYSSNNKNYLAWYQQKPGQPPKLLIYWASIRESGVPDRFSGSG SGTDFTLTINSLQAEDVAVYYCQQYSRPPTFGQGTKVEIK |
| 239 | AT14-015 | Light chain | QSALTQPPSASGSPGQSVTISCTGTSSDVGGYNSVSWYQHHPGKAPKLMIYEVYKRPLGVPDRFSGSKSGN TASLTVSGLQAEDEAYYYCSSYGGTVLFGGGTKLTVL |
| 240 | AT14-016 | Light chain | SYVLTQPPSVSVAPGKTARITCGGNNIGSESVHWYQQKPGQAPVVVIYYDTDRPSGIPERFSGSNSGNTATL TISRVEAGDEADYYCQVWDNTSDHPVVFGGGTKLTVL |
| 241 | AT14-013 | Heavy chain CDR1 | agt cct aac tgg tgg act |
| 242 | AT14-014 | Heavy chain CDR1 | gac gcc tgg atg agc |
| 243 | AT14-015 | Heavy chain CDR1 | gat ttt gct atg agt |
| 244 | AT14-016 | Heavy chain CDR1 | agc tat gcc atg acc |
| 245 | AT14-013 | Heavy chain CDR2 | gaa atc tat tat ggt ggg aga gtg agc tac aac tcg gcc ctc agg agt |
| 246 | AT14-014 | Heavy chain CDR2 | cat att aac acc aaa gtt gat ggt ggg aca aca gag tac gct gca ccc gtg aaa ggc |

TABLE 1B-continued

Preferred anti-AML antibodies according to the invention (CDR numbering according to Kabat et al. 1991)

| SEQ ID NO. | Antibody | Identity | Sequence |
|---|---|---|---|
| 247 | AT14-015 | Heavy chain CDR2 | ttc att aga acc aaa gct aat gat ggg aca aca gaa tac gcc gcg tct gtg aaa ggc |
| 248 | AT14-016 | Heavy chain CDR2 | agt att agt ggt agt ggt ggt agc aca tac tac gca gac tcc gtg agg ggc |
| 249 | AT14-013 | Heavy chain CDR3 | gcg ggt caa aaa aat att ggc tgt ggt tac agc agt tgc ttt atc agt tgg ttc gac acc |
| 250 | AT14-014 | Heavy chain CDR3 | acc aca gag gcg ata tat gat agt agt ggt tat ttc cat gac tat |
| 251 | AT14-015 | Heavy chain CDR3 | gct agc gat ccc ttc atg act aca gac tat tac tac tac tac atg gac gtc |
| 252 | AT14-016 | Heavy chain CDR3 | gcg aaa gga tat gtg ggg tgt agt ggt ggg aac tgc tac tcg ggg ggt gct ttt gat atc |
| 253 | AT14-013 | Light chain CDR1 | aag tcc agc cag act att tta caa agg tcc aac cat ttg aac tac tta gct |
| 254 | AT14-014 | Light chain CDR1 | aag tcc agc cgg agt gtt tta tac agc tcc aac aat aag aac tac tta gct |
| 255 | AT14-015 | Light chain CDR1 | act ggg acc agc agt gac gtt ggt ggt tat aac tct gtc tcc |
| 256 | AT14-016 | Light chain CDR1 | ggg ggg aac aac att gga agt gaa agt gtt cac |
| 257 | AT14-013 | Light chain CDR2 | tgg gca tct acc cgg gaa tcc |
| 258 | AT14-014 | Light chain CDR2 | tgg gca tct atc cgg gaa tcc |
| 259 | AT14-015 | Light chain CDR2 | gag gtc tat aag cgg ccc tta |
| 260 | AT14-016 | Light chain CDR2 | tat gat acc gac cgg ccc tca |
| 261 | AT14-013 | Light chain CDR3 | cac caa tat tat act act ccg cag act |
| 262 | AT14-014 | Light chain CDR3 | cag caa tat tct cgt cct ccg acg |
| 263 | AT14-015 | Light chain CDR3 | agc tca tat gga ggc acc gtg cta ttc |
| 264 | AT14-016 | Light chain CDR3 | cag gtg tgg gat aac act agt gat cat cct gtg gta ttc |

TABLE 1B-continued

Preferred anti-AML antibodies according to the invention (CDR numbering according to Kabat et al. 1991)

| SEQ ID NO. | Antibody | Identity | Sequence |
|---|---|---|---|
| 265 | AT14-013 | Heavy chain | cag ggg cga ctg cag gag tcg ggc cca gga ctg gtg aag cct tcg gag acc ctg acc ctc acg tgc gct gtg tcc ggt ggc tcc tcc gtc agc agt cct aac tgg tgg act tgg gtc cgc cag gcc ccc ggg aag ggg ctg gag tgg att gga gaa tct tat tat ggt ggg aga gtg agc tac aac tcg gcc ctc agg agt cga gtc acc att tca tca gac agg tcc aaa gag gag ttc tcc ctg aaa ctg agg tct gtg acc gcc gcg gac acg gcc ata tat tat tgt gcg ggt caa aaa aat att ggc tgt ggt tac agc agt tgc ttt atc agt tgg ttc gac acc tgg gga cag gga att gcg gtc acc gtc tcc tca |
| 266 | AT14-014 | Heavy chain | gag gtg cag ctg gtg gag tct ggg gga ggt ttg gta aag cct ggg ggg tcc ctt aga ctc tcc tgt gca gcc tct gga ttc act ttc agt gac gcc tgg atg agc tgg gtc cgc cag gct cca ggg aag ggg ctg gag tgg gtt ggc cat att aac acc aaa gtt gat ggt ggg aca aca gag tac gct gca ccc gtg aaa ggc aga ttc acc atc tca aga gat gat tca aaa aat tcg ctg tat ctg cac atg gac agc ctg aaa acc gag gac aca gcc gtg tat tac tgt acc aca gag gcg ata tat gat agt agt ggt tat ttc cat gac tat tgg ggc cag gga tcc ctg gtc acc gtc tcc tca |
| 267 | AT14-015 | Heavy chain | gag gtg cag ctg gtg gag tcg ggg gga ggc ttg gca cag cca ggg cgg tcc ctg aga ctc tcc tgt aca gct tct gga ttc agg ttt ggt gat ttt gct atg agt tgg gtc cgc cag gct cca ggg aag gga ctg gag tgg gta ggt ttc att aga acc aaa gct aat gat ggg aca aca gaa tac gcc gcg tct gtg aaa ggc aga ttc atc atc tca aga gat gat tcc aaa agt atc gcc tat ctg caa atg aac agc ctg aaa acc gag gac aca gcc gtt tat tac tgt gct agc gat ccc ttc atg act aca gac tat tac tac tac atg gac gtc tgg ggc aaa ggg acc acg gtc acc gtc tcc tca |
| 268 | AT14-016 | Heavy chain | gag gtg caa gtg ttg gag tct ggg gga gac tcg gta cag cct ggg ggg tcc ctg aga ctc tcc tgt gca gcc tct gga ttc acc ttt agc agc tat gcc atg acc tgg gtc cgc cag gct cca ggg aag ggg ctg aaa tgg gtc tca agt att agt ggt agt ggt ggt agc aca tac tac gca gac tcc gtg agg ggc cgg ttc acc atc tcc aga gac aat tcc aag aac acg ctg tat gtg cag atg aac agc ctg aga gcc gag gac acg gcc gta tat tac tgt gcg aaa gga tat gtg ggg tgt agt ggt ggg aac tgc tac tcg ggg gct ttt gat atc tgg ggc caa ggg aca tgg gtc acc gtc tct tca |
| 269 | AT14-013 | Light chain | gac atc gtg atg acc cag tct cca gac tcc ctg gct gtg tct ctg ggc gag agg gcc acc atc gcc tgc aag tcc agc cag att tta caa agg tcc aac cat ttg aac tac tta gct tgg tac cag cag aaa cca gga cag cct cct aaa gtg ctc att tat tgg gca tct acc cgg gaa tcc ggg gtc cct gac cga ttc agt ggc agc ggg tct ggg aca gat ttc act ctc acc atc aac agc ctg cag gct gag gat gtg gca gtt tat tac tgt cac caa tat tat act act ccg cag act ttt ggc cag ggg acc aag gtg gag atc aaa |
| 270 | AT14-014 | Light chain | gac atc gtg atg acc cag tct cca gac tcc ctg gct gtg tct ctg ggc gag agg gcc acc atc aac tgc aag tcc agc cgg agt gtt tta tac agc tcc aac aat aag aac tac tta gct tgg tac cag cag aaa cca gga cag cct cct aag ctg ctc att tac tgg gca tct atc cgg gaa tcc ggg gtc cct gac cga ttc agt ggc agc ggg tct ggg aca gat ttc act ctc acc atc aac agc ctg cag gct gaa gat gtg gca gtt tat tac tgt cag caa tat tct cgt cct ccg acg ttc ggc caa ggg acc aag gtg gaa atc aaa |
| 271 | AT14-015 | Light chain | cag tct gcc ctg act cag cct ccc tcc gcg tcc ggg tct cct gga cag tca gtc acc atc tcc tgc act ggg acc agc agt gac gtt ggt ggt tat aac tct gtc tcc tgg tac caa cat cac cca ggc aaa gcc ccc aaa ctc atg att tat gag gtc tat aag cgg ccc tta ggg gtc cct gat cgc ttc tct ggc tcc aag tct ggc aac acg gcc tcc ctg acc gtc tct ggg ctc cag gct gag gat gag gct tat tat tac tgc agc tca tat gga ggc acc gtg cta ttc ggc gga ggg acc aag ctg acc gtc cta |
| 272 | AT14-016 | Light chain | tcc tat gtg ctg act cag cca ccc tca gtg tca gtg gcc cca gga aag acg gcc cgg att acc tgt ggg gga aac aac att gga agt gaa agt gtt cac tgg tac cag cag aag cca ggc cag gcc cct gtg ctg gtc atc tat tat gat acc gac cgg ccc tca ggg atc cct gag cgc ttc tct ggc tcc aac tct ggg aac acg gcc acc ctg acc atc agc agg gtc gaa gcc ggg gat gag gcc gac tat tac tgt cag gtg tgg gat aac act agt gat cat cct gtg gta ttc ggc gga ggg acc aag ctg acc gtc cta |

TABEL 2 mAb are specific for AML

| mAbs | | Cell lines | | | | | | | | | | | Prim cells | |
|---|---|---|---|---|---|---|---|---|---|---|---|---|---|---|
| Name | Ig class | Mel[1] | Mel[2] | Mel[3] | BJ | FB | Col[1] | Col[2] | Col[3] | Vero | HUVEC | HepG2 | PBMC | BM |
| AT12-019 | IgG1 κ | − | − | − | − | − | − | − | − | − | − | − | − | − |
| AT13-023 | IgG1 κ | − | − | − | − | − | − | − | − | − | − | − | − | − |
| AT13-031 | IgG1 κ | − | − | − | − | − | − | − | − | − | − | − | − | − |
| AT12-020 | IgG3 κ | − | − | − | − | − | − | − | − | − | − | − | − | − |
| AT12-023 | IgG3 λ | − | − | − | − | − | − | − | − | − | − | − | − | − |
| AT12-025 | IgG3 κ | − | − | − | − | − | − | − | − | − | − | − | − | − |
| AT13-022 | IgG3 λ | − | − | − | − | − | − | − | − | − | − | − | − | − |
| AT13-024 | IgG3 κ | − | − | − | − | − | − | − | − | − | − | − | − | − |

Mel[1]: Mel 126.2;
Mel[2]: Mel BLM;
Mel[3]: Mel WBO;
BJ: Fibroblast cell line;
FB: primary fibroblasts (skin);
Col[1]: Colo205;
Col[2]: Caco-2;
Col[3]: HT29;
Vero: non-human kidney;
PBMC: peripheral blood mononuclear cells;
BM: bone marrow.

TABEL 3

Overview AML-specific mAbs derived from a patient with a potent GvL response (donor 59)

| mAbs | | | | AML | | Primary AML* | | | | |
|---|---|---|---|---|---|---|---|---|---|---|
| Name | Ig class | CD27 | SHM $V_H/V_L$ | THP-1 | MM6 | M0 | M1 | M1 | M1 | M4 |
| AT12-019 | IgG1 κ | + | 10/9 | ++ | + | + | + | ++ | +/− | − |
| AT13-023 | IgG1 κ | + | 8/4 | ++ | | ++ | + | | | |
| AT13-031 | IgG1 κ | + | 1/1 | ++ | + | − | + | − | − | +/− |
| AT12-020 | IgG3 κ | + | 4/2 | ++ | | | | | | |
| AT12-023 | IgG3 λ | − | Germline/6 | +++ | ++ | + | ++ | ++ | +/− | ++ |
| AT12-025 | IgG3 κ | − | 1/1 | ++ | ++ | − | +/− | + | − | − |
| AT13-022 | IgG3 λ | + | Germline | ++ | | ++ | ++ | | | |
| AT13-024 | IgG3 κ | − | 6/3 | ++ | ++ | ++ | ++ | ++ | | |

MM6: MonoMac6;
M0: donor 77; M1 donor 69, 79, 86 respectively; M4 donor 78
*AML according to the FAB classification; SHM: number of somatic hypermutations

TABEL 4

Some mAb bind other hematologic tumors

| mAbs | | Other hematologic tumor cell lines | | | | Primary tumors | |
|---|---|---|---|---|---|---|---|
| Name | Ig class | OCI-Ly1 | OCI-Ly7 | U266 | NCI-H929 | NHL pt | ALL pt |
| AT12-019 | IgG1 κ | + | − | − | − | − | − |
| AT13-023 | IgG1 κ | | | | | | |
| AT13-031 | IgG1 κ | ++ | + | − | +/− | ++ | − |
| AT12-020 | IgG3 κ | | | | | | |
| AT12-023 | IgG3 λ | − | − | +/− | − | ++ | − |
| AT12-025 | IgG3 κ | − | − | + | − | − | − |
| AT13-022 | IgG3 λ | | | | | | |
| AT13-024 | IgG3 κ | ++ | + | − | − | − | − |

OCI-Ly1 and OCI-Ly7: diffuse large B cell lymphoma cell lines;
U266 and NCI-H929: multiple myeloma cell lines;
NHL pt: B-non Hodgkin lymphoma cells freshly isolated from a newly diagnosed patient;
ALL pt: B-acute lymphatic leukemia cells freshly isolated from a newly diagnosed patient.

TABLE 5

Some mAb show in vitro activity

| mAbs | | | | Killing | |
|---|---|---|---|---|---|
| Name | Ig class | CD27 | SHM $V_H/V_L$ | THP-1 | M0/5 |
| AT12-019 | IgG1 κ | + | 10/9 | no | no |
| AT13-023 | IgG1 κ | + | 8/4 | | |
| AT13-031 | IgG1 κ | + | 1/1 | | |
| AT12-020 | IgG3 κ | + | 4/2 | | |
| AT12-023 | IgG3 λ | − | Germline/6 | yes | |
| AT12-025 | IgG3 κ | − | 1/1 | yes | yes |
| AT13-022 | IgG3 λ | + | Germline | | |
| AT13-024 | IgG3 κ | − | 6/3 | no | yes |

AT13-023, AT13-031, AT12-020 and AT13-022 were not yet tested for in vitro activity

TABEL 6

2nd AML patient with GvL response (donor 58)

| | mAbs | | | AML | | Not binding to | | | |
|---|---|---|---|---|---|---|---|---|---|
| Clone | CD27 | Ig class | SHM $V_H/V_L$ | THP-1 | MM6 | PBMC | Caco | HT-29 | HepG2 |
| AT13-033 | + | IgG3 λ | 18/5 | ++ | ++ | − | − | − | − |
| AT13-034 | + | IgG3 κ | 14/6 | ++ | ++ | − | − | − | − |
| AT13-035 | − | IgG3 λ | 0/0 | ++ | ++ | − | − | − | − |
| AT13-036 | − | IgG3 λ | 4/9 | ++ | ++ | − | − | − | − |
| AT13-037 | + | IgG3 κ | 4/8 | ++ | ++ | − | − | − | − |

SHM: number of somatic hypermutations

TABLE 7

Overview of AML-specific mAbs derived from a 3rd patient with a potent GvL response (donor 101)

| | mAbs | | | AML | | Primary AML* | | | |
|---|---|---|---|---|---|---|---|---|---|
| Name | Ig class | CD27 | SWM $V_H/V_L$ | THP-1 | Molm13 | M0 | M4 | M5[1] | M5[2] |
| AT14-013 | IgG1 κ | + | 26/11 | +++ | +++ | +++ | ++ | +/− | + |
| AT14-014 | IgG3 κ | + | 9/6 | ++ | ++ | − | − | − | − |
| AT14-015 | IgG3 λ | + | 9/9 | ++ | − | − | + | − | − |
| AT14-016 | IgG3 λ | + | 9/5 | ++ | ++ | − | + | − | − |

M1: donor 77;
M4: donor BL-046;
M5[1]: donor BL-034,
M5[2]: donor BL-038
*AML according to the FAB classification; SHM: number of somatic hypermutations

TABLE 8 mAb are specific for AML (donor 101)

| | mAbs | Cell lines | | | | PBMCs | | | | Primary cells |
|---|---|---|---|---|---|---|---|---|---|---|
| Name | Ig class | FB | Col | Liv[1] | Liv[2] | CD3 | CD14 | CD19 | CD56 | Fetal liver cells |
| AT14-013 | IgG1 κ | +/− | − | +/− | − | − | − | − | − | − |
| AT14-014 | IgG3 κ | − | − | − | − | − | − | − | − | − |
| AT14-015 | IgG3 λ | − | − | − | − | − | − | − | − | − |
| AT14-016 | IgG3 λ | − | − | − | − | − | − | − | − | − |

FB: primary fibroblasts (skin);
Col: Caco-2;
Liv[1]: Huh7 liver cell line;
Liv[2]: HepG2 liver cell line
PBMC: peripheral blood mononuclear cells;

TABEL 9A

Overview of AML-specific mAbs derived from a 2nd patient with a potent GvL response (donor 58)

| | mAbs | | | AML | | Primary AML* | | | |
|---|---|---|---|---|---|---|---|---|---|
| Clone | CD27 | Ig class | SHM $V_H/V_L$ | THP-1 | MM6 | M0 | M0 | M1 | M4 |
| AT13-033 | + | IgG3 λ | 18/5 | ++ | ++ | − | − | − | − |
| AT13-034 | + | IgG3 κ | 14/6 | ++ | ++ | +/− | − | − | − |
| AT13-035 | − | IgG3 λ | 0/0 | ++ | ++ | − | − | − | − |
| AT13-036 | − | IgG3 λ | 4/9 | ++ | ++ | − | − | − | − |
| AT13-037 | + | IgG3 κ | 4/8 | ++ | ++ | − | − | − | − |

MM6: MonoMac6;
M0: donor 77, BL-030; M1 donor 69, respectively; M4 donor 78
*AML according to the FAB classification; SHM: number of somatic hypermutations

TABLE 9B

Some mAb show in vitro activity (donor 59)

| | mAbs | | | Killing | |
|---|---|---|---|---|---|
| Name | Ig class | CD27 | SHM $V_H/V_L$ | THP-1 | M1 |
| AT12-019 | IgG1 κ | + | 10/9 | no | no |
| AT13-023 | IgG1 κ | + | 8/4 | no | nd |
| AT13-031 | IgG1 κ | + | 1/1 | yes* | nd |
| AT12-020 | IgG3 κ | + | 4/2 | nd | nd |
| AT12-023 | IgG3 λ | − | Germline/6 | yes | nd |
| AT12-025 | IgG3 κ | − | 1/1 | yes | yes |
| AT13-022 | IgG3 λ | + | Germline | no | nd |
| AT13-024 | IgG3 κ | − | 6/3 | no | yes |

*Only at 37 C.;
nd = not determined

TABLE 10

Some mAb show in vitro activity (donor 58)

| Clone | CD27 | Ig class | SHM $V_H/V_L$ | Killing THP-1 |
|---|---|---|---|---|
| AT13-033 | + | IgG3 λ | 18/5 | yes |
| AT13-034 | + | IgG3 κ | 14/6 | no |
| AT13-035 | − | IgG3 λ | 0/0 | yes |
| AT13-036 | − | IgG3 λ | 4/9 | yes |
| AT13-037 | + | IgG3 κ | 4/8 | yes |

REFERENCES

Bakker A B, van den Oudenrijn S, Bakker A Q, Feller N, van Meijer M, Bia J A, Jongeneelen M A, Visser T J, Bijl N, Geuijen C A, Marissen W E, Radosevic K, Throsby M, Schuurhuis G J, Ossenkoppele G J, de Kruif J, Goudsmit J, Kruisbeek A M. 2004. C-type lectin-like molecule-1: a novel myeloid cell surface marker associated with acute myeloid leukemia. Cancer Res 64:8443-50.

Bennett J M, Catovsky D, Daniel M T, Flandrin G, Galton D A, Gralnick H R, Sultan C. 1976. Proposals for the classification of the acute leukaemias. French-American-British (FAB) co-operative group. Br J Haematol 33:451-458.

Bhat N M, Bieber M M, Hsu F J, Chapman C J, Spellerberg M, Stevenson F K, Teng N N H. 1997. Rapid cytotoxicity of human B lymphocytes induced by VH4-34 (VH4.21) gene-encoded monoclonal antibodies. Clin Exp Immunol 108: 151-159

Biernacki M A, Marina O, Zhang W, Liu F, Bruns I, Cai A, Neuberg D, Canning C M, Alyea E P, Soiffer R J, Brusic V, Ritz J, Wu C J. 2010. Efficacious immune therapy in chronic myelogenous leukemia (CML) recognizes antigens that are expressed on CML progenitor cells. Cancer Research 70:906-915.

Chen Y, Wiesmann C, Fuh G, Li B, Christinger H W, McKay P, de Vos A M, Lowman H B. 1999. Selection and analysis of an optimized anti-VEGF antibody: crystal structure of an affinity-matured Fab in complex with antigen. J Mol Biol 293:865-881.

Diehl S A, Schmidlin H, Nagasawa M, van Haren S D, Kwakkenbos M J, Yasuda E, Beaumont T, Scheeren F A, Spits H. 2008. STAT3-mediated up-regulation of BLIMP1 Is coordinated with BCL6 down-regulation to control human plasma cell differentiation. J Immunol 180:4805-4815.

Drexler H G, Minowada J. 1998. History and classification of human leukemia-lymphoma cell lines. Leuk Lymphoma 31:305-316.

Hernandez A M, Rodriguez N, Gonzalez J E, et al. Anti-NeuGcGM3 Antibodies, Actively Elicited by Idiotypic Vaccination in Nonsmall Cell Lung Cancer Patients, Induce Tumor Cell Death by an Oncosis-Like Mechanism. J Immunol 2011; 186(6):3735-3744.

Hugh J. M et al, 2004 Methods in Molecular biology Vol. 282

Kattah N H, Kattah M G, Utz P J. The U1-snRNP complex: structural properties relating to autoimmune pathogenesis in rheumatic diseases. Immunol Reviews. 2010; 233(1): 126-145.

Kepp O, Galluzzi L, Lipinski M, Yuan J, Kroemer G. Cell death assays for drug discovery. Nat Rev Drug Discov 2011; 1-17.

Kwakkenbos M J, Diehl S A, Yasuda E, Bakker A Q, Van Geelen C M M, Lukens M V, Van Bleek G M, Widjojoatmodjo M N, Bogers W M J M, Mei H, Radbruch A, Scheeren F A, Spits H, Beaumont T. 2010. Generation of stable monoclonal antibody-producing B cell receptor-positive human memory B cells by genetic programming. Nat Med 16:123-128.

Majeti R, Chao M P, Alizadeh A A, Pang W W, Jaiswal S, Gibbs K D, Van Rooijen N, Weissman I L. 2009. CD47 is an adverse prognostic factor and therapeutic antibody target on human acute myeloid leukemia stem cells. Cell 138:286-299

Schlenk R F, Döhner K, Krauter J, Fröhling S, Corbacioglu A, Bullinger L, Habdank M, Späth D, Morgan M, Benner A, Schlegelberger B, Heil G, Ganser A, Döhner H, German-Austrian Acute Myeloid Leukemia Study Group. 2008. Mutations and treatment outcome in cytogenetically normal acute myeloid leukemia. N Engl J Med 358:1909-1918.

Schmid C, Labopin M, Nagler A, Bornhäuser M, Finke J, Fassas A, Volin L, Gürman G, Maertens J, Bordigoni P, Holler E, Ehninger G, Polge E, Gorin N-C, Kolb H-J, Rocha V, EBMT Acute Leukemia Working Party. Donor lymphocyte infusion in the treatment of first hematological relapse after allogeneic stem-cell transplantation in adults with acute myeloid leukemia: a retrospective risk factors analysis and comparison with other strategies by the EBMT Acute Leukemia Working Party. Journal of Clinical Oncology 25:4938-4945.

Schmiedel B J, Werner A, Steinbacher J, et al. Generation and Preclinical Characterization of a Fc-optimized GITR-Ig Fusion Protein for Induction of NK Cell Reactivity Against Leukemia. Mol Ther. 2013; 21(4):877-886.

Singh R, Cadeddu R-P, Fröbel J, et al. The non-steroidal anti-inflammatory drugs Sulindac sulfide and Diclofenac induce apoptosis and differentiation in human acute myeloid leukemia cells through an AP-1 dependent pathway. Apoptosis. 2011; 16(9):889-901.

Tsuchiya S, Yamabe M, Yamaguchi Y, Kobayashi Y, Konno K, Tada K. 1988. Establishment and characterization of a human acute monocytic leukemia cell line (THP-1). Int J Cancer 26:171-176.

Walter R B, Appelbaum F R, Estey E H, Bernstein I D. Acute myeloid leukemia stem cells and CD33-targeted immunotherapy. 2012. Blood 119: 6198-208.

Willingham S B, Volkmer J P, Gentles A J, Sahoo D, Dalerba P, Mitra S S, Wang J, Contreras-Trujillo H, Martin R, Cohen J D, Lovelace P, Scheeren F A, Chao M P, Weiskopf K, Tang C, Volkmer A K, Naik T J, Storm T A, Mosley A R, Edris B, Schmid S M, Sun C K, Chua M S, Murillo O, Rajendran P, Cha A C, Chin R K, Kim D, Adorno M, Raveh T, Tseng D, Jaiswal S, Enger P O, Steinberg G K, Li G, So S K, Majeti R, Harsh G R, van de Rijn M, Teng N N, Sunwoo J B, Alizadeh A A, Clarke M F, Weissman I L. 2012. The CD47-signal regulatory protein alpha (SIRPa) interaction is a therapeutic target for human solid tumors. Proc Natl Acad Sci USA 109: 6662-7.

Wu C J, Yang X F, McLaughlin S, Neuberg D, Canning C, Stein B, Alyea E P, Soiffer R J, Dranoff G, Ritz J. 2000. Detection of a potent humoral response associated with immune-induced remission of chronic myelogenous leukemia. J Clin Invest 106:705-714.

What is claimed is:

1. An antibody, or a functional part thereof,
wherein said functional part thereof is defined as a single chain variable fragment (scFv), a Fab fragment or a F(ab')2 fragment;
wherein said antibody or functional part is able to bind a cell surface component of acute myeloid leukemia (AML) cells, comprising:
a heavy chain CDR1 sequence comprising SEQ ID NO: 209;
a heavy chain CDR2 sequence comprising SEQ ID NO: 213;
a heavy chain CDR3 sequence comprising SEQ ID NO: 217;
a light chain CDR1 sequence comprising SEQ ID NO: 221;
a light chain CDR2 sequence comprising SEQ ID NO: 225; and
a light chain CDR3 sequence comprising SEQ ID NO: 229; and
wherein said antibody is, synthetic or recombinant; and
wherein said antibody or functional part is coupled to a detectable label, a chemotherapeutic drug, a toxic moiety, a CD3-specific binding compound, another AML-specific binding compound, or a radioactive compound.

2. The antibody or functional part according to claim 1, comprising a variable heavy chain sequence having at least 95% sequence identity with a sequence selected from the group consisting of SEQ ID NO: 233.

3. The antibody or functional part according to claim 1, comprising a variable light chain sequence having at least 95% sequence identity with a sequence selected from the group consisting of SEQ ID NO: 237.

4. A composition comprising:
an antibody or functional part, wherein said functional part is defined as a single chain variable fragment (scFv), a Fab fragment or a F(ab')2 fragment; and
wherein said antibody or functional part is able to bind a cell surface component of acute myeloid leukemia (AML) cells, comprising:
a heavy chain CDR1 sequence comprising SEQ ID NO: 209;
a heavy chain CDR2 sequence comprising SEQ ID NO: 213;
a heavy chain CDR3 sequence comprising SEQ ID NO: 217;
a light chain CDR1 sequence comprising SEQ ID NO: 221;
a light chain CDR2 sequence comprising SEQ ID NO: 225; and
a light chain CDR3 sequence comprising SEQ ID NO: 229; and wherein said antibody or functional part is coupled to a detectable label, a chemotherapeutic drug, a toxic moiety, a CD3-specific binding compound, another AML-specific binding compound, or a radioactive compound.

5. The composition according to claim 4, wherein said composition is a pharmaceutical composition which comprises a pharmaceutically acceptable carrier, diluent or excipient.

6. The composition according to claim 5, comprising at least two antibodies, or functional parts.

7. The composition according to claim 5, wherein said composition is for use as a medicament.

8. The composition according to claim 5, wherein said composition is for use in a method for at least in part treating a myeloproliferative or lymphoproliferative disorder.

9. The composition according to claim 5, wherein said composition is for use in diagnosis of a myeloproliferative or lymphoproliferative disorder.

10. The composition according to claim 9, wherein said myeloproliferative disorder is acute myeloid leukemia (AML).

11. The composition according to claim 9, wherein said lymphoproliferative disorder is lymphoma, B-non-Hodgkin lymphoma or multiple myeloma.

12. The composition according to claim 4, wherein said composition is used for determining whether a sample comprises myeloproliferative or lymphoproliferative cells.

13. A bispecific or multispecific binding compound that is able to bind a cell surface component of acute myeloid leukemia (AML) cells, comprising:
an antibody or a functional part thereof, wherein said functional part thereof is defined as a single chain variable fragment (scFv), a Fab fragment or a F(ab')2 fragment, wherein said antibody or functional part is able to bind a cell surface component of acute myeloid leukemia (AML) cells, comprising a heavy chain CDR1 sequence comprising SEQ ID NO: 209 and a heavy chain CDR2 sequence comprising SEQ ID NO: 213 and a heavy chain CDR3 sequence comprising SEQ ID NO: 217 and a light chain CDR1 sequence comprising SEQ ID NO: 221 and a light chain CDR2 sequence comprising SEQ ID NO: 225 and a light chain CDR3 sequence comprising SEQ ID NO: 229; and
an immunomodulatory molecule.

14. A synthetic or recombinant antibody or immunoglobulin that is able to bind a cell surface component of acute myeloid leukemia (AML) cells, comprising:
one Fab fragment comprising a heavy chain CDR1 sequence comprising SEQ ID NO: 209 and a heavy chain CDR2 sequence comprising SEQ ID NO: 213 and a heavy chain CDR3 sequence comprising SEQ ID NO: 217 and a light chain CDR1 sequence comprising SEQ ID NO: 221 and a light chain CDR2 sequence comprising SEQ ID NO: 225 and a light chain CDR3 sequence comprising SEQ ID NO: 229; and
one Fab fragment of another antibody.

15. A chimeric antigen receptor (CAR) T cell that is able to bind a cell surface component of acute myeloid leukemia (AML) cells, said CAR comprising:
a heavy chain CDR1 sequence comprising SEQ ID NO: 209;
a heavy chain CDR2 sequence comprising SEQ ID NO: 213;
a heavy chain CDR3 sequence comprising SEQ ID NO: 217;
a light chain CDR1 sequence comprising SEQ ID NO: 221;
a light chain CDR2 sequence comprising SEQ ID NO: 225; and
a light chain CDR3 sequence comprising SEQ ID NO: 229.

16. The bispecific or multispecific binding compound according to claim 13, wherein said immunomodulatory molecule is a CD3-specific binding compound.

* * * * *

SEQUENCE LISTING

<160> NUMBER OF SEQ ID NOS: 272

<210> SEQ ID NO 1
<211> LENGTH: 5
<212> TYPE: PRT
<213> ORGANISM: Homo sapiens

<400> SEQUENCE: 1

Gly Tyr Tyr Trp Ser
1               5

<210> SEQ ID NO 2
<211> LENGTH: 5
<212> TYPE: PRT
<213> ORGANISM: Homo sapiens

<400> SEQUENCE: 2

Gly Tyr Tyr Trp Ser
1               5

<210> SEQ ID NO 3
<211> LENGTH: 5
<212> TYPE: PRT
<213> ORGANISM: Homo sapiens

<400> SEQUENCE: 3

Ser Tyr Gly Met His
1               5

<210> SEQ ID NO 4
<211> LENGTH: 5
<212> TYPE: PRT
<213> ORGANISM: Homo sapiens

<400> SEQUENCE: 4

Ser Tyr Ala Met Ser
1               5

<210> SEQ ID NO 5
<211> LENGTH: 5
<212> TYPE: PRT
<213> ORGANISM: Homo sapiens

<400> SEQUENCE: 5

Ser Tyr Gly Met His
1               5

<210> SEQ ID NO 6
<211> LENGTH: 5
<212> TYPE: PRT
<213> ORGANISM: Homo sapiens

<400> SEQUENCE: 6

Gly Tyr Phe Trp Thr
1               5

<210> SEQ ID NO 7
<211> LENGTH: 5
<212> TYPE: PRT
<213> ORGANISM: Homo sapiens

<400> SEQUENCE: 7

Gly Tyr Tyr Trp Ser
1               5

```
<210> SEQ ID NO 8
<211> LENGTH: 5
<212> TYPE: PRT
<213> ORGANISM: Homo sapiens

<400> SEQUENCE: 8

Thr Tyr Ser Met Asn
1               5

<210> SEQ ID NO 9
<211> LENGTH: 5
<212> TYPE: PRT
<213> ORGANISM: Homo sapiens

<400> SEQUENCE: 9

Asn Tyr Gly Met His
1               5

<210> SEQ ID NO 10
<211> LENGTH: 5
<212> TYPE: PRT
<213> ORGANISM: Homo sapiens

<400> SEQUENCE: 10

Ser His Ala Ile His
1               5

<210> SEQ ID NO 11
<211> LENGTH: 5
<212> TYPE: PRT
<213> ORGANISM: Homo sapiens

<400> SEQUENCE: 11

Ser Tyr Gly Met His
1               5

<210> SEQ ID NO 12
<211> LENGTH: 5
<212> TYPE: PRT
<213> ORGANISM: Homo sapiens

<400> SEQUENCE: 12

Ser Tyr Ser Met Asn
1               5

<210> SEQ ID NO 13
<211> LENGTH: 5
<212> TYPE: PRT
<213> ORGANISM: Homo sapiens

<400> SEQUENCE: 13

Thr Tyr Gly Met His
1               5

<210> SEQ ID NO 14
<211> LENGTH: 16
<212> TYPE: PRT
<213> ORGANISM: Homo sapiens

<400> SEQUENCE: 14

Glu Ile Asn His Ser Gly Ser Thr Asn Tyr Asn Pro Ser Leu Lys Ser
1               5                   10                  15

<210> SEQ ID NO 15
```

```
<211> LENGTH: 16
<212> TYPE: PRT
<213> ORGANISM: Homo sapiens

<400> SEQUENCE: 15

Glu Ile Asn His Ser Gly Ser Thr Asn Tyr Asn Pro Ser Leu Lys Ser
1               5                   10                  15

<210> SEQ ID NO 16
<211> LENGTH: 17
<212> TYPE: PRT
<213> ORGANISM: Homo sapiens

<400> SEQUENCE: 16

Phe Ile Arg Tyr Asp Gly Ser Asn Lys Tyr Phe Ala Asp Ser Val Arg
1               5                   10                  15

Gly

<210> SEQ ID NO 17
<211> LENGTH: 17
<212> TYPE: PRT
<213> ORGANISM: Homo sapiens

<400> SEQUENCE: 17

Thr Ile Arg Ala Ser Gly Gly Ser Thr Ser Tyr Ala Asp Ser Val Lys
1               5                   10                  15

Gly

<210> SEQ ID NO 18
<211> LENGTH: 16
<212> TYPE: PRT
<213> ORGANISM: Homo sapiens

<400> SEQUENCE: 18

Ile Ser Tyr Asp Gly Ser Asn Lys Tyr Tyr Ala Asp Ser Val Lys Gly
1               5                   10                  15

<210> SEQ ID NO 19
<211> LENGTH: 16
<212> TYPE: PRT
<213> ORGANISM: Homo sapiens

<400> SEQUENCE: 19

Glu Thr Val His Ser Gly Gly Thr Asn Tyr Asn Pro Ser Leu Lys Ser
1               5                   10                  15

<210> SEQ ID NO 20
<211> LENGTH: 16
<212> TYPE: PRT
<213> ORGANISM: Homo sapiens

<400> SEQUENCE: 20

Glu Ile Asn His Ser Gly Ser Thr Asn Tyr Asn Pro Ser Leu Lys Ser
1               5                   10                  15

<210> SEQ ID NO 21
<211> LENGTH: 17
<212> TYPE: PRT
<213> ORGANISM: Homo sapiens

<400> SEQUENCE: 21

Ser Ile Ser Ser Ser Ser Gly Tyr Ile Tyr Tyr Ala Asp Ser Val Lys
1               5                   10                  15
```

Gly

<210> SEQ ID NO 22
<211> LENGTH: 17
<212> TYPE: PRT
<213> ORGANISM: Homo sapiens

<400> SEQUENCE: 22

Val Ile Ser His Asp Gly Ser Lys Thr Tyr Tyr Gly His Ser Val Lys
1               5                   10                  15

Gly

<210> SEQ ID NO 23
<211> LENGTH: 17
<212> TYPE: PRT
<213> ORGANISM: Homo sapiens

<400> SEQUENCE: 23

Leu Ile Trp Tyr Asp Gly Ser Asn Asn Tyr Tyr Ala Asp Ser Val Lys
1               5                   10                  15

Gly

<210> SEQ ID NO 24
<211> LENGTH: 17
<212> TYPE: PRT
<213> ORGANISM: Homo sapiens

<400> SEQUENCE: 24

Val Ile Ser Tyr Asp Gly Ser Asn Lys Tyr Tyr Ala Asp Ser Val Lys
1               5                   10                  15

Gly

<210> SEQ ID NO 25
<211> LENGTH: 17
<212> TYPE: PRT
<213> ORGANISM: Homo sapiens

<400> SEQUENCE: 25

Ser Ile Ser Ser Ser Ser Thr Tyr Ile Tyr Tyr Ala Asp Ser Val Lys
1               5                   10                  15

Gly

<210> SEQ ID NO 26
<211> LENGTH: 17
<212> TYPE: PRT
<213> ORGANISM: Homo sapiens

<400> SEQUENCE: 26

Val Ile Trp Tyr Asp Gly Ser Asn Thr Tyr Tyr Ala Asp Ser Val Lys
1               5                   10                  15

Gly

<210> SEQ ID NO 27
<211> LENGTH: 16
<212> TYPE: PRT
<213> ORGANISM: Homo sapiens

<400> SEQUENCE: 27

Gly Arg Ser Thr Ser Pro Leu Asp Tyr Tyr Tyr Tyr Tyr Met Asp Val
1               5                   10                  15

<210> SEQ ID NO 28
<211> LENGTH: 11
<212> TYPE: PRT
<213> ORGANISM: Homo sapiens

<400> SEQUENCE: 28

Gly Ser Met Ala Arg Pro Lys Pro Phe Asp Tyr
1               5                   10

<210> SEQ ID NO 29
<211> LENGTH: 17
<212> TYPE: PRT
<213> ORGANISM: Homo sapiens

<400> SEQUENCE: 29

Asp Pro Gln Glu Arg Ile Tyr Tyr Ser Asp Thr Ser Gly Tyr Leu Asp
1               5                   10                  15

Tyr

<210> SEQ ID NO 30
<211> LENGTH: 16
<212> TYPE: PRT
<213> ORGANISM: Homo sapiens

<400> SEQUENCE: 30

Ser Pro Ala Met Ile Arg Gly Val Arg Gly Gly Asp Tyr Phe Asp Tyr
1               5                   10                  15

<210> SEQ ID NO 31
<211> LENGTH: 16
<212> TYPE: PRT
<213> ORGANISM: Homo sapiens

<400> SEQUENCE: 31

Asp Gly Lys Gly Ile Val Val Ile Tyr Tyr Tyr Tyr Gly Met Asp Val
1               5                   10                  15

<210> SEQ ID NO 32
<211> LENGTH: 8
<212> TYPE: PRT
<213> ORGANISM: Homo sapiens

<400> SEQUENCE: 32

Gly Leu Asn Ser Pro Phe Asp Tyr
1               5

<210> SEQ ID NO 33
<211> LENGTH: 13
<212> TYPE: PRT
<213> ORGANISM: Homo sapiens

<400> SEQUENCE: 33

Gly Pro Arg Gly Met Tyr Ser Ser Ser Gly Asp Tyr
1               5                   10

<210> SEQ ID NO 34
<211> LENGTH: 12
<212> TYPE: PRT
<213> ORGANISM: Homo sapiens

<400> SEQUENCE: 34

Asp Gly Thr Phe Ser Tyr Tyr Tyr Tyr Met Asp Val
1               5                   10

```
<210> SEQ ID NO 35
<211> LENGTH: 20
<212> TYPE: PRT
<213> ORGANISM: Homo sapiens

<400> SEQUENCE: 35

Ala Gly Leu Asn Tyr Tyr Gly Asn Leu Leu Ser Asn Tyr Phe Tyr Tyr
1               5                   10                  15

Gly Met Asp Val
            20

<210> SEQ ID NO 36
<211> LENGTH: 15
<212> TYPE: PRT
<213> ORGANISM: Homo sapiens

<400> SEQUENCE: 36

Ala Arg Asp Gly Cys Thr Gly Gly Ser Cys Cys Tyr Phe Asp Asn
1               5                   10                  15

<210> SEQ ID NO 37
<211> LENGTH: 19
<212> TYPE: PRT
<213> ORGANISM: Homo sapiens

<400> SEQUENCE: 37

Ala Lys Asp Ser Tyr Tyr Tyr Gly Ser Gly Arg Arg Trp Gly Tyr Tyr
1               5                   10                  15

Phe Asp Tyr

<210> SEQ ID NO 38
<211> LENGTH: 24
<212> TYPE: PRT
<213> ORGANISM: Homo sapiens

<400> SEQUENCE: 38

Ala Arg Arg Arg Glu Val Gly Arg Asp Gly Tyr Ser Leu Tyr Pro Arg
1               5                   10                  15

Gly Tyr His Tyr Gly Met Asp Val
            20

<210> SEQ ID NO 39
<211> LENGTH: 20
<212> TYPE: PRT
<213> ORGANISM: Homo sapiens

<400> SEQUENCE: 39

Ala Arg Gly Arg Gly Tyr Ser Ala Gln Gly Asn Arg Asn Arg Ala Tyr
1               5                   10                  15

Tyr Phe Asp Tyr
            20

<210> SEQ ID NO 40
<211> LENGTH: 11
<212> TYPE: PRT
<213> ORGANISM: Homo sapiens

<400> SEQUENCE: 40

Gln Gly Asp Phe Leu Arg Ser Tyr Tyr Ala Ser
1               5                   10

<210> SEQ ID NO 41
<211> LENGTH: 11
```

<212> TYPE: PRT
<213> ORGANISM: Homo sapiens

<400> SEQUENCE: 41

Arg Ala Ser Gln Ser Ile Ser Arg Tyr Leu Asn
1               5                   10

<210> SEQ ID NO 42
<211> LENGTH: 11
<212> TYPE: PRT
<213> ORGANISM: Homo sapiens

<400> SEQUENCE: 42

Arg Ala Ser Gln Ser Ile Ser Ser Trp Leu Ala
1               5                   10

<210> SEQ ID NO 43
<211> LENGTH: 11
<212> TYPE: PRT
<213> ORGANISM: Homo sapiens

<400> SEQUENCE: 43

Arg Ala Ser Gln Ala Phe Ser Ser Tyr Leu Val
1               5                   10

<210> SEQ ID NO 44
<211> LENGTH: 11
<212> TYPE: PRT
<213> ORGANISM: Homo sapiens

<400> SEQUENCE: 44

Ser Gly Asp Lys Leu Gly Asp Lys Tyr Ala Cys
1               5                   10

<210> SEQ ID NO 45
<211> LENGTH: 11
<212> TYPE: PRT
<213> ORGANISM: Homo sapiens

<400> SEQUENCE: 45

Arg Ala Ser Gln Gly Ile Arg Asn Val Leu Gly
1               5                   10

<210> SEQ ID NO 46
<211> LENGTH: 11
<212> TYPE: PRT
<213> ORGANISM: Homo sapiens

<400> SEQUENCE: 46

Arg Ala Ser Gln Gly Ile Arg Asn Asp Leu Gly
1               5                   10

<210> SEQ ID NO 47
<211> LENGTH: 11
<212> TYPE: PRT
<213> ORGANISM: Homo sapiens

<400> SEQUENCE: 47

Arg Ala Ser Gln Asp Ile Ser Ser Leu Ala
1               5                   10

<210> SEQ ID NO 48
<211> LENGTH: 14
<212> TYPE: PRT
<213> ORGANISM: Homo sapiens

<400> SEQUENCE: 48

Thr Gly Thr Ser Ser Asp Ile Gly Gly Tyr Asn Tyr Val Ser
1               5                   10

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Ser Asn Asn Leu Gly
1               5                   10

<210> SEQ ID NO 50
<211> LENGTH: 11
<212> TYPE: PRT
<213> ORGANISM: Homo sapiens

<400> SEQUENCE: 50

Gln Gly Asp Ser Leu Arg Ser Tyr Tyr Ala Ser
1               5                   10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Tyr Val Ser
1               5                   10

<210> SEQ ID NO 52
<211> LENGTH: 11
<212> TYPE: PRT
<213> ORGANISM: Homo sapiens

<400> SEQUENCE: 52

Arg Ala Ser Gln Ser Val Ser Ser Asn Leu Ala
1               5                   10

<210> SEQ ID NO 53
<211> LENGTH: 7
<212> TYPE: PRT
<213> ORGANISM: Homo sapiens

<400> SEQUENCE: 53

Gly Lys Asn Lys Arg Pro Ser
1               5

<210> SEQ ID NO 54
<211> LENGTH: 7
<212> TYPE: PRT
<213> ORGANISM: Homo sapiens

<400> SEQUENCE: 54

Ala Ala Ser Ser Leu Gln Ser
1               5

<210> SEQ ID NO 55
<211> LENGTH: 7
<212> TYPE: PRT
<213> ORGANISM: Homo sapiens

<400> SEQUENCE: 55

Lys Ala Ser Ser Leu Glu Ser
1               5

<210> SEQ ID NO 56
<211> LENGTH: 7
<212> TYPE: PRT
<213> ORGANISM: Homo sapiens

<400> SEQUENCE: 56

Ala Thr Ser Thr Leu Gln Gly
1               5

<210> SEQ ID NO 57
<211> LENGTH: 7
<212> TYPE: PRT
<213> ORGANISM: Homo sapiens

<400> SEQUENCE: 57

Gln Asp Ser Lys Arg Pro Ser
1               5

<210> SEQ ID NO 58
<211> LENGTH: 7
<212> TYPE: PRT
<213> ORGANISM: Homo sapiens

<400> SEQUENCE: 58

Ala Ala Ser Ser Leu Gln Ser
1               5

<210> SEQ ID NO 59
<211> LENGTH: 7
<212> TYPE: PRT
<213> ORGANISM: Homo sapiens

<400> SEQUENCE: 59

Ala Ala Val Ser Leu Gln Ser
1               5

<210> SEQ ID NO 60
<211> LENGTH: 7
<212> TYPE: PRT
<213> ORGANISM: Homo sapiens

<400> SEQUENCE: 60

Ala Ala Ser Thr Leu Gln Ser
1               5

<210> SEQ ID NO 61
<211> LENGTH: 7
<212> TYPE: PRT
<213> ORGANISM: Homo sapiens

<400> SEQUENCE: 61

Glu Val Thr Lys Arg Pro Ser
1               5

<210> SEQ ID NO 62
<211> LENGTH: 7
<212> TYPE: PRT
<213> ORGANISM: Homo sapiens

<400> SEQUENCE: 62

Gly Ala Ser Thr Arg Ala Thr

<210> SEQ ID NO 63
<211> LENGTH: 7
<212> TYPE: PRT
<213> ORGANISM: Homo sapiens

<400> SEQUENCE: 63

Gly Lys Asn Asn Arg Pro Ser
1               5

<210> SEQ ID NO 64
<211> LENGTH: 7
<212> TYPE: PRT
<213> ORGANISM: Homo sapiens

<400> SEQUENCE: 64

Asp Val Asn Asp Arg Pro Ser
1               5

<210> SEQ ID NO 65
<211> LENGTH: 7
<212> TYPE: PRT
<213> ORGANISM: Homo sapiens

<400> SEQUENCE: 65

Gly Ala Phe Thr Arg Val Thr
1               5

<210> SEQ ID NO 66
<211> LENGTH: 11
<212> TYPE: PRT
<213> ORGANISM: Homo sapiens

<400> SEQUENCE: 66

Asn Ser Arg Asp Arg Ser Gly Asn His Leu Val
1               5                   10

<210> SEQ ID NO 67
<211> LENGTH: 9
<212> TYPE: PRT
<213> ORGANISM: Homo sapiens

<400> SEQUENCE: 67

Gln Gln Ser Tyr Ser Thr Pro Arg Thr
1               5

<210> SEQ ID NO 68
<211> LENGTH: 9
<212> TYPE: PRT
<213> ORGANISM: Homo sapiens

<400> SEQUENCE: 68

Gln Gln Tyr Asn Thr Tyr Pro Tyr Thr
1               5

<210> SEQ ID NO 69
<211> LENGTH: 9
<212> TYPE: PRT
<213> ORGANISM: Homo sapiens

<400> SEQUENCE: 69

Gln Gln Tyr Tyr Ser Tyr Pro Pro Thr
1               5

```
<210> SEQ ID NO 70
<211> LENGTH: 10
<212> TYPE: PRT
<213> ORGANISM: Homo sapiens

<400> SEQUENCE: 70

Gln Ala Trp Asp Ser Ser Thr Val Val Phe
1               5                   10

<210> SEQ ID NO 71
<211> LENGTH: 9
<212> TYPE: PRT
<213> ORGANISM: Homo sapiens

<400> SEQUENCE: 71

Leu Gln His Asn Ser His Pro Arg Thr
1               5

<210> SEQ ID NO 72
<211> LENGTH: 9
<212> TYPE: PRT
<213> ORGANISM: Homo sapiens

<400> SEQUENCE: 72

Leu Gln His Asn Ser Tyr Pro Arg Thr
1               5

<210> SEQ ID NO 73
<211> LENGTH: 9
<212> TYPE: PRT
<213> ORGANISM: Homo sapiens

<400> SEQUENCE: 73

Gln Gln Tyr Tyr Ser Tyr Pro Pro Thr
1               5

<210> SEQ ID NO 74
<211> LENGTH: 10
<212> TYPE: PRT
<213> ORGANISM: Homo sapiens

<400> SEQUENCE: 74

Ser Ser Tyr Ala Gly Ser Asn Asp Leu Leu
1               5                   10

<210> SEQ ID NO 75
<211> LENGTH: 10
<212> TYPE: PRT
<213> ORGANISM: Homo sapiens

<400> SEQUENCE: 75

Gln Gln Tyr Asn Asn Trp Pro Arg Leu Thr
1               5                   10

<210> SEQ ID NO 76
<211> LENGTH: 11
<212> TYPE: PRT
<213> ORGANISM: Homo sapiens

<400> SEQUENCE: 76

Asn Ser Arg Asp Ser Ser Gly Asn His Val Val
1               5                   10

<210> SEQ ID NO 77
```

```
<211> LENGTH: 10
<212> TYPE: PRT
<213> ORGANISM: Homo sapiens

<400> SEQUENCE: 77

Ser Ser Tyr Thr Arg Ser Asn Thr Val Ile
1               5                   10

<210> SEQ ID NO 78
<211> LENGTH: 10
<212> TYPE: PRT
<213> ORGANISM: Homo sapiens

<400> SEQUENCE: 78

Gln Gln Tyr Asn Asp Arg Pro Pro Tyr Thr
1               5                   10

<210> SEQ ID NO 79
<211> LENGTH: 124
<212> TYPE: PRT
<213> ORGANISM: Homo sapiens

<400> SEQUENCE: 79

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Ser Thr Ser Pro Leu Asp Tyr Tyr Tyr Tyr Met Asp
            100                 105                 110

Val Trp Ala Lys Gly Thr Thr Val Thr Val Ser Ser
        115                 120

<210> SEQ ID NO 80
<211> LENGTH: 119
<212> TYPE: PRT
<213> ORGANISM: Homo sapiens

<400> SEQUENCE: 80

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Met Ala Arg Pro Lys Pro Phe Asp Tyr Trp Gly Gln Gly
```

```
                100               105               110
Thr Leu Val Thr Val Ser Ser
        115

<210> SEQ ID NO 81
<211> LENGTH: 126
<212> TYPE: PRT
<213> ORGANISM: Homo sapiens

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Phe Ala Asp Ser Val
    50                  55                  60

Arg Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Asp Pro Gln Glu Arg Ile Tyr Tyr Ser Asp Thr Ser Gly Tyr
            100                 105                 110

Leu Asp Tyr Trp Gly Gln Gly Thr Leu Val Thr Val Ser Ser
        115                 120                 125

<210> SEQ ID NO 82
<211> LENGTH: 125
<212> TYPE: PRT
<213> ORGANISM: Homo sapiens

<400> SEQUENCE: 82

Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Arg Ala Ser Gly Gly Ser Thr Ser Tyr Ala Asp Ser Val
    50                  55                  60

Lys Gly Arg Phe Thr Ile Ser Arg Asp Asn Ser Gln Ser Arg Leu Tyr
65                  70                  75                  80

Leu Gln Met Asn Ser Leu Thr Ala Glu Asp Thr Ala Val Tyr Tyr Cys
                85                  90                  95

Ala Lys Ser Pro Ala Met Ile Arg Gly Val Arg Gly Gly Asp Tyr Phe
            100                 105                 110

Asp Tyr Trp Gly Gln Gly Thr Leu Val Thr Val Ser Ser
        115                 120                 125

<210> SEQ ID NO 83
<211> LENGTH: 125
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Gly Ile Val Val Ile Tyr Tyr Tyr Gly Met
            100                 105                 110

Asp Val Trp Gly Gln Gly Thr Thr Val Thr Val Ser Ser
            115                 120                 125

<210> SEQ ID NO 84
<211> LENGTH: 116
<212> TYPE: PRT
<213> ORGANISM: Homo sapiens

<400> SEQUENCE: 84

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Phe Trp Thr Trp Ile Arg Gln Pro Pro Gly Lys Gly Leu Glu Trp Ile
            35                  40                  45

Gly Glu Thr Val His Ser Gly Gly Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Arg Leu Asn Ser Val Thr Ala Ala Asp Thr Ala Val Tyr Tyr Cys Val
                85                  90                  95

Arg Gly Leu Asn Ser Pro Phe Asp Tyr Trp Gly Gln Gly Thr Leu Val
            100                 105                 110

Thr Val Ser Ser
        115

<210> SEQ ID NO 85
<211> LENGTH: 121
<212> TYPE: PRT
<213> ORGANISM: Homo sapiens

<400> SEQUENCE: 85

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Arg Gly Met Tyr Ser Ser Ser Gly Asp Tyr Trp Gly
            100                 105                 110

Gln Gly Thr Leu Val Thr Val Ser Ser
        115                 120

<210> SEQ ID NO 86
<211> LENGTH: 121
<212> TYPE: PRT
<213> ORGANISM: Homo sapiens

<400> SEQUENCE: 86

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Phe Ser Tyr Tyr Tyr Tyr Met Asp Val Trp Gly
            100                 105                 110

Lys Gly Thr Thr Val Thr Val Ser Ser
        115                 120

<210> SEQ ID NO 87
<211> LENGTH: 129
<212> TYPE: PRT
<213> ORGANISM: Homo sapiens

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Val Ser Gly Leu Ser Phe Arg Asn Tyr
            20                  25                  30

Gly Met His Trp Val Arg Gln Ala Pro Gly Lys Gly Leu Glu Trp Val
        35                  40                  45

Ala Val Ile Ser His Asp Gly Ser Lys Thr Tyr Tyr Gly His Ser Val
    50                  55                  60

Lys Gly Arg Phe Thr Ile Ser Arg Asp Lys Ser Lys Thr Met Leu Phe
65                  70                  75                  80

Leu Gln Met Asn Ser Leu Arg Pro Glu Asp Thr Ala Val Tyr Tyr Cys
                85                  90                  95

Ala Lys Ala Gly Leu Asn Tyr Tyr Gly Asn Leu Leu Ser Asn Tyr Phe
            100                 105                 110

Tyr Tyr Gly Met Asp Val Trp Gly Gln Gly Thr Thr Val Thr Val Ser
        115                 120                 125

Ser

<210> SEQ ID NO 88
<211> LENGTH: 122
<212> TYPE: PRT
<213> ORGANISM: Homo sapiens

<400> SEQUENCE: 88

Gln Val His Leu Val Glu Ser Gly Gly Gly Val Val Gln Pro Gly Thr
1               5                   10                  15

Ser Leu Arg Leu Ser Cys Ala Ala Ser Glu Phe Thr Phe Ser Ser His
            20                  25                  30

Ala Ile His Trp Val Arg Gln Ala Pro Gly Lys Gly Leu Glu Trp Val
        35                  40                  45

Ala Leu Ile Trp Tyr Asp Gly Ser Asn Asn Tyr Tyr Ala Asp Ser Val
    50                  55                  60

Lys Gly Arg Phe Thr Ile Ser Arg Asp Ser Lys Asn Thr Val His
65                  70                  75                  80

Leu Gln Met Asn Ser Leu Arg Val Glu Asp Thr Ala Val Tyr Tyr Cys
                85                  90                  95

Ala Arg Asp Gly Cys Thr Gly Gly Ser Cys Cys Tyr Phe Asp Asn Trp
            100                 105                 110

Gly Gln Gly Thr Leu Val Thr Val Ser Ser
            115                 120

<210> SEQ ID NO 89
<211> LENGTH: 126
<212> TYPE: PRT
<213> ORGANISM: Homo sapiens

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Tyr Tyr Tyr Gly Ser Gly Arg Arg Trp Gly Tyr Tyr
            100                 105                 110

Phe Asp Tyr Trp Gly Gln Gly Thr Leu Val Thr Val Ser Ser
        115                 120                 125

<210> SEQ ID NO 90
<211> LENGTH: 131
<212> TYPE: PRT
<213> ORGANISM: Homo sapiens

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Thr Tyr Ile Tyr Ala Asp Ser Val
    50                  55                  60

Lys Gly Arg Phe Thr Ile Ser Arg Asp Asn Ala Arg Asn Ser Leu Tyr

```
              65                  70                  75                  80
Leu Gln Met Asn Ser Leu Arg Ala Glu Asp Thr Ala Val Tyr Tyr Cys
                     85                  90                  95

Ala Arg Arg Arg Glu Val Gly Arg Asp Gly Tyr Ser Leu Tyr Pro Arg
                100                 105                 110

Gly Tyr His Tyr Gly Met Asp Val Trp Gly Gln Gly Thr Thr Val Thr
                115                 120                 125

Val Ser Ser
        130

<210> SEQ ID NO 91
<211> LENGTH: 127
<212> TYPE: PRT
<213> ORGANISM: Homo sapiens

<400> SEQUENCE: 91

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Thr Tyr
                 20                  25                  30

Gly Met His Trp Val Arg Gln Ala Pro Gly Lys Gly Leu Glu Trp Val
                 35                  40                  45

Ala Val Ile Trp Tyr Asp Gly Ser Asn Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Ile Lys Ser Leu Arg Ala Glu Asp Thr Ala Val Tyr Tyr Cys
                     85                  90                  95

Ala Arg Gly Arg Gly Tyr Ser Ala Gln Gly Asn Arg Asn Arg Ala Tyr
                100                 105                 110

Tyr Phe Asp Tyr Trp Gly Gln Gly Thr Leu Val Thr Val Ser Ser
                115                 120                 125

<210> SEQ ID NO 92
<211> LENGTH: 108
<212> TYPE: PRT
<213> ORGANISM: Homo sapiens

<400> SEQUENCE: 92

Ser Ser Glu Leu Thr Gln Asp Pro Ala Val Ser Val Ala Leu Gly Gln
  1               5                  10                  15

Thr Val Arg Ile Thr Cys Gln Gly Asp Phe Leu Arg Ser Tyr Tyr Ala
                 20                  25                  30

Ser Trp Tyr Gln Gln Lys Pro Gly Gln Ala Pro Val Leu Val Ile Phe
                 35                  40                  45

Gly Lys Asn Lys Arg Pro Ser Gly Ile Pro Asp Arg Phe Ser Gly Ser
             50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Arg Ser Gly Asn His
                     85                  90                  95

Leu Val Phe Gly Gly Gly Thr Lys Leu Thr Val Leu
                100                 105

<210> SEQ ID NO 93
<211> LENGTH: 107
<212> TYPE: PRT
```

<213> ORGANISM: Homo sapiens

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Pro Gly Thr Lys Val Asp Ile Lys
            100                 105
```

<210> SEQ ID NO 94
<211> LENGTH: 107
<212> TYPE: PRT
<213> ORGANISM: Homo sapiens

<400> SEQUENCE: 94

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Thr Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Pro Tyr
                85                  90                  95

Thr Phe Gly Gln Gly Thr Lys Leu Glu Ile Lys
            100                 105
```

<210> SEQ ID NO 95
<211> LENGTH: 107
<212> TYPE: PRT
<213> ORGANISM: Homo sapiens

<400> SEQUENCE: 95

```
Ala Ile Arg Leu Thr Gln Ser Pro Ser Ser Val Ser Ala Ser Thr Gly
1               5                   10                  15

Asp Arg Val Thr Ile Thr Cys Arg Ala Ser Gln Ala Phe Ser Ser Tyr
            20                  25                  30

Leu Val Trp Tyr Gln Gln Lys Pro Gly Lys Ala Pro Asn Leu Leu Ile
        35                  40                  45

Tyr Ala Thr Ser Thr Leu Gln Gly Gly Val Pro Ser Arg Phe Ser Gly
    50                  55                  60

Ser Gly Ser Gly Thr Asp Phe Thr Leu Thr Ile Ser Asn Leu Gln Ser
65                  70                  75                  80

Glu Asp Phe Ala Thr Tyr Tyr Cys Gln Gln Tyr Tyr Ser Tyr Pro Pro
                85                  90                  95
```

Thr Phe Gly Gln Gly Thr Lys Leu Glu Ile Lys
            100                 105

<210> SEQ ID NO 96
<211> LENGTH: 106
<212> TYPE: PRT
<213> ORGANISM: Homo sapiens

<400> SEQUENCE: 96

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 97
<211> LENGTH: 107
<212> TYPE: PRT
<213> ORGANISM: Homo sapiens

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Cys Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser His Pro Arg
                85                  90                  95

Thr Phe Gly Gln Gly Thr Lys Val Glu Ile Lys
            100                 105

<210> SEQ ID NO 98
<211> LENGTH: 107
<212> TYPE: PRT
<213> ORGANISM: Homo sapiens

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

```
Tyr Ala Val Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Leu Glu Ile Lys
                100                 105
```

<210> SEQ ID NO 99
<211> LENGTH: 107
<212> TYPE: PRT
<213> ORGANISM: Homo sapiens

<400> SEQUENCE: 99

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Asp Ile Ser Ser Ser
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro Pro
                85                  90                  95

Thr Phe Gly Gln Gly Thr Arg Leu Glu Ile Lys
                100                 105
```

<210> SEQ ID NO 100
<211> LENGTH: 110
<212> TYPE: PRT
<213> ORGANISM: Homo sapiens

<400> SEQUENCE: 100

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
                20                  25                  30

Asn Tyr Val Ser Trp Tyr Gln His His Pro Gly Lys Ala Pro Lys Leu
            35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala His Tyr Tyr Cys Ser Ser Tyr Ala Gly Ser
                85                  90                  95

Asn Asp Leu Leu Phe Gly Gly Gly Thr Lys Leu Thr Val Leu
                100                 105                 110
```

<210> SEQ ID NO 101
<211> LENGTH: 108
<212> TYPE: PRT
<213> ORGANISM: Homo sapiens

<400> SEQUENCE: 101

```
Glu Val Val Met Thr Gln Ser Pro Ala Thr Leu Ser Val Ser Pro Gly
```

```
                1               5                  10                 15
              Glu Arg Ala Thr Leu Ser Cys Arg Ala Ser Gln Ser Ile Ser Asn Asn
                              20                  25                 30

Leu Gly Trp Tyr Gln Gln Lys Pro Gly Gln Ala Pro Arg Leu Leu Ile
                         35                  40                 45

Tyr Gly Ala Ser Thr Arg Ala Thr Gly Ile Pro Gly Arg Phe Ser Gly
                    50                  55                 60

Ser Gly Ser Gly Thr Glu Phe Thr Leu Thr Ile Tyr Ser Leu Gln Ser
              65                  70                  75                 80

Glu Asp Phe Ala Val Tyr Tyr Cys Gln Gln Tyr Asn Asn Trp Pro Arg
                              85                  90                 95

Leu Thr Phe Gly Gly Gly Thr Lys Val Glu Ile Lys
                              100                 105

<210> SEQ ID NO 102
<211> LENGTH: 108
<212> TYPE: PRT
<213> ORGANISM: Homo sapiens

<400> SEQUENCE: 102

Ser Ser Glu Leu Thr Gln Asp Pro Ala Val Ser Val Ala Leu Gly Gln
              1               5                  10                 15

Thr Val Arg Ile Thr Cys Gln Gly Asp Ser Leu Arg Ser Tyr Tyr Ala
                              20                  25                 30

Ser Trp Tyr Gln Gln Lys Pro Gly Gln Ala Pro Val Leu Val Ile Tyr
                         35                  40                 45

Gly Lys Asn Asn Arg Pro Ser Gly Ile Pro Asp Arg Phe Ser Gly Ser
                    50                  55                 60

Ser Ser Gly Asn Thr Ala Ser Leu Thr Ile Thr Gly Ala Gln Ala Glu
              65                  70                  75                 80

Asp Glu Ala Asp Tyr Tyr Cys Asn Ser Arg Asp Ser Ser Gly Asn His
                              85                  90                 95

Val Val Phe Gly Gly Gly Thr Lys Leu Thr Val Leu
                              100                 105

<210> SEQ ID NO 103
<211> LENGTH: 110
<212> TYPE: PRT
<213> ORGANISM: Homo sapiens

<400> SEQUENCE: 103

Gln Ser Ala Leu Thr Gln Pro Ala Ser Val Ser Gly Ser Pro Arg Gln
              1               5                  10                 15

Ser Ile Thr Ile Ser Cys Thr Gly Thr Ser Ser Asp Val Gly Gly Tyr
                              20                  25                 30

Asn Tyr Val Ser Trp Tyr Gln Gln Leu Pro Gly Lys Ala Pro Lys Leu
                         35                  40                 45

Met Ile Tyr Asp Val Asn Asp Arg Pro Ser Gly Val Ser Ile Arg Phe
                    50                  55                 60

Ser Gly Ser Lys Ser Gly Asn Thr Ala Ser Leu Thr Ile Ser Gly Leu
              65                  70                  75                 80

Gln Ala Glu Asp Glu Ala Asp Tyr Tyr Cys Ser Ser Tyr Thr Arg Ser
                              85                  90                 95

Asn Thr Val Ile Phe Gly Gly Gly Thr Lys Leu Thr Val Leu
                              100                 105                110
```

<210> SEQ ID NO 104
<211> LENGTH: 108
<212> TYPE: PRT
<213> ORGANISM: Homo sapiens

<400> SEQUENCE: 104

```
Glu Ile Val Met Thr Gln Ser Pro Ala Thr Leu Ser Val Ser Pro Gly
1               5                   10                  15

Glu Arg Val Ile Leu Ser Cys Arg Ala Ser Gln Ser Val Ser Ser Asn
            20                  25                  30

Leu Ala Trp Tyr Gln Gln Lys Pro Gly Gln Pro Pro Arg Leu Leu Ile
        35                  40                  45

Tyr Gly Ala Phe Thr Arg Val Thr Gly Val Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Arg Pro Pro
                85                  90                  95

Tyr Thr Phe Gly Gln Gly Thr Lys Leu Glu Ile Lys
            100                 105
```

<210> SEQ ID NO 105
<211> LENGTH: 15
<212> TYPE: DNA
<213> ORGANISM: Homo sapiens

<400> SEQUENCE: 105
ggttactact ggagc                                                     15

<210> SEQ ID NO 106
<211> LENGTH: 15
<212> TYPE: DNA
<213> ORGANISM: Homo sapiens

<400> SEQUENCE: 106
ggttattact ggagc                                                     15

<210> SEQ ID NO 107
<211> LENGTH: 15
<212> TYPE: DNA
<213> ORGANISM: Homo sapiens

<400> SEQUENCE: 107
agctatggca tgcac                                                     15

<210> SEQ ID NO 108
<211> LENGTH: 15
<212> TYPE: DNA
<213> ORGANISM: Homo sapiens

<400> SEQUENCE: 108
agctatgcca tgagt                                                     15

<210> SEQ ID NO 109
<211> LENGTH: 15
<212> TYPE: DNA
<213> ORGANISM: Homo sapiens

<400> SEQUENCE: 109
agctatggca tgcac                                                     15

```
<210> SEQ ID NO 110
<211> LENGTH: 15
<212> TYPE: DNA
<213> ORGANISM: Homo sapiens

<400> SEQUENCE: 110
ggttacttct ggacc                                                    15

<210> SEQ ID NO 111
<211> LENGTH: 15
<212> TYPE: DNA
<213> ORGANISM: Homo sapiens

<400> SEQUENCE: 111
ggttactact ggagc                                                    15

<210> SEQ ID NO 112
<211> LENGTH: 15
<212> TYPE: DNA
<213> ORGANISM: Homo sapiens

<400> SEQUENCE: 112
acctatagca tgaac                                                    15

<210> SEQ ID NO 113
<211> LENGTH: 15
<212> TYPE: DNA
<213> ORGANISM: Homo sapiens

<400> SEQUENCE: 113
aattatggca tgcac                                                    15

<210> SEQ ID NO 114
<211> LENGTH: 15
<212> TYPE: DNA
<213> ORGANISM: Homo sapiens

<400> SEQUENCE: 114
tcccatgcca tacac                                                    15

<210> SEQ ID NO 115
<211> LENGTH: 15
<212> TYPE: DNA
<213> ORGANISM: Homo sapiens

<400> SEQUENCE: 115
agctatggca tgcac                                                    15

<210> SEQ ID NO 116
<211> LENGTH: 15
<212> TYPE: DNA
<213> ORGANISM: Homo sapiens

<400> SEQUENCE: 116
agttatagca tgaac                                                    15

<210> SEQ ID NO 117
<211> LENGTH: 15
<212> TYPE: DNA
<213> ORGANISM: Homo sapiens

<400> SEQUENCE: 117
acctatggca tgcac                                                    15
```

<210> SEQ ID NO 118
<211> LENGTH: 48
<212> TYPE: DNA
<213> ORGANISM: Homo sapiens

<400> SEQUENCE: 118
gaaatcaatc atagtggaag caccaactac aacccgtccc tcaagagt        48

<210> SEQ ID NO 119
<211> LENGTH: 48
<212> TYPE: DNA
<213> ORGANISM: Homo sapiens

<400> SEQUENCE: 119
gaaatcaatc atagtggaag caccaactac aacccgtccc tcaagagt        48

<210> SEQ ID NO 120
<211> LENGTH: 51
<212> TYPE: DNA
<213> ORGANISM: Homo sapiens

<400> SEQUENCE: 120
tttatacggt atgatggaag taataaatac tttgcagact ccgtgagggg c     51

<210> SEQ ID NO 121
<211> LENGTH: 51
<212> TYPE: DNA
<213> ORGANISM: Homo sapiens

<400> SEQUENCE: 121
actattaggg ctagtggtgg tagcacaagc tacgcagact ccgtgaaggg c     51

<210> SEQ ID NO 122
<211> LENGTH: 48
<212> TYPE: DNA
<213> ORGANISM: Homo sapiens

<400> SEQUENCE: 122
atatcatatg atggaagtaa taaatactat gcagactccg tgaagggc         48

<210> SEQ ID NO 123
<211> LENGTH: 48
<212> TYPE: DNA
<213> ORGANISM: Homo sapiens

<400> SEQUENCE: 123
gaaaccgttc atagtggagg caccaactac aacccgtccc tcaagagt         48

<210> SEQ ID NO 124
<211> LENGTH: 48
<212> TYPE: DNA
<213> ORGANISM: Homo sapiens

<400> SEQUENCE: 124
gaaatcaatc atagtggaag caccaactac aacccgtccc tcaagagt         48

<210> SEQ ID NO 125
<211> LENGTH: 51
<212> TYPE: DNA
<213> ORGANISM: Homo sapiens

<400> SEQUENCE: 125
tccattagta gtagtagtgg ttacatatac tacgcagact cagtgaaggg c     51

-continued

<210> SEQ ID NO 126
<211> LENGTH: 51
<212> TYPE: DNA
<213> ORGANISM: Homo sapiens

<400> SEQUENCE: 126
gtcatttcgc atgatggaag taagacatac tatggacact ccgtgaaggg c         51

<210> SEQ ID NO 127
<211> LENGTH: 51
<212> TYPE: DNA
<213> ORGANISM: Homo sapiens

<400> SEQUENCE: 127
cttatatggt atgatggaag taataattat tatgcagact ccgtgaaggg c         51

<210> SEQ ID NO 128
<211> LENGTH: 51
<212> TYPE: DNA
<213> ORGANISM: Homo sapiens

<400> SEQUENCE: 128
gttatatcat atgatggaag taataaatac tatgcagact ccgtgaaggg c         51

<210> SEQ ID NO 129
<211> LENGTH: 51
<212> TYPE: DNA
<213> ORGANISM: Homo sapiens

<400> SEQUENCE: 129
tccattagta gtagtagtac ttacatatac tacgcagact cagtgaaggg c         51

<210> SEQ ID NO 130
<211> LENGTH: 51
<212> TYPE: DNA
<213> ORGANISM: Homo sapiens

<400> SEQUENCE: 130
gttatatggt atgatggaag taatacatac tatgcagact ccgtgaaggg c         51

<210> SEQ ID NO 131
<211> LENGTH: 48
<212> TYPE: DNA
<213> ORGANISM: Homo sapiens

<400> SEQUENCE: 131
ggccgtagta ccagcccgct cgactactac tactactaca tggacgtc            48

<210> SEQ ID NO 132
<211> LENGTH: 33
<212> TYPE: DNA
<213> ORGANISM: Homo sapiens

<400> SEQUENCE: 132
ggctcaatgg caagacccaa gccatttgac tac                            33

<210> SEQ ID NO 133
<211> LENGTH: 57
<212> TYPE: DNA
<213> ORGANISM: Homo sapiens

<400> SEQUENCE: 133

```
gcgaaagatc cccaagagcg tatttattac tctgatacta gtggttacct tgactac        57
```

<210> SEQ ID NO 134
<211> LENGTH: 48
<212> TYPE: DNA
<213> ORGANISM: Homo sapiens

<400> SEQUENCE: 134

```
tctcctgcta tgattcgggg agttaggggg ggtgactact ttgactac                  48
```

<210> SEQ ID NO 135
<211> LENGTH: 48
<212> TYPE: DNA
<213> ORGANISM: Homo sapiens

<400> SEQUENCE: 135

```
gatgggaagg ggattgtagt tatttactac tactacggta tggacgtc                  48
```

<210> SEQ ID NO 136
<211> LENGTH: 24
<212> TYPE: DNA
<213> ORGANISM: Homo sapiens

<400> SEQUENCE: 136

```
ggccttaaca gcccctttga ctac                                            24
```

<210> SEQ ID NO 137
<211> LENGTH: 36
<212> TYPE: DNA
<213> ORGANISM: Homo sapiens

<400> SEQUENCE: 137

```
ccccggggca tgtatagcag ctcgtccggg gactac                               36
```

<210> SEQ ID NO 138
<211> LENGTH: 36
<212> TYPE: DNA
<213> ORGANISM: Homo sapiens

<400> SEQUENCE: 138

```
gatgggactt tctcctacta ctactacatg gacgtc                               36
```

<210> SEQ ID NO 139
<211> LENGTH: 60
<212> TYPE: DNA
<213> ORGANISM: Homo sapiens

<400> SEQUENCE: 139

```
gccgggttga actactatgg aaacctatta tcaaactact tctactacgg aatggacgtc     60
```

<210> SEQ ID NO 140
<211> LENGTH: 45
<212> TYPE: DNA
<213> ORGANISM: Homo sapiens

<400> SEQUENCE: 140

```
gcgagagatg gttgtactgg tggtagctgc tgctattttg acaac                     45
```

<210> SEQ ID NO 141
<211> LENGTH: 57
<212> TYPE: DNA
<213> ORGANISM: Homo sapiens

<400> SEQUENCE: 141

```
gcgaaagact cgtattacta tggttcgggg agacgatggg gctactactt tgactac        57
```

<210> SEQ ID NO 142
<211> LENGTH: 72
<212> TYPE: DNA
<213> ORGANISM: Homo sapiens

<400> SEQUENCE: 142

```
gcgagaagga gggaggtcgg tagagatggc tacagtttgt accccgggg gtaccactac     60 ggtatggacg tc                                                         72
```

<210> SEQ ID NO 143
<211> LENGTH: 60
<212> TYPE: DNA
<213> ORGANISM: Homo sapiens

<400> SEQUENCE: 143

```
gcgagaggcc gtggatatag tgcccaaggg aatcggaata gggcttacta ctttgactac     60
```

<210> SEQ ID NO 144
<211> LENGTH: 33
<212> TYPE: DNA
<213> ORGANISM: Homo sapiens

<400> SEQUENCE: 144

```
caaggagact tcctcagaag ctattatgca agc                                  33
```

<210> SEQ ID NO 145
<211> LENGTH: 33
<212> TYPE: DNA
<213> ORGANISM: Homo sapiens

<400> SEQUENCE: 145

```
cgggcaagtc agagcattag caggtattta aat                                  33
```

<210> SEQ ID NO 146
<211> LENGTH: 33
<212> TYPE: DNA
<213> ORGANISM: Homo sapiens

<400> SEQUENCE: 146

```
cgggccagtc agagtattag tagctggttg gcc                                  33
```

<210> SEQ ID NO 147
<211> LENGTH: 33
<212> TYPE: DNA
<213> ORGANISM: Homo sapiens

<400> SEQUENCE: 147

```
cgggcgagtc aggctttag cagttattta gtc                                   33
```

<210> SEQ ID NO 148
<211> LENGTH: 33
<212> TYPE: DNA
<213> ORGANISM: Homo sapiens

<400> SEQUENCE: 148

```
tctggagata aattggggga taaatatgct tgc                                  33
```

<210> SEQ ID NO 149
<211> LENGTH: 33
<212> TYPE: DNA

-continued

<213> ORGANISM: Homo sapiens

<400> SEQUENCE: 149
cgggcaagtc agggcattag aaatgtttta ggc                33

<210> SEQ ID NO 150
<211> LENGTH: 33
<212> TYPE: DNA
<213> ORGANISM: Homo sapiens

<400> SEQUENCE: 150
cgggcaagtc agggcattag aaatgattta ggc                33

<210> SEQ ID NO 151
<211> LENGTH: 33
<212> TYPE: DNA
<213> ORGANISM: Homo sapiens

<400> SEQUENCE: 151
cgggcgagtc aggatattag cagttcttta gcc                33

<210> SEQ ID NO 152
<211> LENGTH: 42
<212> TYPE: DNA
<213> ORGANISM: Homo sapiens

<400> SEQUENCE: 152
actgggacca gcagtgacat tggtggttat aactatgtct cc      42

<210> SEQ ID NO 153
<211> LENGTH: 33
<212> TYPE: DNA
<213> ORGANISM: Homo sapiens

<400> SEQUENCE: 153
agggccagtc agagcattag caacaactta ggc                33

<210> SEQ ID NO 154
<211> LENGTH: 33
<212> TYPE: DNA
<213> ORGANISM: Homo sapiens

<400> SEQUENCE: 154
caaggagaca gcctcagaag ctattatgca agc                33

<210> SEQ ID NO 155
<211> LENGTH: 42
<212> TYPE: DNA
<213> ORGANISM: Homo sapiens

<400> SEQUENCE: 155
actggaacca gcagtgacgt tggtggttat aactatgtct cc      42

<210> SEQ ID NO 156
<211> LENGTH: 33
<212> TYPE: DNA
<213> ORGANISM: Homo sapiens

<400> SEQUENCE: 156
agggccagtc agagtgttag cagcaactta gcc                33

<210> SEQ ID NO 157
<211> LENGTH: 21

```
<212> TYPE: DNA
<213> ORGANISM: Homo sapiens

<400> SEQUENCE: 157
ggtaaaaaca agcggccctc a                                         21

<210> SEQ ID NO 158
<211> LENGTH: 21
<212> TYPE: DNA
<213> ORGANISM: Homo sapiens

<400> SEQUENCE: 158
gctgcatcca gtttgcaaag t                                         21

<210> SEQ ID NO 159
<211> LENGTH: 21
<212> TYPE: DNA
<213> ORGANISM: Homo sapiens

<400> SEQUENCE: 159
aaggcgtcta gtttagaaag t                                         21

<210> SEQ ID NO 160
<211> LENGTH: 21
<212> TYPE: DNA
<213> ORGANISM: Homo sapiens

<400> SEQUENCE: 160
gctacatcca ctttgcaagg t                                         21

<210> SEQ ID NO 161
<211> LENGTH: 22
<212> TYPE: DNA
<213> ORGANISM: Homo sapiens

<400> SEQUENCE: 161
caagatagca agcggccctc as                                        22

<210> SEQ ID NO 162
<211> LENGTH: 21
<212> TYPE: DNA
<213> ORGANISM: Homo sapiens

<400> SEQUENCE: 162
gctgcatcca gtttgcaaag t                                         21

<210> SEQ ID NO 163
<211> LENGTH: 21
<212> TYPE: DNA
<213> ORGANISM: Homo sapiens

<400> SEQUENCE: 163
gctgcagtca gtttgcaaag t                                         21

<210> SEQ ID NO 164
<211> LENGTH: 21
<212> TYPE: DNA
<213> ORGANISM: Homo sapiens

<400> SEQUENCE: 164
gctgcatcca ctttgcaaag t                                         21

<210> SEQ ID NO 165
```

```
<211> LENGTH: 21
<212> TYPE: DNA
<213> ORGANISM: Homo sapiens

<400> SEQUENCE: 165
gaggtcacta agcggccctc a                                              21

<210> SEQ ID NO 166
<211> LENGTH: 21
<212> TYPE: DNA
<213> ORGANISM: Homo sapiens

<400> SEQUENCE: 166
ggtgcatcca ccagggccac t                                              21

<210> SEQ ID NO 167
<211> LENGTH: 21
<212> TYPE: DNA
<213> ORGANISM: Homo sapiens

<400> SEQUENCE: 167
ggtaaaaaca accggccctc a                                              21

<210> SEQ ID NO 168
<211> LENGTH: 21
<212> TYPE: DNA
<213> ORGANISM: Homo sapiens

<400> SEQUENCE: 168
gatgtcaatg atcggccctc a                                              21

<210> SEQ ID NO 169
<211> LENGTH: 21
<212> TYPE: DNA
<213> ORGANISM: Homo sapiens

<400> SEQUENCE: 169
ggtgcattca cgagggtcac t                                              21

<210> SEQ ID NO 170
<211> LENGTH: 33
<212> TYPE: DNA
<213> ORGANISM: Homo sapiens

<400> SEQUENCE: 170
aactcccggg accgcagtgg taaccacctg gtg                                 33

<210> SEQ ID NO 171
<211> LENGTH: 27
<212> TYPE: DNA
<213> ORGANISM: Homo sapiens

<400> SEQUENCE: 171
caacagagtt acagtacccc tcgcact                                        27

<210> SEQ ID NO 172
<211> LENGTH: 27
<212> TYPE: DNA
<213> ORGANISM: Homo sapiens

<400> SEQUENCE: 172
caacagtata atacttaccc gtacact                                        27
```

```
<210> SEQ ID NO 173
<211> LENGTH: 27
<212> TYPE: DNA
<213> ORGANISM: Homo sapiens

<400> SEQUENCE: 173
caacagtatt atagttaccc tccgact                                         27

<210> SEQ ID NO 174
<211> LENGTH: 30
<212> TYPE: DNA
<213> ORGANISM: Homo sapiens

<400> SEQUENCE: 174
caggcgtggg acagcagcac tgtggtattc                                      30

<210> SEQ ID NO 175
<211> LENGTH: 27
<212> TYPE: DNA
<213> ORGANISM: Homo sapiens

<400> SEQUENCE: 175
ctacagcata atagtcaccc ccggacg                                         27

<210> SEQ ID NO 176
<211> LENGTH: 27
<212> TYPE: DNA
<213> ORGANISM: Homo sapiens

<400> SEQUENCE: 176
ctacagcata atagttaccc tcggact                                         27

<210> SEQ ID NO 177
<211> LENGTH: 27
<212> TYPE: DNA
<213> ORGANISM: Homo sapiens

<400> SEQUENCE: 177
caacagtatt atagttaccc tccgacg                                         27

<210> SEQ ID NO 178
<211> LENGTH: 30
<212> TYPE: DNA
<213> ORGANISM: Homo sapiens

<400> SEQUENCE: 178
agctcatatg caggcagcaa cgatttgcta                                      30

<210> SEQ ID NO 179
<211> LENGTH: 30
<212> TYPE: DNA
<213> ORGANISM: Homo sapiens

<400> SEQUENCE: 179
caacaatata ataactggcc tcggctcact                                      30

<210> SEQ ID NO 180
<211> LENGTH: 33
<212> TYPE: DNA
<213> ORGANISM: Homo sapiens

<400> SEQUENCE: 180
aactcccggg acagcagtgg taaccatgtg gta                                  33
```

<210> SEQ ID NO 181
<211> LENGTH: 30
<212> TYPE: DNA
<213> ORGANISM: Homo sapiens

<400> SEQUENCE: 181
agctcatata caagaagcaa cactgtgata                                       30

<210> SEQ ID NO 182
<211> LENGTH: 30
<212> TYPE: DNA
<213> ORGANISM: Homo sapiens

<400> SEQUENCE: 182
cagcagtaca atgaccggcc cccgtacact                                       30

<210> SEQ ID NO 183
<211> LENGTH: 372
<212> TYPE: DNA
<213> ORGANISM: Homo sapiens

<400> SEQUENCE: 183
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattgggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag gggccgtagt     300
accagcccgc tcgactacta ctactactac atggacgtct gggccaaagg gaccacggtc     360
accgtctcct ca                                                         372

<210> SEQ ID NO 184
<211> LENGTH: 357
<212> TYPE: DNA
<213> ORGANISM: Homo sapiens

<400> SEQUENCE: 184
caggtgcagc tacagcagtg gggcgcagga ctgttgaagc cttcggagac cctgtccctc      60
acctgcgctg tctatggtgg gtccttcagt ggttattact ggagctggat ccgccagccc     120
ccagggaagg ggctggagtg gattgggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcgag aggctcaatg     300
gcaagaccca agccatttga ctactggggc cagggaaccc tggtcaccgt ctcctca       357

<210> SEQ ID NO 185
<211> LENGTH: 378
<212> TYPE: DNA
<213> ORGANISM: Homo sapiens

<400> SEQUENCE: 185
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcattt atacggtatg atggaagtaa taaatacttt     180
gcagactccg tgagggggccg attcaccatc tccagagaca attccaagaa cacgctgttt     240
ctgcaaatga acagcctgag agctgaggac acggctgtgt attactgtgc gaaagatccc     300

```
caagagcgta tttattactc tgatactagt ggttaccttg actactgggg ccagggaacc      360
ctggtcaccg tctcctca                                                    378

<210> SEQ ID NO 186
<211> LENGTH: 375
<212> TYPE: DNA
<213> ORGANISM: Homo sapiens

<400> SEQUENCE: 186
gaggtgcacc tgttggagtc tgggggaggc ttggtacagc ctgggggtc cctgagactc        60 tcctgtgcag cctctggatt cacctttagc agctatgcca tgagttgggt ccgccaggct      120
ccagggaagg ggctggagtg ggtctcaact attagggcta gtggtggtag cacaagctac      180
gcagactccg tgaagggccg gttcaccatc tccagagaca attcccagag caggttgtat      240
ctgcaaatga acagtctgac agccgaggac acggccgtat attactgtgc gaaatctcct      300
gctatgattc ggggagttag ggggggtgac tactttgact actggggcca gggaaccctg      360
gtcaccgtct cctca                                                       375

<210> SEQ ID NO 187
<211> LENGTH: 375
<212> TYPE: DNA
<213> ORGANISM: Homo sapiens

<400> SEQUENCE: 187
caggtgcagc tggtggagtc tgggggaggc gtggtccagc ctggggaggtc cctgagactc      60 tcctgtgcag cctctggatt caccttcagt agctatggca tgcactgggt ccgccaggct      120
ccaggcaagg ggctggagtg ggtggcagtt atatcatatg atggaagtaa taaatactat      180
gcagactccg tgaagggccg attcaccatc tccagagaca attccaagaa cacgctgtat      240
ctgcaaatga acagcctgag agctgaggac acggctgtgt attactgtgc gaaagatggg      300 aagggggattg tagttatttta ctactactac ggtatggacg tctggggcca agggaccacg      360
gtcaccgtct cctca                                                       375

<210> SEQ ID NO 188
<211> LENGTH: 348
<212> TYPE: DNA
<213> ORGANISM: Homo sapiens

<400> SEQUENCE: 188
caggtacagc tacagcagtg gggcgcagga ctgttgaagc cttcggagac cctgtccctc       60
acctgcgctg tctatggtgg gtccttcagt ggttacttct ggacctggat ccgccagccc      120
ccagggaagg ggctggagtg gattgggaa accgttcata gtggaggcac caactacaac      180
ccgtccctca agagtcgagt caccatatca gtcgacacgt ccaagaacca gttctccctg      240
aggctgaact ctgtgaccgc cgcggacacg gctgtgtatt actgtgtgag aggccttaac      300 agccccttttg actactgggg ccagggaacc ctagtcaccg tctcctca                  348

<210> SEQ ID NO 189
<211> LENGTH: 363
<212> TYPE: DNA
<213> ORGANISM: Homo sapiens

<400> SEQUENCE: 189
caggtgcagc tacagcagtg gggcgcagga ctgttgaagc cttcggagac cctgtccctc       60
```

| | |
|---|---|
| acctgcgctg tctatggtgg gtccttcagt ggttactact ggagctggat ccgccagccc | 120 |
| ccagggaagg ggctggagtg gattggggaa atcaatcata gtggaagcac caactacaac | 180 |
| ccgtccctca agagtcgagt caccatatca gtagacacgt ccaagaagca gttctccctg | 240 |
| aagctgagct ctgtgaccgc cgcggacacg gctgtgtatt attgtgcgag aggcccccgg | 300 |
| ggcatgtata gcagctcgtc cggggactac tggggccagg gaaccctggt caccgtctcc | 360 |
| tca | 363 |

<210> SEQ ID NO 190
<211> LENGTH: 363
<212> TYPE: DNA
<213> ORGANISM: Homo sapiens

<400> SEQUENCE: 190

| | |
|---|---|
| gaggtgcagc tggtggagtc tggggqaggc ctggtcaagc ctggggggtc cctgagactc | 60 |
| tcctgtgcag cctctggatt caccttcagt acctatagca tgaactgggt ccgccaggct | 120 |
| ccagggaagg ggctggagtg ggtctcatcc attagtagta gtagtggtta catatactac | 180 |
| gcagactcag tgaagggccg attcaccatc tccagagaca acgccaagaa ctcactgtat | 240 |
| ctgcaaatga acagcctgag agccgaggac acggctgtgt attactgtgc gagagatggg | 300 |
| actttctcct actactacta catggacgtc tggggcaaag gaccacggt caccgtctcc | 360 |
| tca | 363 |

<210> SEQ ID NO 191
<211> LENGTH: 387
<212> TYPE: DNA
<213> ORGANISM: Homo sapiens

<400> SEQUENCE: 191

| | |
|---|---|
| caggtgcagc tggtggagtc tggggqaggc gtggtccagc ctgggaggtc cctgagactc | 60 |
| tcctgtgcag tctctggact cagtttcagg aattatggca tgcactgggt ccgccaggct | 120 |
| cccggcaagg ggctggagtg ggtggcagtc atttcgcatg atggaagtaa gacatactat | 180 |
| ggacactccg tgaagggccg attcaccata tccagagaca atccaagac tatgttgttt | 240 |
| ctccaaatga acagcctgag acctgaggac acggctgttt attactgtgc gaaagccggg | 300 |
| ttgaactact atggaaacct attatcaaac tacttctact acggaatgga cgtctgggc | 360 |
| caagggacca cagtcaccgt ctcgtca | 387 |

<210> SEQ ID NO 192
<211> LENGTH: 366
<212> TYPE: DNA
<213> ORGANISM: Homo sapiens

<400> SEQUENCE: 192

| | |
|---|---|
| caggtgcacc tggtggagtc tggggqaggc gtggtccagc ctgggacgtc cctgagactc | 60 |
| tcctgtgcag cgtctgaatt caccttcagt tcccatgcca tacactgggt ccgccaggct | 120 |
| ccaggcaagg ggctggagtg ggtggcactt atatggtatg atggaagtaa taattattat | 180 |
| gcagactccg tgaagggccg attcaccatc tccagagaca gttccaagaa cacggtgcat | 240 |
| ctgcaaatga acagcctgag agtcgaggac acggctgtgt attactgtgc gagagatggt | 300 |
| tgtactggtg gtagctgctg ctatttttgac aactggggcc agggaaccct agtcaccgtc | 360 |
| tcctcg | 366 |

<210> SEQ ID NO 193
<211> LENGTH: 378
<212> TYPE: DNA
<213> ORGANISM: Homo sapiens

<400> SEQUENCE: 193
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagactcg   300
tattactatg gttcggggag acgatggggc tactactttg actactgggg ccagggaacc   360
ctggtcaccg tctcctca                                                 378

<210> SEQ ID NO 194
<211> LENGTH: 393
<212> TYPE: DNA
<213> ORGANISM: Homo sapiens

<400> SEQUENCE: 194
gaggtgcagc tggtggagtc tgggggaggc ctggtcaagc ctgggggatc cctgagactc    60
tcctgtgcag cctctggatt caccttcagt agttatagca tgaactgggt ccgccaggct   120
ccagggaagg ggctggagtg ggtctcatcc attagtagta gtagtactta catatactac   180
gcagactcag tgaagggccg attcaccatc tccagagaca acgccaggaa ctcactgtat   240
ctgcaaatga acagcctgag agccgaggac acggctgtgt attattgtgc gagaaggagg   300
gaggtcggta gagatggcta cagtttgtac ccccgggggt accactacgg tatggacgtc   360
tggggccaag ggaccacggt caccgtctcc tca                                393

<210> SEQ ID NO 195
<211> LENGTH: 381
<212> TYPE: DNA
<213> ORGANISM: Homo sapiens

<400> SEQUENCE: 195
caggtgcagc tggtggagtc tgggggaggc gtggtccagc ctgggaggtc cctgagactc    60
tcctgtgcag cgtctggatt caccttcagt acctatggca tgcactgggt ccgccaggct   120
ccaggcaagg ggcttgagtg ggtggcagtt atatggtatg atggaagtaa tacatactat   180
gcagactccg tgaagggccg attcaccatc tccagagaca attccaagaa cacactgtat   240
ctgcaaataa agagcctgag agccgaggac acggctgtct attactgtgc gagaggccgt   300
ggatatagtg cccaagggaa tcggaatagg gcttactact ttgactactg gggccaggga   360
accctggtca ccgtctcctc a                                             381

<210> SEQ ID NO 196
<211> LENGTH: 324
<212> TYPE: DNA
<213> ORGANISM: Homo sapiens

<400> SEQUENCE: 196
tcttctgagc tgactcagga ccctgctgtg tctgtggcct tgggacagac agtcaggatc    60
acatgccaag agacttcct cagaagctat tatgcaagct ggtaccagca gaagccagga   120
caggcccctg tacttgtcat ctttggtaaa aacaagcggc cctcagggat cccagaccga   180

```
ttctctggct ccagctcagg aaacacagct tccttgacca tcactggggc tcaggcggaa    240
gatgaggctg actattactg taactcccgg gaccgcagtg gtaaccacct ggtgttcggc    300
ggagggacca agctgaccgt ccta                                          324

<210> SEQ ID NO 197
<211> LENGTH: 321
<212> TYPE: DNA
<213> ORGANISM: Homo sapiens

<400> SEQUENCE: 197
gacatccaga tgacccagtc tccatcctcc ctgtctgcat ctgtaggaga cagagtcacc     60
atcacttgcc gggcaagtca gagcattagc aggtatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcgcac tttcggccct    300
gggaccaaag tggatatcaa a                                             321

<210> SEQ ID NO 198
<211> LENGTH: 321
<212> TYPE: DNA
<213> ORGANISM: Homo sapiens

<400> SEQUENCE: 198
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcactggatc tgggacagaa ttcactctca ccatcagcag cctgcagcct    240
gatgattttg caacttatta ctgccaacag tataatactt acccgtacac ttttggccag    300
gggaccaagc tggagatcaa a                                             321

<210> SEQ ID NO 199
<211> LENGTH: 321
<212> TYPE: DNA
<213> ORGANISM: Homo sapiens

<400> SEQUENCE: 199
gccatccggt tgacccagtc tccatcctca gtctctgcat ctacaggaga cagagtcacc     60
atcacttgtc gggcgagtca ggcttttagc agttatttag tctggtatca gcaaaaacca    120
gggaaagccc ctaacctcct gatctacgct acatccactt tgcaaggtgg ggtcccatca    180
aggttcagcg gcagtggatc tgggacagat ttcactctca ccatcagcaa cctgcagtct    240
gaagattttg caacttatta ctgtcaacag tattatagtt accctccgac ttttggccag    300
gggaccaagt tggagatcaa a                                             321

<210> SEQ ID NO 200
<211> LENGTH: 318
<212> TYPE: DNA
<213> ORGANISM: Homo sapiens

<400> SEQUENCE: 200
tcctatgagc tgactcagcc accctcagtg tccgtgtccc caggacagac agccagcatc     60
acctgctctg gagataaatt gggggataaa tatgcttgct ggtatcagca gaagccaggc    120
cagtcccctg tgctggtcat ctatcaagat agcaagcggc cctcagggat ccctgagcga    180
```

```
ttctctggct ccaactctgg gaacacagcc actctgacca tcagcgggac ccaggctatg    240
gatgaggctg actattactg tcaggcgtgg gacagcagca ctgtggtatt cggcggaggg    300
accaagctga ccgtccta                                                  318
```

<210> SEQ ID NO 201
<211> LENGTH: 321
<212> TYPE: DNA
<213> ORGANISM: Homo sapiens

<400> SEQUENCE: 201

```
gacatccaga tgacccagtc tccatcctcc ctgtctgcat ctgtaggaga cagagtcacc    60
atcacttgcc gggcaagtca gggcattaga aatgttttag ctggtatca gcagaaacca   120 gggaaagccc ctaagtgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtc accccggac gttcggccaa    300 gggaccaagg tggaaatcaa a                                              321
```

<210> SEQ ID NO 202
<211> LENGTH: 321
<212> TYPE: DNA
<213> ORGANISM: Homo sapiens

<400> SEQUENCE: 202

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcagtcagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcggac ttttggccag   300
gggaccaagc tggagatcaa a                                              321
```

<210> SEQ ID NO 203
<211> LENGTH: 321
<212> TYPE: DNA
<213> ORGANISM: Homo sapiens

<400> SEQUENCE: 203

```
gccatccgga tgacccagtc tccatcctca ttctctgcat ctacaggaga cagagtcacc    60
atcacttgtc gggcgagtca ggatattagc agttctttag cctggtatca gcaaaaacca   120
gggaaagccc ctaagctcct gatctatgct gcatccactt tgcaaagtgg agtcccatca   180
aggttcagcg gcagtggatc tgggacagac ttcactctca ccatcagctg cctgcagtct   240
gaagattttg caacttatta ctgtcaacag tattatagtt accctccgac gttcggccaa    300
gggaccaggt tggaaatcaa a                                              321
```

<210> SEQ ID NO 204
<211> LENGTH: 330
<212> TYPE: DNA
<213> ORGANISM: Homo sapiens

<400> SEQUENCE: 204

```
cagtctgccc tgactcagcc tccctccgcg tccgggtctc ctggtcagtc agtcaccatc    60
tcctgtactg gaccagcag tgacattggt ggttataact atgtctcctg gtaccaacac   120
```

```
cacccaggca aagcccccaa attgatgatt tatgaggtca ctaagcggcc ctcaggggtc        180
cctgatcgtt tctctggctc caagtctggc aacacggcct ccctgaccgt ctctggactc        240
caggctgagg atgaggctca ttattactgc agctcatatg caggcagcaa cgatttgcta        300
ttcggcggag ggaccaagct gaccgtcctg                                         330

<210> SEQ ID NO 205
<211> LENGTH: 324
<212> TYPE: DNA
<213> ORGANISM: Homo sapiens

<400> SEQUENCE: 205
gaagtagtga tgacgcagtc tccagccacc ctgtctgtgt ctccagggga aagagccacc         60
ctctcctgca gggccagtca gagcattagc aacaacttag ctggtatca gcagaaacct        120 ggccaggctc ccaggctcct catctacggt gcatccacca gggccactgg tatcccaggc        180
aggttcagtg gcagtgggtc tgggacagag ttcactctca ccatctacag cctgcagtct        240
gaggattttg cagtttatta ctgtcaacaa tataataact ggcctcggct cactttcggc        300
ggagggacca aggtggagat caaa                                               324

<210> SEQ ID NO 206
<211> LENGTH: 324
<212> TYPE: DNA
<213> ORGANISM: Homo sapiens

<400> SEQUENCE: 206
tcttctgagc tgactcagga ccctgctgtg tctgtggcct tgggacagac agtcaggatc         60
acatgccaag agacagcct cagaagctat tatgcaagct ggtaccagca gaagccagga        120
caggcccctg tacttgtcat ctatggtaaa aacaaccggc cctcagggat cccagaccga        180
ttctctggct ccagctcagg aaacacagct tccttgacca tcactggggc tcaggcggaa        240
gatgaggctg actattactg taactcccgg gacagcagtg gtaaccatgt ggtattcggc        300
ggagggacca agctgaccgt ccta                                               324

<210> SEQ ID NO 207
<211> LENGTH: 330
<212> TYPE: DNA
<213> ORGANISM: Homo sapiens

<400> SEQUENCE: 207
cagtctgccc tgactcagcc tgcctccgtg tctgggtctc ctagacagtc gatcaccatc         60
tcctgcactg gaaccagcag tgacgttggt ggttataact atgtctcctg gtaccaacaa        120
ctcccaggca aagcccccaa actcatgatt tatgatgtca atgatcggcc ctcaggggtt        180
tctattcgct tctctggctc caagtctggc aacacggcct ccctgaccat ctctgggctc        240
caggctgagg acgaggctga ttattactgc agctcatata caagaagcaa cactgtgata        300
ttcggcggag ggaccaaact gaccgtccta                                         330

<210> SEQ ID NO 208
<211> LENGTH: 324
<212> TYPE: DNA
<213> ORGANISM: Homo sapiens

<400> SEQUENCE: 208
gaaatagtga tgacgcagtc tccagccacc ctgtctgtgt ctccagggga aagggtcatc         60
ctctcctgca gggccagtca gagtgttagc agcaacttag cctggtacca gcagaaacct        120
```

```
ggccagcctc ccaggctcct catctatggt gcattcacga gggtcactgg tgtcccagcc    180
aggttcagtg gcagtgggtc tgggacagaa ttcactctca ccatcagcag cctgcagtct    240
gaagattttg cagtttatta ctgtcagcag tacaatgacc ggccccgta cacttttggc    300 caggggacca agctggagat caaa                                           324
```

<210> SEQ ID NO 209
<211> LENGTH: 6
<212> TYPE: PRT
<213> ORGANISM: Homo sapiens

<400> SEQUENCE: 209

Ser Pro Asn Trp Trp Thr
1               5

<210> SEQ ID NO 210
<211> LENGTH: 5
<212> TYPE: PRT
<213> ORGANISM: Homo sapiens

<400> SEQUENCE: 210

Asp Ala Trp Met Ser
1               5

<210> SEQ ID NO 211
<211> LENGTH: 5
<212> TYPE: PRT
<213> ORGANISM: Homo sapiens

<400> SEQUENCE: 211

Asp Phe Ala Met Ser
1               5

<210> SEQ ID NO 212
<211> LENGTH: 5
<212> TYPE: PRT
<213> ORGANISM: Homo sapiens

<400> SEQUENCE: 212

Ser Tyr Ala Met Thr
1               5

<210> SEQ ID NO 213
<211> LENGTH: 16
<212> TYPE: PRT
<213> ORGANISM: Homo sapiens

<400> SEQUENCE: 213

Glu Ile Tyr Tyr Gly Gly Arg Val Ser Tyr Asn Ser Ala Leu Arg Ser
1               5                   10                  15

<210> SEQ ID NO 214
<211> LENGTH: 19
<212> TYPE: PRT
<213> ORGANISM: Homo sapiens

<400> SEQUENCE: 214

His Ile Asn Thr Lys Val Asp Gly Gly Thr Thr Glu Tyr Ala Ala Pro
1               5                   10                  15

Val Lys Gly

<210> SEQ ID NO 215

-continued

```
<211> LENGTH: 19
<212> TYPE: PRT
<213> ORGANISM: Homo sapiens

<400> SEQUENCE: 215

Phe Ile Arg Thr Lys Ala Asn Asp Gly Thr Thr Glu Tyr Ala Ala Ser
1               5                   10                  15
Val Lys Gly

<210> SEQ ID NO 216
<211> LENGTH: 17
<212> TYPE: PRT
<213> ORGANISM: Homo sapiens

<400> SEQUENCE: 216

Ser Ile Ser Gly Ser Gly Gly Ser Thr Tyr Tyr Ala Asp Ser Val Arg
1               5                   10                  15
Gly

<210> SEQ ID NO 217
<211> LENGTH: 20
<212> TYPE: PRT
<213> ORGANISM: Homo sapiens

<400> SEQUENCE: 217

Ala Gly Gln Lys Asn Ile Gly Cys Gly Tyr Ser Ser Cys Phe Ile Ser
1               5                   10                  15
Trp Phe Asp Thr
            20

<210> SEQ ID NO 218
<211> LENGTH: 15
<212> TYPE: PRT
<213> ORGANISM: Homo sapiens

<400> SEQUENCE: 218

Thr Thr Glu Ala Ile Tyr Asp Ser Ser Gly Tyr Phe His Asp Tyr
1               5                   10                  15

<210> SEQ ID NO 219
<211> LENGTH: 17
<212> TYPE: PRT
<213> ORGANISM: Homo sapiens

<400> SEQUENCE: 219

Ala Ser Asp Pro Phe Met Thr Thr Asp Tyr Tyr Tyr Tyr Met Asp
1               5                   10                  15
Val

<210> SEQ ID NO 220
<211> LENGTH: 20
<212> TYPE: PRT
<213> ORGANISM: Homo sapiens

<400> SEQUENCE: 220

Ala Lys Gly Tyr Val Gly Cys Ser Gly Gly Asn Cys Tyr Ser Gly Gly
1               5                   10                  15
Ala Phe Asp Ile
            20

<210> SEQ ID NO 221
<211> LENGTH: 17
```

```
<212> TYPE: PRT
<213> ORGANISM: Homo sapiens

<400> SEQUENCE: 221

Lys Ser Ser Gln Thr Ile Leu Gln Arg Ser Asn His Leu Asn Tyr Leu
1               5                   10                  15

Ala

<210> SEQ ID NO 222
<211> LENGTH: 17
<212> TYPE: PRT
<213> ORGANISM: Homo sapiens

<400> SEQUENCE: 222

Lys Ser Ser Arg Ser Val Leu Tyr Ser Ser Asn Asn Lys Asn Tyr Leu
1               5                   10                  15

Ala

<210> SEQ ID NO 223
<211> LENGTH: 14
<212> TYPE: PRT
<213> ORGANISM: Homo sapiens

<400> SEQUENCE: 223

Thr Gly Thr Ser Ser Asp Val Gly Gly Tyr Asn Ser Val Ser
1               5                   10

<210> SEQ ID NO 224
<211> LENGTH: 11
<212> TYPE: PRT
<213> ORGANISM: Homo sapiens

<400> SEQUENCE: 224

Gly Gly Asn Asn Ile Gly Ser Glu Ser Val His
1               5                   10

<210> SEQ ID NO 225
<211> LENGTH: 7
<212> TYPE: PRT
<213> ORGANISM: Homo sapiens

<400> SEQUENCE: 225

Trp Ala Ser Thr Arg Glu Ser
1               5

<210> SEQ ID NO 226
<211> LENGTH: 7
<212> TYPE: PRT
<213> ORGANISM: Homo sapiens

<400> SEQUENCE: 226

Trp Ala Ser Ile Arg Glu Ser
1               5

<210> SEQ ID NO 227
<211> LENGTH: 7
<212> TYPE: PRT
<213> ORGANISM: Homo sapiens

<400> SEQUENCE: 227

Glu Val Tyr Lys Arg Pro Leu
1               5
```

```
<210> SEQ ID NO 228
<211> LENGTH: 7
<212> TYPE: PRT
<213> ORGANISM: Homo sapiens

<400> SEQUENCE: 228

Tyr Asp Thr Asp Arg Pro Ser
1               5

<210> SEQ ID NO 229
<211> LENGTH: 9
<212> TYPE: PRT
<213> ORGANISM: Homo sapiens

<400> SEQUENCE: 229

His Gln Tyr Tyr Thr Thr Pro Gln Thr
1               5

<210> SEQ ID NO 230
<211> LENGTH: 8
<212> TYPE: PRT
<213> ORGANISM: Homo sapiens

<400> SEQUENCE: 230

Gln Gln Tyr Ser Arg Pro Pro Thr
1               5

<210> SEQ ID NO 231
<211> LENGTH: 9
<212> TYPE: PRT
<213> ORGANISM: Homo sapiens

<400> SEQUENCE: 231

Ser Ser Tyr Gly Gly Thr Val Leu Phe
1               5

<210> SEQ ID NO 232
<211> LENGTH: 13
<212> TYPE: PRT
<213> ORGANISM: Homo sapiens

<400> SEQUENCE: 232

Gln Val Trp Asp Asn Thr Ser Asp His Pro Val Val Phe
1               5                   10

<210> SEQ ID NO 233
<211> LENGTH: 128
<212> TYPE: PRT
<213> ORGANISM: Homo sapiens

<400> SEQUENCE: 233

Gln Gly Arg Leu Gln Glu Ser Gly Pro Gly Leu Val Lys Pro Ser Glu
1               5                   10                  15

Thr Leu Thr Leu Thr Cys Ala Val Ser Gly Gly Ser Val Ser Ser
            20                  25                  30

Pro Asn Trp Trp Thr Trp Val Arg Gln Ala Pro Gly Lys Gly Leu Glu
        35                  40                  45

Trp Ile Gly Glu Ile Tyr Tyr Gly Gly Arg Val Ser Tyr Asn Ser Ala
    50                  55                  60

Leu Arg Ser Arg Val Thr Ile Ser Ser Asp Arg Ser Lys Glu Glu Phe
65                  70                  75                  80

Ser Leu Lys Leu Arg Ser Val Thr Ala Ala Asp Thr Ala Ile Tyr Tyr
                85                  90                  95
```

```
Cys Ala Gly Gln Lys Asn Ile Gly Cys Gly Tyr Ser Ser Cys Phe Ile
                100                 105                 110

Ser Trp Phe Asp Thr Trp Gln Gly Ile Ala Val Thr Val Ser Ser
            115                 120                 125
```

<210> SEQ ID NO 234
<211> LENGTH: 124
<212> TYPE: PRT
<213> ORGANISM: Homo sapiens

<400> SEQUENCE: 234

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Ser Trp Val Arg Gln Ala Pro Gly Lys Gly Leu Glu Trp Val
        35                  40                  45

Gly His Ile Asn Thr Lys Val Asp Gly Gly Thr Thr Glu Tyr Ala Ala
    50                  55                  60

Pro Val Lys Gly Arg Phe Thr Ile Ser Arg Asp Asp Ser Lys Asn Ser
65                  70                  75                  80

Leu Tyr Leu His Met Asp Ser Leu Lys Thr Glu Asp Thr Ala Val Tyr
                85                  90                  95

Tyr Cys Thr Thr Glu Ala Ile Tyr Asp Ser Ser Gly Tyr Phe His Asp
            100                 105                 110

Tyr Trp Gly Gln Gly Ser Leu Val Thr Val Ser Ser
        115                 120
```

<210> SEQ ID NO 235
<211> LENGTH: 126
<212> TYPE: PRT
<213> ORGANISM: Homo sapiens

<400> SEQUENCE: 235

```
Glu Val Gln Leu Val Glu Ser Gly Gly Gly Leu Ala Gln Pro Gly Arg
1               5                   10                  15

Ser Leu Arg Leu Ser Cys Thr Ala Ser Gly Phe Arg Phe Gly Asp Phe
            20                  25                  30

Ala Met Ser Trp Val Arg Gln Ala Pro Gly Lys Gly Leu Glu Trp Val
        35                  40                  45

Gly Phe Ile Arg Thr Lys Ala Asn Asp Gly Thr Thr Glu Tyr Ala Ala
    50                  55                  60

Ser Val Lys Gly Arg Phe Ile Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ser Asp Pro Phe Met Thr Thr Asp Tyr Tyr Tyr Tyr Tyr
            100                 105                 110

Met Asp Val Trp Gly Lys Gly Thr Thr Val Thr Val Ser Ser
        115                 120                 125
```

<210> SEQ ID NO 236
<211> LENGTH: 127
<212> TYPE: PRT
<213> ORGANISM: Homo sapiens

<400> SEQUENCE: 236

Glu Val Gln Val Leu Glu Ser Gly Gly Asp Ser Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Lys Trp Val
        35                  40                  45

Ser Ser Ile Ser Gly Ser Gly Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Gly Tyr Val Gly Cys Ser Gly Gly Asn Cys Tyr Ser Gly Gly
            100                 105                 110

Ala Phe Asp Ile Trp Gly Gln Gly Thr Val Thr Val Ser Ser
            115                 120                 125

<210> SEQ ID NO 237
<211> LENGTH: 113
<212> TYPE: PRT
<213> ORGANISM: Homo sapiens

<400> SEQUENCE: 237

Asp Ile Val Met Thr Gln Ser Pro Asp Ser Leu Ala Val Ser Leu Gly
1               5                   10                  15

Glu Arg Ala Thr Ile Ala Cys Lys Ser Ser Gln Thr Ile Leu Gln Arg
            20                  25                  30

Ser Asn His Leu Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys His Gln
                85                  90                  95

Tyr Tyr Thr Thr Pro Gln Thr Phe Gly Gln Gly Thr Lys Val Glu Ile
            100                 105                 110

Lys

<210> SEQ ID NO 238
<211> LENGTH: 112
<212> TYPE: PRT
<213> ORGANISM: Homo sapiens

<400> SEQUENCE: 238

Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln 85                  90                  95

Tyr Ser Arg Pro Pro Thr Phe Gly Gln Gly Thr Lys Val Glu Ile Lys
                100                 105                 110

<210> SEQ ID NO 239
<211> LENGTH: 108
<212> TYPE: PRT
<213> ORGANISM: Homo sapiens

<400> SEQUENCE: 239

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Ser Val Ser Trp Tyr Gln His Pro Gly Lys Ala Pro Lys Leu
            35                  40                  45

Met Ile Tyr Glu Val Tyr Lys Arg Pro Leu Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Tyr Tyr Tyr Cys Ser Ser Tyr Gly Gly Thr
                85                  90                  95

Val Leu Phe Gly Gly Gly Thr Lys Leu Thr Val Leu
                100                 105

<210> SEQ ID NO 240
<211> LENGTH: 109
<212> TYPE: PRT
<213> ORGANISM: Homo sapiens

<400> SEQUENCE: 240

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Glu Ser Val
                20                  25                  30

His Trp Tyr Gln Gln Lys Pro Gly Gln Ala Pro Val Val Val Ile Tyr
            35                  40                  45

Tyr Asp Thr Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Thr Ser Asp His
                85                  90                  95

Pro Val Val Phe Gly Gly Gly Thr Lys Leu Thr Val Leu
                100                 105

<210> SEQ ID NO 241
<211> LENGTH: 18
<212> TYPE: DNA
<213> ORGANISM: Homo sapiens

<400> SEQUENCE: 241
agtcctaact ggtggact                                                18

<210> SEQ ID NO 242
<211> LENGTH: 15
<212> TYPE: DNA
<213> ORGANISM: Homo sapiens

```
<400> SEQUENCE: 242
gacgcctgga tgagc                                                  15

<210> SEQ ID NO 243
<211> LENGTH: 15
<212> TYPE: DNA
<213> ORGANISM: Homo sapiens

<400> SEQUENCE: 243
gattttgcta tgagt                                                  15

<210> SEQ ID NO 244
<211> LENGTH: 15
<212> TYPE: DNA
<213> ORGANISM: Homo sapiens

<400> SEQUENCE: 244
agctatgcca tgacc                                                  15

<210> SEQ ID NO 245
<211> LENGTH: 48
<212> TYPE: DNA
<213> ORGANISM: Homo sapiens

<400> SEQUENCE: 245
gaaatctatt atggtgggag agtgagctac aactcggccc tcaggagt              48

<210> SEQ ID NO 246
<211> LENGTH: 57
<212> TYPE: DNA
<213> ORGANISM: Homo sapiens

<400> SEQUENCE: 246
catattaaca ccaaagttga tggtgggaca acagagtacg ctgcacccgt gaaaggc    57

<210> SEQ ID NO 247
<211> LENGTH: 57
<212> TYPE: DNA
<213> ORGANISM: Homo sapiens

<400> SEQUENCE: 247
ttcattagaa ccaaagctaa tgatgggaca acagaatacg ccgcgtctgt gaaaggc    57

<210> SEQ ID NO 248
<211> LENGTH: 51
<212> TYPE: DNA
<213> ORGANISM: Homo sapiens

<400> SEQUENCE: 248
agtattagtg gtagtggtgg tagcacatac tacgcagact ccgtgagggg c          51

<210> SEQ ID NO 249
<211> LENGTH: 60
<212> TYPE: DNA
<213> ORGANISM: Homo sapiens

<400> SEQUENCE: 249
gcgggtcaaa aaatattgg ctgtggttac agcagttgct ttatcagttg gttcgacacc  60

<210> SEQ ID NO 250
<211> LENGTH: 45
<212> TYPE: DNA
<213> ORGANISM: Homo sapiens
```

```
<400> SEQUENCE: 250
accacagagg cgatatatga tagtagtggt tatttccatg actat            45

<210> SEQ ID NO 251
<211> LENGTH: 51
<212> TYPE: DNA
<213> ORGANISM: Homo sapiens

<400> SEQUENCE: 251
gctagcgatc ccttcatgac tacagactat tactactact acatggacgt c      51

<210> SEQ ID NO 252
<211> LENGTH: 60
<212> TYPE: DNA
<213> ORGANISM: Homo sapiens

<400> SEQUENCE: 252
gcgaaaggat atgtggggtg tagtggtggg aactgctact cgggggtgc ttttgatatc  60

<210> SEQ ID NO 253
<211> LENGTH: 51
<212> TYPE: DNA
<213> ORGANISM: Homo sapiens

<400> SEQUENCE: 253
aagtccagcc agactatttt acaaaggtcc aaccatttga actacttagc t      51

<210> SEQ ID NO 254
<211> LENGTH: 51
<212> TYPE: DNA
<213> ORGANISM: Homo sapiens

<400> SEQUENCE: 254
aagtccagcc ggagtgtttt atacagctcc aacaataaga actacttagc t      51

<210> SEQ ID NO 255
<211> LENGTH: 42
<212> TYPE: DNA
<213> ORGANISM: Homo sapiens

<400> SEQUENCE: 255
actgggacca gcagtgacgt tggtggttat aactctgtct cc               42

<210> SEQ ID NO 256
<211> LENGTH: 33
<212> TYPE: DNA
<213> ORGANISM: Homo sapiens

<400> SEQUENCE: 256 gggggggaaca acattggaag tgaaagtgtt cac                       33

<210> SEQ ID NO 257
<211> LENGTH: 21
<212> TYPE: DNA
<213> ORGANISM: Homo sapiens

<400> SEQUENCE: 257
tgggcatcta cccgggaatc c                                    21

<210> SEQ ID NO 258
<211> LENGTH: 21
<212> TYPE: DNA
<213> ORGANISM: Homo sapiens
```

```
<400> SEQUENCE: 258
tgggcatcta tccgggaatc c                                                21

<210> SEQ ID NO 259
<211> LENGTH: 21
<212> TYPE: DNA
<213> ORGANISM: Homo sapiens

<400> SEQUENCE: 259
gaggtctata agcggccctt a                                                21

<210> SEQ ID NO 260
<211> LENGTH: 21
<212> TYPE: DNA
<213> ORGANISM: Homo sapiens

<400> SEQUENCE: 260
tatgataccg accggccctc a                                                21

<210> SEQ ID NO 261
<211> LENGTH: 27
<212> TYPE: DNA
<213> ORGANISM: Homo sapiens

<400> SEQUENCE: 261
caccaatatt atactactcc gcagact                                          27

<210> SEQ ID NO 262
<211> LENGTH: 24
<212> TYPE: DNA
<213> ORGANISM: Homo sapiens

<400> SEQUENCE: 262
cagcaatatt ctcgtcctcc gacg                                             24

<210> SEQ ID NO 263
<211> LENGTH: 27
<212> TYPE: DNA
<213> ORGANISM: Homo sapiens

<400> SEQUENCE: 263
agctcatatg gaggcaccgt gctattc                                          27

<210> SEQ ID NO 264
<211> LENGTH: 39
<212> TYPE: DNA
<213> ORGANISM: Homo sapiens

<400> SEQUENCE: 264
caggtgtggg ataacactag tgatcatcct gtggtattc                             39

<210> SEQ ID NO 265
<211> LENGTH: 384
<212> TYPE: DNA
<213> ORGANISM: Homo sapiens

<400> SEQUENCE: 265 cagggggcgac tgcaggagtc gggcccagga ctggtgaagc cttcggagac cctgaccctc     60
acgtgcgctg tgtccggtgg ctcctccgtc agcagtccta actggtggac ttgggtccgc    120
caggcccccg ggaaggggct ggagtggatt ggagaaatct attatggtgg gagagtgagc    180
tacaactcgg ccctcaggag tcgagtcacc atttcatcag acaggtccaa agaggagttc    240
```

```
tccctgaaac tgaggtctgt gaccgccgcg gacacggcca tatattattg tgcgggtcaa    300
aaaaatattg gctgtggtta cagcagttgc tttatcagtt ggttcgacac ctggggacag    360
ggaattgcgg tcaccgtctc ctca                                           384
```

<210> SEQ ID NO 266
<211> LENGTH: 372
<212> TYPE: DNA
<213> ORGANISM: Homo sapiens

<400> SEQUENCE: 266

```
gaggtgcagc tggtggagtc tgggggaggt ttggtaaagc ctggggggtc ccttagactc     60
tcctgtgcag cctctggatt cactttcagt gacgcctgga tgagctgggt ccgccaggct    120
ccagggaagg ggctggagtg ggttggccat attaacacca agttgatgg tgggacaaca    180 gagtacgctg cacccgtgaa aggcagattc accatctcaa gagatgattc aaaaaattcg    240
ctgtatctgc acatggacag cctgaaaacc gaggacacag ccgtgtatta ctgtaccaca    300
gaggcgatat atgatagtag tggttatttc catgactatt ggggccaggg atccctggtc    360
accgtctcct ca                                                        372
```

<210> SEQ ID NO 267
<211> LENGTH: 378
<212> TYPE: DNA
<213> ORGANISM: Homo sapiens

<400> SEQUENCE: 267

```
gaggtgcagc tggtggagtc ggggggaggc ttggcacagc cagggcggtc cctgagactc     60
tcctgtacag cttctggatt caggtttggt gattttgcta tgagttgggt ccgccaggct    120
ccagggaagg gactggagtg ggtaggtttc attagaacca agctaatga tgggacaaca    180 gaatacgccg cgtctgtgaa aggcagattc atcatctcaa gagatgattc caaaagtatc    240
gcctatctgc aaatgaacag cctgaaaacc gaggacacag ccgtttatta ctgtgctagc    300
gatcccttca tgactacaga ctattactac tactacatgg acgtctgggg caaagggacc    360
acggtcaccg tctcctca                                                  378
```

<210> SEQ ID NO 268
<211> LENGTH: 381
<212> TYPE: DNA
<213> ORGANISM: Homo sapiens

<400> SEQUENCE: 268

```
gaggtgcaag tgttggagtc tgggggagac tcggtacagc ctggggggtc cctgagactc     60
tcctgtgcag cctctggatt cacctttagc agctatgcca tgacctgggt ccgccaggct    120
ccagggaagg ggctgaaatg ggtctcaagt attagtggta gtggtggtag cacatactac    180
gcagactccg tgaggggccg gttcaccatc tccagagaca attccaagaa cacgctgtat    240
gtgcagatga acagcctgag agccgaggac acggccgtat attactgtgc gaaaggatat    300
gtggggtgta gtggtgggaa ctgctactcg ggggtgctt ttgatatctg ggccaaggg    360 acagtggtca ccgtctcttc a                                              381
```

<210> SEQ ID NO 269
<211> LENGTH: 339
<212> TYPE: DNA
<213> ORGANISM: Homo sapiens

<400> SEQUENCE: 269

```
gacatcgtga tgacccagtc tccagactcc ctggctgtgt ctctgggcga gagggccacc    60
atcgcctgca agtccagcca gactattta caaaggtcca accatttgaa ctacttagct   120
tggtaccagc agaaaccagg acagcctcct aaagtgctca tttattgggc atctacccgg   180
gaatccgggg tccctgaccg attcagtggc agcgggtctg ggacagattt cactctcacc   240
atcaacagcc tgcaggctga ggatgtggca gtttattact gtcaccaata ttatactact   300
ccgcagactt ttggccaggg gaccaaggtg gagatcaaa                          339
```

<210> SEQ ID NO 270
<211> LENGTH: 336
<212> TYPE: DNA
<213> ORGANISM: Homo sapiens

<400> SEQUENCE: 270

```
gacatcgtga tgacccagtc tccagactcc ctggctgtgt ctctgggcga gagggccacc    60
atcaactgca gtccagccg gagtgtttta tacagctcca acaataagaa ctacttagct   120
tggtaccagc agaaaccagg acagcctcct aagctgctca tttactgggc atctatccgg   180
gaatccgggg tccctgaccg attcagtggc agcgggtctg ggacagattt cactctcacc   240
atcaacagcc tgcaggctga agatgtggca gtttattact gtcagcaata ttctcgtcct   300
ccgacgttcg gccaagggac caaggtggaa atcaaa                             336
```

<210> SEQ ID NO 271
<211> LENGTH: 324
<212> TYPE: DNA
<213> ORGANISM: Homo sapiens

<400> SEQUENCE: 271

```
cagtctgccc tgactcagcc tccctccgcg tccgggtctc ctggacagtc agtcaccatc    60
tcctgcactg gaaccagcag tgacgttggt ggttataact ctgtctcctg gtaccaacat   120
cacccaggca aagcccccaa actcatgatt tatgaggtct ataagcggcc cttagggggtc   180
cctgatcgct tctctggctc caagtctggc aacacggcct ccctgaccgt ctctgggctc   240
caggctgagg atgaggctta ttattactgc agctcatatg gaggcaccgt gctattcggc   300
ggagggacca gctgaccgt ccta                                           324
```

<210> SEQ ID NO 272
<211> LENGTH: 327
<212> TYPE: DNA
<213> ORGANISM: Homo sapiens

<400> SEQUENCE: 272

```
tcctatgtgc tgactcagcc accctcagtg tcagtggccc caggaaagac ggcccggatt    60
acctgtgggg gaacaacat ggaagtgaa agtgttcact ggtaccagca gaagccaggc    120
caggcccctg tggtggtcat ctattatgat accgaccggc cctcagggat ccctgagcgc   180
ttctctggct ccaactctgg gaacacggcc accctgacca tcagcagggt cgaagccggg   240
gatgaggccg actattactg tcaggtgtgg gataacacta gtgatcatcc tgtggtattc   300
ggcggaggga ccaagctgac cgtccta                                       327
```